US008546500B2

(12) United States Patent
Hoveyda et al.

(10) Patent No.: US 8,546,500 B2
(45) Date of Patent: Oct. 1, 2013

(54) COMPLEXES FOR USE IN METATHESIS REACTIONS

(75) Inventors: Amir H. Hoveyda, Lincoln, MA (US); Richard R. Schrock, Winchester, MA (US); Simon J. Meek, Newtonville, MA (US); Steven J. Malcolmson, Brighton, MA (US); Elizabeth T. Kiesewetter, Brighton, MA (US)

(73) Assignees: Massachusetts Institute of Technology, Cambridge, MA (US); Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 13/481,157

(22) Filed: May 25, 2012

(65) Prior Publication Data

US 2012/0302710 A1    Nov. 29, 2012

Related U.S. Application Data

(60) Provisional application No. 61/490,784, filed on May 27, 2011.

(51) Int. Cl.
*C08F 36/14* (2006.01)

(52) U.S. Cl.
USPC ............... 526/170; 548/402; 546/10; 546/12; 526/127; 502/167

(58) Field of Classification Search
USPC ...................... 526/170; 548/402; 546/10, 12
See application file for complete search history.

(56) References Cited

U.S. PATENT DOCUMENTS

| | | | |
|---|---|---|---|
| 5,055,628 A | 10/1991 | Lin et al. | |
| 5,889,128 A | 3/1999 | Schrock et al. | |
| 6,121,473 A | 9/2000 | Schrock et al. | |
| 6,271,325 B1 | 8/2001 | McConville et al. | |
| 6,306,988 B1 | 10/2001 | Grubbs et al. | |
| 6,316,555 B1 | 11/2001 | Schrock et al. | |
| 6,346,652 B1 | 2/2002 | Schrock et al. | |
| 6,414,097 B1 | 7/2002 | Grubbs et al. | |
| 6,610,806 B2 | 8/2003 | Schrock et al. | |
| 6,855,839 B2 | 2/2005 | McConville et al. | |
| 7,135,544 B2 | 11/2006 | Schrock et al. | |
| 7,932,397 B2 * | 4/2011 | Hock et al. .................... 548/101 |
| 2008/0119678 A1 | 5/2008 | Hock et al. | |
| 2011/0015430 A1 | 1/2011 | Schrock et al. | |
| 2011/0065915 A1 | 3/2011 | Malcolmson et al. | |
| 2011/0077421 A1 | 3/2011 | Schrock et al. | |
| 2011/0237815 A1 | 9/2011 | Hock et al. | |
| 2011/0245477 A1 | 10/2011 | Hoveyda et al. | |

OTHER PUBLICATIONS

[No Author Listed] New catalysts promise faster, cleaner, and more efficient research platform. Science Daily. 2 pages. (Nov. 16, 2008).
Aeilts et al., A readily available and user-friendly chiral catalyst for efficient enantioselective olefin metathesis, Angew Chem Int Ed. 40(8):1452-6 (2001).

Agbossou et al., Synthesis and Reactivity of Chiral Rhenium Alcohol Complexes of the Formula [(η5-C5H5)Re(NO)(PPH3)(ROH)] ⊕ BF4⊖. Chem Berichte. 123(6):129-9 (1990).
Al Obaidi, N. et al., Steric and Electronic Effects on the Chemistry of Molybdenum Octahedrally Co-ordinated by Six Nitrogen Atoms. The Molecular Structure of [Mo{HB(3,5-Me2C3N2H)3}(NO)(pyrollide)2],J. Chem. Soc., Chem. Commun. 690-692 (1984).
Altmann, K. H. et al., The Chemistry and Biology of Epothilones—The Wheel Keeps Turning. ChemMedChem. 2, 396-423 (2007).
Anderson et al., Kinetic selectivity of olefin metathesis catalysts bearing cyclic (alkyl)(amino)carbenes. Organometallics. 27(4):563-6 (2008).
Ascenso et al., Synthesis and characterization of [W(NC4Me4)2(Cl2] and [W(NC4Me4)2(CH3)2], the first azametallocene tungsten complexes with pyrrolyl ligands. Electronic structure and bonding of tungsten bispyrrolyl complexes. Inorg Chem Acta. 356: 249-58 (2003).
Bailey et al., Evaluation of molybdenum and tungsten metathesis catalysts for homogeneous tandem alkane metathesis. Organometallics. 28(1):355-60 (2009).
Balog, A., et al., A Novel Aldol Condensation with 2-Methyl-4-pentenal and Its Application to an Improved Total Synthesis of Epothilone B**. Angew. Chem., Int. Ed. 37, 2675-2678 (1998).
Barluenga et al., Zirconium-Mediated Coupling Reactions of Amines and Enol or Allyl Ethers: Synthesis of Allyl- and Homoallylamines. Chemistry—A European Journal, vol. 10 Iss1, pp. 109-116 (Abstract) 2004.
Bazan et al., Living ring-opening metathesis polymerization of 2,3-difunctionalized 7-oxanorbornenes and 7-oxanorbornadienes by Mo(CHCMe2R)(N-2,6-C6H3-iso-Pr2)(O-tert-Bu)2 and Mo(CHCMe2R)(N-2,6-C6H3-iso-Pr2)(OCMe2CF3)2. J Am Chem Soc. 113(18):6899-907 (1991).
Bei et al., Highly efficient olefin-metathesis catalysts. Pharm Technol. 2008:s18.
Bindl, M., et al., Molybdenum Nitride Complexes with Ph3SiO Ligands Are Exceedingly Practical and Tolerant Precatalysts for Alkyne Metathesis and Efficient Nitrogen Transfer Agents. J. Am. Chem. Soc.131, 9468-9470 (2009).
Blackwell et al., New approaches to olefin cross-metathesis. J Am Chem Soc. 122:58-71 (2000).
Blackwell, J. et al., Enediynes via sequential acetylide reductive coupling and alkyne metathesis: Easy access to well-defined molybdenum initiators for alkyne metathesis. Organometallics 22, 3351-3353 (2003).
Blanc, F. et al., Dramatic Improvements of Well-Defined Silica Supported Mo-Based Olefin Metathesis Catalysts by Tuning the N-Containing Ligands. J. Am. Chem. Soc.129(27), 8434-8435 (2007).
Blanc, F. et al., Highly Active, Stable, and Selective Well-Defined Silica Supported Mo Imido Olefin Metathesis Catalysts. J. Am. Chem. Soc.129(17), 1044-1045 (2007).
Blanc, F. et al., Surface versus molecular siloxy ligands in well-defined olefin metathesis catalysis: [{(RO)3SiO}Mo(=NAr)(=CHtBu)(CH2tBu)], Angew. Chem. Int. Ed. 45, 1216-1220 (2006).
Blosch, L., et al., Synthesis of an Air-Stable, Moisture-Stable, and Thermally Stable Tungsten (VI) Oxo Alkylidene Complex. Precursor to an Air- and Moisture-Stable ROMP Catalyst. J. Am. Chem. Soc. 113, 7066-7068 (1991).

(Continued)

Primary Examiner — Robert D. Harlan
(74) Attorney, Agent, or Firm — Choate, Hall & Stewart, LLP; Andrea L. C. Robidoux; Xiadong Li

(57) ABSTRACT

The present invention relates generally to metal complexes, methods for preparation and uses of the same.

20 Claims, 10 Drawing Sheets

(56) References Cited

OTHER PUBLICATIONS

Blosch, L., et al., Synthesis of Stable Tungsten (VI) Imido Alkylidene Complexes: Crystal Structure of an Air-Stable Cationic Alkylidene Complex. Organometallics. 11, 2342 (1992).

Bornand et al., Mechanism-based design of a ROMP catalyst for sequence-selective copolyerization. Angew Chem Int Ed Engl. 44(48):7909-11 (2005).

Brunner et al., Catalytic hydrosilylation or hydrogenation at one coordination site of Cp'Fe(CO)(X)] fragments. Angewandte Chemie Intl Ed Engl. 29(10):1131-2 (1990).

Brunner et al., Optisch aktive Übergangsmetall-Komplexe, LI: P-Liganden als optisch aktive Hilfsstoffe in den Komplexen C5H5M(CO)(NO)L, M=Cr, Mo, W. Chem Ber. 11:673-91.—Abstract only (1978).

Brunner, Optical activity at an asymmetrical manganese atom. Angew Chem. Int Ed Engl. 8:382-3 (1969).

Brunner, Optically active organometallic compounds of transition elements with chiral metal atoms. Angew Chemie Intl Ed. 38(9):1194-1208 (1999).

Brunner, Stability of the metal configuration in chiral-at-metal half-sandwich compounds. Eur J Inorg Chem. 905-12 (2001).

Burdett et al., Renewable monomer feedstocks via olefin metathesis: fundamental mechanistic studies of methyl oleate ethenolysis with the first-generation grubbs catalyst. Organometallics. 23(9):2027-47 (2004).

Cantrell et al., Ring-Opening Metathesis of a Cyclic Imine. Organometallics, vol. 19, pp. 3562-3568 (2000).

Chatterjee et al., Olefin Cross-Metathesis. Handbook Metathesis. 2003;2:246-95.

Chen, Y., et al., Regioselective Substitution of Fluorine in F8BINOL as a Versatile Route to New Ligands with Axial Chirality. Org. Lett. 2, 3433-3436 (2000).

Clark, D, N., et al., Multiple Metal-Carbon Bonds. 12.[1] Tungsten and Molybdenum Neopentylidyne and Some Tungsten Neopentylidene Complexes. J. Am. Chem. Soc. 100, 6774-6776 (1978).

Connon et al., Recent developments in olefin cross-metathesis. Angew Chem Int Ed Engl. 42(17):1900-23(2003).

Corma et al., Chemical routes for the transformation of biomass into chemicals. Chem Rev. 107(6):2411-502. (2007).

Coutelier, O., et al., Terminal alkyne metathesis: A further step towards selectivity. Adv. Synth. Catal. 348, 2038-2042 (2006).

Deiter, A., et al., Synthesis of oxygen- and nitrogen-containing heterocycles by ring-closing metathesis. Chem. Rev. 104, 2199-2238 (2004).

Dias, A. et al., Synthesis, characterisation, crystal structure, reactivity and bonding in titanium complexes containing 2,3,4,5-tetramethylpyrrolyl. J. Chem. Soc., Dalton Trans.1055-1061 (1997).

Dinger et al., High turnover numbers with ruthenium-based metathesis catalysts. Adv Synth Catal. 344(6-7):671-7 (2002).

Dolman et al., Efficient catalytic enantioselective synthesis of unsaturated amines: preparation of small- and medium-ring cyclic amines through mo-catalyzed asymmetric ring-closing metathesis in the absence of solvent. J Am Chem Soc.124(24):6991-7 (2002).

Dolman, New chiral molybdenum metathesis catalysts; application of the enantioselective preparation of cyclic amines, Ph.D. Thesis. MIT. 234 pages. (Jun. 2004).

Duarte, M. et al., Chlorobis(dimethylamido)($\eta^5$-2,5-dimethylpyrrolyl)titanium(IV), [Ti(NMe$_2$)2(DMP)CI]. Acta Cryst. C.61, 104-106 (2005).

Edwards, D. S., et al., Rhenium (VII) Neopentylidene and Neopentylidyne Complexes and the X-ray Structure of Re(CCME$_3$) (CHCMe$_3$) (C$_5$H$_5$N)$_2$I$_2$[1]. Organometallics. 2, 1505 (1983).

Feldman, J. et al., Recent advances in the schnistry of "d0" alkylidine metallacyclobutane complexes. Prog. Inorg. Chem.39, 1-74 (1991).

Flook et al., Z-selective olefin metathesis processes catalyzed by a molybdenum hexaisopropylterphenoxide monopyrrolide complex. J. Am Chem Soc.131(23):7962-3 (2009).

Flook, M. M. Thesis: Z-Selective Olefin Metathesis Processes and Cis/Syndioselective ROMP with High Oxidation State Molybdenum Alkylidenes. Massachusetts Institute of Technology (2012).

Flook, M. M., et al. Z-Selective and Syndioselective Ring-Opening Metathesis Polymerization (ROMP) Inititated by Monoaryloxidepyrrolide (MAP) Catalysts. Macromolecule.43, 7515-7522 (2010).

Flook, M. M., et al., Synthesis of cis, syndiotactic ROMP Polymers Containing Alternating Enantiomers. J. Am. Chem. Soc.133, 1784-1786 (2011).

Fontecave et al., Chiral-at-metal complexes as asymmetric catalysts, In Chiral Diazaligands for Asymmetric Synthesis. Top Organometallic Chem.15(2005):271-88 (2005).

Forman et al., A stable ruthenium catalyst for productive olefin metathesis. Organometallics. 23(21);4824-7 (2004).

Fox, H. H., et al., Synthesis of Five- and Six- Coordinate Alkylidene Complexes of the Type Mo (CHR) (NAr) [OCMe(CF$_3$)$_2$]$_2$S$_x$ and Their Use as Living ROMP Initiators or Wittig Reagents. Organometallics.12, 759-768 (1993).

Freudenberger, H. H., et al., Preparation of Di-tert-butoxytungsten(VI) Alkylidene Complexes by Protonation of Tri-tert-butoxytungsten(VI) Alkylidene Complexes[1]. Organometallics. 4, 1937-1944 (1985).

Fürstner et al., Cationic ruthenium allenylidene complexes as catalysts for ring closing olefin metathesis. Chemistry. 6(10):1847-57 (2000).

Fürstner, A. et al., Alkyne metathesis: Development of a novel molybdenum-based catalyst system and its application to the total synthesis of Epothilone A and C. Chem. Eur. J. 7(24), 5299-5317 (2001).

Fürstner, A. et al., Mo[N(t-Bu)(Ar)]3 complexes as catalyst precursors: in situ activation and application to metathesis reactions of alkynes and diynes. J. Am. Chem. Soc. 121, 9453-9454 (1999).

Fürstner, A., et al., Conformationally Unbiased Macrocyclization Reactions by Ring Closing Metathesis. J. Org. Chem. 61, 3942-3943 (1996).

Fürstner, A., et al., Macrocycles by ring-closing metathesis. Synthesis 792-803 (1997).

Fürstner, A., et al., Ring Closing Alkyne Metathesis. Comparative Investigation of Two Different Catalyst Systems and Application to the Stereoselective Synthesis of Olfactory Lactones, Azamacrolides, and the Macrocyclic Perimter of the Marine Alkaloid Nakadomarin A. J. Am. Chem. Soc.121, 11108-11113 (1999).

Fürstner, A., et al., Total synthesis of the turrianes and evaluation of their DNA-cleaving properties. Che. Eur. J. 8, 1856-1871 (2002).

Ganter, Chiral organometallic half-sandwich complexes with defined metal configuration. Chem Soc Rev. 32(3):130-8 (2003).

Garber, S. B., et al., Efficient and recyclable monomeric and dendritic Ru-based metathesis catalysts. J. Am. Chem. Soc. 122, 8168-8179 (2000).

Gerber, L. C., et al., Synthesis of Molybenum Alkylidene Complexes That Contain the 2,6-Dimesitylphenylimido Ligand. J. Am. Chem. Soc.133, 18142-18144 (2011).

Giessert et al., Intermolecular enol ether-alkyne metathesis, Org Lett. 5(10):1793-6 (2003).

Gillingham et al., Chiral N-heterocyclic carbenes in natural product synthesis: application of Ru-catalyzed asymmetric ring-opening/cross-metathesis and Cu-catalyzed allylic alkylation to total synthesis of baconipyrone C. Agnew Chem Int Ed Engl. 46(21):3860-4 (2007).

Giudici et al., Directed catalytic asymmetric olefin metathesis. Selectivity control by enoate and ynoate groups in Ru-catalyzed asymmetric ring-opening/cross-metathesis. J Am Chem Soc.129(13):3824-5. (2007).

Gradillas, A., et al., in Metathesis in Natural Product Synthesis (eds Cossy, J., Arseniyadis, S., Meyer, C.)—(Wiley-VCH, 2010).

Gradillas, A., et al., Macrocyclization by ring-closing metathesis in the total synthesis of natural products: reaction conditions and limitations. Angew. Chem. Int. Edn 45, 6086-6101 (2006).

Hadlington, Catalyst flexes for extra control. Chemistry World. Nov. 17, 2008. Last accessed online. Dec. 1, 2008.

Heppekausen, J., et al., Practical New Silyloxy-Based Alkyne Metathesis Catalysts with Optimized Activity and Selectivity Profiles. J. Am. Chem. Soc.132, 11045-11057 (2010).

Heppekausen, J., et al., Rendering Schrock-type Molybdenum Alkylidene Complexes Air Stable: User-Friendly Precatalysts for Alkene Metathesis. Angew. Chem. Int. Ed.50, 7829-7832 (2011).

Herrmann et al., Methyltrioxorhenium als Katalysator für die Olefin-Metathese. Angew Chem 103:1704-1706 (1991).

Herrmann et al., Methyltrioxorhenium as Catalyst for Olefin Metathesis. Angew Chem Int. Ed. Engl. 103:1636-1638 (1991).

Hesek et al., The first asymmetric synthesis of chiral ruthenium tris(bipyridine) from racemic ruthenium bis(bipyridine) complexes. Tetrahedron Lett. 41(15):2617-20 (2000).

Hock, A. et al., Dipyrrolyl Precursors to Bisalkoxide Molybdenum Olefin Metathesis Catalysts. J. Am. Chem. Soc.128(50), 16373-16375 (2006).

Hoveyda, A. et al., The remarkable metal-catalyzed olefin metathesis reaction. Nature 450, 243-251 (2007).

Ibrahem et al., Highly Z- and enantioselective ring-opening/cross-metathesis reactions catalyzed by stereogenic-at-Mo adamantylimido complexes. J Am Chem Soc.131(11):3844-5 (2009).

International Preliminary Report on Patentability for PCT/US2010/002644, issued Apr. 3, 2012.

International Preliminary Report on Patentability for PCT/US2011/024100, issued Aug. 14, 2012.

International Preliminary Report on Patentability from International Patent Application Serial No. PCT/US2007/024318, filed Nov. 21, 2007, mailed May 26, 2009.

International Preliminary Report on Patentability in connection with Application Serial No. PCT/US2009/000465 issued Jul. 27, 2010.

International Search Report and Written Opinion in connection with Application Serial No. PCT/US2009/000465 mailed Jul. 13, 2009.

International Search Report and Written Opinion in PCT/US2007/024318, mailed on May 7, 2008.

International Search Report and Written Opinion in PCT/US2011/024100, mailed on Apr. 23, 2011.

International Search Report for PCT/US2010/002644, mailed Mar. 7, 2011.

International Search Report for PCT/US2012/40574, mailed Sep. 5, 2012.

Jakubec, P., et al., Total synthesis of (−)-nakadomarin A. J. Am. Chem. Soc.131, 16632-16633 (2009).

Jiang et al., Fundamental studies of tungsten alkylidene imido monoalkoxidepyrrolide complexes. J Am Chem Soc.131(22):7770-80 (2009).

Jiang et al., Highly Z-selective metathesis homocoupling of terminal olefins, J Am Chem Soc.131(46):16630-1 (2009).

Kershner, D. et al., η5-Heterocyclic Metal Carbonyls. Coord. Chem. Rev. 79, 279-92 (1987).

Kiely et al., Enantioselective synthesis of medium-ring heterocycles, tertiary ethers, and tertiary alcohols by Mo-catalyzed ring-closing metathesis. J Am Chem Soc. 124(12):2868-9 (2002).

King, A. J. H., Ph.D. Thesis: The Evolution of Molybdenum and Tungsten Olefin Metathesis Catalysts. Massachusetts Institute of Technology (2010).

Knof et al., Predetermined chirality at metal centers. Angew Chemie Intl Ed. 38(3):302-22 (1999).

Kreickmann, T., et al., Imido Alkylidene Bispyrrolyl Complexes of Tungsten. Organometallics. 26, 5702-5711 (2007).

Lacour et al., Recent developments in chiral anion mediated asymmetric chemistry. Chem Soc Rev. 32(6):373-82 (2003).

Lee et al., Enantioselective synthesis of cyclic enol ethers and all-carbon quaternary stereogenic centers through catalytic asymmetric ring-closing metathesis. J Am Chem Soc. 128(15):5153-7 (2006).

Lee et al., Endo-selective enyne ring-closing metathesis promoted by stereogenic-at-Mo monoalkoxide and monoaryloxide complexes. Efficient synthesis of cyclic dienes not accessible through reactions with Ru carbenes. J Am Chem Soc.131(30):10652-61 (2009).

Lichtscheidl, A. G., et al., Molybdenum Monoaryloxide Pyrrolide Alkylidene Complexes That Contain Mono-*ortho*-substituted Phenyl Imido Ligands. Organometallics. 31, 2388-2394 (2012).

Liu et al., Regioselective ring-opening/cross-metathesis reactions of norbornene derivatives with electron-rich olefins. Org Lett. 7(I):131-3 (2005).

Lokare et al., Synthesis, properties, and structure of tethered molybdenum alkylidenes. Organometallics. 27(19):5130-8 (2008).

Malcolmson et al., Highly efficient molybdenum-based catalysts for enantioselective alkene metathesis. Nature. 456(7224):933-7 (2008).

Marinescu et al., Ethenolysis reactions catalyzed by imido alkylidene monoaryloxide monopyrrolide (MAP) complexes of molybdenum. J Am Chem Soc. Aug. 12, 2009;131(31):10840-1 (2009).

Marinescu et al., Inversion of configuration at the metal in diastereomeric imido alkylidene monoaryloxide monopyrrolide complexes of molybdenum. J Am Chem Soc.131 (1):58-9 (2009).

Marinescu, S. C., et al., Isolation of Pure Disubstituted E Olefins through Mo-Catalyzed Z-Selective Ethenolysis of Stereoisomeric Mixtures. J. Am. Chem. Soc. 133, 11512-14 (2011).

Marinescu, S. C., et al., Room-Temperature Z-Selective Homocoupling of α-Olefins by Tungsten Catalysts. Organometallics. 30, 1780-1782 (2011).

Marinescu, S. C., et al., Syntheses and Structures of Molybdenum Imido Alkylidene Pyrrolide and Indolide Complexes. Organometallics. 27, 6570-8 (2008).

Maruoka et al., Efficient synthesis of sterically hindered chiral binaphthol derivatives. Bull Chem Soc Jpn. 61(8):2975-6 (1988).

May, S. A., et al., Total synthesis of (−)-epothilone B. Chem. Commun. 1597-1598 (1998).

McDougal et al., Asymmetric Morita-Baylis-Hillman reactions catalyzed by chiral Brønsted acids. J Am Chem Soc. 125(40):12094-5 (2003).

McDougal et al., The development of the asymmetric morita-baylis-hillman reaction catalyzed by chiral brønsted acids, Adv Synth Cat. 346;1231-40 (2004).

Meek et al., The significance of degenerate processes to enantioselective olefin metathesis reactions promoted by stereogenic-at-Mo complexes. J Am Chem Soc.131(45):16407-9 (2009).

Meek, S. J., et al., Catalytic Z-selective olefin cross-metathesis for natural product synthesis. Nature 471, 461-466 (2011).

Meng, D.; et al., Total Sysntheses of Epothilones A and B. J. Am. Chem. Soc. 119, 10073-10092 (1997).

Monchaud et al., Ion-pair-mediated asymmetric synthesis of a configurationally stable mononuclear tris(diimine)-iron(II) complex. Angew Chem Int Ed Engl. 41(13):2317-9 (2002).

Morrison, D. J., et al., 2,2'-Disubstiuted F12binaphthyl derivatives: stannanes, boranes, and (R)-F12BINOL. Chem. commun.2875-2877 (2006).

Nagata, T., et al., The first total synthesis of nakadomarin A. J. Am. Chem. Soc. 125, 7484-7485 (2003).

Nicolaou et al,, Metathesis reactions in total synthesis. Angew Chem Int Ed Engl. 44(29):4490-527 (2005).

Nicolaou, K. C., et al. Synthesis of epothilones A and B in solid and solution phase. Nature 387, 268-272 (1997).

Nicolaou, K. C., et al. The olefin metathesis approach to epothilone A and its analogues. J. Am. Chem. Soc. 119, 7960-7973 (1997).

Nicolaou, K. C., et al., Chemical Biology of Epothilones. Angew. Chem., Int. Ed. 37, 2014-2045 (1998).

Nicolaou, K. C., et al., Total Syntheses of Epothilones A and B via a Macrolactonization-Based Strategy. J. Am. Chem. Soc. 119, 7974-7991 (1997).

Nilson, M. G., et al., Total synthesis of (−)-nakadomarin A. Org. Lett. 12, 4912-4915 (2010).

Ono, K., et al., Asymmetric total synthesis of (−)-nakadomarin A. Angew. Chem. Int. Edn, 43, 2020-2023 (2004).

Oskam, J. H., et al., Ligand variation in alkylidene complexes of the type Mo(CHR)(NR')(OR'')$_2$. J. Organomet. Chem.459, 185 (1993).

Peryshkov, D. V., et al., Z-Selective Olefin Metathesis Reaction Promoted by Tungsten Oxo Alkylidene Comlexes. J. Am. Chem. Soc. 133, 20754-7 (2011).

Pezet et al., Highly diastereoselective preparation of ruthenium bis(diimine) sulfoxide complexes: new concept in the preparation of optically active octahedral ruthenium complexes. Organometallics. 19(20):4008-15 (2000).

Poater et al., Understanding d(0)-olefin metathesis catalysts: which metal, which ligands? J Am Chem Soc.129(26):8207-16 (2007).

Quintard, D. et al., Synthesis and Conformational Analysis of Macrocycles Related to 10-Oxa-epothilone. Eur. J. Org. Chem. 4762-4770 (2004).

Rhers, B. et al., A well-defined, silica-supported tungsten imido alkylidene olefin metathesis catalyst. Organometallics. 25, 3554-3557 (2006).

Rivkin, A., et al., On the Remarkable Antitumor Properties of Fludelone: How We Got There. Angew. Chem., Int. Ed.44, 2838-2850 (2005).

Sattely et al., Design and stereoselective preparation of a new class of chiral olefin metathesis catalysts and application to enantioselective synthesis of quebrachamine: catalyst development inspired by natural product synthesis. J Am Chem Soc.131(3):943-53 (2009).

Sattely et al., Enantioselective synthesis of cyclic amides and amines through mo-catalyzed asymmetric ring-closing metathesis. J Am Chem Soc.127(23):8526-33 (2005).

Sattely, Cyclic amines and amides through molybdenum-catalyzed asymmetric olefin metathesis: A total synthesis of quebrachamine. Boston College Dissertations and Theses. Paper AAI3256831. http://escholarship.bc.edu/dissertations/AA13256831. 340 pages. (Jan. 1, 2007).

Schaverien, C. J., et al., A Well-Characterized, Highly Active, Lewis Acid Free Olefin Metathesis Catalyst[1]. J. Am. Chem. Soc. 108, 2771-3 (1986).

Schinzer, D. et al., Synthesis of (−)-Epothilone A. Angew. Chem., Int. Ed. 36, 523-524 (1997).

Schinzer, D. et al., Synthesis of (−)-Epothilone A. Chem. Eur. J. 5, 2483-2491 (1999).

Schinzer, D. et al., Syntheses of (−)-Epothilone B. Chem. Eur. J. 5, 2492-2500 (1999).

Scholl, M., et al., Synthesis and activity of a new generation of ruthenium-based olefin metathesis catalysts coordinated with 1,3-dimesityl-4,5-dihydroimidazol-2-ylidine ligands. Org. Lett. 1, 953-956 (1999).

Schrock et al., Further studies of imido alkylidene complexes of tungsten, well-characterized olefin metathesis catalysts with controllable activity. Organometallics, vol. 9, No. 8, pp. 2262-2275 (1990).

Schrock et al., Thousands of catalysts for olefin metathesis: variability, longevity and asymmetry at the metal. Abstract. Presented at Technical University of Berlin (Oct. 24, 2008).

Schrock, R. et al., Molybdenum alkylidyne complexes that contain 3,3'-di-t-butyl-5,5', 6,6'-tetramethyl-1-1, 11-biphenyl-2,21-diolate ([Biphen]2-) ligand. J. Organomet, Chem. 684, 56-67 (2003).

Schrock, R. et al., Molybdenum and tungsten imido alkylidene complexes as efficient olefinmetathesis catalysts. Angew. Chem. Int. Ed. 42, 4592-4633 (2003).

Schrock, R. et al., Preparation of molybdenum and tungsten neopentylidyne complexes of the type $M(CCMe_3)(O_2CR)_3$, their reactions with acetylenes, and the X-ray structure of the $\eta_3$-cyclopropenyl complex $W[C_3(CMe_3)Et_2]O_2CCH_3)_3$. Organometallics. 5, 25-33 (1986).

Schrock, R. et al., Synthesis of Molybdenum Imido Alkylidene Complexes and Some Reactions Involving Acyclic Olefins. J. Am. Chem. Soc. 112, 3875-3886 (1990).

Schrock, R. R. High-Oxidation-State Molybdenum and Tungsten Alklidyne Complexes. Acc. Chem. Res.19, 342-348 (1986).

Schrock, R. R., et al., Preparation and Reactivity of Several Alkylidene Complexes of the Type $W(CHR')(N-2,6-C_6H_3-i-Pr_2)(OR)_2$ and Related Tungstacyclobutane Complexes. Controlling Metathesis Activity through the Choice of Alkoxide Ligand. J. Am. Chem. Soc. 109, 1423-35 (1987).

Schrock, R. R., et al., Preparation of Rhenium(VII) Monoimido Alkylidyne Complexes and Metathesis of Acetylenes via Rhenacyclobutadiene Intermediates. J. Am. Chem. Soc. 110, 2686-7 (1988).

Schrock, R. R., et al., Recent Advances in the Syntheses and Applications of Molybdebnum and Tungsten Alkylidene and Alkylidyne Catalysts for the Metathesis of Alkenes and Alkynes. Adv. Syn. Catal. 349, 55-77 (2007).

Schrock, R. R., et al., Tungsten(VI) Neopentylidyne Complexes. Organometallics. 1, 1645-51 (1982).

Schrock, R., High oxidation state multiple metal-carbon bonds. Chem. Rev.102, 145-179 (2002).

Schrock, Recent advances in high oxidation state Mo and W imido alkylidene chemistry. Chem Rev. 109(8):3211-26 (2009).

Schrodi et al., Ruthenium olefin metathesis catalysts for the ethenolysis of renewable feedstocks. Clean: Soil, Air, Water. 36:669-673 (2008).

She, J., et al., Examination of the olefin-olefin ring-closing metathesis to prepare latrunculin B. Tetrahedron Lett. 50, 298-301 (2009).

Singh, R. et al., Molybdenum Imido Alkylidene Metathesis Catalysts That Contain Electron-Withdrawing Biphenolates or Binaphtholates. Organometallics. 26(10), 2528-2539 (2007).

Singh, R. et al., Synthesis of Monoalkoxide Monopyrrolyl Complexes Mo(NR)(CHR')(OR")(pyrrolyl): Enyne Metathesis with High Oxidation State Catalysts. J. Am. Chem. Soc.129(42), 12654-12655 (2007).

Sinha, A. et al., Diphenylamido precursors to bisalkoxide molybdenum olefin metathesis catalysts. Organometallics. 25, 4621-4626 (2006).

Sinha, A. et al., Reactions of $M(N-2,6-i-Pr2C6H3)(CHR)(CH2R')2$ (M=Mo, W) Complexes with Alcohols to Give Olefin Metathesis Catalysts of the Type $M(N-2,6-i-Pr2C6H3)(CHR)(CH2R')(OR")$. Organometallics. 25, 1412-23 (2006).

Sinha, S. C., et al., Catalytic Antibody Route to the Naturally Occurring Epothilones: Total Synthesis of Epothilones A-F. Chem. Eur. J. 7, 1691-1702 (2001).

Smith, B. J., et al., Total synthesis of (±)-haliclonacyclamine C. Angew. Chem. Int. Edn 49, 1599-1602 (2010).

Solans-Monfort et al., $d^0$ Re-based olefin metathesis catalysts, Re(=CR)(=CHR)(X)(Y): The key role of X and Y ligands for efficient active sites. J Am Chem Soc.127(40):14015-25 (2005).

Takano et al., Enantioselective route to both (+)- and (−)-enantiomers of quebrachamine using a single chiral synthon. J Chem Soc Chem Commun. 1153-5 (1981).

Takemura et al., Stereochemical aspects of asymmetric Diels-Alder reaction catalyzed by chiral alkoxyaluminum dichlorides. Tetrahedron Lett. 1987;28(46):5687-90 (1987).

Tallarico et al., Selectivity in ring-opening metatheses. Tetrahedron. 53(48):16511-20 (1997).

Tayama et al., Activation of ether functionality of allyl vinyl ethers by chiral bis(organoaluminum) Lewis acids: application to asymmetric Claisen rearrangement. Tetrahedron. 58(41):8307-12 (2002).

Tonzetich, Z. et al., Reaction of Phosphoranes with Mo(N-2,6-i-Pr2C6H3)(CHCMe3)[OCMe(CF3)2]2: Synthesis and Reactivity of an Anionic Imido Alkylidyne Complex. Organometallics. 25, 4301-4306 (2006).

Toreki, R., et al., A Well-Defined Rhenium(VII) Olefin Metathesis Catalyst. J. Am. Chem. Soc.112, 2448-9 (1990).

Toreki, R., et al., Synthesis and Characterization of Re(VII) Alkylidene Alkylidyne Complexes of the Type Re(CR')(CHR')(OR)₂ and Related Species. J. Am. Chem. Soc. 114, 3367-80 (1992).

Toró, A., et al., Furanophane Transannular Diels-Adler Approach to (+)-Chatancin: An Asymmentric Total Synthesis of (+)-Anhydrochatancin. J. Org. Chem. 68, 6847-6852 (2003).

Tsai, Y. et al, Facile synthesis of trialkoxymolybdenum(VI) alkylidyne complexes for alkyne metathesis. Organometallics. 19, 5260-5262 (2000).

Van Veldhuizen et al., A readily available chiral Ag-based N-heterocyclic carbene complex for use in efficient and highly enantioselective Ru-catalyzed olefin metathesis and Cu-catalyzed allylic alkylation reactions. J Am Chem Soc.127(18):6877-82 (2005).

Van Veldhuizen et al., A recyclable chiral Ru catalyst for enantioselective olefin metathesis. Efficient catalytic asymmetric ring-opening/cross metathesis in air. J Am Chem Soc. May 8, 2002;124(18):4954-5. Erratum in: J Am Chem Soc.125(41):12666 (2003).

Walls et al., Alkaloids from *Stemmadenia* species-I : The alkaloids of S. *donnell-smithii* and S. Galeottiana. Tetrahedron. 2(3-4):173-82 (1958).

Wang, Y., et al., Control of Olefin Geometry in Macrocyclic Ring-Closing Metathesis Using a Removabel Silyl Group. J. Am. Chem. Soc. 133, 9196-9199 (2011).

Weatherhead et al., Mo-catalyzed asymmetric olefin metathesis in target-oriented synthesis: enantioselective synthesis of (+)-africanol. Proc Natl Acad Sci U S A.101(16):5805-9 (2004).

Weinstock, I. A., et al., Rhenium(VII) Monoimido Alkylidyne Complexes. The Importance of Face Selectivity in the Metathesis of Acetylenes via Rhenacyclobutadiene Intermediates. J. Am. Chem. Soc. 113, 135-44 (1991).

Wengrovius, J. H., et al., Synthesis and Characterization of Tungsten Oxo Neopentylidene Complexes[1]. Organometallics. 1, 148-55 (1982).

Wengrovius, J. H., et al., Tungsten-Oxo Alkylidene Complexes as Olefin Metathesis Catalysts and the Crystal Structure of W(O)(CHCM$_3$)(PEt$_3$)(Cl$_2^1$). J. Am. Chem. Soc. 102, 4515-6 (1980).

Werner et al., Bur Kennfnie dee asymmetrimhen Kobaltatoms. I. Ber Dtsch Chem Ges. 44:1887-98. German. (1911).

Written Opinion for PCT/US2012/040574, mailed Sep. 5, 2012.

Written Opinion for PCT/US2010/002644, mailed Mar. 7, 2011.

Xie, J., et al., Total synthesis of the proposed structure of iriomoteolide-1a. Chem. Commun. 46, 4770-4772 (2010).

Xu, Z. et al. Applications of Zr-catalyzed carbomagnesation and Mo-catalyzed macrocyclic ring-closing metathesis in asymmetric synthesis. Enantioselective total synthesis of Sch 38516(fluvirucin B). J. Am. Chem. Soc. 119, 10302-10316 (1997).

Yang, Z., et al., Total Synthesis of Epothilone A: The Olefin Metathesis Approach. Angew. Chem., Int. Ed. 36, 166-168 (1997).

Yashiro et al., Efficient stereochemical regulation of octahedral cobalt(III) complexes by a chiral bidentate ligand. Part 2. Remarkable effect of the chelate-ring size in the stereoselective formation of sym-cis-(ethylenediamine-N,N'-diacetato)(pentane-2,4-diamine)cobalt(III). J Chem Soc. Dalton Trans.10:1511-6 (1994).

Yashiro et al., Efficient stereochemical regulation of octahedral cobalt(III) complexes by a chiral bidentate ligand. Part I. Effect of N-alkyl substitutions. J Chem Soc, Dalton Trans. 7:1073-7 (1994).

Yi et al., The ruthenium acetylide catalyzed cross-coupling reaction of terminal and internal alkynes: isolation of a catalytically active β-agostic intermediate species. Organometallics. 17(15):3158-60 (1998).

Young, I., et al., Total synthesis of (+)-nakadomarin A. J. Am. Chem. Soc. 129, 1465-1469 (2007).

Yu, M., et al., Enol Ethers as Substrates for Efficient Z- and Enantioselective Ring-Opening/Cross-Metathesis Reactions Promoted by Stereogenic-at-Mo Complexes: Utility in Chemical Synthesis and Mechanistic Attributes. J. Am. Chem. Soc.134, 2788-2799 (2012).

Yu, M., et al., Synthesis of macrocyclic natural products by catalyst-controlled stereoselective ring-closing metathesis. Nature, 479, 88-93 (2011).

Yudin, A. K., et al., F8BINOL, an Electronically Perturbed Version of Binol with Remarkable Configurational Stability. Org. Lett. 2, 41-44 (2000).

Zhang, W. et al., A reductive recycle strategy for the facile synthesis of molybdenum(VI) alkylidyne catalysts for alkyne metathesis. Chem. Commun. 832-833 (2003).

Zhao, Y., et al., *Endo*-Selective Enyne Ring-Closing Metathesis Promoted by Stereogenic-at-W Mono-Pyrrolide Complexes. Org. Lett. 13, 784-787 (2011).

Zhou et al., Synthesis and reactivity of chiral rhenium indenyl complexes of the formula [(μ5-C9H7)Re(NO)(PPh3)(X)]n+. Organometallics.12(10);3918-23 (1993).

Zhu et al., Chiral Mo-Binol complexes: activity, synthesis, and structure. efficient enantioselective six-membered ring synthesis through catalytic metathesis. J Am Chem Soc. 121:8251-9 (1999).

\* cited by examiner (a)

(b)

COMPLEXES FOR USE IN METATHESIS REACTIONS

CROSS-REFERENCE TO RELATED APPLICATIONS

The present invention claims priority to U.S. Provisional Application Ser. No. 61/490,784, filed May 27, 2011, the entirety of which is incorporated herein by reference.

STATEMENT REGARDING FEDERALLY SPONSORED RESEARCH OR DEVELOPMENT

This invention was made with government support under Grant No. R01 GM059426 awarded by the National Institutes of Health. The government has certain rights in this invention.

FIELD OF THE INVENTION

The present invention generally relates to stabilized methatesis catalyst precursors.

BACKGROUND

Catalytic olefin metathesis has transformed chemical synthesis and offers exceptionally efficient pathways for synthesis of alkenes. Among various types of olefin metathesis, cross-metathesis of two different terminal alkenes, a reaction that generates only the easily removable ethylene as the side-product, constitutes a remarkably attractive and efficient strategy for synthesis of disubstituted alkenes. Cross-metathesis, however, is a mechanistically complicated variant of this class of transformations. In ring-closing metathesis, reacting alkenes are tethered and the intramolecular reaction is favored; in ring-opening metathesis, release of strain typically serves as the driving force that results in one of several pathways to be preferred. In contrast, cross-metathesis demands that two different alkenes react without the entropic benefit of an intramolecular reaction or strain release, and under conditions that can also cause homo-coupling of the cross partners.

A great number of commercially important molecules contain olefins. Such specialty chemicals include biologically active molecules, oleochemicals, renewables, fine chemicals, and polymeric materials, to name a few. Moreover, many reactions in organic chemistry require alkenes as starting materials. Accordingly, there remains an unmet need for improved methods and catalysts for metathesis reaction.

SUMMARY

Figure 1:
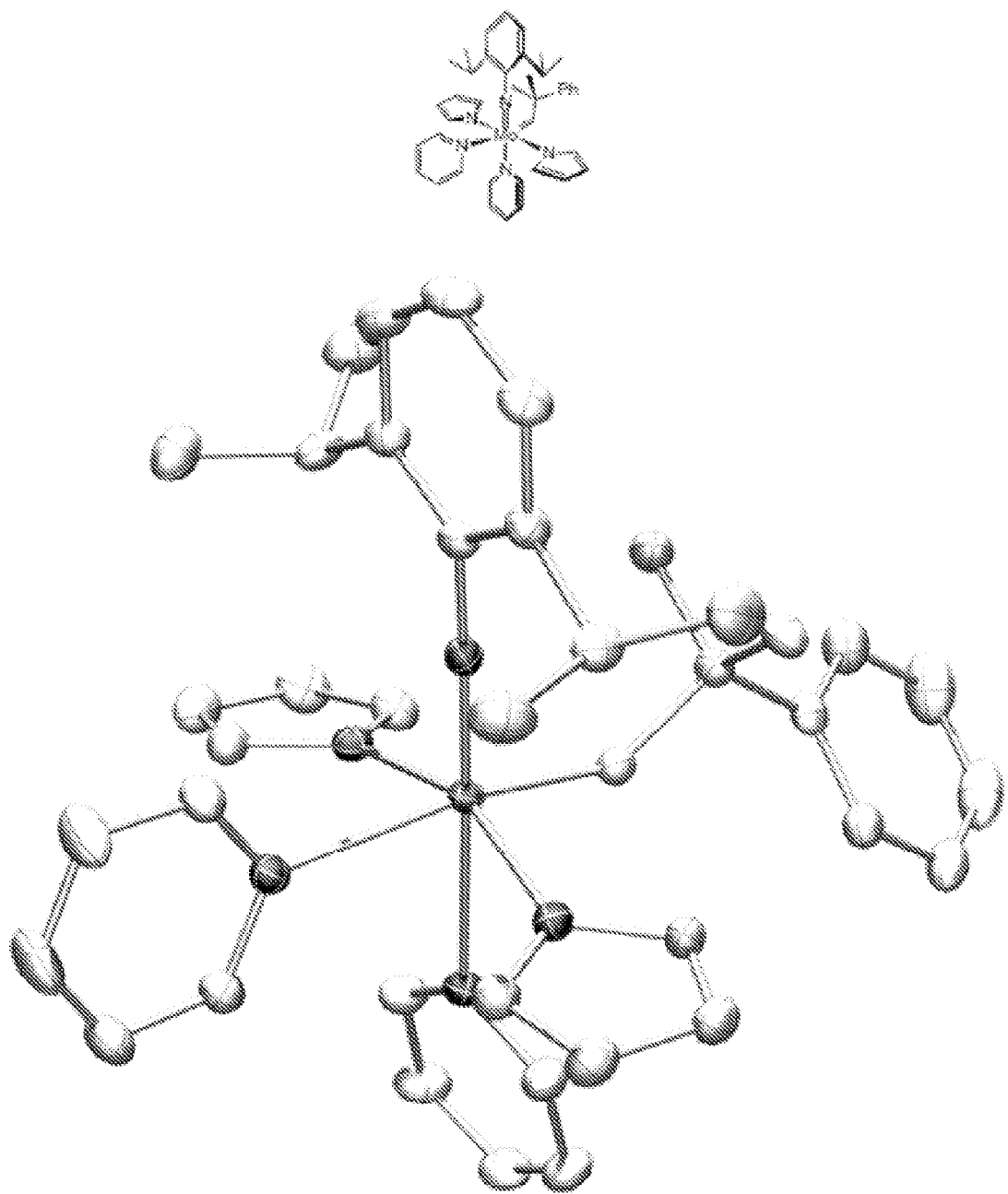
FIG. 1. X-ray crystal structure of alkylidene pyr-5.

In some embodiments, the present invention provides new stabilized metathesis catalyst precursor complexes and methods of using the same. Some embodiments provide moisture- and/or air-stable precursor complexes that can be used outside of an inert environment for an amount of time without substantial degradation to the complex.

In some embodiments, the present invention provides novel complexes which can serve as precursors to stereogenic-at-metal metathesis catalysts. In some embodiments, a provided precursor complex exhibits improved air-stability and/or moisture stability relative to known metathesis catalyst complexes.

In some embodiments, the present invention provides methods of preparing provided precursor complexes which are useful for synthesizing metathesis catalysts.

In some embodiments, the present invention provides methods of generating active metathesis catalysts from provided precursor complexes.

In some embodiments, the present invention provides methods of using provided precursor complexes in metathesis reactions. Exemplary metathesis reactions include ring-closing metathesis reactions, Z-selective homo-coupling reactions, Z-selective cross-metathesis reactions, and the like. In some embodiments, the metathesis reaction is an olefin metathesis reaction. One of skill in the art will appreciate that a provided precursor complex may be useful in any reaction in which the active catalyst generated from the provided precursor complex is useful.

DETAILED DESCRIPTION OF CERTAIN EMBODIMENTS

1. General Description of Certain Embodiments of the Invention

Certain stereogenic-at-metal complexes display unprecedented reactivity and stereoselectivity in olefin metathesis reactions; examples are highly enantioselective ring-closing metathesis (RCM) reactions or Z-selective homo-coupling and cross-metathesis processes. The requisite metal (e.g., Mo and W) complexes are often prepared and used in situ due to their well known instability when exposed to air. While several structurally diverse catalysts can be prepared, many such catalysts are sensitive to air and moisture, thereby limiting the ability to utilize them in an ambient atmosphere. One of ordinary skill in the art would recognize that development of a metathesis catalyst reagent that is usable in ambient atmosphere would be a significant improvement over the state of the art.

It was previously reported that N,N-chelating ligands bind and provide stability to Mo alkylidene bis-alkoxide complexes which are useful in olefin metathesis reactions (e.g., see Fox, H. H.; Lee, J-K.; Park, L. Y.; Schrock, R. R. *Organometallics* 1993, 12, 759-768.). In 1993, it was reported that the addition of an N,N-chelating ligand (e.g., 2,2-bipyridyl) allows for the isolation of a typically unstable Mo-methylidene complex. More recently, Fürstner and coworkers have used the above principle and disclosed phenanthroline adducts of high oxidation state Mo alkylidynes (e.g., see Heppekausen, J.; Stade, R.; Goddard, R.; Fürstner, A. *J. Am. Chem. Soc.* 2010, 131, 11045-11068). Building on previous studies regarding related pyridine complexes (e.g., see Bindl, M.; Stade, R.; Heilmann, E. K.; Picot, A.; Goddard, R.; Fürstner, A. *J. Am. Chem. Soc.* 2009, 131, 9468-9470), octahedral complexes were prepared that display significant stability to air and moisture. However, these complexes then require treatment with $MnCl_2$ at elevated temperature (80° C.) to generate and release the active alkyne metathesis catalysts.

It was surprisingly found that provided precursor complexes of formulae I and II, described in detail below, are easily prepared and are air- and/or moisture-stable. In addition, provided precursor complexes generally do not require the use of additional metal salts or elevated temperature in order to generate the corresponding metathesis catalyst. In certain embodiments, the present invention further provides methods for preparing a metathesis catalyst from a precursor complex of formula I or II. Such methods are described in detail, herein.

In some embodiments, methods described herein using provided precursor complexes are useful in metathesis reactions. In some embodiments, methods described herein using provided precursor complexes exhibit comparable or enhanced activity and/or stereoselectivity relative to known methods, and are useful in the synthesis of a large assortment of compounds, including, but not limited to, those with biological and therapeutical significance.

In some embodiments, the present invention provides a compound of formula I:

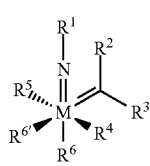

I wherein:
M is a suitable metal;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of $R^2$ and $R^3$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R, provided that $R^2$ and $R^3$ are not simultaneously hydrogen;
each of $R^4$ and $R^5$ is independently halogen, —N(R)$_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;
each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:
  two R groups on the same nitrogen atom are taken together with the nitrogen to form an optionally substituted 3-8 membered saturated, partially unsaturated, or aryl ring having 0-3 additional heteroatoms not including the same nitrogen atom independently selected from nitrogen, oxygen, or sulfur;
each of $R^6$ and $R^{6'}$ is independently a monodentate ligand, or $R^6$ and $R^{6'}$ are taken together with their intervening atoms form an optionally substituted bidentate group.

Further aspects of compounds of formula I are described in detail, infra.

In certain embodiments, the present invention provides a compound of formula II:

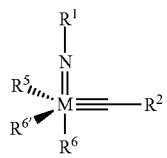

wherein:

M is a suitable metal;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^2$ is —OR, —SR, —N(R)$_2$, —NROR, —OC(O)R, —SOR, —SO$_2$R, —SO$_2$N(R)$_2$, —C(O)N(R)$_2$, —NRC(O)R, —NRC(O)OR, or —NRSO$_2$R, or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^5$ is halogen, —N(R)$_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur, or:

two R groups on the same nitrogen atom are taken together with the nitrogen to form a 3-8 membered saturated, partially unsaturated, or aryl ring having 0-3 additional heteroatoms not including the same nitrogen atom independently selected from nitrogen, oxygen, or sulfur; and each of $R^6$ and $R^{6'}$ is independently a monodentate ligand, or $R^6$ and $R^{6'}$ are taken together with their intervening atoms form an optionally substituted bidentate group.

Further aspects of compounds of formula II are described in detail, infra.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly (ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ C(S)NR^\circ)_2$; $-(CH_2)_{0-4}N(R^\circ)C(O)OR^\circ$; $-N(R^\circ)N(R^\circ C(O)R^\circ$; $-N(R^\circ)N(R^\circ)C(O)NR^\circ)_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_1$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NHR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_1$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NHR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In certain embodiments, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral product. Such metal complexes may exhibit improved catalytic activity and stereoselectivity, relative to previous systems, and may reduce undesired side reactions (e.g., dimerization or oligomerization of the metal complex).

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

As used herein, the term "oxygen-containing ligand" may be used to refer to ligands comprising at least one oxygen atom. In some cases, the oxygen atom binds to the metal atom thereby forming an ether-linkage. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

As defined herein, a "metal complex" is any complex used to form a provided precursor complex or any complex generated from a provided precursor complex (e.g., for use as a catalyst in a reaction such as a metathesis reaction).

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

3. Description of Certain Embodiments of the Invention

In some embodiments, the present invention provides complexes which serve as precursors to metathesis catalysts, including stereogenic-at-metal catalysts. In certain embodiments, provided precursor complexes are used in metathesis reactions, such as olefin metathesis reactions.

As used herein, the term "metathesis reaction" is given its ordinary meaning in the art and refers to a chemical reaction in which two reacting species exchange partners in the presence of a transition-metal catalyst. In some cases, a byproduct of a metathesis reaction may be ethylene. A metathesis reaction may involve reaction between species comprising, for example, olefins and/or alkynes. Examples of different kinds of metathesis reactions include cross metathesis, ring-closing metathesis, ring-opening metathesis, acyclic diene metathesis, alkyne metathesis, enyne metathesis, and the like. The metathesis reaction may occur between two substrates which are not joined by a bond (e.g., intermolecular metathesis reaction) or between two portions of a single substrate (e.g., intramolecular metathesis reaction). In some embodiments, complexes of the present invention are useful in the formation of a metathesis product with high enantioselectivity and/or high ratio of Z:E isomers, and/or high ratio of E:Z isomers.

Provided Precursor Complexes

In some embodiments, a provided precursor complex is isolated as a Lewis base adduct. The terms "Lewis base" and "Lewis base adduct" are known in the art and refer to a chemical moiety capable of donating a pair of electrons to another chemical moiety. In some embodiments, the coordination of Lewis base molecules to a provided precursor complex may result in a complex having a plane of symmetry with respect to the metal center. However, a stereogenic metal center may be formed by facile removal of the Lewis base molecules and/or replacement of one or more Lewis base molecules with one or more molecules that cause the complex to lose the plane of symmetry with respect to the metal center. For example, the provided precursor complex may be formed and stored as a Lewis base adduct, and may be "activated" in a subsequent reaction step to generate a catalyst with a stereogenic metal center.

Some embodiments of the invention provide a composition comprising a provided precursor complex which, upon treatment to generate a metal complex, affords a catalyst suitable for use in reactions described herein. In some embodiments, treatment of the provided precursor complex generates a metal complex comprising a stereogenic metal atom and two or more ligands that bind the metal atom. In some embodiments, each ligand associated with the metal complex comprises an organic group. The ligands may be monodentate ligands, i.e., the ligands bind the stereogenic metal atom via one site of the ligand (e.g., a carbon atom or a heteroatom of the ligand). In some embodiments, a monodentate ligand may bind the metal center via a single bond or a multiple bond. In some embodiments, the metal complex comprises at least one ligand lacking a plane of symmetry. That is, at least one ligand bound to the stereogenic metal atom is a chiral ligand. In some embodiments, the metal complex comprises a nitrogen-containing ligand, including chiral and/or achiral nitrogen-containing ligands. For example, the ligand may be a chiral or achiral nitrogen heterocycle, such as a pyrrolide. In some embodiments, the metal complex comprises an oxygen-containing ligand, including chiral and/or achiral oxygen-containing ligands. For example, the ligand may be a chiral or achiral biphenyl group substituted with at least one oxygen-containing moiety, e.g., a phenol. In some cases, the metal atom may be bound to at least one carbon atom.

Some aspects of the invention can be realized with provided precursor complexes comprising two or more ligands, wherein each ligand is a monodentate ligand, i.e., each ligand binds or coordinates the metal center via one coordination site of the metal only, or via one site of the ligand only. In some embodiments, a provided precursor complex comprises primarily monodentate ligands. In some embodiments, a provided precursor complex comprises at least one bidentate ligand, i.e., the ligand binds or coordinates the metal center via two coordination sites. In some embodiments, a provided precursor complex comprises a monodentate ligand and a bidentate ligand.

In some embodiments, methods of the present invention comprise use of a provided precursor complex wherein, upon generation of a metal complex in situ, the metal complex is present in a diastereomeric ratio greater than 1:1. In some embodiments, the metal complex is present in a diastereomeric ratio greater than about 5:1, greater than about 7:1, greater than about 10:1, greater than about 20:1, or, in some cases, greater. In certain embodiments, the metal complex generated in situ is an active metal catalyst complex. Exemplary such active metal catalyst complexes include metal complexes described herein for use in, inter alia, olefin metathesis reactions.

In some embodiments, a provided precursor complex is of formula I:

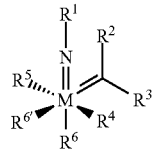

I wherein each of $R^1$, $R^2$, $R^3$, $R^4$, $R^5$, $R^6$ and $R^{6'}$ is as defined above and described in embodiments herein, both singly and in combination.

As defined above, the M moiety of formula I is a suitable metal. One of ordinary skill in the art would recognize that a suitable metal, M, is one that can achieve the appropriate valency and also result in a reactive metathesis catalyst. In some embodiments, M is molybdenum, tungsten, rhuthenium, rhenium, or tantalum. In certain embodiments, M is molybdenum or tungsten. In some embodiments, M is molybdenum. In other embodiments, M is tungsten.

As defined generally above, the $R^1$ group of formula I is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, the $R^1$ group of formula I is an optionally substituted group selected from $C_{1-20}$ aliphatic, phenyl, a 3-7 membered saturated or partially unsaturated carbocyclic ring, or an 8-10 membered bicyclic saturated, partially unsaturated or aryl ring. In certain embodiments, $R^1$ is optionally substituted phenyl. In some embodiments, $R^1$ is substituted phenyl. In some embodiments, $R^1$ is mono-, di-, or tri-substituted phenyl. In certain embodiments, $R^1$ is 2,6-disubstituted phenyl. In some embodiments, $R^1$ is phenyl disubstituted with halogen or $C_{1-4}$ aliphatic. Such $R^1$ groups include 2,6-dichlorophenyl, 2,6-dibromophenyl, 2,6-dimethylphenyl, 2,6-di-tert-butylphenyl, and 2,6-diisopropylphenyl.

In certain embodiments, the $R^1$ group of formula I is an optionally substituted group selected from $C_{1-20}$ aliphatic. In some embodiments, $R^1$ is an optionally substituted $C_{3-20}$ mono-, di-, or tri-cyclic aliphatic group. In some embodiments, $R^1$ is an optionally substituted bridged bicyclic or tricyclic aliphatic group. In certain embodiments, $R^1$ is an optionally substituted adamantyl group. In other embodiments, $R^1$ is an optionally substituted $C_{3-8}$ membered cycloalkyl group. In some embodiments, $R^1$ is selected from any of those $R^1$ groups depicted or described herein.

In some embodiments, $R^1$ is selected from:

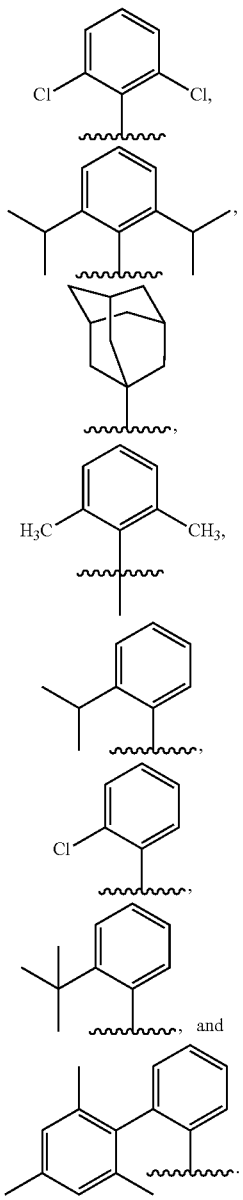

As defined generally above, each of $R^2$ and $R^3$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R, provided that $R^2$ and $R^3$ are not simultaneously hydrogen, wherein R is hydrogen, or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, provided that $R^2$ and $R^3$ are not simultaneously hydrogen.

In some embodiments, one of $R^2$ and $R^3$ is hydrogen and the other is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, the $R^2$ group or the $R^3$ group of formula I is optionally substituted $C_{1-20}$ aliphatic. In some embodiments, $R^2$ or $R^3$ is optionally substituted $C_{1-20}$ alkyl. In certain embodiments, $R^2$ or $R^3$ is $C_{1-6}$ alkyl substituted with phenyl and one or two additional substituents. In certain embodiments, $R^2$ or $R^3$ is a lower alkyl group optionally substituted with one or two methyl groups and phenyl. In certain embodiments, $R^2$ or $R^3$ is —C(Me)$_2$Ph. In certain embodiments, $R^2$ or $R^3$ is —C(Me)$_3$. In some embodiments, $R^2$ or $R^3$ is selected from any of those $R^2$ or $R^3$ groups depicted or described herein. In some embodiments, one of $R^2$ and $R^3$ is hydrogen and the other is —C(Me)$_2$Ph. In some embodiments, one of $R^2$ and $R^3$ is hydrogen and the other is —C(Me)$_3$.

As defined generally above, each of $R^4$ and $R^5$ is independently halogen, —N(R)$_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur.

In some embodiments, at least one of $R^4$ and $R^5$ is halogen. In other embodiments, each $R^4$ and $R^5$ is independently —N(R)$_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur, wherein $R^4$ and $R^5$ are coordinated to M via a nitrogen.

In certain embodiments, at least one of $R^4$ and $R^5$ is —N(R)$_2$. In some embodiments, both of $R^4$ and $R^5$ are —N(R)$_2$, wherein one R is hydrogen and the other is optionally substituted $C_{1-20}$ aliphatic.

In other embodiments, $R^4$ and $R^5$ are —N(R)$_2$, wherein the two R groups are taken together with the nitrogen to form an optionally substituted 3-8 membered saturated, partially unsaturated, or aryl ring having 0-3 additional heteroatoms not including the N atom from N(R)$_2$ independently selected from nitrogen, oxygen, or sulfur, wherein $R^4$ and $R^5$ are coordinated to M via a nitrogen. In some embodiments, the two R groups are taken together with the nitrogen to form an optionally substituted 5-membered heteroaryl ring having 0-3 additional nitrogen atoms not including the N atom from N(R)$_2$. Such rings include optionally substituted pyrrol-1-yl, pyrazol-1-yl, imidazol-1-yl, and triazol-1-yl. In some embodiments, such rings are unsubstituted pyrrol-1-yl, pyrazol-1-yl, imidazol-1-yl, and triazol-1-yl.

In some embodiments, at least one of $R^4$ and $R^5$ is an optionally substituted 5-6 membered monocyclic heteroaryl ring having at least one nitrogen and 0-3 additional heteroatoms independently selected from nitrogen, oxygen, or sulfur. In some embodiments, at least one of $R^4$ and $R^5$ is an optionally substituted group selected from pyrrolyl, pyrazolyl, imidazolyl, triazolyl, oxazolyl, isoxazoly, oxadiazoyl, thiazolyl, and thiazolyl. In some embodiments, at least one of $R^4$ and $R^5$ is an unsubstituted group selected from pyrrolyl, pyrazolyl, imidazolyl, triazolyl, oxazolyl, isoxazoly, oxadiazoyl, thiazolyl, and thiazolyl. In some embodiments, at least one of $R^4$ and $R^5$ is unsubstituted pyrrolyl. In some embodiments, each of $R^4$ and $R^5$ is unsubstituted pyrrolyl.

In other embodiments, at least one of $R^4$ and $R^5$ is an optionally substituted 8-10 membered bicyclic heteroaryl ring having at least one nitrogen and 0-4 additional heteroatoms independently selected from nitrogen, oxygen, or sulfur. In some embodiments, at least one of $R^4$ and $R^5$ is an optionally substituted group selected from indolyl, benzimidazolyl, and indazolyl. In some embodiments, at least one of $R^4$ and $R^5$ is an unsubstituted group selected from indolyl, benzimidazolyl, and indazolyl.

In certain embodiments, at least one of $R^4$ and $R^5$ is an optionally substituted group selected from

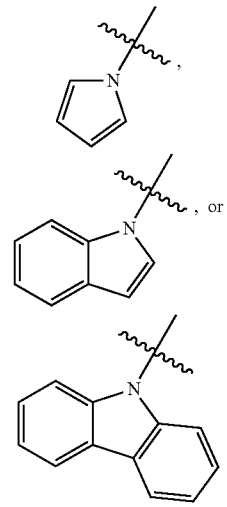

wherein each $\xi$ represents the point of attachment to the metal. In some embodiments, at least one of $R^4$ and $R^5$ is an unsubstituted group selected from

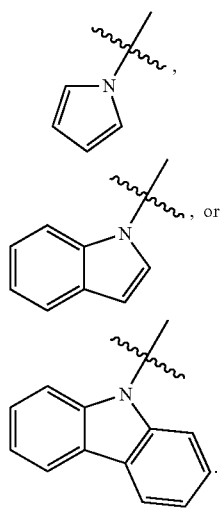

As defined generally above, each of $R^6$ and $R^{6'}$ is independently a monodentate ligand, or $R^6$ and $R^{6'}$ are taken together with their intervening atoms form an optionally substituted bidentate group. In some embodiments, each of $R^6$ and $R^{6'}$ is independently a nitrogen-donating ligand, or $R^6$ and $R^{6'}$ are taken together with their intervening atoms form an optionally substituted bidentate group. One of ordinary skill in the art will appreciate that $R^6$ and $R^{6'}$ can be any suitable ligand capable of coordinating with M. In some embodiments, such ligands are depicted herein.

In some embodiments, each of $R^6$ and $R^{6'}$ is independently nitrogen-containing ligand capable of coordinating with M via the nitrogen atom. Accordingly, in some embodiments, each of $R^6$ and $R^{6'}$ is independently —N(R)$_2$, —NRC(O)R, —NRC(O)OR, —NRC(O)N(R)$_2$, —NRSO$_2$R, —NRSO$_2$N(R)$_2$, —NROR, a 5-6 membered monocyclic heteroaryl ring having at least one nitrogen atom and 0-3 additional heteroatoms independently selected from nitrogen, oxygen, or sulfur, a 4-7 membered saturated or partially unsaturated heterocyclic ring having at least one nitrogen atom and 0-2 additional heteroatoms independently selected from nitrogen, oxygen, or sulfur, a 7-10 membered bicyclic saturated or partially unsaturated heterocyclic ring having at least one nitrogen atom and 0-4 additional heteroatoms independently selected from nitrogen, oxygen, or sulfur, or an 8-14 membered bicyclic or tricyclic heteroaryl ring having at least one nitrogen atom and 0-4 additional heteroatoms independently selected from nitrogen, oxygen, or sulfur, or $R^6$ and $R^{6'}$ are taken together with their intervening atoms form an optionally substituted bidentate group.

In some embodiments, at least one of $R^6$ and $R^{6'}$ is independently selected from an optionally substituted 6-membered heteroaryl ring having 1-3 nitrogens. Such $R^6$ and $R^{6'}$ groups include optionally substituted pyridine, pyrimidine, or triazine groups.

In certain embodiments, at least one of $R^6$ and $R^{6'}$ is optionally substituted pyridine. In some embodiments, both of $R^6$ and $R^{6'}$ is optionally substituted pyridine.

In other embodiments, at least one of $R^6$ and $R^{6'}$ is independently selected from an optionally substituted 5-membered heteroaryl ring having one nitrogen and 0-2 additional heteroatoms independently selected from nitrogen, oxygen, or sulfur. Such $R^6$ and $R^{6'}$ groups include optionally substituted pyrrole, pyrazole, imidazole, triazole, oxazole, isoxazole, oxadiazole, thiazole, and thiadiazole rings.

In some embodiments, at least one of $R^6$ and $R^{6'}$ is independently —N(R)$_2$, —NHC(O)R, —NHC(O)OR, —NHC(O)N(R)$_2$, or —NHSO$_2$R. In some embodiments, at least one of $R^6$ and $R^{6'}$ is —N(R)$_2$.

In certain embodiments, each of $R^6$ and $R^{6'}$ is —N(R)$_2$ wherein each R is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, one R group is hydrogen and the other is and optionally substituted group selected from phenyl, napthyl, cyclohexyl, pyridyl, pyrimidinyl, cyclopentyl, methyl, ethyl, propyl, or butyl.

In certain embodiments, each of $R^6$ and $R^{6'}$ is —N(R)$_2$, wherein the two R groups are taken together with the nitrogen atom to form an optionally substituted 3-8 membered saturated, partially unsaturated, or aryl ring having 0-3 additional heteroatoms not including the N atom from N(R)$_2$ independently selected from nitrogen, oxygen, or sulfur. In some embodiments, the two R groups are taken together with the nitrogen to form an optionally substituted 5-membered heteroaryl ring having 1-3 nitrogen atoms. Such rings include optionally substituted pyrrol-1-yl, pyrazol-1-yl, imidazol-1-yl, and triazol-1-yl.

In certain embodiments, each of $R^6$ and $R^{6'}$ is —NHC(O)R. In some embodiments, each of $R^6$ and $R^{6'}$ is —NHC(O)R, wherein R is an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, R is an optionally substituted group selected from phenyl, napthyl, cyclohexyl, pyridyl, pyrimidinyl, cyclopentyl, methyl, ethyl, propyl, or butyl.

In some embodiments, $R^6$ and $R^{6'}$ are taken together with their intervening atoms to form an optionally substituted bidentate moiety. In certain embodiments, $R^6$ and $R^{6'}$ are taken together to form optionally substituted bipyridyl. In certain embodiments, $R^6$ and $R^{6'}$ are taken together to form:

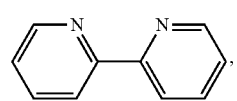

-continued

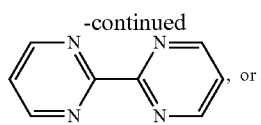, or

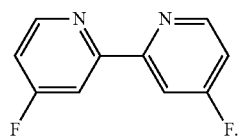

In some embodiments, $R^6$ and $R^{6'}$ are taken together with their intervening atoms to form a bidentate optionally substituted bicyclic or tricyclic heteroaryl ring having 1-3 heteroatoms independently selected from nitrogen, oxygen, or sulfur. In certain embodiments, $R^6$ and $R^{6'}$ are taken together to form optionally substituted phenanthroline. In certain embodiments, $R^6$ and $R^{6'}$ are taken together to form

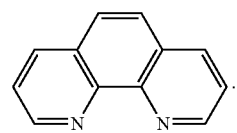 [SMILES: c1cnc2c(c1)ccc1cccnc12]

In some embodiments, a provided precursor complex of formula I is selected from the structures depicted below:

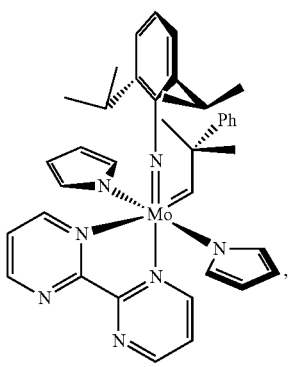

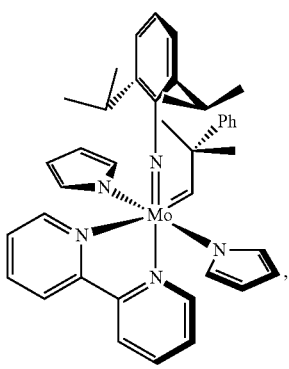

-continued

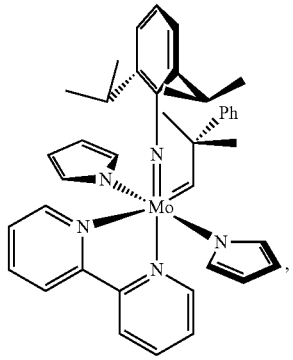

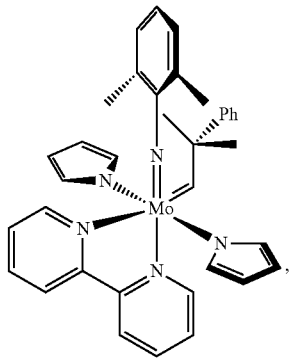

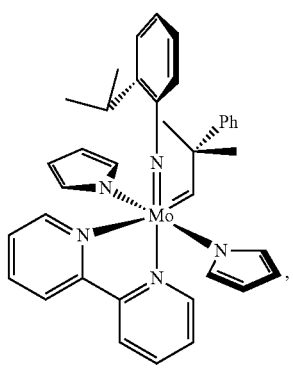

23
-continued
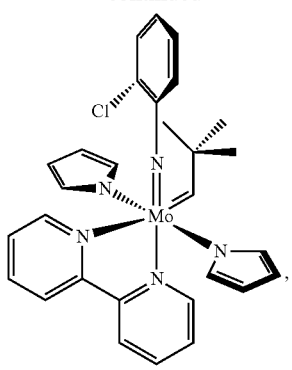
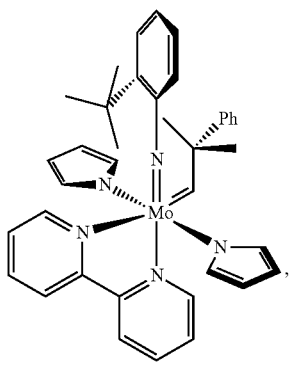
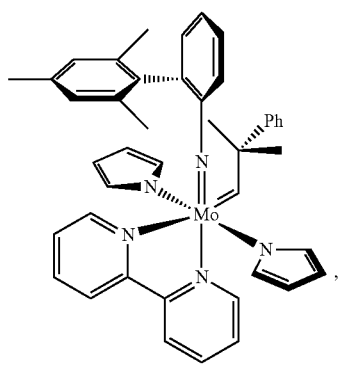
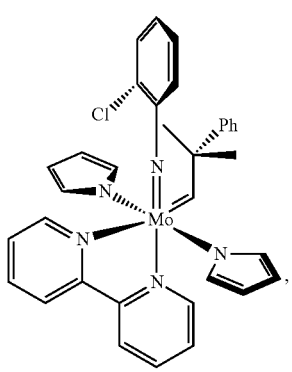
24
-continued
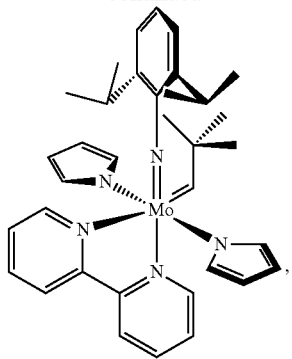
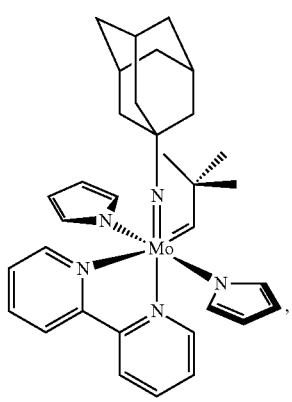
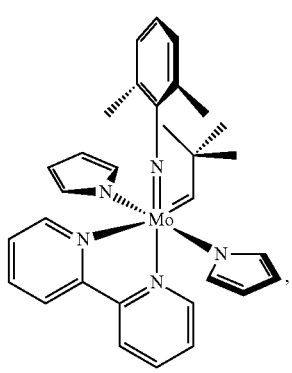
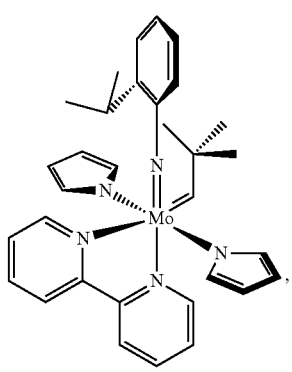

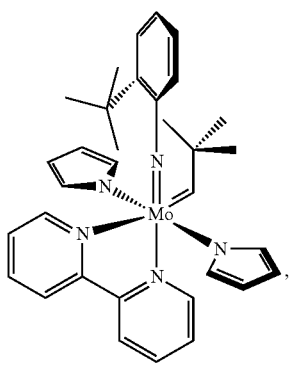

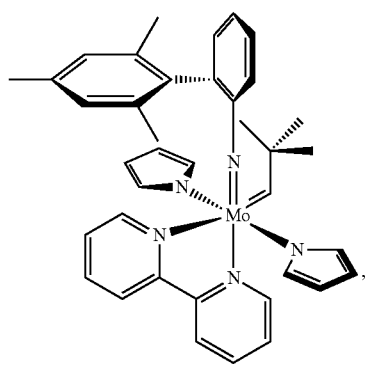

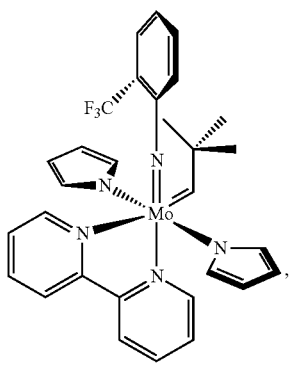

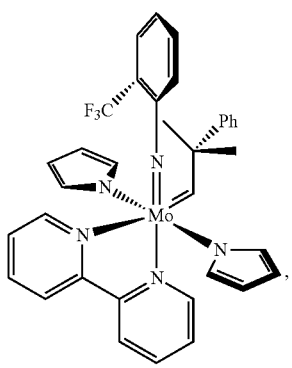

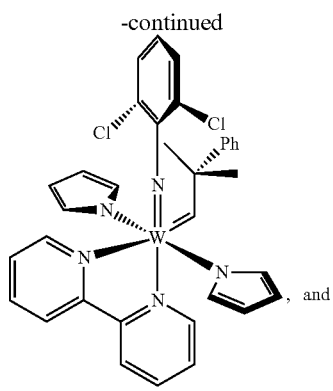

, and

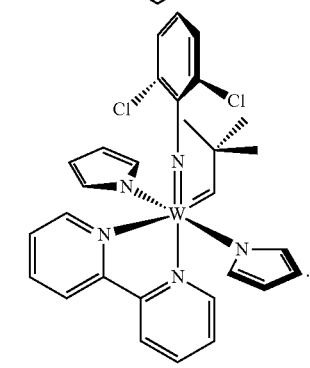

.

In some embodiments, a provided precursor complex of formula I is any of the above structures, wherein the Mo metal center is replaced with a W metal center.

In some embodiments, the present invention provides a compound of formula II:

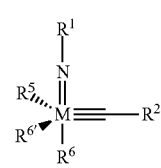

II wherein each of $R^1$, $R^2$, $R^5$, $R^6$, and $R^{6'}$ is as defined above and described in embodiments herein, both singly and in combination.

As defined above, the M moiety of formula II is a suitable metal. One of ordinary skill in the art would recognize that a suitable metal, M, is one that can achieve the appropriate valency and also result in a reactive metathesis catalyst. In some embodiments, M is molybdenum, tungsten, rhuthenium, rhenium, or tantalum. In certain embodiments, M is molybdenum or tungsten. In some embodiments, M is molybdenum. In other embodiments, M is tungsten.

As defined generally above, the $R^1$ group of formula II is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, the $R^1$ group of formula II is an optionally substituted group selected from $C_{1-20}$ aliphatic, phenyl, a 3-7 membered saturated or partially unsaturated carbocyclic ring, or an 8-10 membered bicyclic saturated, partially unsaturated or aryl ring. In certain embodiments, $R^1$ is optionally substituted phenyl. In some embodiments, $R^1$ is substituted phenyl. In some embodiments, $R^1$ is mono-, di-, or tri-substituted phenyl. In certain embodiments, $R^1$ is 2,6-disubstituted phenyl. In some embodiments, $R^1$ is phenyl disubstituted with halogen or $C_1$ aliphatic. Such $R^1$ groups include 2,6-dichlorophenyl, 2,6-dibromophenyl, 2,6-dimethylphenyl, 2,6-di-tert-butylphenyl, and 2,6-diisopropylphenyl.

In certain embodiments, the $R^1$ group of formula II is an optionally substituted group selected from $C_{1-20}$ aliphatic. In some embodiments, $R^1$ is an optionally substituted $C_{3-20}$ mono-, di-, or tri-cyclic aliphatic group. In some embodiments, $R^1$ is an optionally substituted bridged bicyclic or tricyclic aliphatic group. In certain embodiments, $R^1$ is an optionally substituted adamantyl group. In other embodiments, $R^1$ is an optionally substituted $C_{3-8}$ membered cycloalkyl group. In some embodiments, $R^1$ is selected from any of those $R^1$ groups depicted or described herein.

In some embodiments, $R^1$ is selected from:

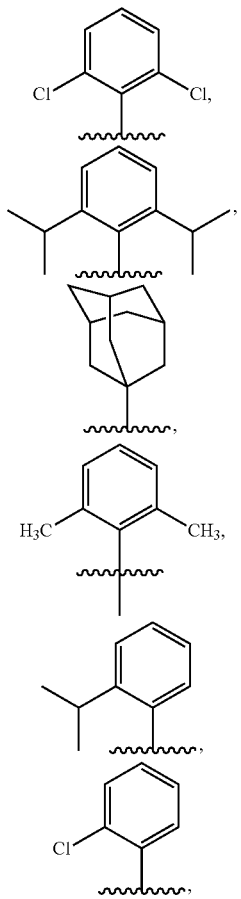

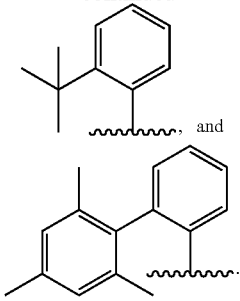

As defined generally above, the $R^2$ group of formula II is $R^2$ is —OR, —SR, —N(R)$_2$, —NROR, —OC(O)R, —SOR, —SO$_2$R, —SO$_2$N(R)$_2$, —C(O)N(R)$_2$, —NRC(O)R, —NRC(O)OR, or —NRSO$_2$R, or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^2$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, the $R^2$ group of formula II is optionally substituted $C_{1-20}$ aliphatic. In some embodiments, $R^2$ is optionally substituted $C_{1-20}$ alkyl. In certain embodiments, $R^2$ is $C_{1-6}$ alkyl substituted with phenyl and one or two additional substituents. In certain embodiments, $R^2$ is a lower alkyl group optionally substituted with one or two methyl groups and phenyl. In certain embodiments, $R^2$ is —C(Me)$_2$Ph. In certain embodiments, $R^2$ is —C(Me)$_3$. In some embodiments, $R^2$ is selected from any of those $R^2$ groups depicted or described herein.

As defined generally above, the $R^5$ group of formula II is halogen, —N(R)$_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur.

In some embodiments, at least one of $R^4$ and $R^5$ is halogen. In other embodiments, each $R^4$ and $R^5$ is independently —$N(R)_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur, wherein $R^4$ and $R^5$ are coordinated to M via a nitrogen.

In certain embodiments, $R^5$ is —$N(R)_2$. In some embodiments, $R^5$ is —$N(R)_2$, wherein one R is hydrogen and the other is optionally substituted $C_{1-20}$ aliphatic.

In other embodiments, $R^5$ is —$N(R)_2$, wherein the two R groups are taken together with the nitrogen to form an optionally substituted 3-8 membered saturated, partially unsaturated, or aryl ring having 0-3 additional heteroatoms not including the N atom from $N(R)_2$ independently selected from nitrogen, oxygen, or sulfur. In some embodiments, the two R groups are taken together with the nitrogen to form an optionally substituted 5-membered heteroaryl ring having 0-3 additional nitrogen atoms not including the N atom from $N(R)_2$. Such rings include optionally substituted pyrrol-1-yl, pyrazol-1-yl, imidazol-1-yl, and triazol-1-yl. In some embodiments, such rings are substituted pyrrol-1-yl, pyrazol-1-yl, imidazol-1-yl, and triazol-1-yl.

In some embodiments, $R^5$ is an optionally substituted 5-6 membered monocyclic heteroaryl ring having at least one nitrogen and 0-3 additional heteroatoms independently selected from nitrogen, oxygen, or sulfur. In some embodiments, $R^5$ is an optionally substituted group selected from pyrrolyl, pyrazolyl, imidazolyl, triazolyl, oxazolyl, isoxazoly, oxadiazoyl, thiazolyl, and thiazolyl. In some embodiments, $R^5$ is a substituted group selected from pyrrolyl, pyrazolyl, imidazolyl, triazolyl, oxazolyl, isoxazoly, oxadiazoyl, thiazolyl, and thiazolyl. In certain embodiments, $R^5$ is dimethylpyrrolyl. In some embodiments, $R^5$ is

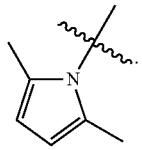

In other embodiments, $R^5$ is an optionally substituted 8-10 membered bicyclic heteroaryl ring having at least one nitrogen and 0-4 additional heteroatoms independently selected from nitrogen, oxygen, or sulfur. In some embodiments, $R^5$ is an optionally substituted group selected from indolyl, benz-imidazolyl, and indazolyl. In some embodiments, $R^5$ is a substituted group selected from indolyl, benzimidazolyl, and indazolyl.

As defined generally above, each of $R^6$ and $R^{6'}$ is independently a monodentate ligand, or $R^6$ and $R^{6'}$ are taken together with their intervening atoms form an optionally substituted bidentate group. In some embodiments, each of $R^6$ and $R^{6'}$ is independently a nitrogen-donating ligand, or $R^6$ and $R^{6'}$ are taken together with their intervening atoms form an optionally substituted bidentate group. One of ordinary skill in the art will appreciate that $R^6$ and $R^{6'}$ can be any suitable ligand capable of coordinating with M. In some embodiments, such ligands are depicted herein.

In some embodiments, each of $R^6$ and $R^{6'}$ is independently nitrogen-containing ligand capable of coordinating with M via the nitrogen atom. Accordingly, in some embodiments, each of $R^6$ and $R^{6'}$ is independently —$N(R)_2$, —NHC(O)R, —NHC(O)OR, —NHC(O)N(R)$_2$, —NHSO$_2$R, —NHSO$_2$N(R)$_2$, —NHOR, a 5-6 membered monocyclic heteroaryl ring having at least one nitrogen atom and 0-3 additional heteroatoms independently selected from nitrogen, oxygen, or sulfur, a 4-7 membered saturated or partially unsaturated heterocyclic ring having at least one nitrogen atom and 0-2 additional heteroatoms independently selected from nitrogen, oxygen, or sulfur, a 7-10 membered bicyclic saturated or partially unsaturated heterocyclic ring having at least one nitrogen atom and 0-4 additional heteroatoms independently selected from nitrogen, oxygen, or sulfur, or an 8-14 membered bicyclic or tricyclic heteroaryl ring having at least one nitrogen atom and 0-4 additional heteroatoms independently selected from nitrogen, oxygen, or sulfur, or $R^6$ and $R^{6'}$ are taken together with their intervening atoms form an optionally substituted bidentate group.

In some embodiments, at least one of $R^6$ and $R^{6'}$ is independently selected from an optionally substituted 6-membered heteroaryl ring having 1-3 nitrogens. Such $R^6$ and $R^{6'}$ groups include optionally substituted pyridine, pyrimidine, or triazine groups.

In certain embodiments, at least one of $R^6$ and $R^{6'}$ is optionally substituted pyridine. In some embodiments, both of $R^6$ and $R^{6'}$ is optionally substituted pyridine.

In other embodiments, at least one of $R^6$ and $R^{6'}$ is independently selected from an optionally substituted 5-membered heteroaryl ring having one nitrogen and 0-2 additional heteroatoms independently selected from nitrogen, oxygen, or sulfur. Such $R^6$ and $R^{6'}$ groups include optionally substituted pyrrole, pyrazole, imidazole, triazole, oxazole, isoxazole, oxadiazole, thiazole, and thiadiazole rings.

In some embodiments, at least one of $R^6$ and $R^{6'}$ is independently —$N(R)_2$, —NHC(O)R, —NHC(O)OR, —NHC(O)N(R)$_2$, or —NHSO$_2$R. In some embodiments, at least one of $R^6$ and $R^{6'}$ is —$N(R)_2$.

In certain embodiments, each of $R^6$ and $R^{6'}$ is —$N(R)_2$ wherein each R is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, one R group is hydrogen and the other is and optionally substituted group selected from phenyl, napthyl, cyclohexyl, pyridyl, pyrimidinyl, cyclopentyl, methyl, ethyl, propyl, or butyl.

In certain embodiments, each of $R^6$ and $R^{6'}$ is —$N(R)_2$, wherein the two R groups are taken together with the nitrogen atom to form an optionally substituted 3-8 membered saturated, partially unsaturated, or aryl ring having 0-3 additional heteroatoms not including the N atom from $N(R)_2$ independently selected from nitrogen, oxygen, or sulfur. In some embodiments, the two R groups are taken together with the nitrogen to form an optionally substituted 5-membered heteroaryl ring having 1-3 nitrogen atoms. Such rings include optionally substituted pyrrol-1-yl, pyrazol-1-yl, imidazol-1-yl, and triazol-1-yl.

In certain embodiments, each of $R^6$ and $R^{6'}$ is —NHC(O)R. In some embodiments, each of $R^6$ and $R^{6'}$ is —NHC(O)R, wherein R is an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur. In some embodiments, one R group is hydrogen and the other is and optionally substituted group selected from phenyl, napthyl, cyclohexyl, pyridyl, pyrimidinyl, cyclopentyl, methyl, ethyl, propyl, or butyl.

In some embodiments, $R^6$ and $R^{6'}$ are taken together with their intervening atoms to form an optionally substituted bidentate moiety. In certain embodiments, $R^6$ and $R^{6'}$ are taken together to form optionally substituted bipyridyl. In certain embodiments, $R^6$ and $R^{6'}$ are taken together to form:

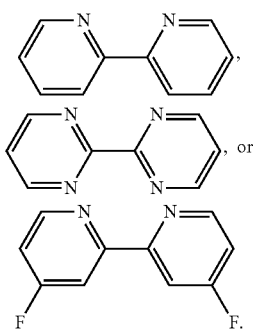

In some embodiments, $R^6$ and $R^{6'}$ are taken together with their intervening atoms to form a bidentate optionally substituted bicyclic or tricyclic heteroaryl ring having 1-3 heteroatoms independently selected from nitrogen, oxygen, or sulfur. In certain embodiments, $R^6$ and $R^{6'}$ are taken together to form optionally substituted phenanthroline. In certain embodiments, $R^6$ and $R^{6'}$ are taken together to form

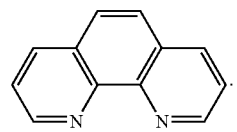 [SMILES: c1cnc2c(c1)ccc1cccnc12]

In some embodiments, a provided precursor complex of formula II is of any one of the structures depicted below:

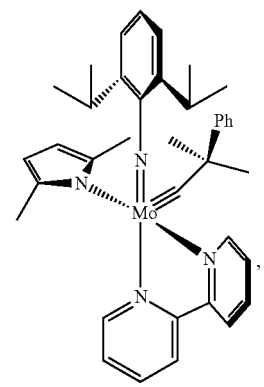

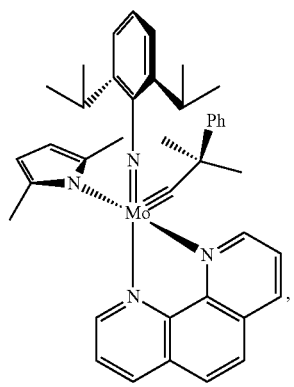

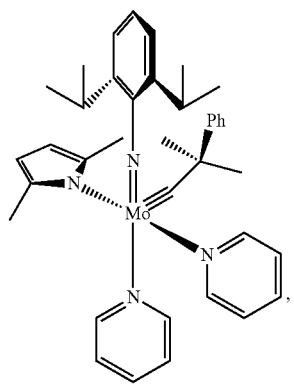

33
-continued
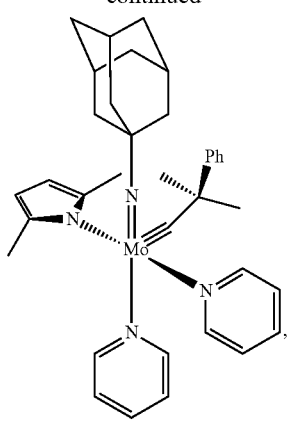
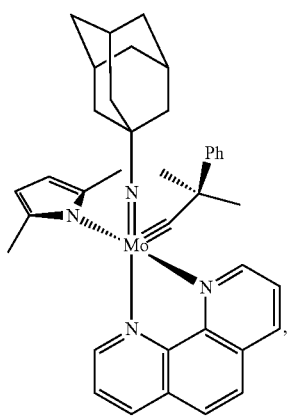
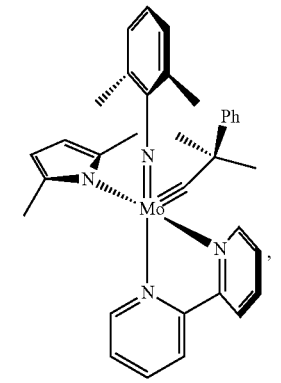
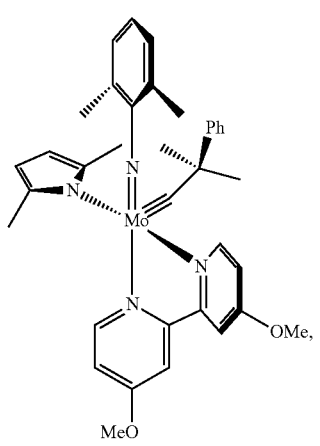
34
-continued
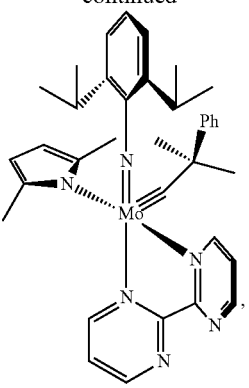
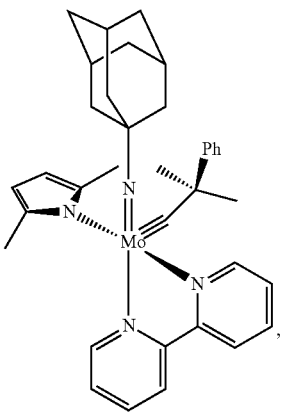
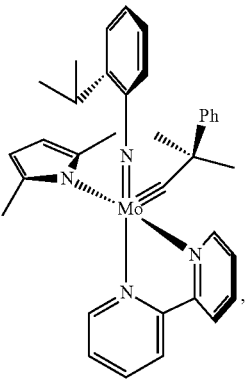
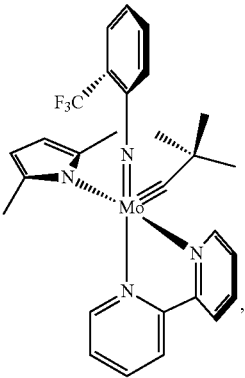

-continued
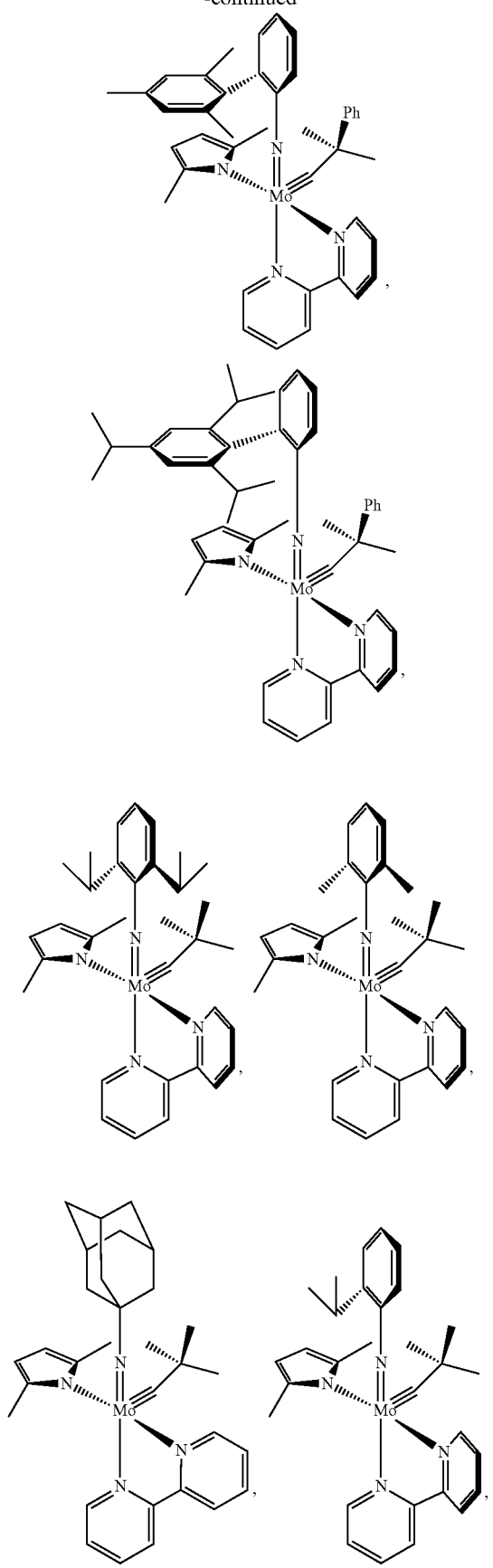
-continued
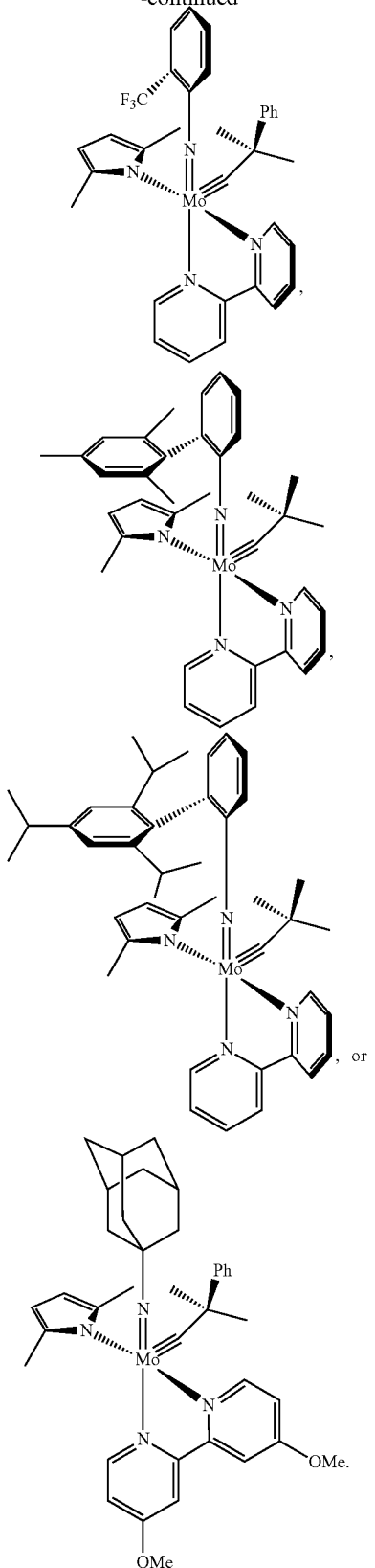
In some embodiments, a provided precursor complex of formula II is of any one of the above structures, wherein the Mo metal center is replaced with a W metal center.

In some embodiments, a suitable ligand corresponding to the $R^6$ or $R^{6'}$ groups of formulae I and II is an optionally substituted group selected from:
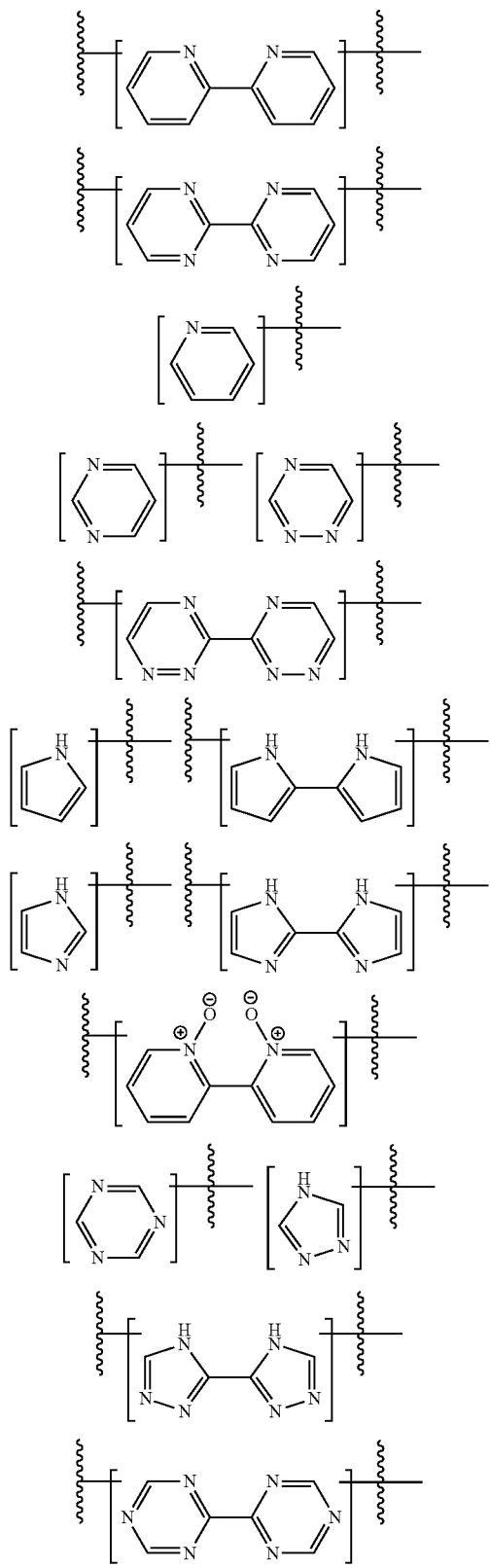
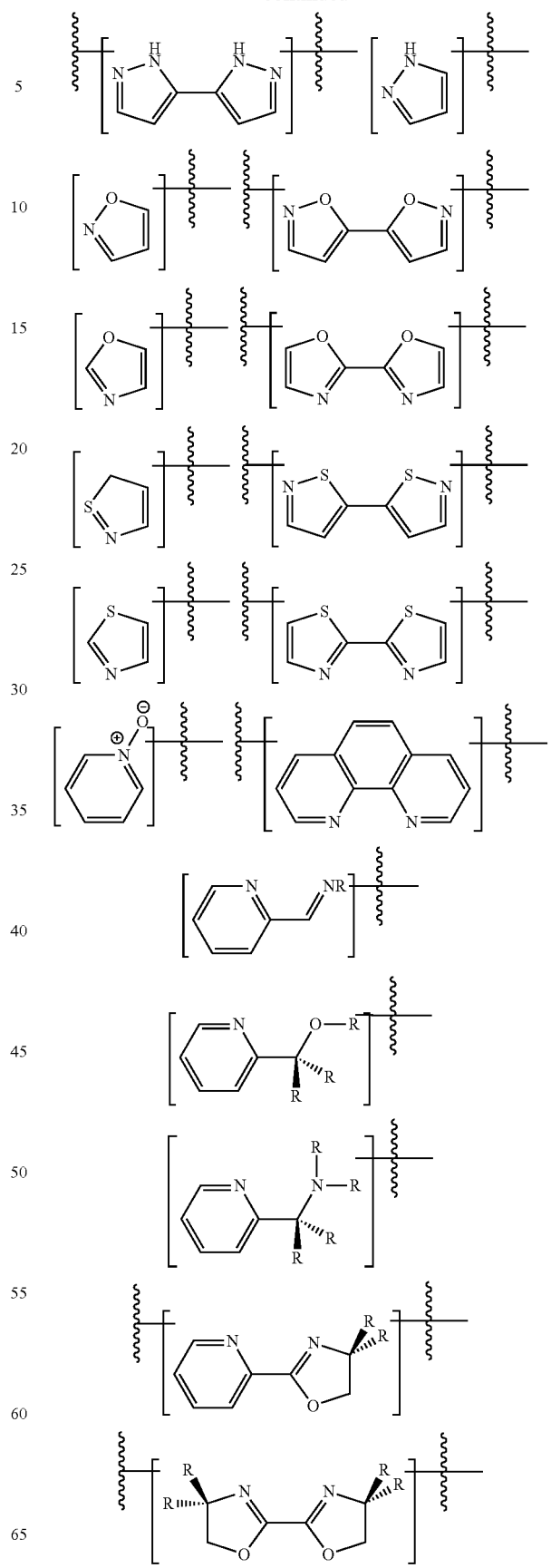

-continued

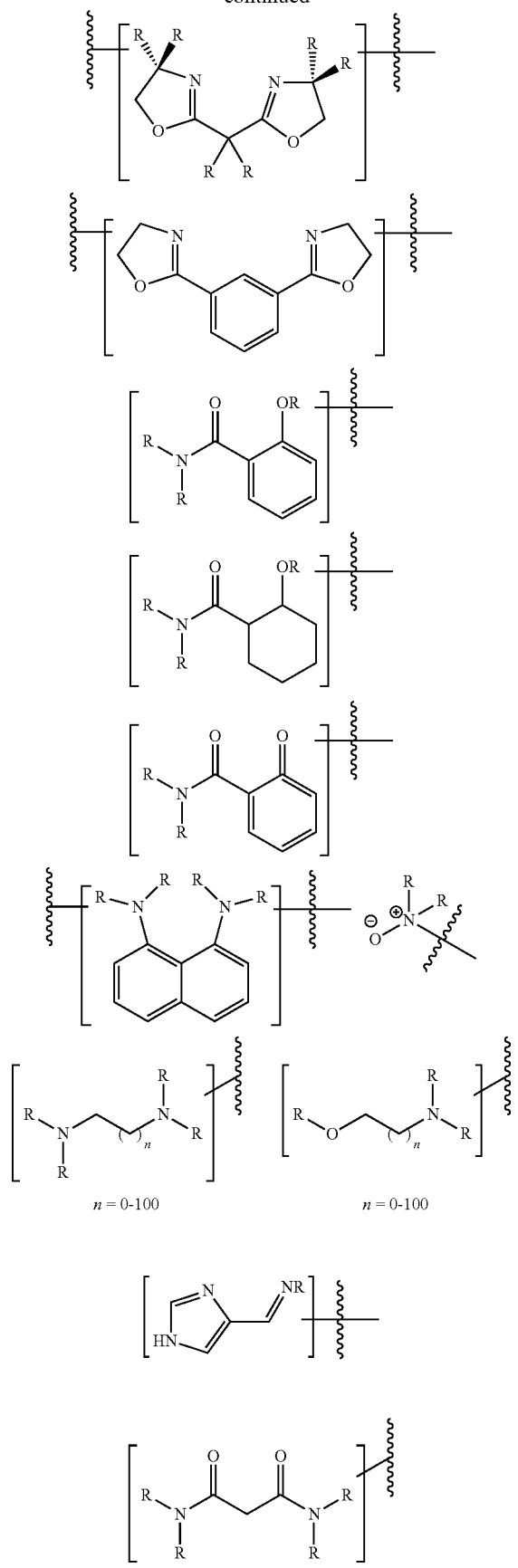

-continued wherein each R is independently as defined and described herein and each wavy line corresponds to the point of coordination to M. One of ordinary skill in the art will appreciate that moieties having two wavy lines correspond to bidentate ligands (i.e., those where $R^6$ and $R^{6'}$ are taken together with their intervening atoms to form a bidentate ligand), and that $R^6$ and $R^{6'}$ ligands can coordinate with M via one or more heteroatoms (e.g., nitrogen), one or more aromatic rings systems, one or more pi-bonds, etc. Those of ordinary skill in the art will understand that, in addition to the examples of ligands depicted specifically above, another set of examples involves those depicted as bidentate but which coordinate to M via only one point such that the ligand is monodentate, and those depicted above as monodentate but which coordinate to M through two points of attachment such that the ligand is bidentate. Other suitable ligands exist at would be understood from the disclosure herein.

In some embodiments, a suitable ligand corresponding to the $R^6$ or $R^{6'}$ groups of formulae I and II is an optionally substituted group selected from those depicted above, wherein the ligand is coordinated to M via a nitrogen atom.

In some embodiments, a provided precursor complex of formula I or formula II is characterized in that it is reasonably air and/or moisture stable. That is, provided precursor complexes may be characterized in that they are stable to air and moisture for periods of time which allow for handling and/or storing outside of an inert atmosphere. For instance, in certain embodiments, a provided precursor complex is characterized in that it decomposes less than about 90%, 80%, 70%, 60%, 50%, 40%, 30%, 20%, 15%, 10%, 9%, 8%, 7%, 6%, 5%, 4%, 3%, 2%, or 1% after about 12 hours of exposure to air. In some embodiments, a provided precursor complex is characterized in that it decomposes less than about 90%, 80%, 70%, 60%, 50%, 40%, 30%, 20%, 15%, 10%, 9%, 8%, 7%, 6%, 5%, 4%, 3%, 2%, or 1% after about 1 hour of exposure to air. In some embodiments, a provided precursor complex is characterized in that it decomposes less than about 60%, 50%, 40%, 30%, 20%, 15%, 10%, 9%, 8%, 7%, 6%, 5%, 4%, 3%, 2%, or 1% after about 30 minutes of exposure to air. In some embodiments, a provided precursor complex is characterized in that it decomposes less than about 60%, 50%, 40%, 30%, 20%, 15%, 10%, 9%, 8%, 7%, 6%, 5%, 4%, 3%, 2%, or 1% after about 15 minutes of exposure to air. One of ordinary skill in the art would appreciate that, as used herein, the term "air", refers to ambient atmosphere.

One of ordinary skill in the art will recognize that stability (i.e., decomposition rate and/or purity) of a provided precursor complex can be determined by a variety of means well known in the art including $^1H$ NMR and methods described in detail herein, infra.

In certain embodiments, a provided precursor complex is characterized in that it decomposes less than about 15% in about 12 hours. In certain embodiments, a provided precursor complex is characterized in that it decomposes less than about 2% in about 11 hours. In certain embodiments, a provided precursor complex is characterized in that it decomposes less than about 29% in about 1 hour. In certain embodiments, a provided precursor complex is characterized in that it decomposes less than about 12% in about 15 minutes. In certain embodiments, a provided precursor complex is characterized in that it decomposes less than about 7% in about 15 minutes.
Methods of Making Provided Precursor Complexes In certain embodiments, the present invention further provides methods of making provided precursor complexes. In some embodiments, a provided precursor complex is synthesized from a synthetically accessible or commercially available metal complex and one or more suitable ligands. In certain embodiments, provided precursor complexes have improved air and/or moisture stability relative to synthetically accessible or commercially available metal complexes.

In some embodiments, the present invention provides a method of preparing a compound of formula I, comprising reacting a compound of formula III:

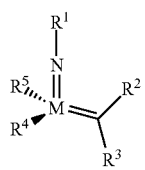
III wherein each of M, $R^1$, $R^2$, $R^3$, $R^4$, and $R^5$ is as defined above with regard to formulae I and II, and described in embodiments, both singly and in combination,
with one or two suitable ligands, as defined and described herein, to form a compound of formula I:

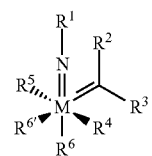
I wherein each of M, $R^1$, $R^2$, $R^3$, $R^4$, $R^5$, $R^6$, and $R^{6'}$ is as defined above with regard to formula I, and described in embodiments, both singly and in combination.

One of ordinary skill in the art will recognize that reacting a compound of formula III with one suitable ligand (ultimately corresponding to $R^6/R^{6'}$ of formula I), results in a compound of formula I wherein $R^6$ and $R^{6'}$ are the same. Reacting a compound of formula III with two different suitable ligands results in a compound of formula I wherein $R^6$ and $R^{6'}$ are different. It will be further recognized that reacting a compound of formula III with one suitable ligand having two atoms capable of coordinating with M, the result will be a compound of formula I wherein $R^6$ and $R^{6'}$ are taken together to form a bidentate ligand.

In some embodiments, the present invention provides a method of preparing a compound of formula II, comprising reacting a metal compound of formula III:

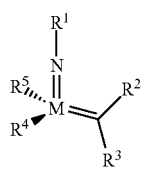
III wherein each of M, $R^1$, $R^2$, $R^3$, $R^4$, and $R^5$ is as defined above with regard to formulae I and II, and described in embodiments, both singly and in combination, with one or more suitable ligands to form a compound of formula II:

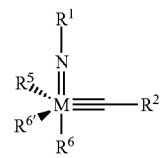
II wherein each of M, $R^1$, $R^2$, $R^5$, $R^6$, and $R^{6'}$ is as defined above with regard to formula II, and described in embodiments, both singly and in combination.

In some embodiments, the metal complex of formula III for use in preparing a compound of formula I is

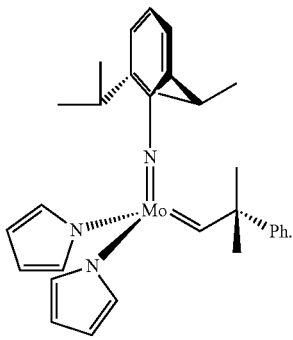

In some embodiments, the metal complex of formula III for use in preparing a compound of formula II is

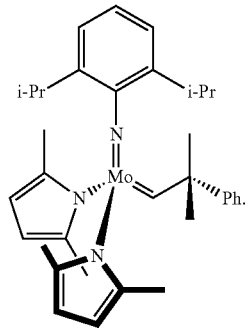

It is understood by one of ordinary skill in the art that a compound of formula III may exist in various forms. Each of the variations is deemed to be within the scope of the present invention. In some embodiments, a compound of formula III having the formula of $Mo(NR^1)(CHR^2)(Pyr)_2$ may exist as:

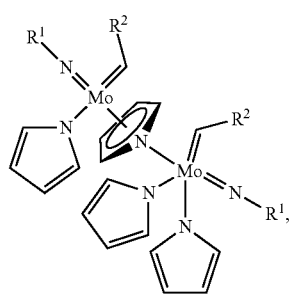

wherein each of $R^1$ and $R^2$ is independently as defined above and described herein. In some embodiments, a compound of formula III is of the formula $Mo(NR^1)(CHR^2)(Pyr)_2$, wherein $R^1$ is 2,6-diisopropylphenyl, adamantyl, 2,6-dimethylphenyl, 2-isopropylphenyl, 2-chlorophenyl, 2-t-butylphenyl, or 2-mesitylphenyl, and $R^2$ is —$CMe_2Ph$ or —$CMe_3$. In some embodiments, $R^1$ is 2,6-diisopropylphenyl or adamantyl, and $R^2$ is —$CMe_2Ph$ or —$CMe_3$. In some embodiments, a compound of formula III is selected from $Mo(NAr)(CHCMe_2Ph)(Pyr)_2$ (Ar=2,6-i-$Pr_2C_6H_3$), $Mo(NAd)(CHCMe_2Ph)(Pyr)_2$ (Ad=adamantyl), $Mo(NAr')(CHCMe_2Ph)(Pyr)_2$ (Ar'=2,6-$Me_2C_6H_3$), $Mo(NAr^{iPr})(CHCMe_2Ph)(Pyr)_2$ ($Ar^{iPr}$=2-i-$PrC_6H_4$), $Mo(NAr^{Cl})(CHCMe_3)(Pyr)_2$ ($Ar^{Cl}$=2-$ClC_6H_4$), $W(N(2,6\text{-dichlorophenyl}))(CHCMe_2Ph)(Pyr)_2$, $Mo(NAr^{tBu})(CHCMe_2Ph)(Pyr)_2$ ($Ar^{tBu}$=2-$tBuC_6H_4$), and $Mo(NAr^M)(CHCMe_2Ph)(Pyr)_2$ ($Ar^M$=2-mesityl$C_6H_4$). In other embodiments, a compound of formula III having the formula of $Mo(NR^1)(CHR^2)(2,5\text{-}Me_2Py)_2$ may exist as:

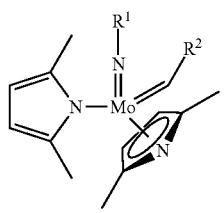

wherein each of $R^1$ and $R^2$ is independently as defined above and described herein. In some embodiments, $R^1$ is an optionally substituted phenyl, and $R^1$ is —$CMe_2Ph$ or —$CMe_3$. In some embodiments, a compound of formula III is selected from:

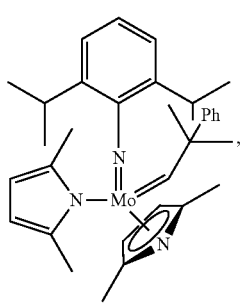, 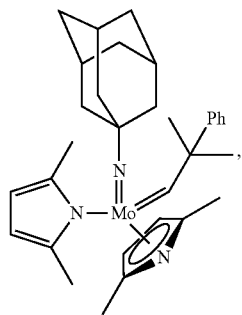, 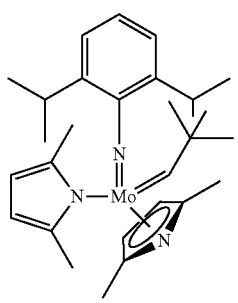, 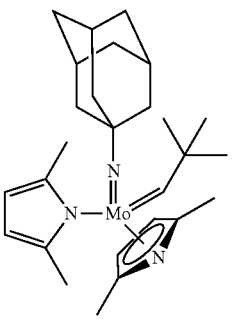

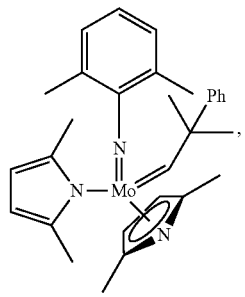, 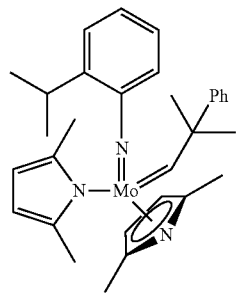, 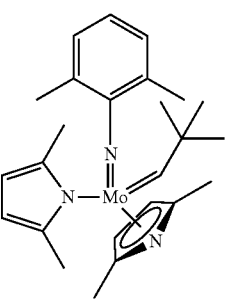, 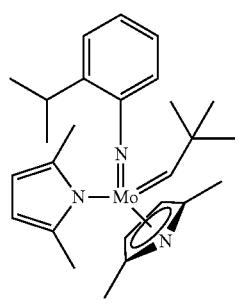

-continued

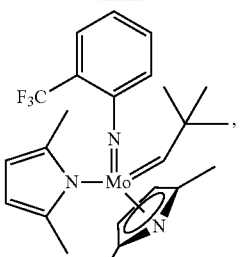,

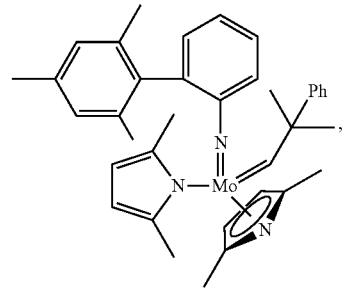,

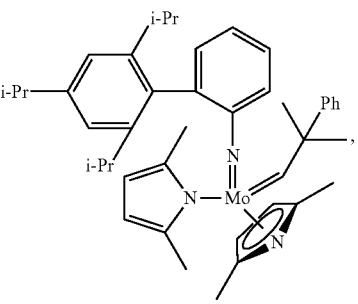,

-continued

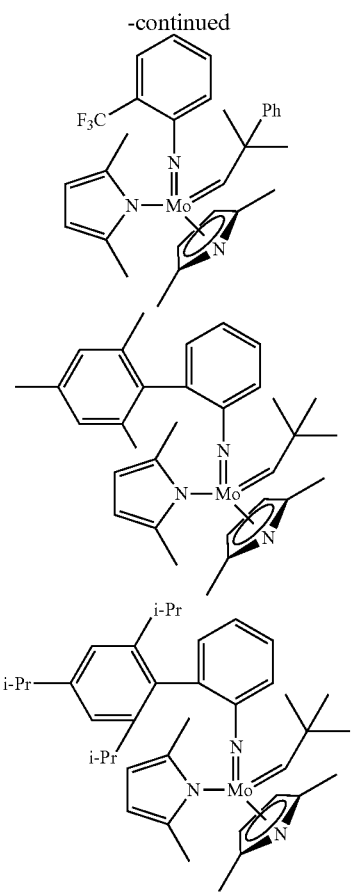

In some embodiments, a compound of formula III is generated in situ. In some embodiments, a compound of formula III is generated from $Mo(NR^1)(CR^2R^3)(OX')_4$, wherein each of $R^1$, $R^2$ and $R^3$ is independently as defined above and described herein, each of OX' is independently an oxygen-containing ligand, and one or more OX' are optionally connected to form a bidentate or multi-dentate ligands. In some embodiments, a compound of formula III is generated in situ from:

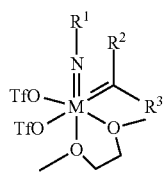

wherein each of $R^1$, $R^2$ and $R^3$ is independently as defined above and described herein.

In some embodiments, the present invention provides a method of preparing a compound of formula I, comprising reacting a compound of formula III-b:

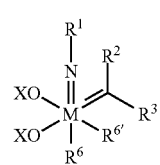

III-b wherein
each of M, $R^1$, $R^2$, $R^3$, $R^4$, and $R^5$ is as defined above with regard to formulae I and II, and described in embodiments, both singly and in combination; and
each OX is independently an oxygen-containing ligand, or two OX are connected together to form a bidentate ligand;
with one or two suitable ligands, as defined and described herein, to form a compound of formula I:

I

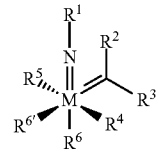

wherein each of M, $R^1$, $R^2$, $R^3$, $R^4$, $R^5$, $R^6$, and $R^{6'}$ is as defined above with regard to formula I, and described in embodiments, both singly and in combination.

One of ordinary skill in the art will recognize that, in some embodiments, reacting a compound of formula III-b with one suitable ligand (ultimately corresponding to $R^6/R^{6'}$ of formula I), results in a compound of formula I wherein $R^6$ and $R^{6'}$ are the same. In some embodiments, reacting a compound of formula III-b with two different suitable ligands results in a compound of formula I wherein $R^6$ and $R^{6'}$ are different. It will be further recognized that reacting a compound of formula III-b with one suitable ligand having two atoms capable of coordinating with M, the result can be a compound of formula I wherein $R^6$ and $R^{6'}$ are taken together to form a bidentate ligand. In some embodiments, at least one of the suitable ligand is

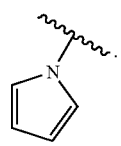

In some embodiments, both of the suitable ligands are

In some embodiments, one of the reactants is

In some embodiments, at least one OX is triflate. In some embodiments, each OX is triflate. In some embodiments, the present invention provides a compound of formula III-b having the structure of:

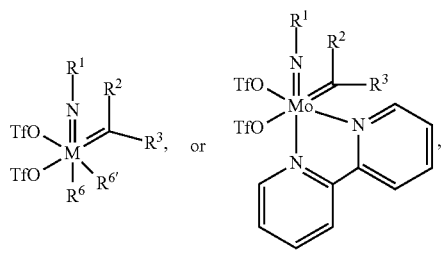
wherein each variable is independently as defined above and described herein.
In some embodiments, a provided compound of formula III-b is of any one of the structures depicted below:
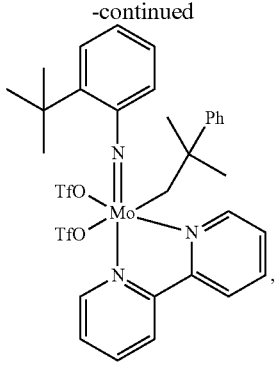
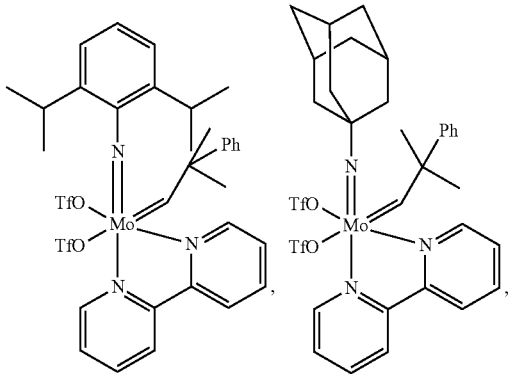
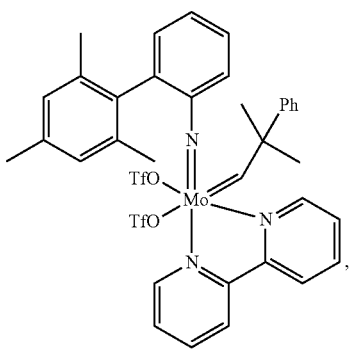
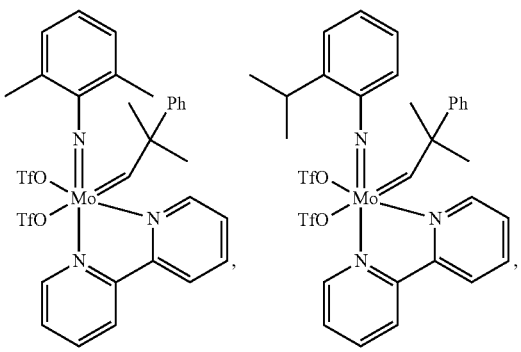
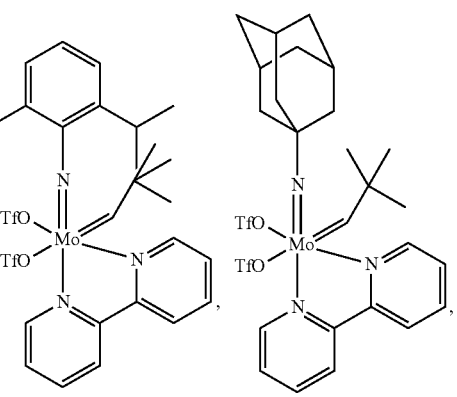
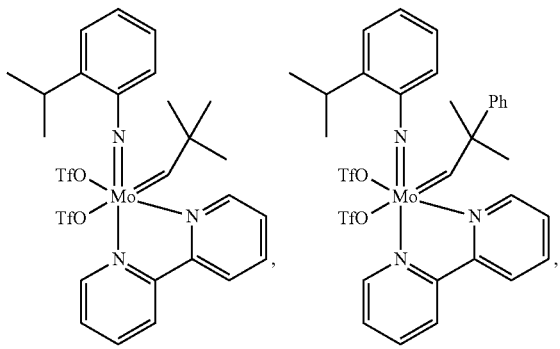

-continued

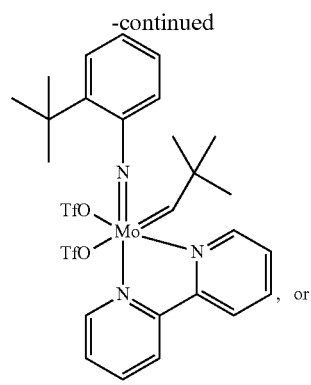, or

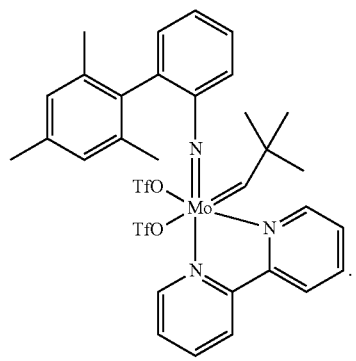.

In some embodiments, a compound of formula III-b is prepared from M(NR$^1$)(CR$^2$R$^3$)(OX')$_4$, wherein each variable is independently as defined above and described herein. In some embodiments, a compound of formula III-b is prepared from

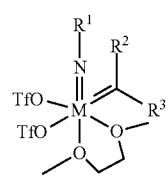

wherein each variable is as defined above and described herein. In some embodiments, a compound of formula III-b having the structure of

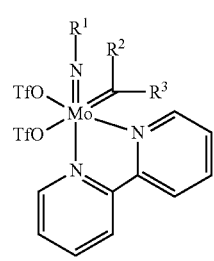

is prepared using

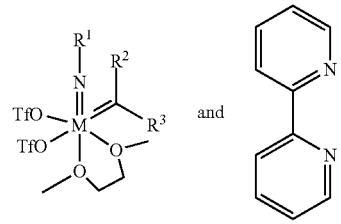

as two of the reagents.

Exemplary compounds of formula

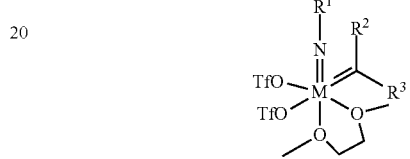

are depicted below:

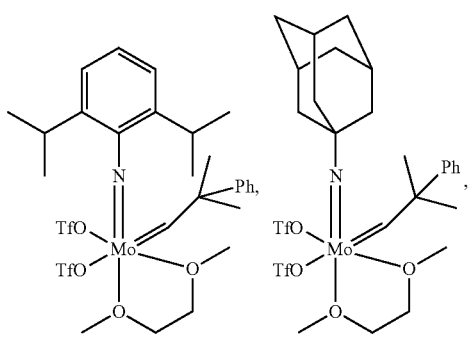

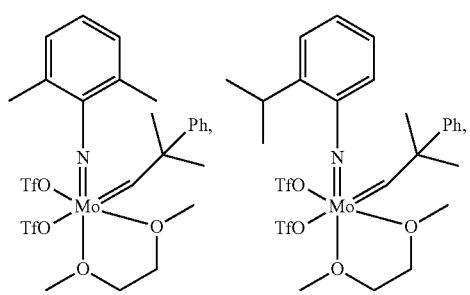

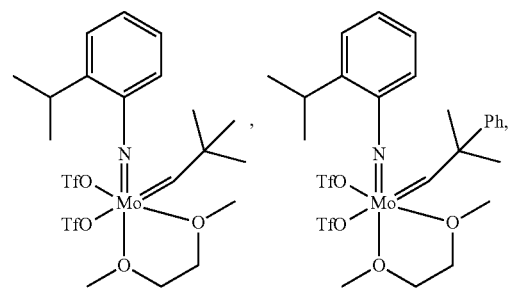

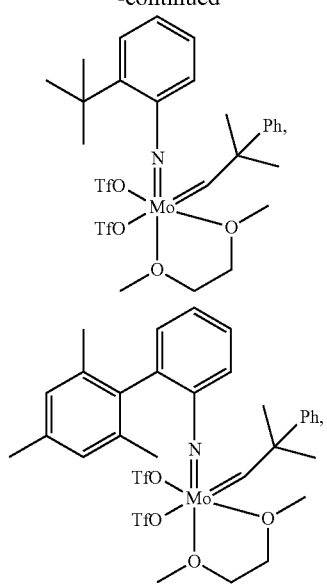

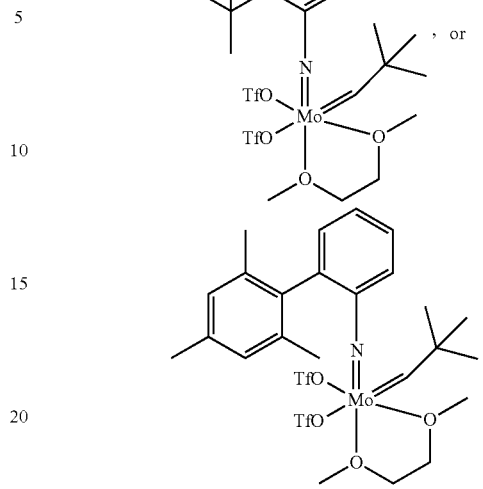

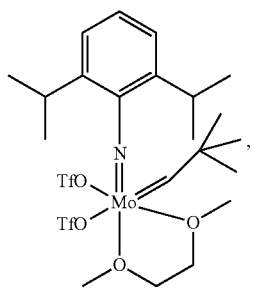

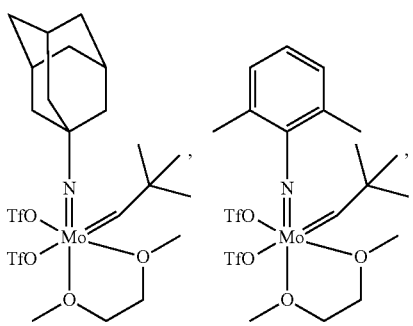

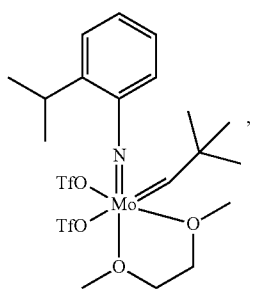

In certain embodiments, a metal complex of formula III or III-b is of either of the above structures, wherein the Mo metal center is replaced with a W metal center.

In some embodiments, a ligand is provided in a molar ratio of about 10:1, 9:1, 8:1, 7:1, 6:1, 5:1, 4:1, 3:1, 2:1, or 1:1 relative to the metal complex of formula III or III-b. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal complex of formula III or In certain embodiments, a ligand is provided in a molar ratio of about 1:1 relative, to the metal complex of formula III or III-b. One of skill in the art will appreciate that the optimal molar ratio of ligand to metal complex will depend on, inter alia, whether the ligand is mono- or bidentate.

Suitable conditions for performing provided methods generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, or polar aprotic solvents, such as ethereal solvents including ether, tetrahydrofuran (THF), or dioxanes, or mixtures thereof. In certain embodiments, one or more solvents are deuterated. In some embodiments, the desired product has different solubility in the solvent than the reagents used and/or the side-products. In some embodiments, the desired product has lower solubility in the solvent than most other species in the reaction. In some embodiments, a compound of formula I as a product has lower solubility than other species in the reaction. The difference in solubility can be used for the isolation and/or purification of products, as exemplified in the "EXEMPLIFICATION" section. Some of the examples are the isolation and/or purification of type 101 complexes in methods A, B, and/or C. In other embodiments, the desired product has higher solubility than most other species in the reaction. Such difference in solubility can also be used for the isolation and/or purification of products, as exemplified in the "EXEMPLIFICATION" section in the synthesis of type 103 complexes.

In some embodiments, a single solvent is used. In certain embodiments, the solvent is benzene. In certain embodiments, the solvent is ether.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. In certain embodiments wherein a solvent mixture comprises an ethereal solvent and a hydrocarbon, the solvents may be present in a ratio of about 20:1, about 10:1, about 9:1, about 8:1, about 7:1, about 6:1, about 5:1, about 4:1, about 3:1, about 2:1, or about 1:1 ethereal solvent:hydrocarbon. In certain embodiments, the solvent mixture comprises a mixture of ether and benzene in a ratio of about 5:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

Suitable conditions for forming a provided precursor complex typically employ ambient reaction temperatures. In some embodiments, a suitable reaction temperature is about 15° C., about 20° C., about 25° C., or about 30° C. In some embodiments, a suitable reaction temperature is from about 15° C. to about 25° C. In certain embodiments, a suitable reaction temperature is about 20° C., 21° C., 22° C., 23° C., 24° C., or 25° C.

In certain embodiments, a provided method for preparing a provided precursor complex is performed at elevated temperature. In some embodiments, a suitable reaction temperature is from about 25° C. to about 110° C. In certain embodiments, a suitable reaction temperature is from about 40° C. to about 100° C., from about 50° C. to about 100° C., from about 60° C. to about 100° C., from about 70° C. to about 100° C., from about 80° C. to about 100° C., or from about 90° C. to about 100° C. In some embodiments, a suitable reaction temperature is about 60° C.

In some embodiments, a provided method, or part of a provided method, is performed at a decreased temperature. In some embodiments, a suitable temperature is from about −80° C. to about 25° C. In some embodiments, a suitable temperature is from about −80° C. to about 25° C., from about −70° C. to about 25° C., from about −60° C. to about 25° C., from about −50° C. to about 25° C., from about −40° C. to about 25° C., from about −30° C. to about 25° C., from about −20° C. to about 25° C., from about −10° C. to about 25° C., from about 0° C. to about 25° C. In some embodiments, a suitable temperature is about −35° C.

Suitable conditions for forming a provided precursor complex typically involve reaction times of about 1 minute to about 1 day. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1 hour. In certain embodiments, the reaction time is about 2, 3, 4, 5, 6, 7, 8, 9, 10, 11, or 12 hours. In some embodiments, the reaction time is about 12 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 30 minutes.

Methods of Generating Active Catalysts from Provided Precursor Complexes

The present invention further provides methods of generating metathesis catalyst complexes from provided precursor complexes of formula I or formula II. In some embodiments, such compounds are active catalyst complexes for use in metathesis reactions, such as an olefin metathesis reaction. In certain embodiments, generation of an active catalyst complex occurs in situ.

In some embodiments, the present invention provides methods of making an active catalyst complex from a provided precursor complex comprising reacting a complex of formula I:

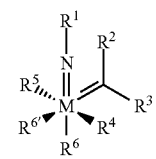

I wherein each of M, $R^1$, $R^2$, $R^3$, $R^4$, $R^5$, $R^6$, and $R^{6'}$ is as defined above with regard to formula I, and described in embodiments, both singly and in combination,
with a suitable alcohol, H—$OR^7$ to form a complex of formula V-a, V-b, or V-c:

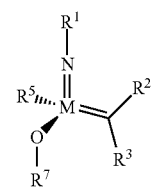

V-a

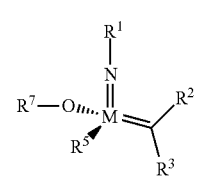

V-b

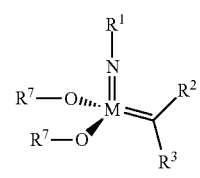

V-c wherein each of M, $R^1$, $R^2$, $R^3$, and $R^5$ is as defined above with regard to formula I, and described in embodiments, both singly and in combination, and each R⁷ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur.

In some embodiments, the present invention provides methods of making an active catalyst complex from a provided precursor complex comprising reacting a complex of formula II:

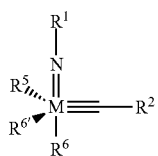

II wherein each of M, R¹, R², R⁵, R⁶, and R⁶' is as defined above with regard to formula II, and described in embodiments, both singly and in combination,
with a suitable alcohol, H—OR⁷ to form a complex of formula VI-a, VI-b, or VI-c:

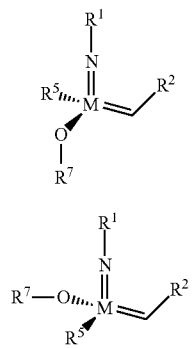

VI

VI-b

VI-c wherein each of M, R¹, R², and R⁵ is as defined above with regard to formula II, and described in embodiments, both singly and in combination, and
each R⁷ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur.

In certain embodiments, the alcohol H—OR⁷ is an optionally substituted phenol.

In some embodiments, —OR⁷ is an asymmetric ligand. In certain embodiments, —OR⁷ is a silyl-protected BINOL derivative.

In some embodiments, —OR⁷ is an optionally substituted group selected from:

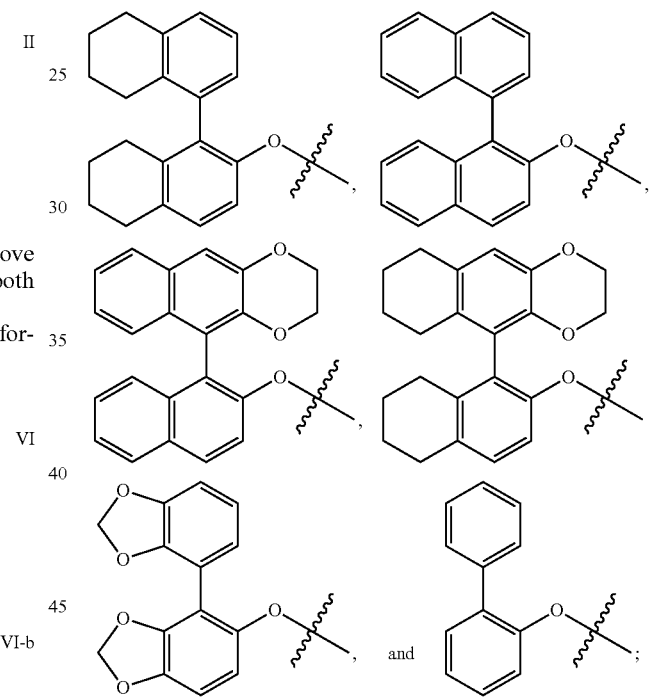

wherein each ⌇ represents the point of attachment to the metal, M.

In other embodiments, —OR⁷ is an optionally substituted

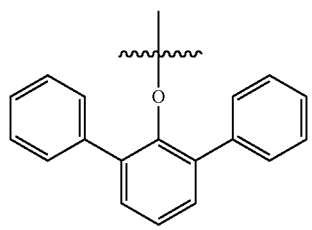 [SMILES: *Oc1c(-c2ccccc2)cccc1-c1ccccc1]

moiety. In some embodiments, —OR⁷ is

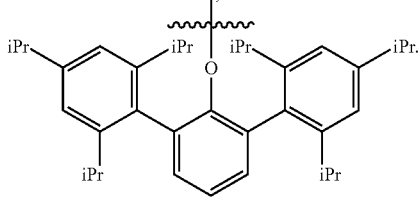

In some embodiments, the methods of making an active catalyst complex from a provided precursor complex further comprising the presence of a Lewis acid. In some embodiments, the Lewis acid comprises Zn(II). In some embodiments, the Lewis acid is $ZnCl_2$(dioxane).

In some embodiments, alcohol H—OR⁷ is provided in a molar ratio of about 10:1, 9:1, 8:1, 7:1, 6:1, 5:1, 4:1, 3:1, 2:1, or 1:1 relative to the provided precursor complex. In some embodiments, alcohol H—OR⁷ is provided in a molar ratio of about 0.9:1, 0.8:1, 0.7:1, 0.6:1, 0.5:1, 0.4:1, 0.3:1, 0.2:1, or 0.1:1 relative to the metal complex of formula III. In certain embodiments, alcohol H—OR⁷ is provided in a molar ratio of about 1:1 relative to a provided precursor complex. In certain embodiments, alcohol —OR⁷ is provided in a molar ratio of about 2:1 relative to a provided precursor complex.

In some embodiments, a complex of formula V is any of the following structures:

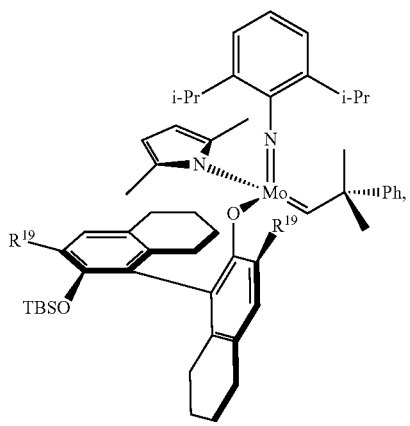

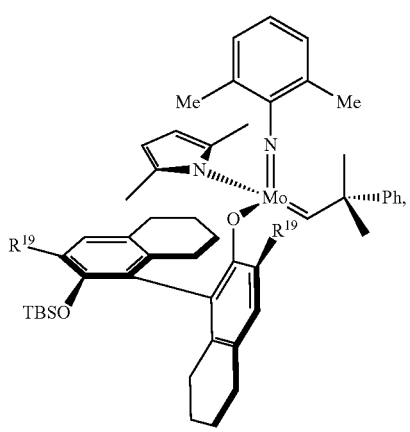

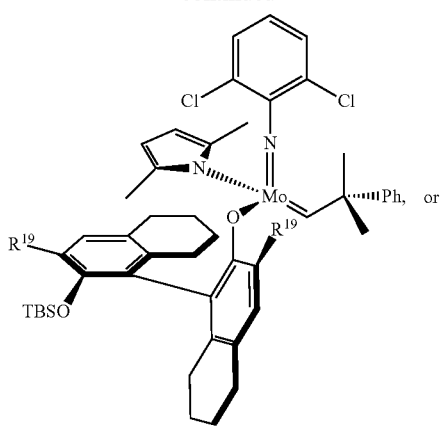

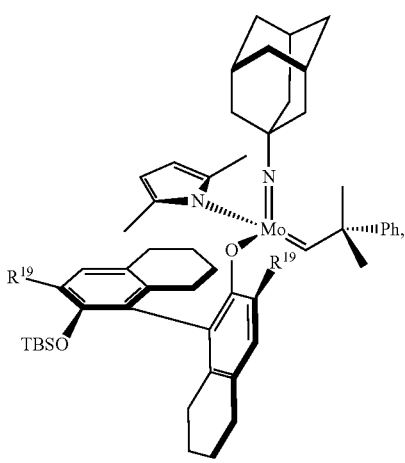

wherein each $R^{19}$ is independently F, Cl, Br, or I. In certain embodiments, $R^{19}$ is Br.

In some embodiments, a complex of formula V prepared by methods of the present invention is any of the following structures:

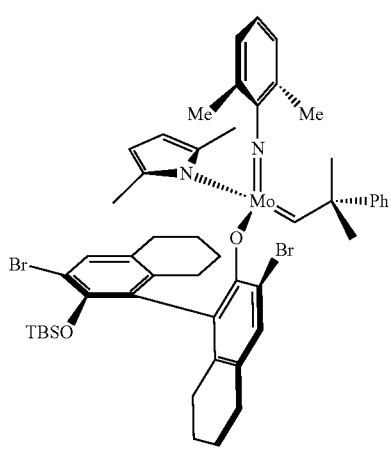

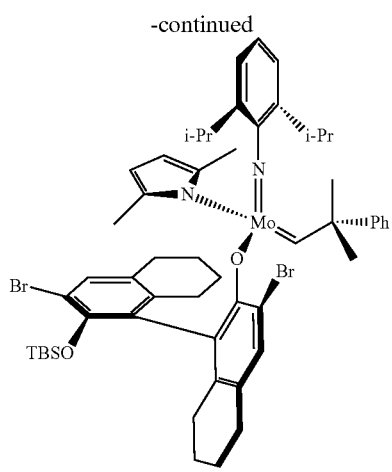
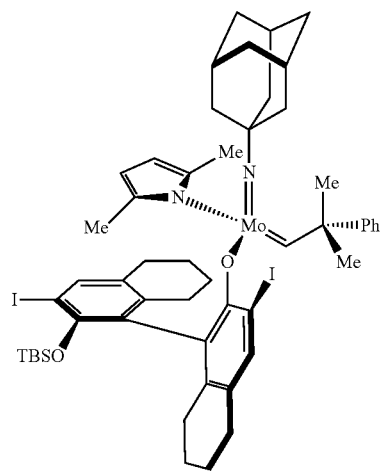
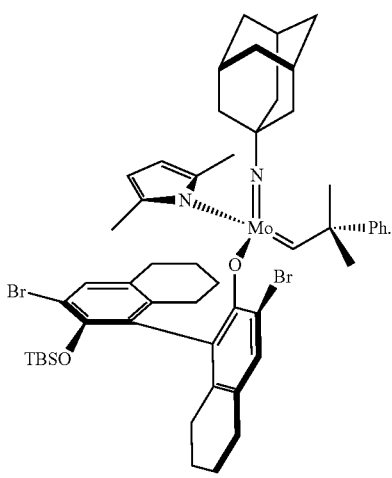
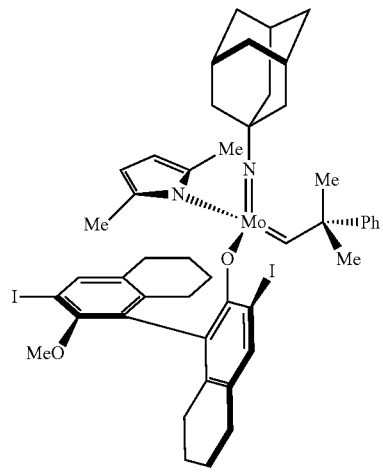
In some embodiments, a complex of formula V prepared by methods of the present invention is of the following formula:
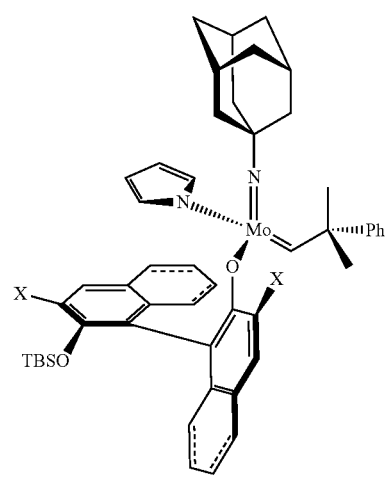
wherein each X is independently Br or I.
In some embodiments, a complex of formula V prepared by methods of the present invention is any of the following structures:
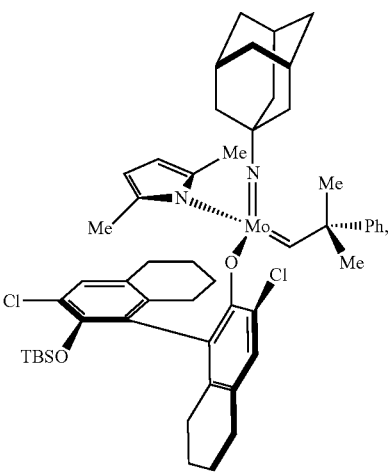

61
-continued
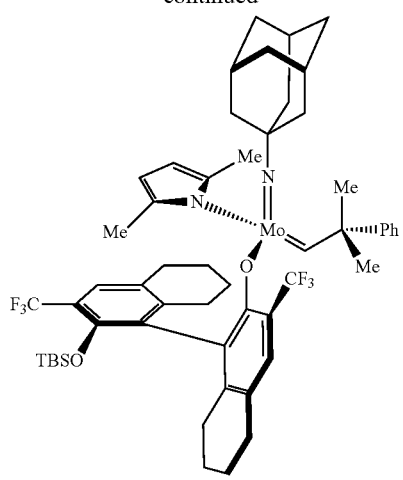
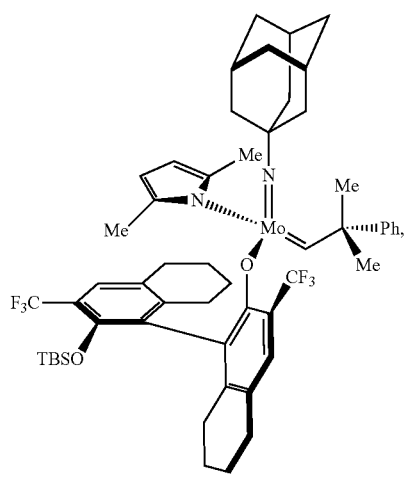
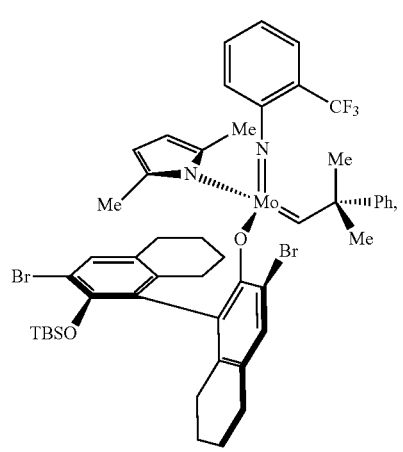
62
-continued
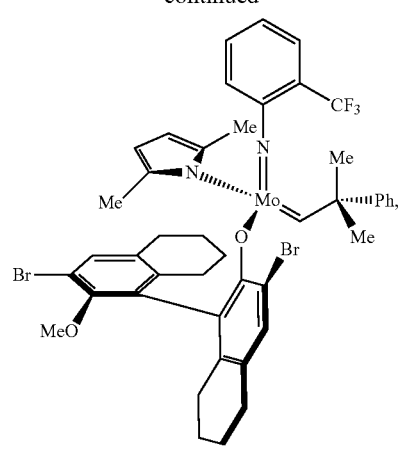
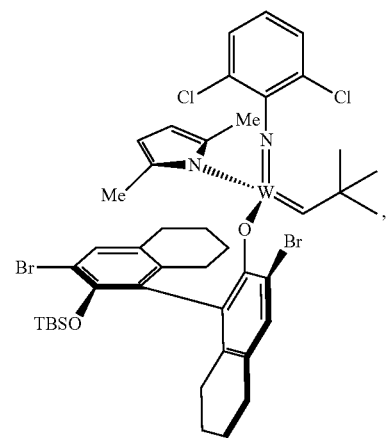
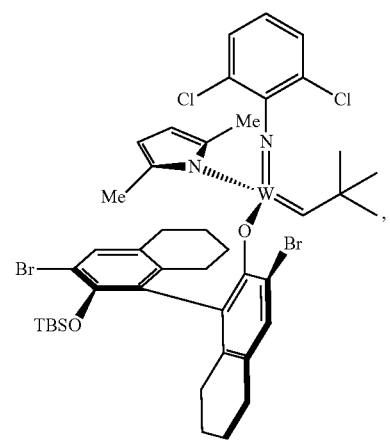

-continued
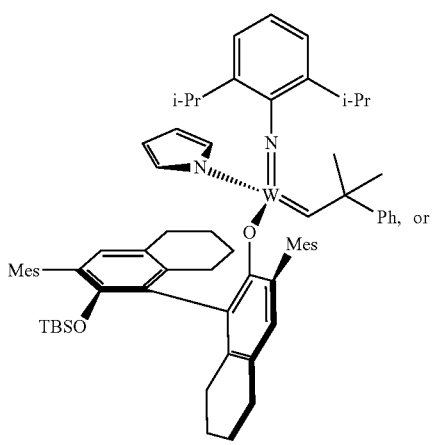
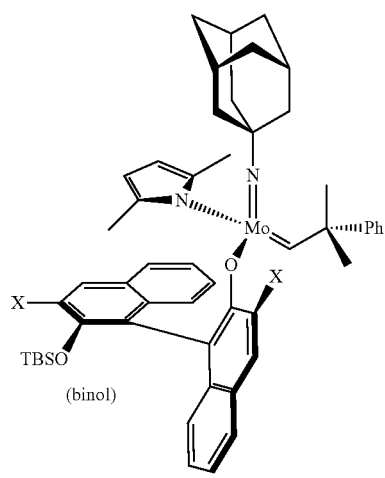
(binol)
wherein Mes is 2,4,6-trimethyl phenyl, and wherein each X is independently Br, I, or $CF_3$.
In some embodiments, a complex of formula V prepared by methods of the present invention is any of the following structures:
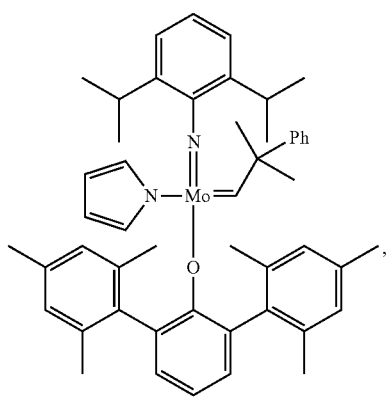
-continued
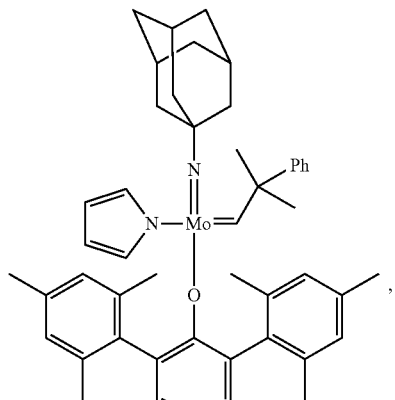
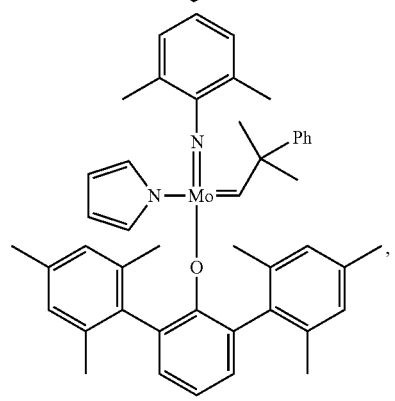
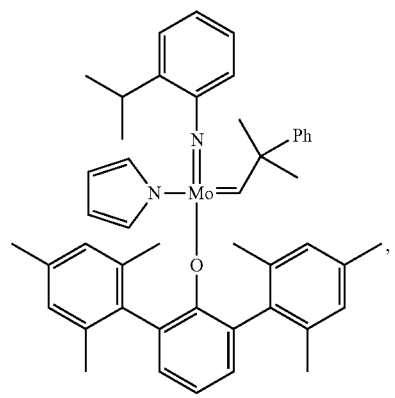
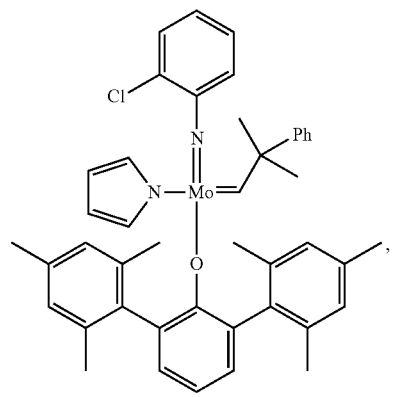

-continued
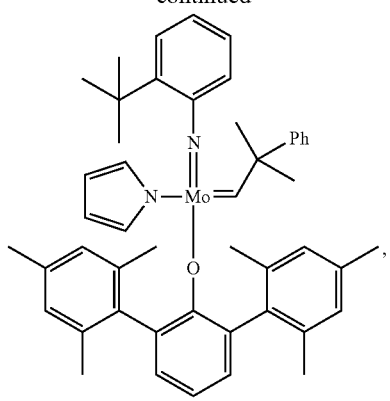
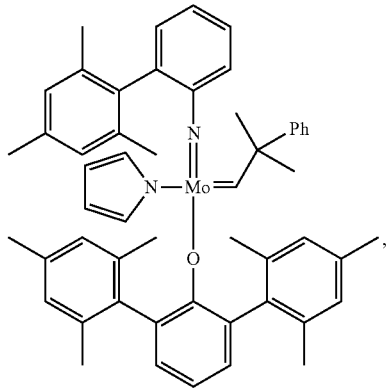
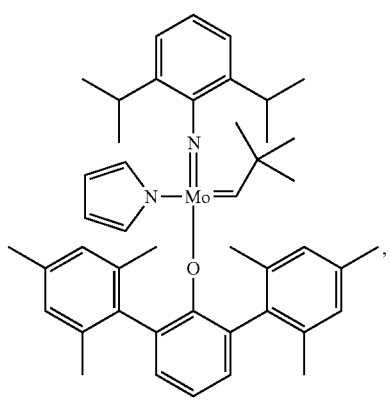
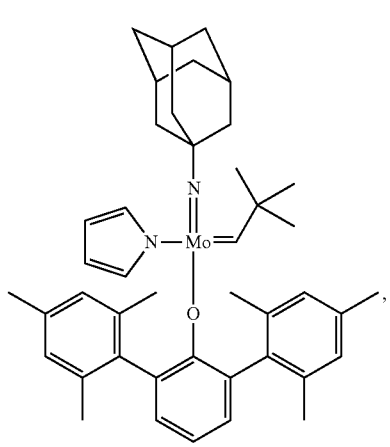
-continued
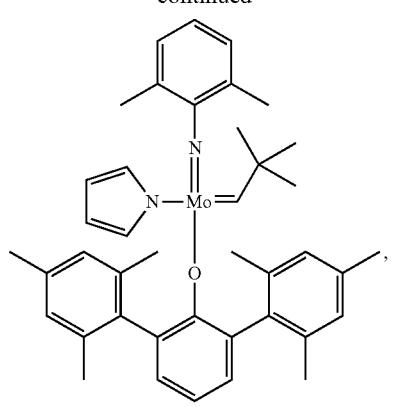
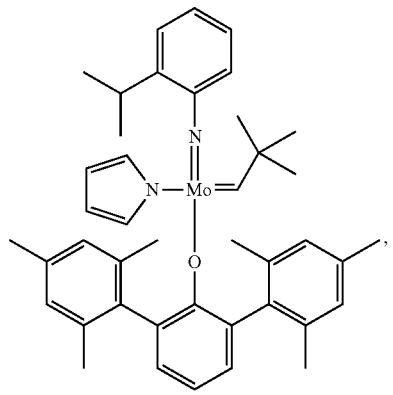
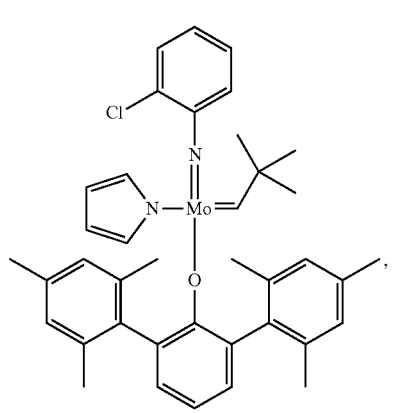
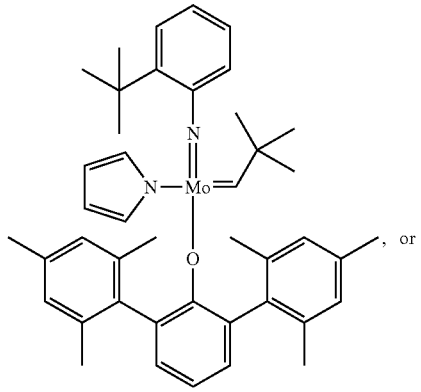, or

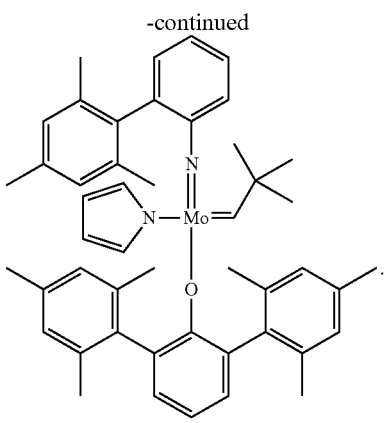

Exemplary Uses of Provided Precursor Complexes

As described herein, provided compounds of formula I and formula II are stable and particularly useful in generating active metathesis catalysts. Accordingly, in further embodiments, the present invention provides a method for performing a metathesis reaction comprising the steps of:
(a) providing a compound of formula I, wherein said compound is as defined above and described in embodiments herein;
(b) reacting the compound of formula I with a suitable alcohol to form an active catalyst; and
(c) performing a metathesis reaction with the active catalyst.

In other embodiments, the present invention provides a method for performing a metathesis reaction comprising the steps of:
(a) providing a compound of formula II, wherein said compound is as defined above and described in embodiments herein;
(b) reacting the compound of formula II with a suitable alcohol to form an active catalyst; and
(c) performing a metathesis reaction with the active catalyst.

In some embodiments, the suitable alcohol is of formula —OR$^7$ as defined above and described in embodiments herein.

In certain embodiments, the active catalyst is of formula V-a, V-b, or V-c, as defined above and described in embodiments herein.

In certain embodiments, the active catalyst is of formula VI-a, VI-b, or VI-c, as defined above and described in embodiments herein.

In some embodiments, the metathesis reaction is ring-opening metathesis. In some embodiments, the metathesis reaction is ring-opening metathesis polymerization (ROMP). In some embodiments, the metathesis reaction is the ring-opening metathesis polymerization of dicarbomethoxynorbornadiene (DCMNBD).

In some embodiments, the active catalyst generated in step (b) is generated and utilized in situ, i.e., in a "one-pot" reaction. In this regard, metathesis reagents can be added to the catalyst after it is generated. Alternatively, metathesis reagents are added to the catalyst precursor complex (i.e., compound of formula I or II) along with the suitable alcohol such that active catalyst and metathesis reaction occur in situ.

In some embodiments, methods using provided precursor complexes involve reacting a first species and a second species to form a product comprising a double bond, wherein the double bond comprises an atom of the first species and an atom of the second species. In some embodiments, the double bond may comprise a carbon atom from the first species and a carbon atom from the second species. The double bond produced may have a Z (e.g., cis) or E (e.g., trans) configuration. Those of ordinary skill in the art would understand the meaning of the terms "cis" or "Z" and "trans" or "E," as used within the context of the invention.

Some embodiments may provide the ability to selectively synthesize, via a metathesis reaction, products having a Z or E configuration about a double bond. In some embodiments, methods using precursor complexes of the present invention may provide the ability to synthesize compounds comprising a Z-disubstituted olefin. In some embodiments, such methods are useful when applied to a wide range of olefin substrates, including those having sterically small or large groups adjacent the olefin. In some embodiments, complexes of the present invention are useful in methods for synthesizing Z-disubstituted enol ethers. In some embodiments, complexes of the present invention are useful in methods for synthesizing Z-disubstituted allylic amines. In some embodiments, complexes of the present invention are useful in methods for synthesizing Z-disubstituted allylic amides.

In some embodiments, a metathesis reaction using a complex of the present invention produces a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

In some embodiments, a metathesis reaction using a complex of the present invention produces a double bond in an E:Z ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC). In some cases, about 100% of the double bond produced in the metathesis reaction may have an E configuration. The E or trans selectivity may also be expressed as a percentage of product formed. In some cases, the product may be greater than about 50% E, greater than about 60% E, greater than about 70% E, greater than about 80% E, greater than about 90% E, greater than about 95% E, greater than about 96% E, greater than about 97% E, greater than about 98% E, greater than about 99% E, or, in some cases, greater than about 99.5% E.

In some embodiments, a method of the present invention produces a chiral product. In some embodiments, a method of the present invention produces a product in an enantiomeric ratio greater than 50:50. In some embodiments, a method of the present invention produces a product in an enantiomeric ratio greater than 60:40. In some embodiments, a method of the present invention produces a product in an enantiomeric ratio greater than 70:30. In some embodiments, a method of the present invention produces a product in an enantiomeric ratio greater than 80:20. In some embodiments, a method of the present invention produces a product in an enantiomeric ratio greater than 90:10. In some embodiments, a method of the present invention produces a product in an enantiomeric ratio greater than 95:5. In some embodiments, a method of the present invention produces a product in an enantiomeric ratio greater than 96:4. In some embodiments, a method of the present invention produces a product in an enantiomeric ratio greater than 97:3. In some embodiments, a method of the present invention produces a product in an enantiomeric ratio greater than 98:2. In some embodiments, a method of the present invention produces a product in an enantiomeric ratio greater than 99:1.

As mentioned above, provided precursor complexes are useful as precursors to stereogenic-at-metal complexes which are capable of catalyzing metathesis reactions. Exemplary such methods and reactions are described below.

It will be appreciated that, in certain embodiments, each variable recited for the above method is as defined above and described in embodiments, herein, singly and in combination.

Exemplification

Stereogenic-at-Mo as well as W— complexes, such as 3 and 4 (Scheme 1), display unprecedented reactivity and stereoselectivity in olefin metathesis reactions; examples are highly enantioselective ring-closing metathesis (RCM) reactions or Z-selective homo-coupling and cross-metathesis processes (e.g., see (a) Malcolmson, S. J.; Meek, S. J.; Sattely, E. S.; Schrock, R. R.; Hoveyda, A. H. *Nature* 2008, 456, 933-937. (b) Sattely, E. S.; Meek, S. J.; Malcolmson, S. J.; Schrock, R. R.; Hoveyda, A. H. *J. Am. Chem. Soc.* 2009, 131, 943-953. (c) Ibrahem, I.; Yu, M.; Schrock, R. R.; Hoveyda, A. H. *J. Am. Chem. Soc.* 2009, 131, 3844-3845. (d) Flook, M. M.; Jiang, A. J.; Schrock, R. R.; Müller, P.; Hoveyda, A. H. *J. Am. Chem. Soc.* 2009, 131, 7962-7963. (e) Lee, Y-J.; Schrock, R. R.; Hoveyda, A. H. *J. Am. Chem. Soc.* 2009, 131, 10652-10661. (f) Jiang, A. J.; Zhao, Y.; Schrock, R. R.; Hoveyda, A. H. *J. Am. Chem. Soc.* 2009, 131, 16630-16631. (g) Zhao, Y; Hoveyda, A. H.; Schrock, R. R. *Org. Lett.* 2011, 13, 784-787. (h) Meek, S. J.; O'Brien, R. V.; Llaveria, J.; Schrock, R. R.; Hoveyda, A. H. *Nature,* 2011, 471, 461-466). For an additional transformation (not stereoselective) catalyzed by this class of complexes, see: (i) Marinescu, S. C.; Schrock, R. R; Müller, P.; Hoveyda, A. H. *J. Am. Chem. Soc.* 2009, 131, 10840-10841). The requisite Mo and W complexes are prepared and used in situ by protonation of a pyrrolide ligand with a chiral phenol (2) from a bis-pyrrolide precursor (Scheme 1).

Scheme 1. Synthesis of Stereogenic-at-Metal Complexes

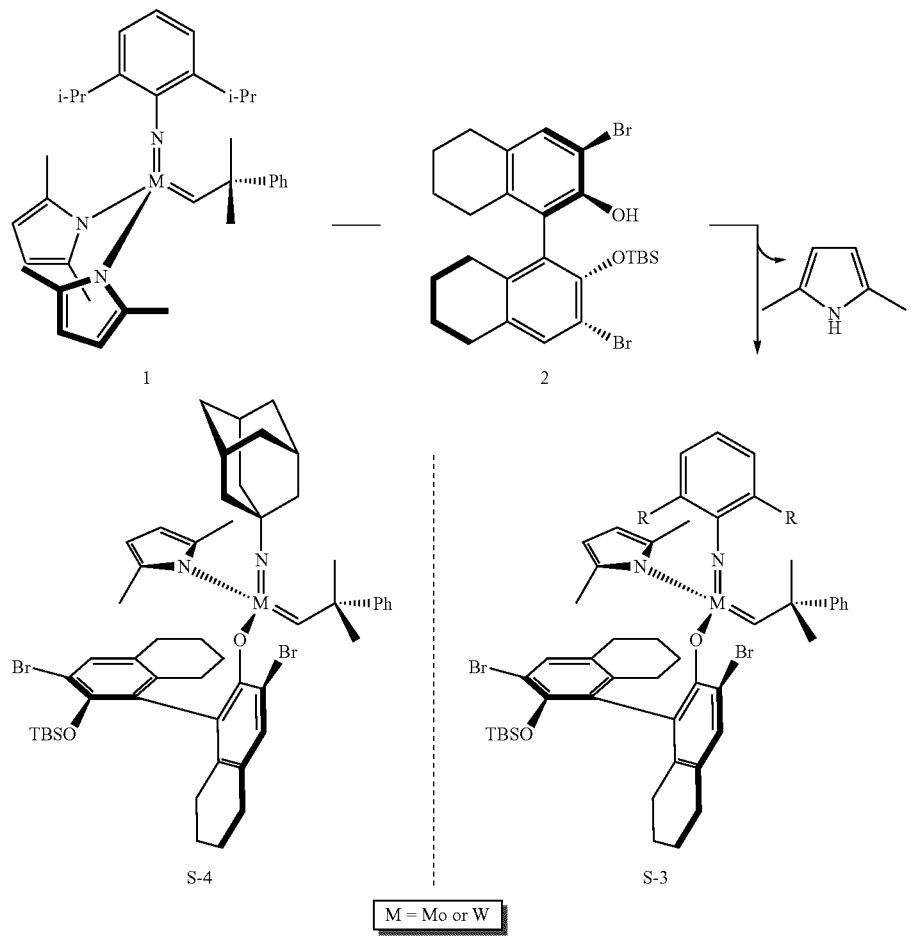

Although several structurally diverse catalysts can be prepared, bis-pyrrolide complexes (e.g., 1) are sensitive to air and moisture, thus limiting the ability to weigh them on the bench. A more convenient protocol would permit the user to weigh an air-stable catalyst precursor, in addition to all other reagents, on the bench-top in a fume hood. It has been previously noted that N,N-chelating ligands bind and provide stability to Mo alkylidene bis-alkoxide complexes (e.g., see Fox, H. H.; Lee, J-K.; Park, L. Y.; Schrock, R. R. *Organometallics* 1993, 12, 759-768). In 1993, it was noted that the addition of an N,N-chelating ligand (e.g., 2,2-bipyridyl) allows for the isolation of a typically unstable Mo-methylidene complex. More recently, Fürstner and coworkers have used the above principle and disclosed phenanthroline adducts of high oxidation state Mo alkylidynes (e.g., see Heppekausen, J.; Stade, R.; Goddard, R.; Fürstner, A. *J. Am. Chem. Soc.* 2010, 131, 11045-11068). Building on previous studies regarding related pyridine complexes (e.g., see Bindl, M.; Stade, R.; Heilmann, E. K.; Picot, A.; Goddard, R.; Fürstner, A. *J. Am. Chem. Soc.* 2009, 131, 9468-9470), octahedral complexes were prepared that display significant stability to air and moisture. The corresponding Mo alkylidynes are then generated by treatment with $MnCl_2$ at elevated temperature (80° C.) to release the active alkyne metathesis catalysts. The present invention discloses the isolation of air stable Mo alkylidene and alkylidyne complexes, which serve as precursors to stereogenic-at-Mo olefin metathesis catalysts, and which surprisingly do not require elevated temperatures (ca. 80 C) or treatment with an additional metal to generate the active catalyst.

Initial investigations began with the reaction of Mo complex 5, bearing two unsubstituted pyrrolide ligands, with 2,2'-bipyridyl (bpy). Under the reaction conditions shown in Scheme 2, a yellow precipitate formed, which on standing in solution quickly (<5 min) rearranged to octahedral bpy-5 (orange crystals) whose structure was confirmed by X-ray analysis. The yellow powder as well as orange crystalline forms were bench stable under air in the solid state (<2% decomposition in 11 h).

Scheme 2. Isolation and X-ray Crystal Structure of bpy-5

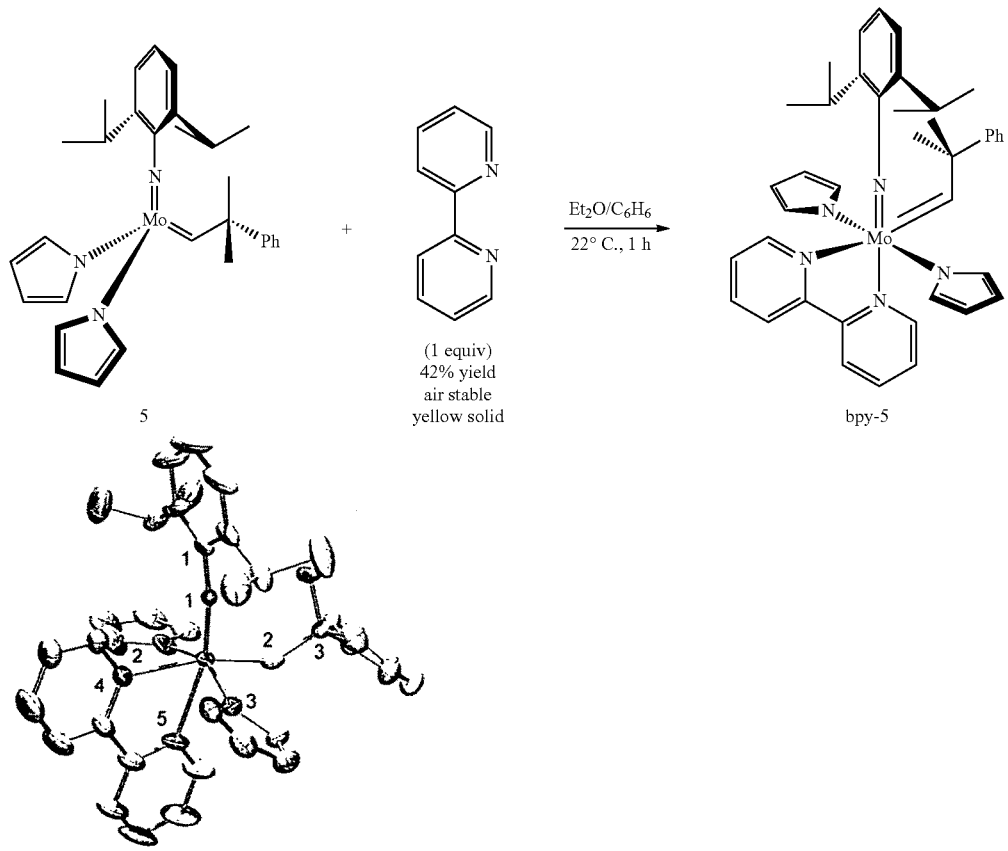

| bond lengths (Å): | bond angles (deg): |
|---|---|
| Mo-C1 = 1.932 | N1-Mo-N2 = 100.6 |
| Mo-N1 = 1.730 | N1-Mo-N3 = 101.1 |
| Mo-N2 = 2.135 | N1-Mo-C2 = 98.6 |
| Mo-N3 = 2.143 | N1-Mo-N4 = 93.5 |
| Mo-N4 = 2.353 | N1-Mo-C4 = 162.8 |
| | Mo-N1-C1 = 171.0 |
| | Mo-C2-C3 = 138.3 |
| | N4-Mo-N5 = 69.3 |
| | N2-Mo-C2 = 95.2 |
| | N3-Mo-C2 = 92.2 |
| | N3-Mo-C2 = 80.5 |
| | N2-Mo-N4 = 87.4 |

Furthermore, on treatment with two equivalents of phenol 2 (60° C., 2 h), there was 81% conversion to a 1:5 mixture of the tetrahedral monoaryloxide complex and its bpy-adduct; reaction at 22° C. led to a significantly slower substitution (10% conversion in 2 h with one equivalent 2). Exposure of triene 6 to this mixture (2 mol % bpy-5 and 4 mol % 2) led to 38% conversion to 7 in 58:42 er (eq 1, R-enantiomer of 7 is major). Notably, similar selectivity to that obtained from the catalyst synthesis outlined in Scheme 1 (1 mol %, 30 min, 54% conv, 56.5:43.5 er) was observed. Importantly, unlike formerly reported cases regarding precursors to catalysts for alkyne metathesis, heating (80° C.) or addition of a new metal salt (such as $MnCl_2$ or $ZnCl_2$) was not needed.

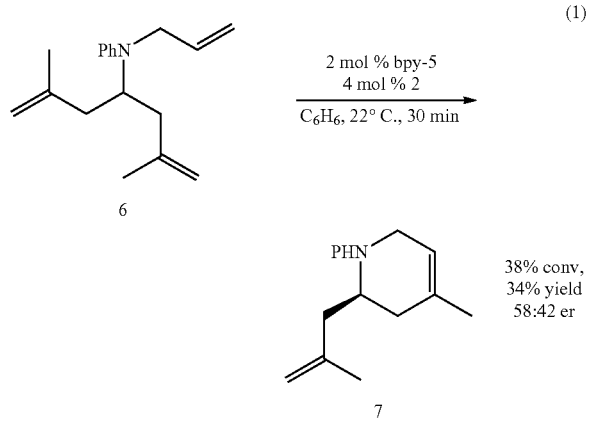

(1)

Monodentate N-donating ligands such as pyridine also impart significant stability to corresponding octahedral Mo alkylidene complexes. As illustrated in FIG. 1, exposure of bis-pyrrolide 5 to 5 equivalents of pyridine delivered complex pyr-5 in 52% yield as an orange complex.

Figure 2:
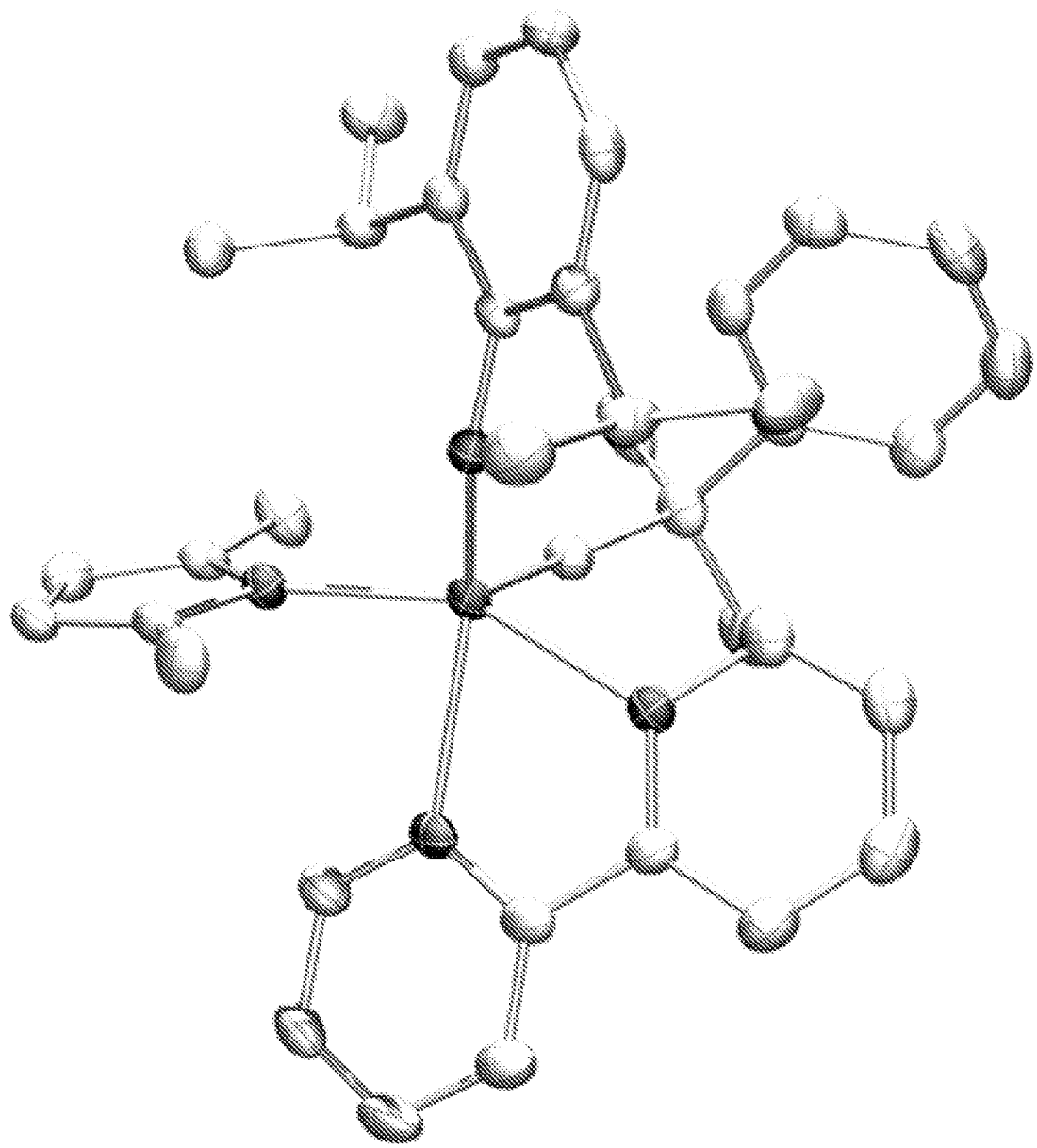
FIG. 2. X-ray crystal structure of alkylidyne bpy-6.

In some instances, substituted pyrrolide ligands were desired. Accordingly, preparation of the corresponding 2,5-dimethylpyrrolide adduct was also investigated. Treatment of bis-pyrrolide 1 with bpy led to the clean formation of a reasonably air-stable purple complex (12% decomposition in 15 min, 29% in 1 h as confirmed by 400 MHz $^1$H NMR analysis), but one which lacked an alkylidene signal in the $^1$H NMR spectrum. Further investigations revealed that the complex generated on the reaction of bis-pyrrolide 1 with bpy is Mo imido, monopyrrolide alkylidyne complex bpy-6 (FIG. 2), formed by net α-abstraction of the alkylidene proton by a pyrrolide ligand on bipyridyl complexation.

Exposure of bpy-6 to one equivalent of 2 (22° C., 1.5 h), however, led to the clean formation of monoaryloxide 3 (98% conv, 1:1 dr), which catalyzed the ring-closing metathesis of triene 7 to deliver 8 with equal efficiency and nearly equal selectivity (94:6 er vs 96.5:3.5 er with catalyst generated directly from bis-pyrrolide 1, Scheme 1).

In this manner, several alkylidyne complexes, bearing N,N-chelating ligands as well as monodentate N-donating ligands (e.g., pyridine), have been prepared from dimethylpyrrolide precursors (9-13, Scheme 3).

Scheme 3. Synthesis of bpy-6 and Use in Catalytic RCM

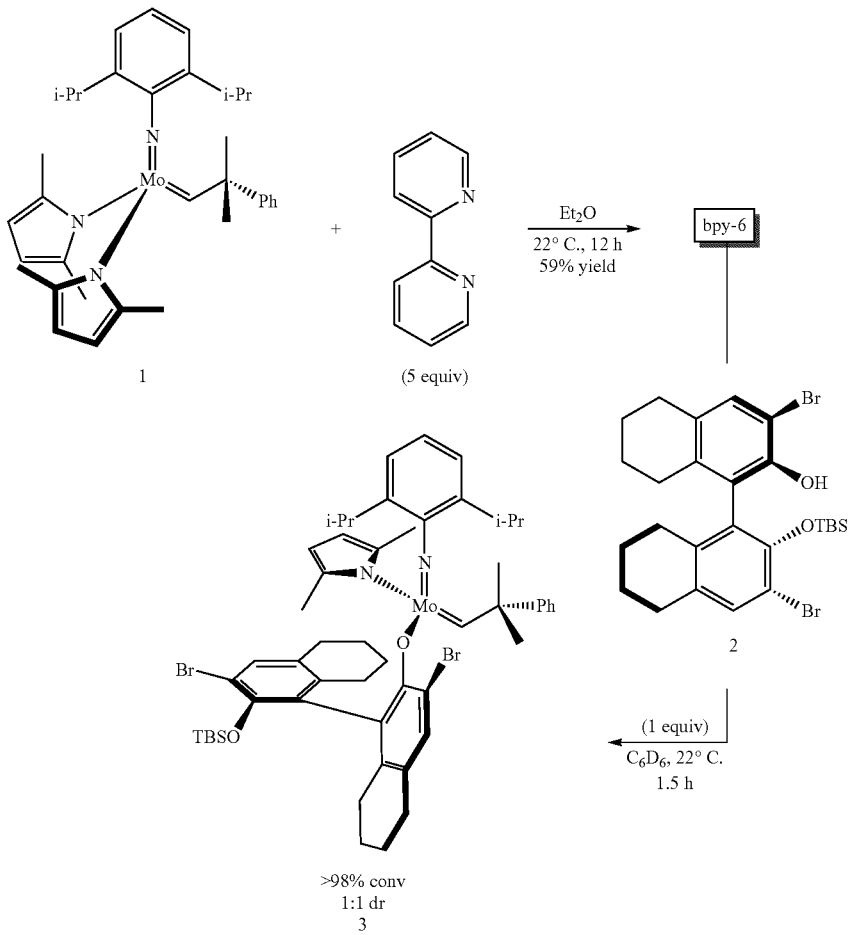

-continued

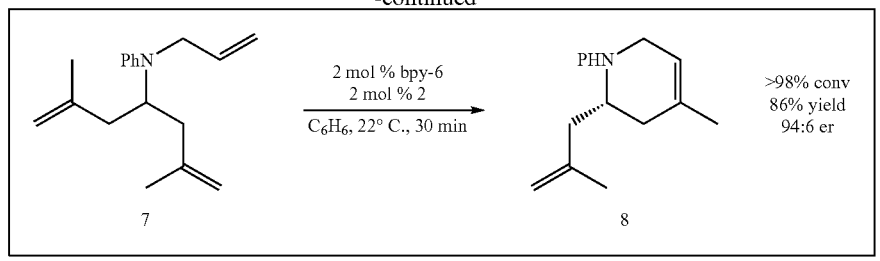

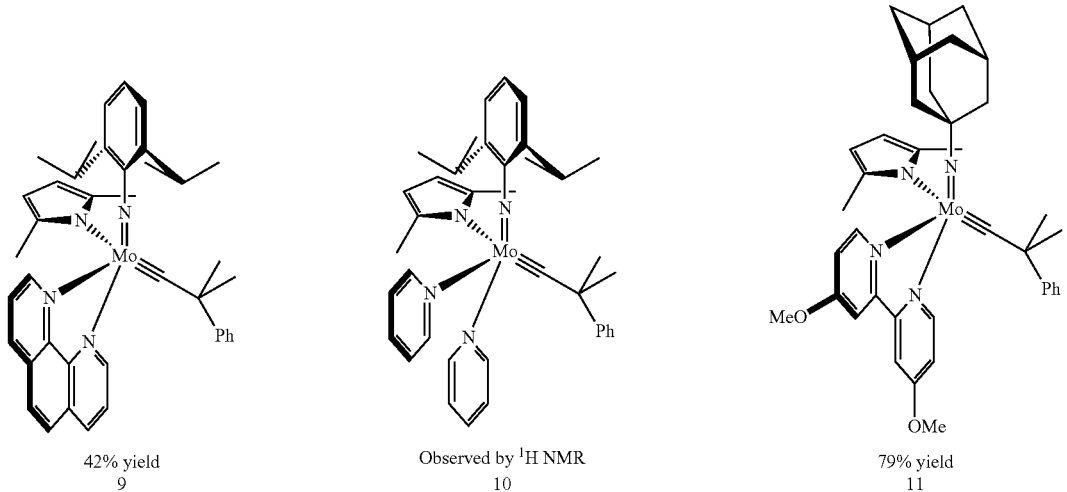

42% yield
9

Observed by ¹H NMR
10

79% yield
11

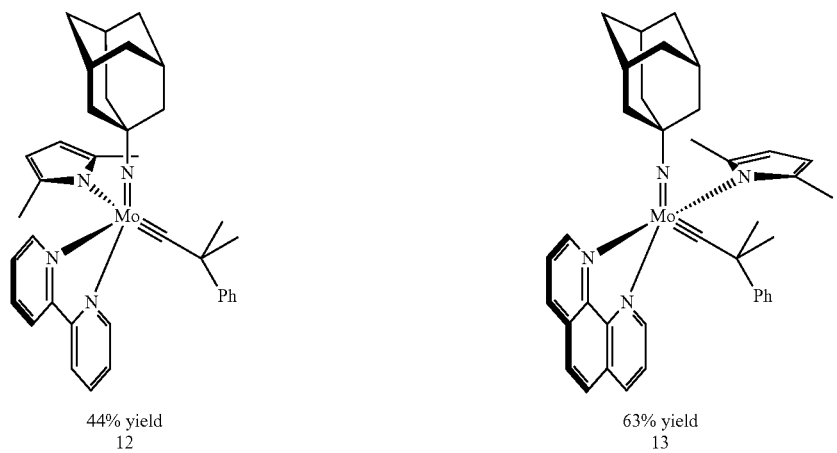

44% yield
12

63% yield
13

In addition to bipyridyl and pyridine, phenanthroline may be employed as the bidentate ligand (9). A sterically less hindered adamantylimido bis-pyrrolide complex furnished alkylidyne complexes with the same set of N,N-bidentate ligands (11-13), as well as an electronically modified bipyridyl (11). The alkylidyne complexes displayed varying levels of air stability, with those containing a 2,6-diisopropylarylimido ligand being the most stable, although none were as stable as octahedral bpy-5. Compared to bpy-6, phenanthroline complex 9 offers a slightly enhanced stability (7% decomposition in 15 min). Bipyridyl adducts bearing adamantylimido ligands decomposed completely within 1 min in air.

Contrary to the situation involving arylimido ligands, the phenanthroline adduct of the adamantylimido Mo (13) offered significantly enhanced stability over bpy (50% decomposition after 12 h).

Several alkylidyne complexes served as effective precursors to monoaryloxide-monopyrrolide alkylidene catalysts (e.g., S-3 and S-4, Scheme 1) (e.g., see (a) Freudenberger, H. H.; Schrock, R. R. *Organometallics*, 1985, 4, 1937-1944. (b) Schrock, R. R. *Acc. Chem. Res.* 1986, 19, 342-348). In addition to the combination of bpy-1 and phenol 2 (Scheme 3), treatment of adamantyl-containing bipyridyl adducts 11 or 12 with one equivalent of 2 delivered S-4 as a 1:1 mixture of diastereomers (22° C., 10 min, eq 2). In contrast to bipyridyl-substituted alkylidynes, those than bear a phenanthroline ligand (9 and 13) did not lead to monoaryloxide catalysts; instead, on treatment of either of these Mo complexes with phenol 2, a complex mixture of products was obtained. Several other alcohols yielded similar results. Control experiments have indicated that, unlike with bipyridyl, phenanthroline was capable of reacting with monoaryloxide complexes. Binding of phenanthroline to stereogenic-at-Mo 3 (generated in situ) causes formation of alkylidyne 8 and gives rise to a number of other unidentified compounds.

(2)

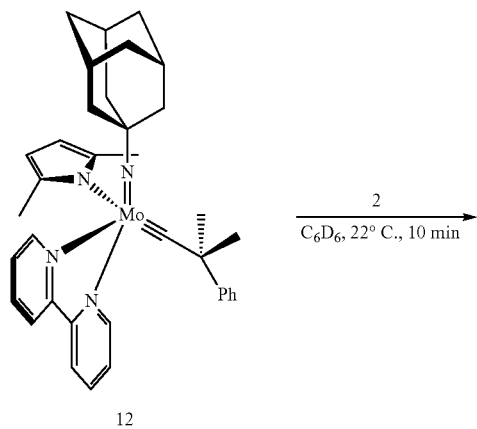

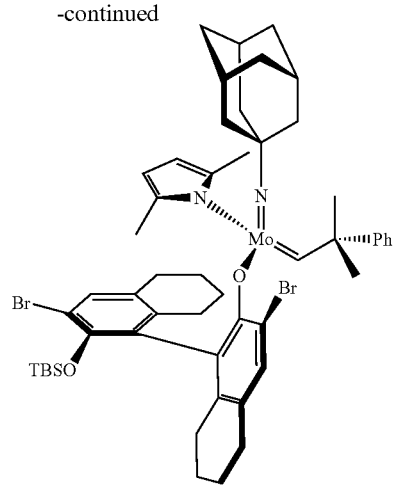

>98% conv 1:1 d.r.
Similar result obtained with 12.
4

In addition to increased air-stability, several other aspects of the chelated alkylidyne complexes contribute to their practicality. For instance, formation of the monoaryloxide catalyst prior to the olefin metathesis reaction is not required. Simply mixing bpy-6 and phenol 2 together in the presence of triene 7 leads to >98% conversion to 8 (87% yield, 93.5:6.5 er) within 1 h (eq 3). Highly Z-selective ring-opening cross-metathesis reactions were achieved with monoaryloxide catalyst 4, obtained from bpy complex 12 and phenol 2 (91% conv, >98:2 Z:E, with 1.5 mol % catalyst, 30 min); similar results were obtained when the catalyst was generated directly from the bis-pyrrolide complex and phenol 2. As before, heating or addition of a new metal salt was not required.

(3)

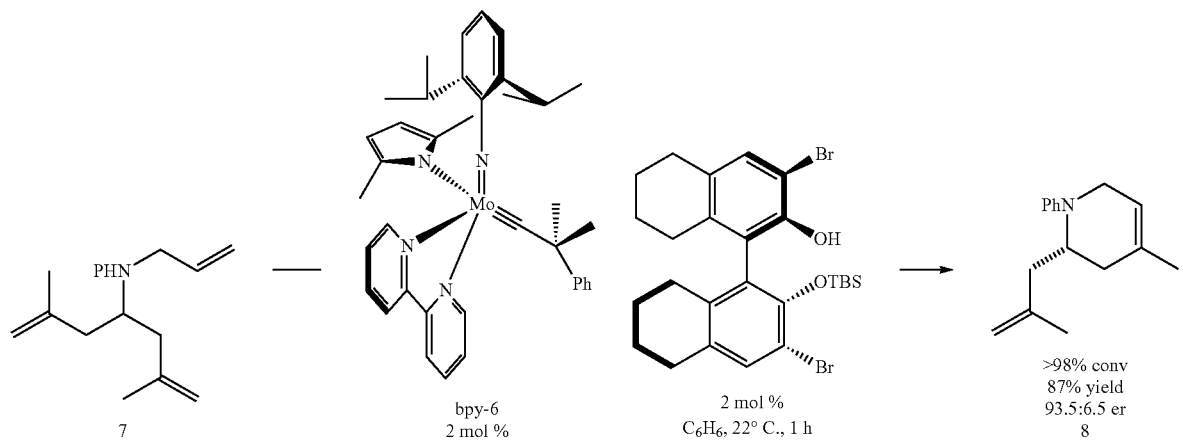

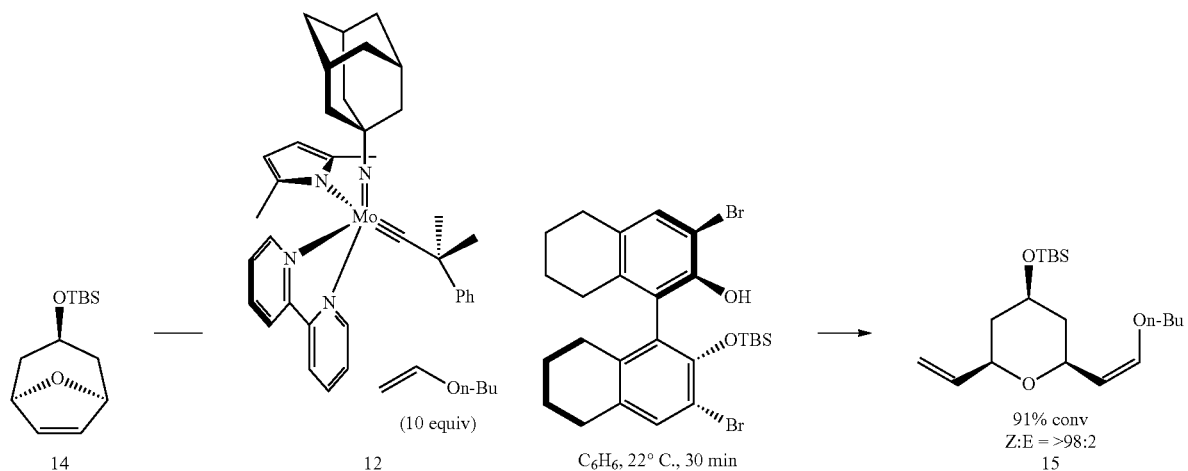

(4)

Thus, it was surprisingly found that the addition of N-donor ligands to Mo bis-pyrrolide complexes imparts a great deal of air-stability to the otherwise unstable complexes. This process is also applicable to the analogous tungsten bis-pyrrolides complexes. With unsubstituted pyrrolide ligands, octahedral complexes (such as bpy-5) were formed, which can undergo substitution with a chiral (or achiral) phenol to render a metathesis active catalyst. In the case of bis-dimethylpyrrolide complexes, steric crowding at the metal on ligand complexation led to alkylidyne formation through an α-abstraction mechanism. Five-coordinate alkylidyne complexes are significantly more air-stable than their parent alkylidenes and can serve as precursors to tetrahedral alkylidene metathesis catalysts.

These technologies can be applied to the corresponding W-based complexes. The air-stable Mo or W pyrrolide adducts (an example is shown in eq 3), handled at the bench without an inert environment, can be used to generate alkylidene complexes for olefin metathesis in the fume hood. Moreover, the present approach is applicable to a wide range of mono- and bidentate N-based ligands. Representative examples of different ligands are listed in Appendix A, provided below.

(3)

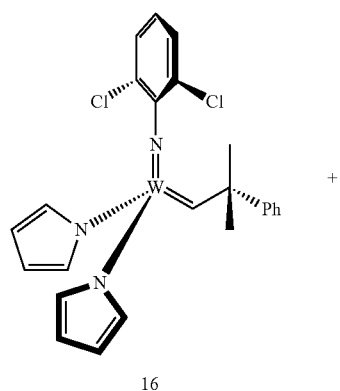

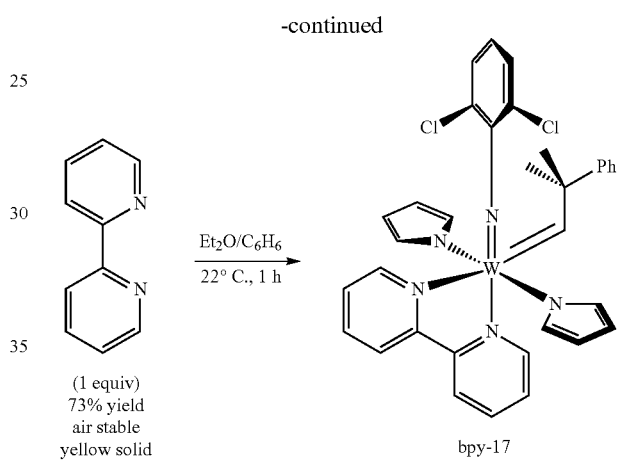

Experimental Procedures:
Octahedral Mo Complex bpy-5:
In an $N_2$-filled dry box, a 25-mL round-bottom flask containing a magnetic stir bar was charged with Mo bis-pyrrolide complex 5 (116 mg, 0.217 mmol), 2,2'-bipyridyl (35.8 mg, 0.229 mmol), $Et_2O$ (10 mL), and $C_6H_6$ (2 mL); the mixture instantly became homogenous and was allowed to stir (solution is a red-orange color). After 1 h, some yellow solids had precipitated. The mixture was concentrated to a yellow solid. $Et_2O$ (3 mL) was added and the suspension concentrated (to remove residual $C_6H_6$). $Et_2O$ (3 mL) was again added and the suspension placed in the freezer (−40° C.). After 1 h, the solids were filtered while cold and washed with cold $Et_2O$ (10 mL, −40° C.). The solids were dried by pulling the dry box atmosphere through the frit and crushing them with a spatula. A stereoisomer of octahedral complex bpy-5 (63.8 mg, 92.2 μmol, 42.5% yield) was recovered as a yellow solid. The yellow solid rearranges in $C_6D_6$ to stereoisomer bpy-5; at first both isomers were observed in the $^1H$ NMR spectrum and eventually only the presumably more stable bpy-5. Thus, the $^1H$ NMR data for octahedral bpy-5 are reported. $^1H$ NMR (400 MHz, $C_6D_6$): δ 14.06 (1H, s), 9.03-8.95 (2H, m), 7.81-7.76 (2H, m), 7.37-7.32 (2H, m), 7.18-7.12 (3H, m), 7.06 (1H, dd, J=8.8, 6.8 Hz), 6.92-6.88 (1H, m), 6.88-6.82 (1H, m), 6.60 (1H, d, J=8.0 Hz), 6.42 (1H, dt, J=7.6, 1.6 Hz), 6.30 (4H, t, J=2.0 Hz), 6.25 (1H, ddd, J=7.2, 5.2, 1.6 Hz), 6.23 (4H, t, J=2.0 Hz), 6.11 (1H, ddd, J=7.6, 5.2, 1.2 Hz), 4.01 (2H, septuplet, J=6.8 Hz), 2.18 (6H, s), 1.29 (6H, d, J=6.8 Hz), 1.25 (6H, d, J=6.8 Hz). X-ray quality crystals were obtained by crystallization from 1:1 $CH_2Cl_2$:n-pentane at −45° C.

2,6-Diisopropylarylimdo bpy Alkylidyne Complex bpy-6:

In an $N_2$-filled dry box, a 10-mL round-bottom flask containing a magnetic stir bar was charged with Mo bis-pyrrolide complex 1 (120. mg, 0.203 mmol), 2,2'-bipyridyl (158 mg, 1.01 mmol), and $Et_2O$ (2 mL). The mixture was allowed to stir and after 2 h was diluted with n-pentane (7 mL) and placed in the freezer (−50° C.). After 18 h, the purple solids were filtered and washed with n-pentane (22° C.). The solids were dried by pulling the dry box atmosphere through the frit and crushing them with a spatula. Alkylidyne bpy-6 (78.5 mg, 0.120 mmol, 59.1% yield) was recovered as a purple solid. $^1$H NMR (400 MHz, $C_6D_6$): δ 8.13 (1H, d, J=5.2 Hz), 7.36 (2H, d, J=7.6 Hz), 7.18-7.07 (3H, m), 7.01-6.98 (2H, m), 6.80-6.65 (7H, m), 6.51-6.47 (1H, m), 6.44 (1H, ddd, J=6.8, 5.2, 1.2 Hz), 6.18 (1H, ddd, J=7.2, 5.6, 1.6 Hz), 4.36 (2H, septuplet, J=6.8 Hz), 3.18 (3H, s), 2.60 (3H, s), 1.76 (3H, s), 1.41 (6H, d, J=6.8 Hz), 1.33 (3H, s), 1.16 (6H, d, J=7.2 Hz). X-ray quality crystals were obtained by crystallization from 1:7 $CH_2Cl_2$:n-pentane at −45° C.

Adamantylimido bpy Alkylidyne Complex 12:

In an $N_2$-filled dry box, a 50-mL pear-shaped flask containing a magnetic stir bar was charged with adamantylimido Mo bis-pyrrolide complex of 1 (100. mg, 0.177 mmol), 2,2'-bipyridyl (138 mg, 0.884 mmol), and $Et_2O$ (8.8 mL); the mixture was allowed to stir for 1 h. At that time, the mixture was concentrated to a black/blue solid, which was redissolved in a minimal amount of $Et_2O$ (5 mL). n-Pentane was added until solids began to precipitate (ca. 5 mL). The mixture was placed in the freezer (−35° C.) for 1 h. The solids were then filtered and washed with n-pentane (22° C.). The solids were then dried by pulling the dry box atmosphere through the frit and crushing them with a spatula. Alkylidyne 12 (56.0 mg, 77.6 μmol, 43.8% yield) was recovered as a blue/purple solid. $^1$H NMR (400 MHz, $C_6D_6$): δ 8.94 (1H, dd, J=5.6, 0.8 Hz), 8.60 (1H, br s), 7.32-7.27 (2H, m), 7.00-6.95 (1H, m), 6.92-6.87 (2H, m), 6.86-6.81 (1H, m), 6.76-6.62 (3H, m), 6.57-6.50 (2H, m), 6.16 (1H, ddd, J=7.2, 5.6, 1.2 Hz), 3.05 (3H, s), 2.71 (3H, s), 2.31 (5H, br s), 2.18 (4H, br s), 1.92 (3H, s), 1.78 (3H, d, JAB=10.8 Hz), 1.70 (3H, d, JAB=10.8 Hz), 1.67 (3H, s).

Representative Procedure for Testing Air-Stability of Mo-Based Complexes:

In an $N_2$— filled dry box, a 4-mL vial was charged with a Mo complex (3-5 mg). The vial with compound was removed from the dry box and exposed to air for a length of time. The vial containing the Mo complex was then reintroduced to the dry box and an NMR sample prepared in $C_6D_6$. The percent decomposition was then determined by 400 MHz NMR spectroscopy by comparing the amount of free chelating ligand in solution to the remaining Mo complex.

Stereogenic-at-Mo Catalyst Formation from Octahedral Complex bpy-5:

In an $N_2$-filled dry box, a 4-mL vial containing a magnetic stir bar was charged with complex bpy-5 (5.2 mg, 7.5 μmol), phenol 2 (8.5 mg, 0.015 mmol), and $C_6D_6$ (500 μL). The mixture was allowed to stir at 60° C. for 2 h at which time $^1$H NMR spectroscopy was performed. The spectrum indicated 81% conversion to products based on complex bpy-5: the products were a 1:5 mixture of alkylidene 3 (alkylidene signal at 12.90 ppm) and its bpy adduct (alkylidene signal at 13.38 ppm).

Representative Procedure for Stereogenic-at-Mo Catalyst Formation from bpy Alkylidyne Complexes:

In an $N_2$-filled dry box, a 4-mL vial containing a magnetic stir bar was charged with the alkylidyne complex (3-5 mg), phenol 2 (1 equiv with respect to the Mo complex), and benzene (concentration of catalyst=0.02 M). The mixture was allowed to stir for the required period of time (15-90 min) and then used in catalytic olefin metathesis reactions. Alkylidene diastereomers of the stereogenic-at-Mo catalysts were obtained in ca. 1:1 dr.

Enantioselective RCM from Air-Stable Precursor bpy-5:

In an $N_2$-filled dry box, a 4-mL vial containing a magnetic stir bar was charged with octahedral Mo complex bpy-5 (2.0 mg, 2.9 μmol), phenol 2 (3.2 mg, 5.8 μmol), and $C_6H_6$ (140 mL). The mixture was allowed to stir for 3 h at 60° C. A separate 4-mL vial containing a magnetic stir bar was charged with triene 7 (17.4 mg, 68.0 mmol) and $C_6H_6$ (280 μL). A portion (65 μL, 0.021 M, 1.4 mmol) of the 22° C. catalyst solution, prepared as described above, was then added by syringe. The mixture was allowed to stir for 30 min at which time the reaction was quenched by exposure to air and concentrated. The unpurified brown oil was dissolved in minimal MeOH (0.5 mL), and KF (15.2 mg, 0.262 mmol) was added (to desilylate phenol 2, which has the same Rf as 8). The mixture was allowed to stir for 30 min. Silica gel was added and the mixture concentrated and purified by silica gel chromatography (100% hexanes to 50:1 hexanes:$Et_2O$) to afford 8 (5.1 mg, 22 mmol, 33% yield) as a white solid. The physical and spectral data were identical to those previously reported for compound 4.12. $^1$H NMR (400 MHz, $CDCl_3$): δ 7.26 (2H, dd, J=8.8, 8.8 Hz), 6.89 (2H, d, J=8.8 Hz), 6.77 (1H, dddd, J=7.2, 7.2, 0.8, 0.8 Hz), 5.54-5.50 (1H, m), 4.79-4.75 (1H, m), 4.69-4.66 (1H, m), 4.23 (1H, dddd, JABX=10.0, 5.2, 4.0, 0.8 Hz), 3.80 (1H, app dt, JABX=16.8, 1.6 Hz), 3.51 (1H, ddddd, JABX=16.8, 3.6, 2.4, 2.0, 2.0 Hz), 2.40 (1H, br d, JAB=16.8 Hz), 2.21 (1H, dd, JAB=13.2, 10.6 Hz), 2.07 (1H, dd, JABX=13.6, 4.0 Hz), 2.03 (1H, d, JAB=17.2 Hz), 1.76 (3H, br s), 1.74 (3H, d, J=0.8 Hz). The enantiomeric purity of 8 (58:42 er) was determined by GLC analysis (CDGTA column, 20 psi, 130° C.). The enantiomer formed in this reaction was assigned through inference with that detailed previously (e.g., see Dolman, S. J.; Sanely, E. S.; Hoveyda, A. H.; Schrock, R. R. *J. Am. Chem. Soc.* 2002, 124, 6991-6997).

Enantioselective RCM from Air-Stable Alkylidyne Precursor bpy-6:

In an $N_2$-filled dry box, a 4-mL vial containing a magnetic stir bar was charged with triene 7 (20.9 mg, 81.8 μmol) and $C_6H_6$ (340 μL). 2 mol % of stereogenic-at-Mo catalyst 3 (82 μL, 0.020 M, 1.6 μmol), prepared from alkylidyne bpy-6 and phenol 2 as detailed above, was added by syringe and the mixture allowed to stir. After 30 min, the reaction was quenched by exposure to air and concentrated. The unpurified brown solid was dissolved in minimal MeOH (0.5 mL), and KF (9.5 mg, 0.16 mmol) was added (to desilylate phenol 2, which has the same Rf as 8). The mixture was allowed to stir for 30 min. Silica gel was added and the mixture concentrated and purified by silica gel chromatography (50:1 hexanes:$Et_2O$) to afford 8 (16.1 mg, 70.8 μmol, 86.6% yield) as a white solid. The enantiomeric purity of 8 (94:6 er) was determined by GLC analysis (CDGTA column, 20 psi, 130° C.).

Enantioselective RCM without Preforming the Stereogenic-at-Mo Catalyst from Alkylidyne bpy-6:

In an $N_2$-filled dry box, a 4-mL vial containing a magnetic stir bar was charged with alkylidyne bpy-6 (0.80 mg, 1.2 μmol) and phenol 2 (0.70 mg, 1.2 mop. A separate 4-mL vial was charge with triene 7 (15.8 mg, 61.9 μmol) and $C_6H_6$ (200 μL). The solution of 7 was transferred by pipet to the reaction vessel; the vial containing triene 7 was rinsed with $C_6H_6$ (100 μL), which was similarly transferred. The mixture was allowed to stir for 1 h. At that time, the reaction was quenched by exposure to air and concentrated. The unpurified brown solid was dissolved in minimal MeOH (0.5 mL), and KF (7.1 mg, 0.12 mmol) was added (to desilylate phenol 2, which has the same Rf as 8). The mixture was allowed to stir for 30 min. Silica gel was added and the mixture concentrated and purified by silica gel chromatography (50:1 hexanes:$Et_2O$) to afford 8 (12.3 mg, 54.1 μmol, 87.4% yield) as a white solid. The enantiomeric purity of 8 (93.5:6.5 er) was determined by GLC analysis (CDGTA column, 20 psi, 130° C.).

Bipyridine Adducts of Molybdenum Imido Alkylidene and Imido Alkylidyne Complexes High oxidation state molybdenum and tungsten imido alkylidene complexes ((a) Schrock, R. R. *Chem. Rev.* 2009, 109, 3211. (b) Schrock, R. R. *Chem. Rev.* 2002, 102, 145. (c) Schrock, R. R.; Hoveyda, A. H. *Angew. Chem. Int. Ed.* 2003, 42, 4592. (d) Schrock, R. R.; Czekelius, C. C. *Adv. Syn. Catal.* 2007, 349, 55) were discovered before ((a) Schaverien, C. J.; Dewan, J. C.; Schrock, R. R. *J. Am. Chem. Soc.* 1986, 108, 2771. (b) Schrock, R. R.; DePue, R. T.; Feldman, J.; Schaverien, C. J.; Dewan, J. C.; Liu, A. H. *J. Am. Chem. Soc.* 1987, 109, 1423). In the last several years new types of imido alkylidene complexes with the formula M(NR)(CHR')(OR'')(Pyr)=2,6-i-$Pr_2C_6H_3$ (Ar), adamantyl (Ad), 2,6-$Me_2C_6H_3$ (Ar'), 2-i-$PrC_6H_4$ (Ar$^{iPr}$), 2-Cl$C_6H_4$ (Ar$^{Cl}$), 2-t-Bu$C_6H_4$ (Ar$^{tBu}$), and 2-Mesityl$C_6H_4$ (Ar$^M$), respectively; R'=Me, Ph), where Pyr is a pyrrolide or substituted pyrrolide ligand and OR'' usually is an aryloxide, have been prepared and explored ((a) Singh, R.; Schrock, R. R.; Müller, P.; Hoveyda, A. H. *J. Am. Chem. Soc.* 2007, 129, 12654. (b) Flook, M. M.; Gerber, L. C. H.; Debelouchina, G. T.; Schrock, R. R. *Macromolecules* 2010, 43, 7515. (c) Marinescu, S. C.; Schrock, R. R.; Müller, P.; Takase, M. K.; Hoveyda, A. H. *Organometallics* 2011, 30, 1780. (d) Sattely, E. S.; Meek, S. J.; Malcolmson, S. J.; Schrock, R. R.; Hoveyda, A. H. *J. Am. Chem. Soc.* 2009, 131, 943. (e) Ibrahem, I; Yu, M.: Schrock, R. R.; Hoveyda, A. H. *J. Am. Chem. Soc.* 2009, 131, 3844. (f) Jiang, A. J.; Simpson, J. H.; Müller, P.; Schrock, R. R. *J. Am. Chem. Soc.* 2009, 131, 7770. (g) Marinescu, S. C.; Levine, D.; Zhao, Y.; Schrock, R. R.; Hoveyda, A. H. *J. Am. Chem. Soc.* 2011, 133, 11512. (h) Jiang, A. J.; Zhao, Y.; Schrock, R. R.; Hoveyda, A. H. *J. Am. Chem. Soc.* 2009, 131, 16630. (i) Flook, M. M.; Jiang, A. J.; Schrock, R. R.; Müller, P.; Hoveyda, A. H. *J. Am. Chem. Soc.* 2009, 131, 7962. (j) Peryshkov, D. V.; Schrock, R. R.; Takase, M. K.; Müller, P.; Hoveyda, A. H. *J. Am. Chem. Soc.* 2011, 133, 20754. (k) Marinescu, S. C.; Schrock, R. R.; Müller, P.; Hoveyda, A. H. *J. Am. Chem. Soc* 2009, 131, 10840. (l) Gerber, L. C.; Schrock, R. R.; Müller, P.; Takase, K. M. *J. Am. Chem. Soc.* 2011, 133, 18142. (m) Yu, M.; Ibrahem, I.; Hasegawa, M.; Schrock, R. R.; Hoveyda, A. H. *J. Am. Chem. Soc.* 2012, 134, 2788. (n) Schrock, R. R. *Chem. Rev.* 2009, 109, 3211); we refer to these monoaryloxide monopyrrolide complexes as MAP species. MAP species were discovered in the process of adding alcohols or phenols to bispyrrolide complexes with the general formula M(NR)(CHR')(Pyr)$_2$ (R=2,6-i-$Pr_2C_6H_3$ (Ar), adamantyl (Ad), 2,6-$Me_2C_6H_3$ (Ar'), 2-i-$PrC_6H_4$ (Ar$^{iPr}$), 2-Cl$C_6H_4$ (Ar$^{Cl}$), 2-t-Bu$C_6H_4$ (Ar$^{tBu}$), and 2-Mesityl$C_6H_4$ (Ar$^M$), respectively; R'=Me, Ph) ((a) Hock, A. S.; Schrock, R. R.; Hoveyda, A. H. *J. Am. Chem. Soc.* 2006, 128, 16373). (b) Singh, R; Czekelius, C.; Schrock, R. R.; Müller, P. *Organometallics*, 2007, 26, 2528. (c) Marinescu, S. C.; Singh, R.; Hock, A. S.; Wampler, K. M.; Schrock, R. R.; Müller, P. *Organometallics* 2008, 27, 6570. (d) King, A. J. H., Ph.D. Thesis, 2010, Massachusetts Institute of Technology) in order to prepare bisalkoxide or biphenolate catalysts in situ and screen them for olefin metathesis activity.

Bispyrrolide complexes have been prepared that contain pyrrolide ((a) Hock, A. S.; Schrock, R. R.; Hoveyda, A. H. *J. Am. Chem. Soc.* 2006, 128, 16373), 2,5-$Me_2$pyrrolide (Singh, R; Czekelius, C.; Schrock, R. R.; Miller, P. *Organometallics*, 2007, 26, 2528), 2,3,4,5-$Me_4$pyrrolide (Marinescu, S. C.; Singh, R.; Hock, A. S.; Wampler, K. M.; Schrock, R. R.; Müller, P. *Organometallics* 2008, 27, 6570), 2,5-i-$Pr_2$pyrrolide (Marinescu, S. C.; Singh, R.; Hock, A. S.; Wampler, K. M.; Schrock, R. R.; Müller, P. *Organometallics* 2008, 27, 6570), 2,5-$Ph_2$pyrrolide (Marinescu, S. C.; Singh, R.; Hock, A. S.; Wampler, K. M.; Schrock, R. R.; Müller, P. *Organometallics* 2008, 27, 6570), and 2-Mesitylpyrrolide (King, A. J. H., Ph.D. Thesis, 2010, Massachusetts Institute of Technology). The majority of MAP species that have been prepared contain 2,5-dimethylpyrrolide. The relatively small number of MAP compounds that contain an unsubstituted pyrrolide is a consequence of the often poor crystallinity and instability of Mo(NR)(CHR')(pyrrolide)$_2$ (R=2,6-i-$Pr_2C_6H_3$ (Ar), adamantyl (Ad), 2,6-$Me_2C_6H_3$ (Ar'), 2-i-$PrC_6H_4$ (Ar$^{iPr}$), 2-Cl$C_6H_4$ (Ar$^{Cl}$), 2-t-Bu$C_6H_4$ (Ar$^{tBu}$), and 2-Mesityl$C_6H_4$ (Ar$^M$), respectively; R'=Me, Ph) species over a period of days, even in the solid state. Two exceptions are compounds in which the imido substituent (R) is 2,6-i-$Pr_2C_6H_3$ (Ar) or adamantyl (Ad), which are stable for many days at –35° C. Mo(NAd)(CHCMe$_2$Ph)(NC$_4$H$_4$)$_2$ has been employed as a precursor to Mo(NAd)(CHCMe$_2$Ph)(NC$_4$H$_4$)(OAr) complexes that are especially useful as Z-selective olefin metathesis catalysts ((a) Flook, M. M.; Gerber, L. C. H.; Debelouchina, G. T.; Schrock, R. R. *Macromolecules* 2010, 43, 7515. (b) Marinescu, S. C.; Schrock, R. R.; Müller, P.; Takase, M. K.; Hoveyda, A. H. *Organometallics* 2011, 30, 1780. (c) Ibrahem, I; Yu, M.: Schrock, R. R.; Hoveyda, A. H. *J. Am. Chem. Soc.* 2009, 131, 3844. (d) Marinescu, S. C.; Levine, D.; Zhao, Y.; Schrock, R. R.; Hoveyda, A. H. *J. Am. Chem. Soc.* 2011, 133, 11512. (e) Jiang, A. J.; Zhao, Y.; Schrock, R. R.; Hoveyda, A. H. *J. Am. Chem. Soc.* 2009, 131, 16630. (f) Flook, M. M.; Jiang, A. J.; Schrock, R. R.; Müller, P.; Hoveyda, A. H. *J. Am. Chem. Soc.* 2009, 131, 7962. (g) Peryshkov, D. V.; Schrock, R. R.; Takase, M. K.; Müller, P.; Hoveyda, A. H. *J. Am. Chem. Soc.* 2011, 133, 20754. (h) Flook, M. M.; Ng, V. W. L.; Schrock, R. R. *J. Am. Chem. Soc.* 2011, 133, 1784. (i) Flook, M. M. Ph.D. Thesis, 2011, Massachusetts Institute of Technology), where OAr is a large 2,6-disubstituted phenoxide. Only one equivalent of a large 2,6-terphenol adds to the metal in bispyrrolide complexes for steric reasons, a circumstance that allows the MAP species to be generated and/or isolated in relatively high yields.

14 electron bisalkoxide catalysts may form 16 or 18 electron adducts with donor ligands (Schrock, R. R. *Chem. Rev.* 2002, 102, 145). Bipyridine was first employed as a ligand in imido alkylidene chemistry in order to isolate the methylidene complex, yellow crystalline Mo(NAr)(CH$_2$)[OC(CF$_3$)$_2$Me]$_2$(bipy) in high yield (Fox, H. H.; J.-K. Lee; Park, L. Y.; Schrock, R. R. *Organometallics* 1993, 12, 759). Eighteen electron Mo(NAr)(CH$_2$)[OC(CF$_3$)$_2$Me]$_2$(bipy) is inactive as a metathesis catalyst and stable toward bimolecular decomposition reactions. Fürstner has reported that bipyridine adducts of several related molybdenum species are relatively stable to air and can be activated toward metathesis in the absence of air in solution through addition of $ZnCl_2$ to remove bipyridine (Heppekausen, J.; Fürstner, A. *Angew. Chem. Int. Ed.* 2011, 50, 7829); little exchange of alkoxide for chloride on the molybdenum is observed during the activation process. He has also reported examples of 18 electron alkylidyne complexes that are relatively stable in air and can be activated through addition of Lewis acids (Heppekausen, J.; Stade, R.; Goddard, A.; Fürstner, A. *J. Am. Chem. Soc.* 2010, 132, 11045). Other types of 18 electron alkylidene complexes that are activated upon addition of Lewis acids are known ((a) Wengrovius, J. H.; Schrock, R. R.; Churchill, M. R.; Missert, J. R.; Youngs, W. J. *J. Am. Chem. Soc.* 1980, 102, 4515. (b) Wengrovius, J. H.; Schrock, R. R. *Organometallics* 1982, 1, 148. (c) Blosch, L. L.; Abboud, K.; Boncella, J. M. *J. Am. Chem. Soc.* 1991, 113, 7066. (d) Blosch, L. L.; Gamble, A. S.; Abboud, K.; Boncella, J. M. *Organometallics* 1992, 11, 2342).

In some embodiments, this application provides relatively air-stable bipyridine adducts of bispyrrolide complexes that contain a variety of different imido groups, their preparation and their use as catalyst precursors for the preparation of Mo(NR)(CHCMe$_2$Ph)(NC$_4$H$_4$)(OAr) species (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), or 2-MesitylC$_6$H$_4$ (Ar$^M$)). In some embodiments, the relatively air-stable bipyridine adducts of bispyrrolide complexes are of the type Mo(NR)(CHCMe$_2$R')(Pyr)$_2$(bipy) (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively; R'=Me, Ph). Some of the exemplary complexes are described below (101a-101g). In some embodiments, the MAP species can be prepared more efficiently through the species and methods disclosed in this application. In some embodiments, some MAP species can be prepared only through the species and methods disclosed in this application. In other embodiments, this application provide imido alkylidyne complexes of the type Mo(NR)(CCMe$_2$R')(Me$_2$Pyr)(bipy) (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively; R'=Me, Ph), their preparation methods and their use. In some embodiments, imido alkylidyne complexes of the type Mo(NR)(CCMe$_2$R')(Me$_2$Pyr)(bipy) (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively; R'=Me, Ph) are prepared using bis-2,5-dimethylpyrrolide complexes as one of the reactants. In some embodiments, imido alkylidyne complexes of the type Mo(NR)(CCMe$_2$R')(Me$_2$Pyr)(bipy) (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively; R'=Me, Ph) are prepared using bis-2,5-dimethylpyrrolide complexes and bispyridine as two of the reactants. Without the intention to be limited by any theory, in some embodiments, imido alkylidyne complexes of the type Mo(NR)(CCMe$_2$R')(Me$_2$Pyr)(bipy) (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively; R'=Me, Ph) are prepared using bis-2,5-dimethylpyrrolide complexes and bispyridine as reactants through sterically-induced a abstraction of the alkylidene proton by one of the dimethylpyrrolide ligands.

Addition of one equivalent of bipyridine to Mo(NR)(CHCMe$_2$Ph)(Pyr)$_2$ in diethyl ether led to precipitation of complexes with the general formula Mo(NR)(CHCMe$_2$Ph)(Pyr)$_2$(bipy) (R=Ar, 101a; R=Ad, 101b) in good yields (equation 101). This procedure is referred to as method A. Mo(NR)(CHCMe$_2$Ph)(Pyr)$_2$(bipy) (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively) species are relatively insoluble, a property that allows them to be isolated readily. A proton NMR spectrum of 101b was obtained in CD$_2$Cl$_2$. Without the intention to be limited by any theory, the three alkylidene isomers of 101b are proposed to arise from one adduct with trans pyrrolide ligands and two adducts that contain cis pyrrolide ligands; all are proposed to be syn alkylidene isomers. Both $^1$H and $^{13}$C NMR spectra were obtained for 101a. Only one isomer of 101a is observed.

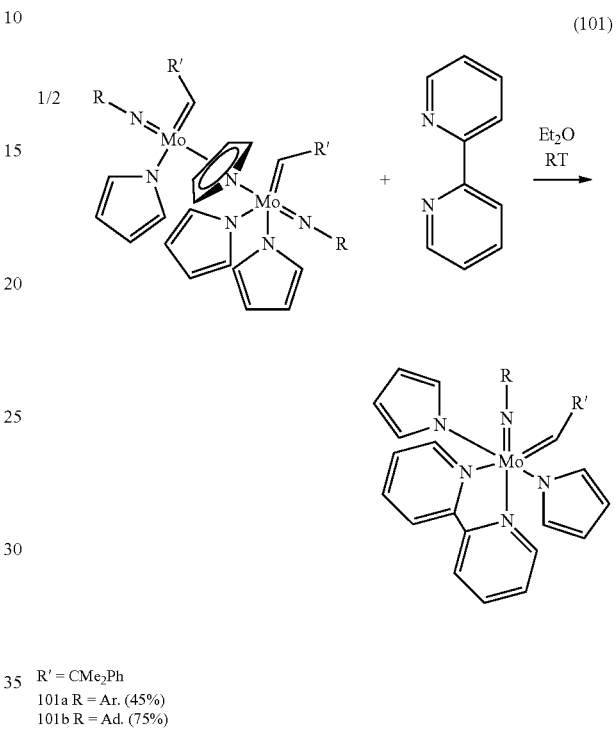

(101)

R' = CMe$_2$Ph
101a R = Ar. (45%)
101b R = Ad. (75%)

Figure 3:
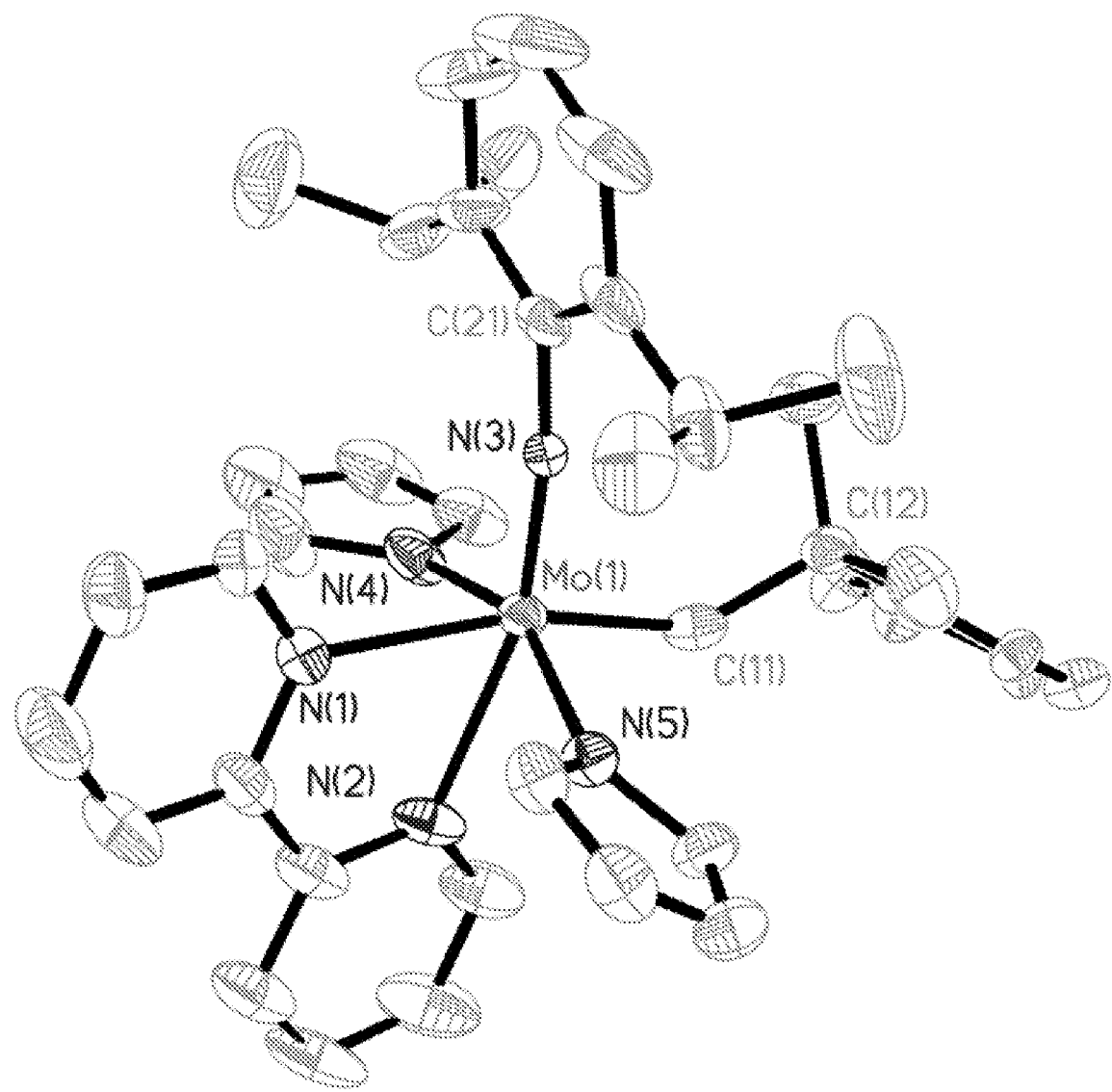
FIG. 3. A drawing of the solid-state structure of Mo(NAr)(CHCMe$_2$Ph)(Pyr)$_2$ (bipy) (101a; 50% probability ellipsoids). The solvent molecule, hydrogen atoms, and the disorder are omitted for clarity. Selected bond lengths (Å) and angles (°): Mo(1)-C(11)=1.932(3), Mo(1)-N(1)=2.330(3), Mo(1)-N(2)=2.354(3), Mo(1)-N(3)=1.730(2), Mo(1)-N(4)=2.135(3), Mo(1)-N(5)=2.143(2), Mo(1)-C(11)-C(12)=138.3(2), Mo(1)-N(3)-C(21)=171.0 (2), N(5)-Mo(1)-N(4)=155.75(10).

An X-ray study of 101a shows it to have a structure (FIG. 3) in which the pyrrolide ligands are trans to one another and bipy is bound trans to the alkylidene and imido ligands. In contrast, Mo(NAr)(CHCMe$_2$Ph)[OC(CF$_3$)$_2$Me]$_2$(bipy) ((a) Heppekausen, J.; Fürstner, A. *Angew. Chem. Int. Ed.* 2011, 50, 7829. (b) Heppekausen, J.; Stade, R.; Goddard, A.; Fürstner, A. *J. Am. Chem. Soc.* 2010, 132, 11045) adopts a cis configuration in which bipy is bound trans to the alkylidene and one of the alkoxide ligands. The Mo—N$_{bipy}$ bond lengths in 101a (2.330(3) and 2.354(3)Å) therefore are similar, whereas the two Mo—N$_{bipy}$ bond lengths in Mo(NAr)(CHCMe$_2$Ph)[OC(CF$_3$)$_2$Me]$_2$(bipy) (2.3503(11)Å and 2.2462(10) 5<) ((a) Heppekausen, J.; Fürstner, A. *Angew. Chem. Int. Ed.* 2011, 50, 7829. (b) Heppekausen, J.; Stade, R.; Goddard, A.; Fürstner, A. *J. Am. Chem. Soc.* 2010, 132, 11045) differ significantly, with the latter bond length (trans to the alkoxide) being the shorter of the two.

Bispyrrolide species were also prepared in situ from Mo(NR)(CHCMe$_2$Ph)(OTf)$_2$ (DME) complexes (R=2,6-i-Pr$_2$C$_6$H$_3$ (Ar), adamantyl (Ad), 2,6-Me$_2$C$_6$H$_3$ (Ar'), 2-i-PrC$_6$H$_4$ (Ar$^{iPr}$), 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively) and treated with 0.8-0.9 equivalents of bipyridine to produce the insoluble compounds of type 101 shown in equation 102 (R'=t-Buor CMe$_2$Ph). This method will be referred to as method B. It is an effective way to make six of the seven bipyridyl adducts of type 101. Compounds 101b-101g were obtained in analytically pure form simply through filtration.

(102)

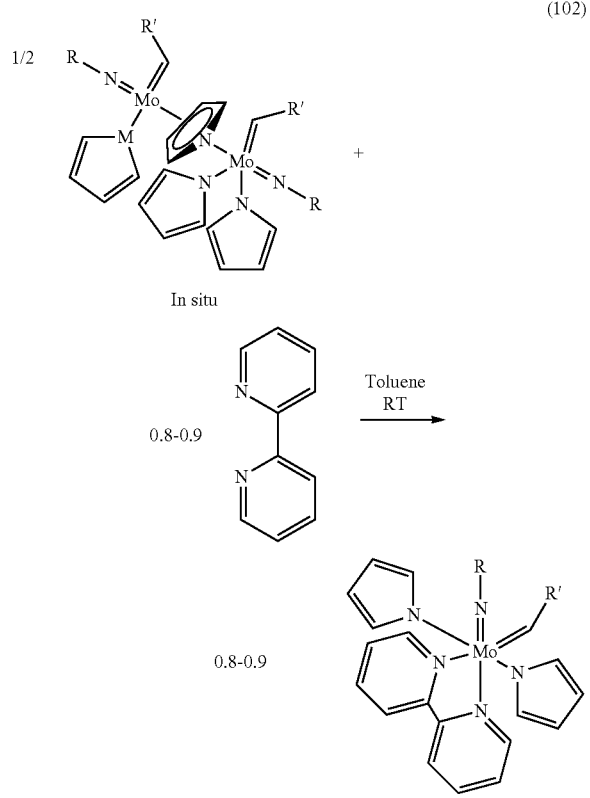

101b R = Ad (36%): 101c R = Ar' (96%): 101d R = Ar$^{iPr}$ (96%)
101e R = Ar$^{Cl}$ (87%): 101f R = Ar$^{tBu}$ (24%): 101g R = Ar$^M$ (74%)

Only one alkylidene resonance is present in the alkylidene region in the $^1$H NMR spectrum (in CD$_2$Cl$_2$) of 101c and 101f, two are present for 101e and 101d, while three are present for 101g. Without the intention to be limited by any theory, all isomers are presumed to arise from cis/trans isomerism of the pyrrolide ligands, as noted earlier, although in the case of 101g restricted rotation of the NAr$^M$ imido ligand could give rise to the third isomer.

Mo(NR)(CHCMe$_2$Ph)(OTf)$_2$(bipy) complexes can be synthesized from Mo(NR)(CHCMe$_2$Ph)(OTf)$_2$(dme) complexes by suspending the latter in benzene that contains one equivalent of bipyridine at room temperature (R=2,6-i-Pr$_2$C$_6$H$_3$ (Ar), 1-adamantyl (Ad), 2,6-Me$_2$C$_6$H$_3$ (Ar'), and 2-MesC$_6$H$_4$ (Ar$^M$), or in diethyl ether (R=2-ClC$_6$H$_4$ (Ar$^{Cl}$), 2-i-PrC$_6$H$_4$ (Ar$^{iPr}$), 2-t-BuC$_6$H$_4$ (Ar$^{tBu}$)) and stirring the mixtures for 12 h at 22° C. (equation 103). In all cases, the relatively insoluble Mo(NR)(CHCMe$_2$Ph)(OTf)$_2$(bipy) complexes can be collected by filtration in good yields. All Mo(NR)(CHCMe$_2$Ph)(OTf)$_2$(bipy)=2,6-i-Pr$_2$C$_6$H$_3$ (Ar), adamantyl (Ad), 2,6-Me$_2$C$_6$H$_3$ (Ar'), 2-i-PrC$_6$H$_4$ 2-ClC$_6$H$_4$ (Ar$^{Cl}$), 2-t-BuC$_6$H$_4$ (Ar$^{tBu}$), and 2-MesitylC$_6$H$_4$ (Ar$^M$), respectively)) complexes are soluble in CD$_2$Cl$_2$ with the exception of 102a and 102b, which are only sparingly soluble. Proton NMR spectra of the complexes in CD$_2$Cl$_2$ show either one or two alkylidene resonances, which arise from cis and trans disposition of the triflates, a proposal that is corroborated by the $^{19}$F NMR spectra of each compound. Two isomers are observed when the imido group has only one substituent.

(103)

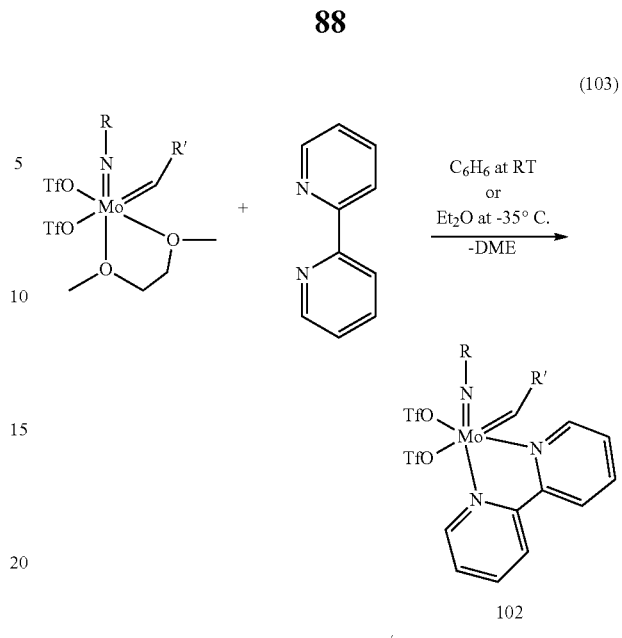

102a R = Ar (84%): 102b R = Ad (91%): 102c R = Ar' (67%):
102d R = Ar$^{iPr}$ (76%): 102e R = Ar$^{Cl}$ (66%): 102f R = Ar$^{tBu}$ (76%):
102g R = Ar$^M$ (73%)

Complexes 102a, 102c and 102d react with 2 equivalents of LiNC$_4$H$_4$ to generate the bispyrrolide species, 101a, 101c and 101d (method C; equation 104). These compounds were isolated in moderate to good yields by running the reaction in diethyl ether for 12 h, collecting the precipitated product by filtration, and washing the precipitate with diethyl ether.

(104)

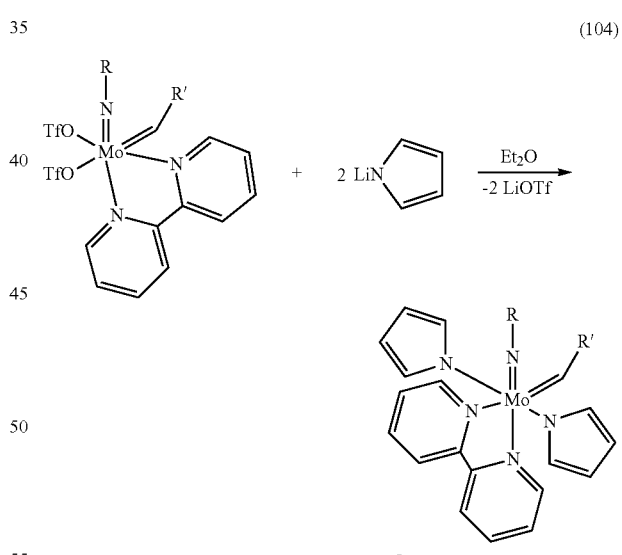

101a R = Ar (61%): 101c R = Ar' (77%): 101d R = Ar$^{iPr}$ (85%)

Bipyridine adducts of type 101 are easy to isolate, handle, and store for long periods of time, and can be used to prepare MAP species for various reactions, for example but not limited to metathesis reactions. Complexes 101a-101g were mixed with one equivalent of ZnCl$_2$(dioxane) and one equivalent of 2,6-dimesitylphenol (HMTOH) in 10-15 mL of toluene in a Teflon-sealed Schlenk flask. The flask was placed in a conventional ultrasonic cleaner for 3-5 h at 22° C. The choice of solvent is key because the reagents, except for HMTOH and the ZnCl$_2$(bipy) byproduct, are only slightly soluble in toluene, whereas the MAP complexes are highly soluble. The MAP complexes 103a-103g are obtained in crystalline form by filtering off any remaining insoluble material(s) and recrystallizing the solid products from pentane at −35° C. (equation 105). Proton NMR and carbon NMR spectra of 103a-103g are consistent with the presence of only one isomer (syn) in solution. Apparently exchange of pyrrolide (on Mo) for chloride (on Zn) is not a significant problem in the reaction shown in equation 105.

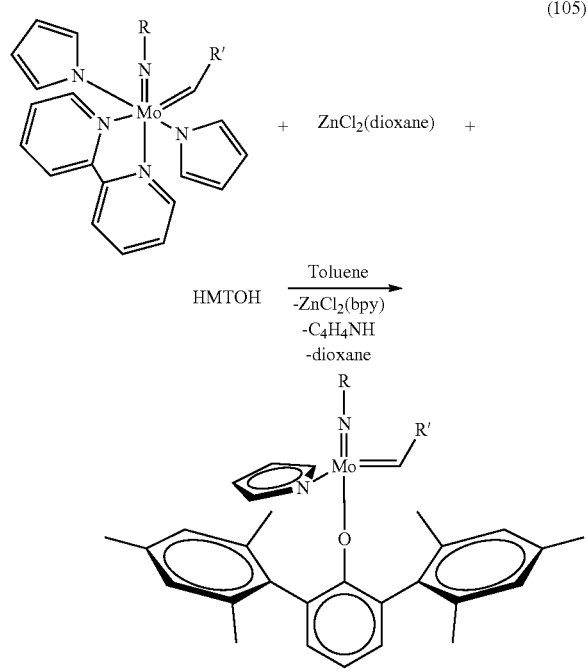

103a R = Ar (46%): 103b R = Ad (64%): 103c R = Ar' (79%):
103d R = Ar$^{iPr}$ (42%): 103e R = Ar$^{Cl}$ (47%): 103f R = Ar$^{tBu}$ (36%):
103g R = Ar$^{M}$ (37%)

Figure 4:
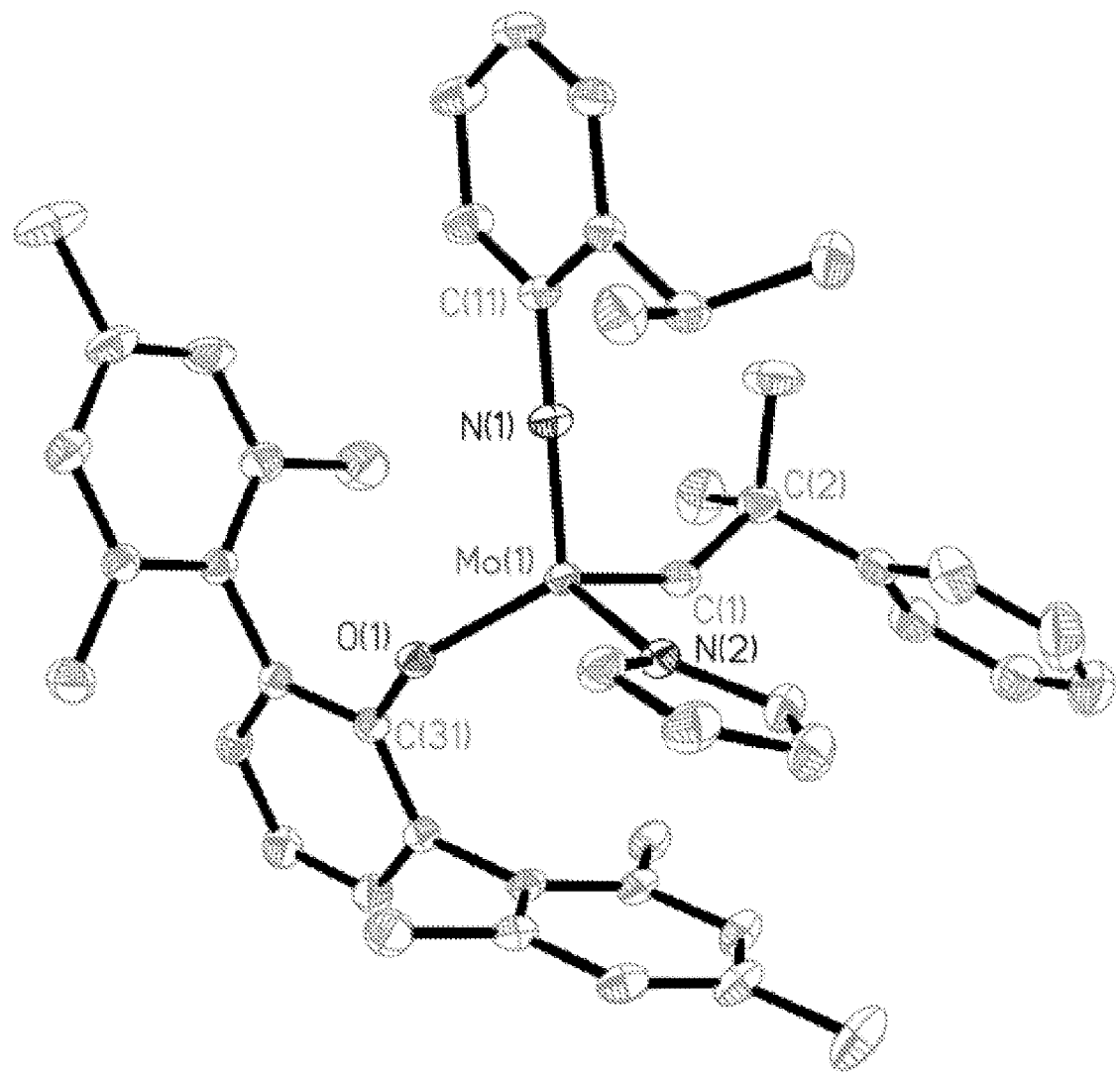
FIG. 4. (a) A drawing of the solid-state structure of (R)—Mo(NAr$^{iPr}$)(CHCMe$_2$Ph)(Pyr)(OHMT) (R-103d, 50% probability ellipsoids). Selected bond lengths (Å) and angles (°): Mo(1)-C(1)=1.8769(15), Mo(1)-N(1)=1.7300 (12), Mo(1)-N(2)=2.0198(13), Mo(1)-O(1)=1.9186(10), Mo(1)-C(1)-C(2)=145.61(11), Mo(1)-N(1)-C(11)=178.12 (11), Mo(1)-O(1)-C(31)=143.14(9). (b) A drawing of the solid-state structure of (S)—Mo(NAr$^{iPR}$)(CHCMe$_2$Ph)(Pyr)(OHMT) (S-103d, 50% probability ellipsoids). Selected bond lengths (Å) and angles (°): Mo(2)-C(101)=1.8759(15), Mo(2)-N(3)=1.7263(12), Mo(2)-N(4)=2.0294(13), Mo(2)-O(2)=1.9168(10), Mo(2)-C(101)-C(102)=143.31(11), Mo(2)-N(3)-C(111)=177.45(11), Mo(2)-O(2)-C(131)=150.15(9).
Figure 4:
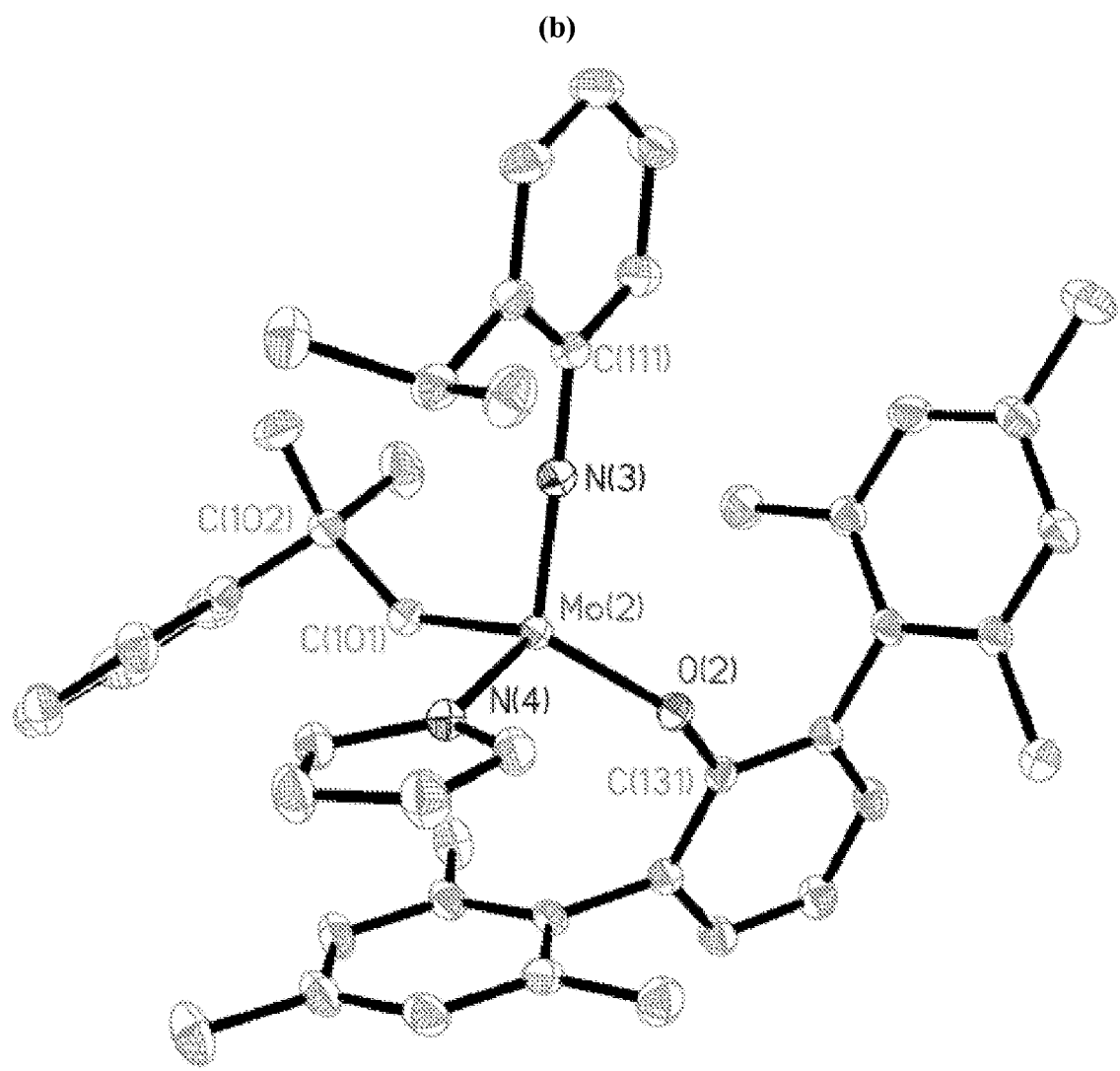

The structure of 103d was obtained through an X-ray study. The complex crystallized in the space group P$\bar{1}$ with both the R and S enantiomers present (FIGS. 4 (a) and (b)).

The efficacies of 103a-103g for polymerization of 50 equivalents of 2,3-dicarbomethoxynorbornadiene (DCMNBD) to give cis poly(DCMNBD) were explored with each as an initiator at 22° C. for 1-2 h. The cis content of poly(DCMNBD) was determined through $^1$H and $^{13}$C NMR spectroscopy. All reactions are relatively fast and all give >98% cis polymer that is syndiotactic on the basis of the similarity of spectra to those for poly(DCMNBD) samples prepared with Mo(NAd)(CHCMe$_2$R')(Pyr)(OHIPT) (R'=Me, Ph) as an initiator and polymers prepared from menthoxy analogs of DCMNBD ((a) Hock, A. S.; Schrock, R. R.; Hoveyda, A. H. *J. Am. Chem. Soc.* 2006, 128, 16373. (b) Singh, R; Czekelius, C.; Schrock, R. R.; Miller, P. *Organometallics,* 2007, 26, 2528. (c) Marinescu, S. C.; Singh, R.; Hock, A. S.; Wampler, K. M.; Schrock, R. R.; Müller, P. *Organometallics* 2008, 27, 6570. (d) King, A. J. H., Ph.D. Thesis, 2010, Massachusetts Institute of Technology). Similar behavior had been observed for the analogous Mo(NR)(CHCMe$_2$R')(Me$_2$Pyr)(OHMT) initiators in which the phenyl imido ligands were monosubstituted in the ortho positions with Cl, CF$_3$, or i-Pr groups, although t-Bu, mesityl, or 2,4,6-triisopropylphenyl groups in the ortho position of the phenylimido ligand led to formation of poly(DCMNBD) samples that contained some trans linkages (Lichtscheidl, A. G.; Ng, V. W. L.; Müller, P.; Takase, M. K.; Schrock, R. R. *Organometallics* 2012, 31, 2388).

In some embodiments, the present application provides the imido alkylidyne complexes 104a-104g and their preparation methods as shown in equation 106. In some embodiments, the reaction is performed at room temperature. In some embodiments, the reaction is performed at 22° C. In some embodiments, the reaction is performed at elevated temperature. In some embodiments, the reaction is performed at 60° C. The reaction between Mo(NAr$^{iPr}$)(CHCMe$_2$Ph)(Me$_2$Pyr)$_2$ and one equivalent of bipy or Mo(NAd(CHCMe$_2$Ph)(Me$_2$Pyr)$_2$ and five equivalents of bipy were carried out to completion at 22° C. in a 1:1 mixture of toluene and pentane or diethyl ether respectively. Other reactions in equation 106 require heating in toluene at 60° C. In all cases the color of the reaction mixture changes from orange-brown to red-purple. Upon completion of the reaction, one equivalent of Me$_2$PyrH can be observed in solution in proton NMR spectra. Upon removing the solvent from the reaction mixture and washing the resulting solids with pentane, compounds 104a-104g can be obtained as purple or red-purple solids in good to very good yields (equation 106).

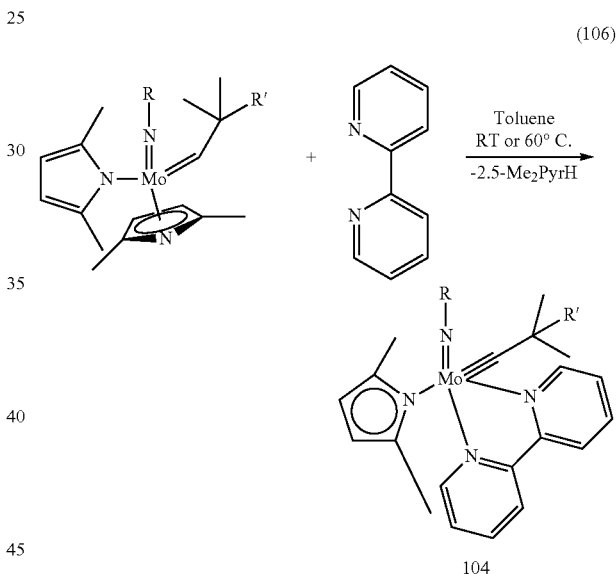

104a R = Ar, R' = Ph, 60° C., (46%); 104b R = Ad, R' = Ph, 60° C., (44%)
104c R = Ar', R' = Ph, 60° C., (60%); 104d R = Ar$^{iPr}$, R' = Ph, 22° C., (86%)
104e R = Ar$^{CF3}$, R' = Me, 60° C., (69%); 104f R = Ar$^{M}$, R' = Ph, 60° C., (53%)
104g R = Ar$^{T}$, R' = Me, 60° C., (69%)

Figure 5:
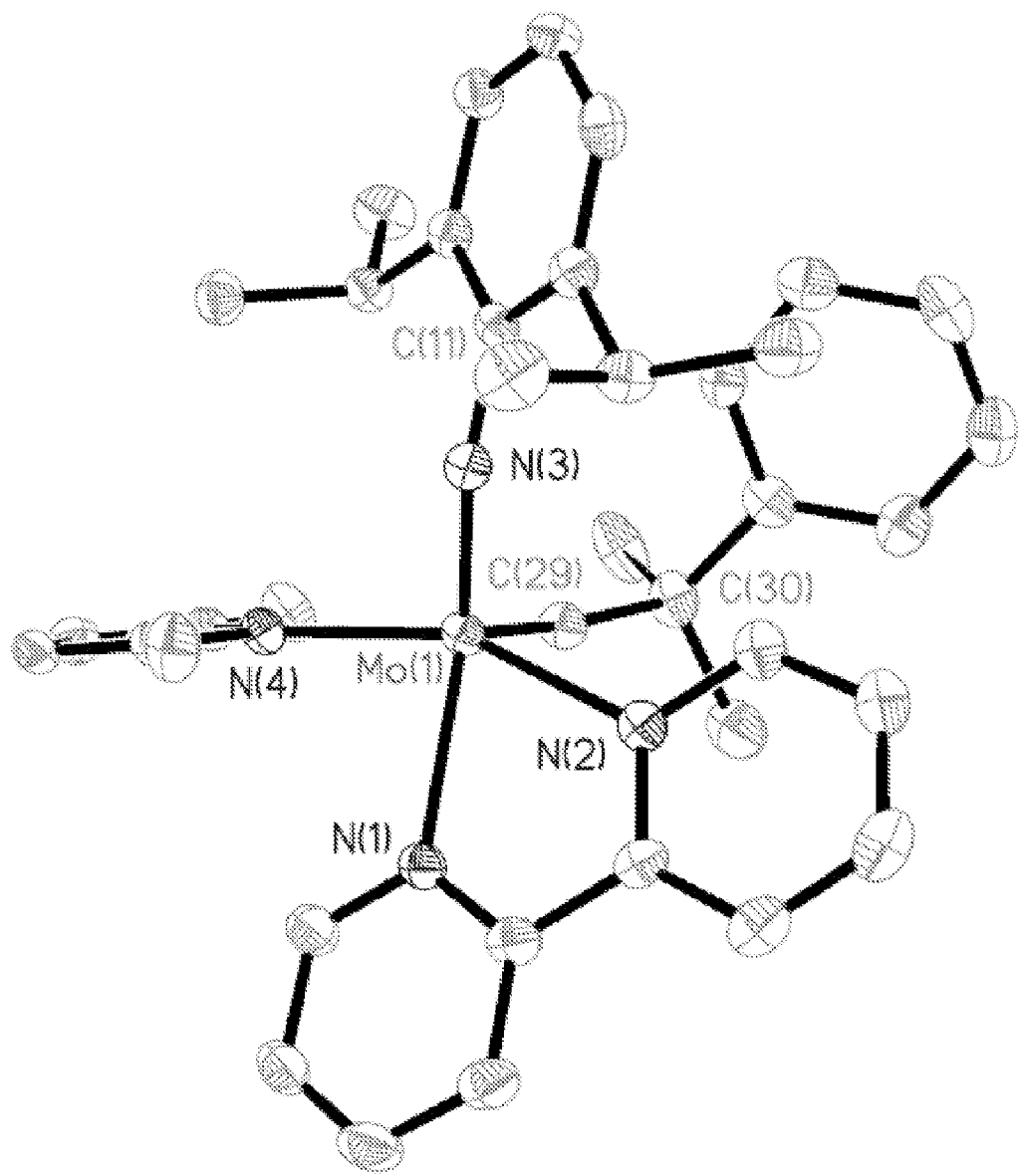
FIG. 5. A drawing of the solid-state structure of (NAr)(CCMe$_2$Ph)(Me$_2$Pyr) (bipy) (104a; 50% probability ellipsoids). Selected bond lengths (Å) and angles (°): Mo(1)-C(29)=1.764(3), Mo(1)-N(1)=2.326(3), Mo(1)-N(2)=2.209 (3), Mo(1)-N(3)=1.804(3), Mo(1)-N(4)=2.098(3), Mo(1)-C(29)-C(30)=161.5(2), Mo(1)-N(3)-C(11)=159.6(2), N(1)-Mo(1)-N(3)=144.12(10), N(2)-Mo(1)-N(4)=153.05(10).
Figure 6:
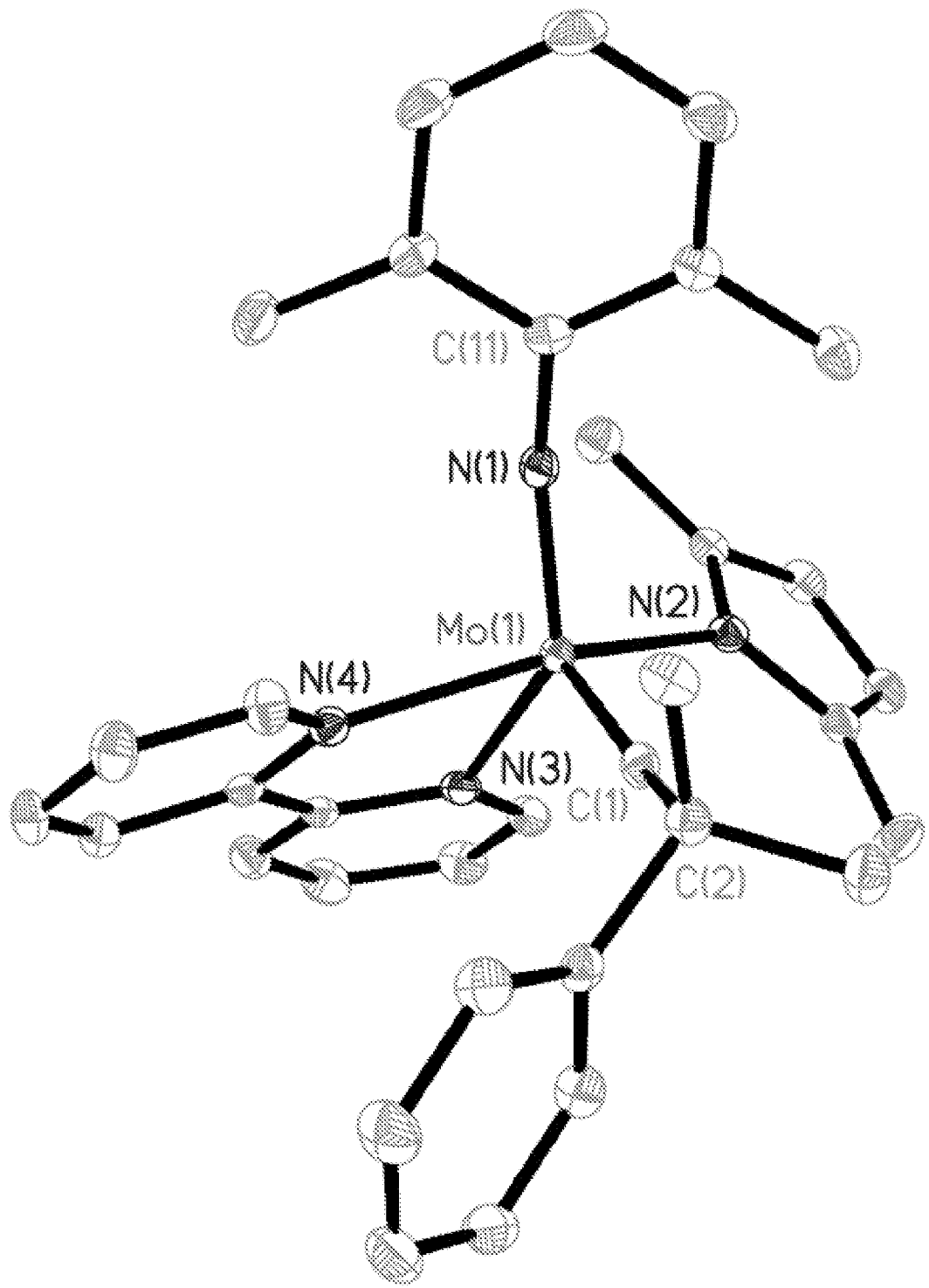
FIG. 6. A drawing of the solid-state structure of Mo(NAr')(CCMe$_2$Ph)(Me$_2$Pyr) (bipy) (104c; 50% probability ellipsoids). Selected bond lengths (Å) and angles (°): Mo(1)-C(1)=1.7643(17), Mo(1)-N(1)=1.7958(14), Mo(1)-N(2)=2.1228(14), Mo(1)-N(3)=2.3165(13), Mo(1)-N(4)=2.2100(13), Mo(1)-C(1)-C(2)=159.05(14), Mo(1)-N(1)-C(11)-162.64(12), N(1)-Mo(1)-N(3)=137.44(6), N(2)-Mo(1)-N(4)=153.09(15).
Figure 7:
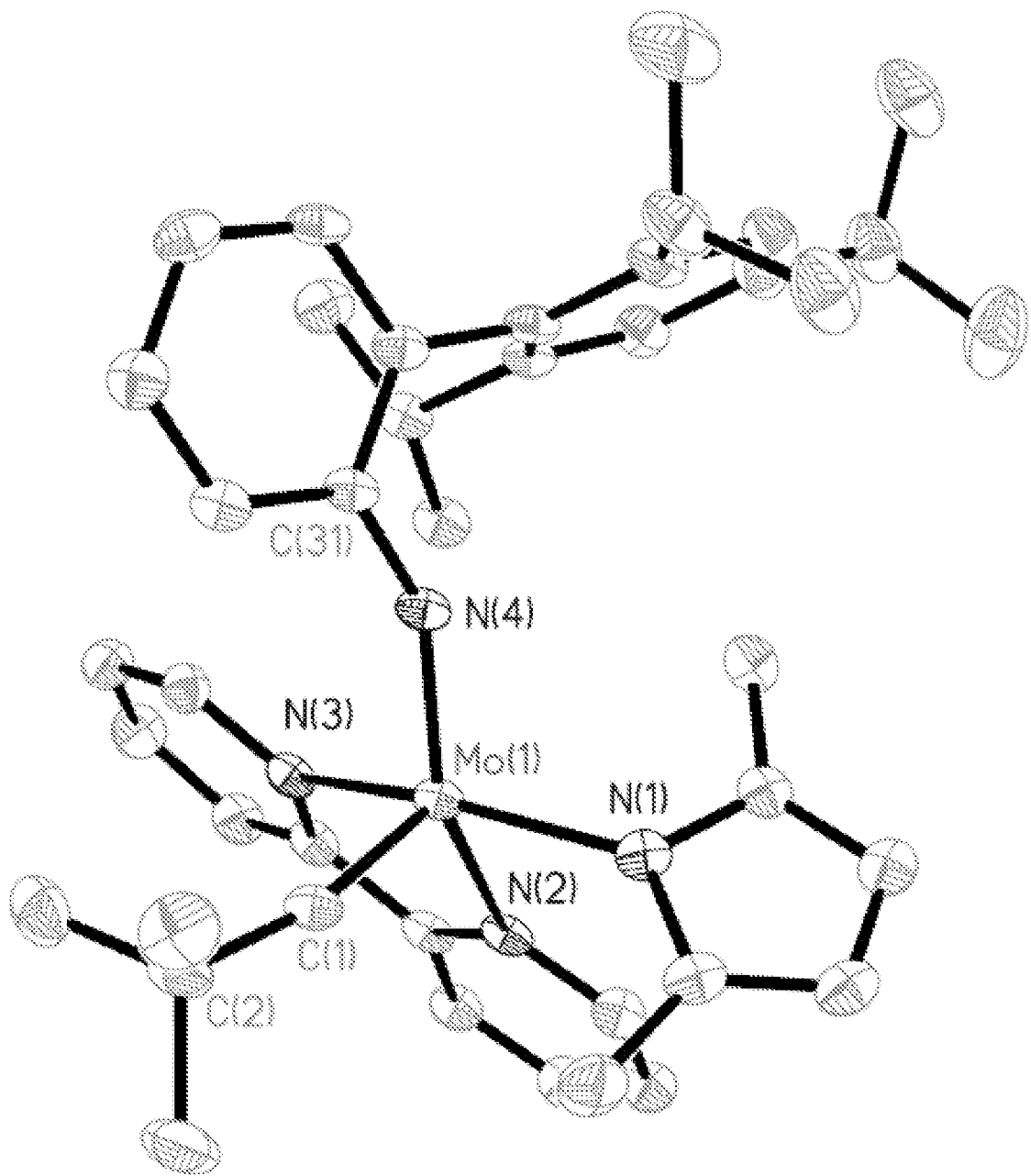
FIG. 7. A drawing of the solid-state structure of Mo(NAr$^T$)(CCMe$_3$)(Me$_2$Pyr) (bipy) (104g, 50% probability ellipsoids). Solvent molecules and the second independent molecule, which shows some disorder, as well as the hydrogen atoms are omitted for clarity. Selected bond lengths (Å) and angles (°): Mo(1)-C(1)=1.780(5), Mo(1)-N(1)=2.105(4), Mo(1)-N(2)=2.306(3), Mo(1)-N(3)=2.225(4), Mo(1)-N(4)=1.823(4), Mo(1)-C(1)-C(2)=167.1(4), Mo(1)-N(4)-C(31)=152.6(3), N(1)-Mo(1)-N(3)=153.28(14), N(2)-Mo(1)-N(4)=140.98(15).
Figure 8:
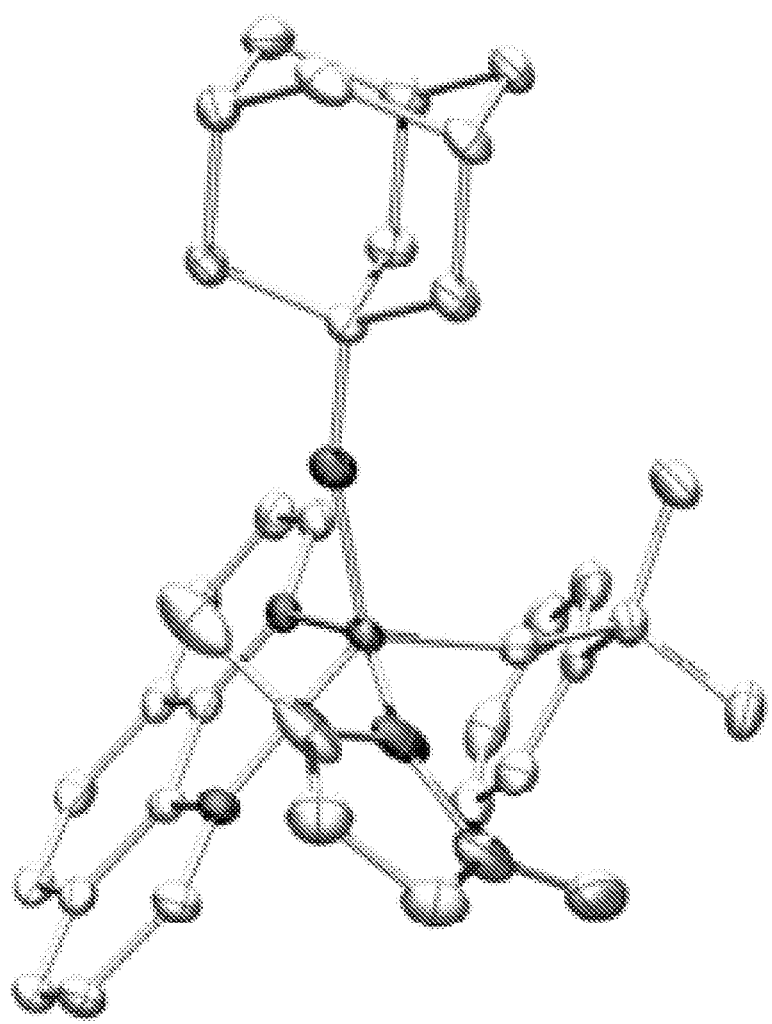
FIG. 8. X-ray of compound 13.
Figure 9:
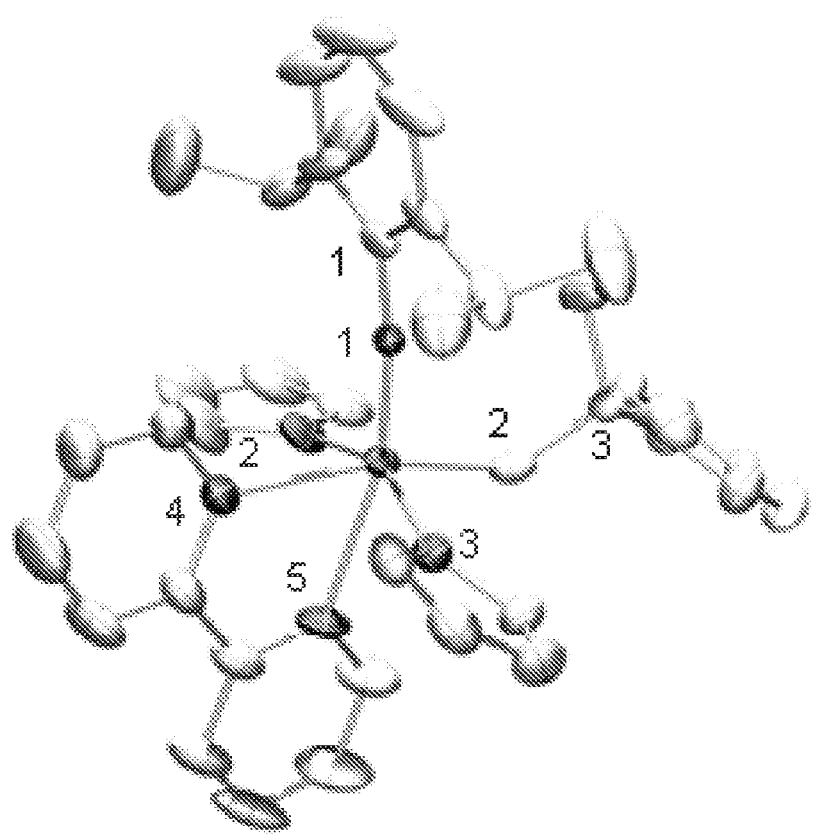
FIG. 9. X-ray crystal structure of alkylidene bpy-5.

X-ray quality crystals of 104a and 104c were grown from a mixture of dichloromethane and pentane at −45° C., while crystals of 104g were grown from benzene at 22° C. Complex 104a crystallized in the monoclinic space group P2(1)/n, whereas 104c and 104g crystallized in the monoclinic space group P2(1)/c. The structures are shown in FIGS. 5-7. In the case of 104g two independent molecules were present in the asymmetric unit along with six benzene molecules. One of the complexes is considerably disordered in the phenyl imido ligand (disorder not shown) while the other is not. Compounds 104a, 104c and 104g can best be regarded as distorted square pyramids with the alkylidyne ligand located in the apical position. The most striking features are the bond lengths Mo(1)-C(29) in 104a (1.764(3)Å), Mo(1)-C(1) in 104c (1.7643(17)Å), and Mo(1)-C(1) in 104g (1.780(5)Å), and the relatively large Mo(1)-C(29)-C(30) bond angle in 104a)(161.5(2)°, the Mo(1)-C(1)-C(2) bond angle in 104c) (159.05(14)°, and the Mo(1)-C(1)-C(2) bond angle in 104g (167.1(4)°); all are consistent with formation of alkylidyne complexes. The Mo=NR bond lengths of 104a (1.804(3)Å), 104c (1.7958(14)Å), and 104g (1.823(4)Å) are longer than in analogous alkylidene complexes, without wishing to be limited by any theory, in view of competition between the imido and alkylidyne ligands for π type d orbitals. The Mo(1)-N(3)-C(11) bond angle in 104a (159.6(2)°), the Mo(1)-N(1)-C(11) bond angle in 104c (162.64(12)°), and the Mo(1)-N(4)-C(31) bond angle in 104g (152.6(3)°) are relatively small, consistent with a Mo—N double bond more than a pseudo triple bond in the bent imido ligands. The imido ligand in {Mo(NAr)(C-t-Bu)[OCMe(CF$_3$)$_2$]$_2$}$^-$ is more bent (Mo—N—C=141.16(17)°. Tonzetich, Z. J.; Schrock, R. R.; Müller, P. Organometallics 2006, 25, 4301, and references therein) than any in 104a, 104c, or 104g. Without the intention to be limited by any theory, we propose that steric interactions between ligands in five-coordinate 104a, 104c and 104g prevent the imido ligands being as bent as the imido ligand in four-coordinate {Mo(NAr)(C-t-Bu)[OCMe(CF$_3$)$_2$]$_2$}$^-$. Although adducts analogous to 101a-101g are not formed readily upon addition of bipyridine to bisdimethylpyrrolide complexes, without the intention to be limited by any theory, we propose that adducts are likely intermediates in the process of forming 104a, 104c, and 104g and that steric crowding leads to an alkylidene with a larger Mo—C—C angle and results in activation of that alkylidene a proton toward migration, ultimately to a pyrrolide, and generation of dimethylpyrrole (equation 107). In some embodiments, phenols may add across the metal-carbon triple bond in complexes 104a-104g to regenerate MAP species.

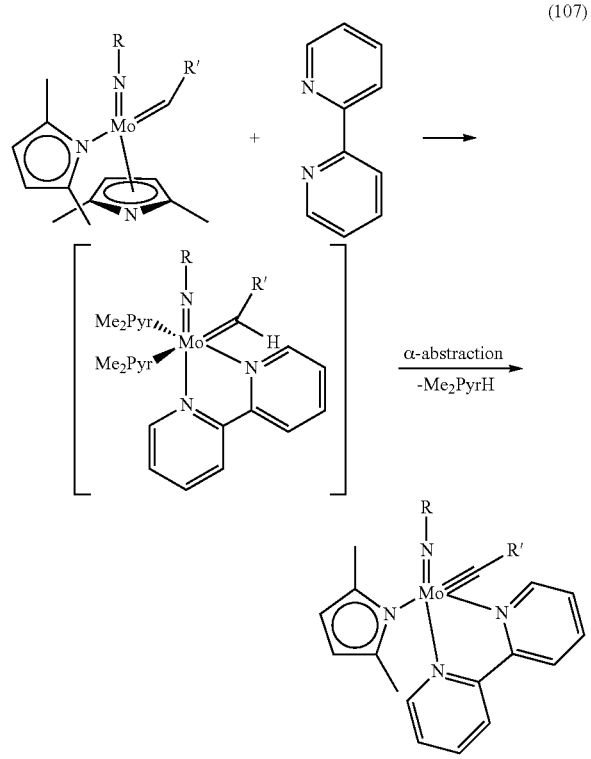

(107)

The above examples provide exemplary bipyridine adducts of molybdenum imido alkylidene bispyrrolide complexes of the type Mo(NR)(CHCMe$_2$R')(Pyr)$_2$(bipy) (as non-limiting examples, 101a-101g), and at least three different exemplary methods for their preparation. The adducts are isolated readily and quite stable thermally over a long period, unlike Mo(NR)(CHCMe$_2$R')(Pyr)$_2$ complexes themselves. In some embodiments, the present invention further provides methods to convert the molybdenum imido alkylidene bispyrrolide complexes into active MAP species for various reactions, for example but not limited to, olefin metathesis. In some embodiments, the exemplary molybdenum imido alkylidene bispyrrolide complexes of the type Mo(NR)(CHCMe$_2$R')(Pyr)$_2$(bipy) are employed as starting materials for formation of MAP species of the type Mo(NR)(CHCMe$_2$R')(Pyr)(OHMT) (103a-103g) through sonication of a mixture containing 101a-101g, HMTOH, and ZnCl$_2$(dioxane). In some embodiments, the present invention provides molybdenum imido alkylidene bispyrrolide complexes that can be converted into active MAP species for efficient Z-selective olefin metathesis reactions. In some embodiments, the present invention provides molybdenum imido alkylidene bispyrrolide complexes that can be converted into active MAP species as initiators for efficient Z-selective formation of >98% cis,syndiotactic poly(DCMNBD). In some embodiments, reactivity studies of 103a-103g with DCMNBD reveal that they are all efficient Z-selective initiators for formation of >98% cis,syndiotactic poly(DCMNBD), more so than analogous MAP complexes that contain dimethylpyrrolide. In some embodiments, the present invention provides imido alkylidyne complexes. In some embodiments, such imido alkylidyne complexes are of the type Mo(NR)(CCMe$_2$R')(Me$_2$Pyr)(bipy) as exemplified by 104a-104g. In some embodiments, certain imido alkylidyne complexes are prepared using bipy and bisdimethylpyrrolide complexes as reactants. Exemplary but not limiting examples are compounds 104a-104g. Without wishing to be bound by any theory, it is understood that in some embodiments, the formation of the imido alkylidyne complexes of the type Mo(NR)(CCMe$_2$R')(Me$_2$Pyr)(bipy) can be through a ligand-induced migration of an alkylidene α proton to a dimethylpyrrolide ligand.

Experimental Procedures
General.

All reactions and manipulations of air- and moisture-sensitive compounds were handled in oven-dried glassware (150° C., 2 hr) under a N$_2$ atmosphere either in a dual Schlenk line or in a Vacuum Atmospheres glove box. HPLC grade solvents (benzene, toluene, diethyl ether, tetrahydrofuran, pentane, and methylene chloride), were purged with N$_2$ and passed through activated alumina and stored over molecular sieves prior to use. 2,2'-bipyridine and benzaldehyde were purchased from Alfa-Aesar and used without further purification. LiNC$_4$H$_4$ (Deiter, T. Z. Anorg. Allgem. Chem. 1971, 384, 136), ZnCl$_2$(dioxane) (Hatch, L. F.; Everett, G. D. J. Org. Chem. 1968, 33, 2551), HMTOH (Stanciu, C.; Olmstead, M. M.; Phillips, A. D.; Stender, M.; Power, P. P. Eur. J. Inorg. Chem. 2003, 3495) and DCMNBD (Tabor, D. C.; White, F. H.; Collier, L. W.; Evans, S. A. J. Org. Chem. 1983, 48, 1638-1643) were prepared according to literature reports. HMTOH was placed under high vacuum for 12 hours before use. All Mo(NR)(CHCMe$_2$Ph)(OTf)$_2$DME ((a) Schrock, R. R.; Murdzek, J. S.; Bazan, G. C.; Robbins, J.; DiMare, M.; O'Regan, M. J. Am. Chem. Soc. 1990, 112, 3875. (b) Oskam, J. H.; Fox, H. H.; Yap, K. B.; McConville, D. H.; O'Dell, R.; Lichtenstein, B. J.; Schrock, R. R. J. Organomet. Chem. 1993, 459, 185), Mo(NR)(CHCMe$_2$Ph)(Pyr)$_2$ (R=2,6-iPr$_2$C$_6$H$_3$, adamantyl) (Hock, A. S.; Schrock, R. R.; Hoveyda, A. H. J. Am. Chem. Soc. 2006, 128, 16373), and Mo(NR)(CHCMe$_2$R')(NC$_4$H$_2$Me$_2$)$_2$ ((a) Singh, R.; Schrock, R. R.;

Müller, P.; Hoveyda, A. H. *J. Am. Chem. Soc.* 2007, 129, 12654. (b) Lichtscheidl, A. G.; Ng, V. W. L.; Müller, P.; Takase, M. K.; Schrock, R. R. *Organometallics* 2012, 31, 2388) complexes were prepared according to literature procedures. All deuterated solvents ($d^6$-benzene, $d^8$-toluene, and $d^2$-dichloromethane) were stored over molecular sieves 12 hours prior to use. All NMR spectra were recorded on Bruker 400 MHz and Varian 500 MHz spectrometers. Sonications were performed on a Bransonic Ultrasonic Cleaner 1510R-MT. purchased from Branson Ultrasonics Corporation. X-ray diffraction data were collected on a Siemens three-circle Platform diffractometer coupled to a Bruker-APEX CCD detector and an Oxford Cryosystems Cryostream 700 diffractometer. Elemental analyses were performed by Midwest Microlab, LLC.

Mo(NAr)(CHCMe$_2$Ph)(OTf)$_2$(bipy) (102a).

Mo(NAr)(CHCMe$_2$Ph)(OTf)$_2$ (DME) (0.5000 g, 0.63 mmol) was dissolved in benzene and bipyridine (0.09864 g, 0.63 mmol) was added in one portion. After a few minutes a yellow precipitate began forming. The mixture was allowed to stir for 12 h and then it was filtered and dried under vacuo; yield 0.4566 g (84%): $^1$H NMR (400. MHz, CD$_2$Cl$_2$) δ 14.59 (s, 1H, Mo=CH, $J_{CH}$=126.4 Hz), 8.85 (d, 1H, bipy), 8.25-8.18 (overlapping peaks, 2H, aromatic), 8.14 (m, 1H, aromatic), 8.08 (m, 1H, aromatic), 7.72 (m, 1H, aromatic), 7.56 (d, 2H, aromatic), 7.47 (t, 2H, aromatic), 7.35 (t, 1H, aromatic), 7.24-7.13 (overlapping peaks, 3H, aromatic), 7.05-6.92 (overlapping peaks, 2H, aromatic), 3.94 (s br, 1H, CHMe$_2$), 2.70 (s br, 1H, CHMe$_2$), 2.10 (s, 3H, MoCHCMe$_2$Ph), 1.59 (s, 3H, MoCHCMe$_2$Ph), 1.34 (s br, 3H, CHMe$_2$), 1.14 (d, 6H, CHMe$_2$), −0.05 (s br, 3H, CHMe$_2$). Anal. Calcd C$_{34}$H$_{37}$F$_6$MoN$_3$O$_6$S$_2$: C, 47.61; H, 4.35; N, 4.90. Found: C, 47.65; H, 4.40; N, 5.01.

Mo(NAd)(CHCMe$_2$Ph)(OTf)$_2$(bipy) (102b).

The procedure is identical to the synthesis of 102a, employing Mo(NAd)(CHCMe$_2$Ph)(OTf)$_2$(DME) (0.5000 g, 0.65 mmol) and bipyridine (0.1021 g, 0.65 mmol); yield 0.4960 g (91%): $^1$H NMR (400 MHz, CD$_2$Cl$_2$) δ 14.29 (s, 1H, Mo=CH, $J_{CH}$=123.6 Hz), 8.94 (d, 1H, bipy), 8.40-8.18 (overlapping peaks, 3H, aromatics), 8.06 (t, 1H, aromatic), 7.78 (m, 1H, aromatic), 7.65-7.10 (overlapping peaks, 5H, aromatics), 6.99 (m, 1H, aromatic), 6.59 (br, 1H, aromatic), 2.40 (s, 3H, Ad), 1.95 (s, 3H, CMe$_2$Ph), 1.78 (s, 6H, Ad), 1.65-1.40 (overlapping peaks, 9H, CMe$_2$Ph+Ad). Anal. Calcd C$_{32}$H$_{25}$F$_6$MoN$_3$O$_6$S$_2$: C, 46.21; H, 4.24; N, 5.05. Found: C, 45.82; H, 4.09; N, 5.19.

Mo(NAr')(CHCMe$_2$Ph)(OTf)$_2$(bipy) (102c).

The procedure is identical to the synthesis of 102a, employing Mo(NAr')(CHCMe$_2$Ph)(OTf)$_2$(DME) (0.4000 g, 0.54 mmol) and bipyridine (0.0850 g, 0.54 mmol); yield 0.2907 g (67%): $^1$H NMR (400 MHz, CD$_2$Cl$_2$) δ 14.55 (s, 1H, Mo=CH, $J_{CH}$=130.4 Hz), 8.83 (d, 1H, bipy), 8.23 (t, 2H, aromatic), 8.10 (m, 2H, aromatic), 7.68 (t, 1H, MoCHCMe$_2$Ph), 7.57 (m, 2H, MoCHCMe$_2$Ph), 7.44-7.32 (overlapping peaks, 3H, aromatics), 7.24 (t, 1H, aromatic), 7.02 (t, 1H, aromatic), 6.96 (t, 1H, aromatic), 6.89 (s br, 2H, Ar'), 2.53 (s br, 3H, Ar' Me), 2.00 (s, 3H, MoCHCMe$_2$Ph), 1.57 (s, 3H, MoCHCMe$_2$Ph), 1.43 (s br, 3H, Ar' Me); $^{13}$C NMR (100 MHz, CD$_2$Cl$_2$) δ 332.4 (Mo=CH), 160.3, 155.4, 152.5, 148.6, 147.1, 142.9, 141.7, 129.4, 129.0, 128.8, 127.9, 127.3, 127.2, 127.2, 123.9, 123.4, 58.0, 30.4, 28.8, 19.7 (br). Anal. Calcd C$_{30}$H$_{29}$F$_6$MoN$_3$O$_6$S$_2$: C, 44.95; H, 3.65; N, 5.24. Found: C, 44.57; H, 3.64; N, 5.32.

Mo(NAr$^{iPr}$)(CHCMe$_2$Ph)(OTf)$_2$(bipy) (102d).

Mo(NAr$^{iPr}$)(CHCMe$_2$Ph)(OTf)$_2$ (DME) (0.2468 g, 0.33 mmol) was dissolved in Et$_2$O and chilled to −35° C. for 1 hr. Then, bipyridine (0.0514 g, 0.33 mmol) was added in one portion. After a few minutes a green precipitate began forming. The mixture was allowed to stir for 12 h and then it was filtered and dried in vacuo; yield 0.2051 g of a yellow solid (76%): $^1$H NMR (400 MHz, CD$_2$Cl$_2$) 14.46 (s, 1H, Mo=CH, $J_{CH}$=125.7 Hz, major), 14.23 (s, 0.12H, Mo=CH, minor), 8.85 (d, 1H, bipy major), 8.80 (d, 0.12H, bipy minor), 8.74 (d, 0.12H, aromatic minor), 8.60 (d, 0.12H, aromatic minor), 8.55 (m, 0.24H, aromatic minor), 8.48 (m, 0.12H, aromatic minor), 8.44 (m, 0.12H, aromatic minor), 8.29 (d, 1H, aromatic major), 8.24 (d, 1H, aromatic major), 8.12 (m, 2.24H, aromatic major+minor), 7.95 (m, 0.12H, aromatic minor), 7.85 (m, 0.12H, aromatic minor), 7.82 (m, 0.12H, aromatic minor), 7.68 (m, 1H, aromatic major), 7.65 (m, 0.12H, aromatic minor), 7.57 (m, 2.12H, aromatic major+minor), 7.45 (t, 2H, aromatic major), 7.34 (t, 1H, aromatic major), 7.30-7.08 (overlapping peaks, 5.36H, aromatic major+minor), 7.02 (t, 1H, aromatic major), 3.13 (m, 1H, CHMe$_2$ major), 2.98 (m, 0.12H, CHMe$_2$ minor), 2.18 (s, 3H, MoCHCMe$_2$Ph major), 1.83 (s, 0.72H, CMe$_2$Ph minor), 1.58 (s, 3H, CMe$_2$Ph major), 1.03 (d, 3H, CHMe$_2$ major), 0.96 (d, 0.36H, CHMe$_2$ minor), 0.74 (d, 3H, CHMe$_2$ major), 0.44 (d, 0.36H, CHMe$_2$ minor); $^{13}$C NMR (100 MHz, CD$_2$Cl$_2$) δ 331.9 (syn MoCH), 160.9, 159.2, 155.5, 155.4, 153.5, 152.9, 152.8, 152.3, 151.6, 151.3, 149.3, 148.6, 148.5, 148.4, 147.3, 146.0, 145.9, 143.7, 143.3, 142.8, 141.9, 131.7, 130.9, 130.2, 130.0, 129.7, 129.5, 128.7, 128.0, 127.9, 127.8, 127.4, 127.3, 127.0, 126.9, 126.7, 126.6, 126.6, 126.4, 125.5, 125.4, 124.1, 123.3, 121.7, 118.6, 155.4, 58.6, 58.3, 30.8, 30.4, 29.7, 29.5, 29.3, 23.7, 23.6, 23.5, 22.8; $^{19}$F NMR (376 MHz, CD$_2$Cl$_2$) δ −77.3 (s, 0.5 F, cis), −79.1 (s br, 0.12 F, trans), −79.4 (s, 0.5 F, cis). Anal. Calcd C$_{31}$H$_{31}$F$_6$MoN$_3$O$_6$S$_2$: C, 45.65; H, 3.83; N, 5.15. Found: C, 45.89; H, 3.90; N, 4.92.

Mo(NAr$^{Cl}$)(CHCMe$_2$Ph)(OTf)$_2$(bipy) (102e).

The procedure is identical to the synthesis of 102d, employing Mo(NAr$^{Cl}$)(CHCMe$_2$Ph)(OTf)$_2$(DME) (0.1664 g, 0.22 mmol) and bipyridine (0.0350 g, 0.22 mmol); yield 0.1204 g (66%): $^1$H NMR (400 MHz, CD$_2$Cl$_2$) δ 14.39 (s, 1H, Mo=CH major, $J_{CH}$=127.1 Hz), 14.20 (s, 0.28H, Mo=CH minor, $J_{CH}$=118.9 Hz), 8.86 (d, 0.28H, bipy minor), 8.81 (d, 1H, bipy major), 8.77 (d, 0.28H, aromatic minor), 8.73 (d, 0.28H, aromatic minor), 8.59 (m, 0.56H, aromatic minor), 8.53 (m, 0.56H, aromatic minor), 8.47 (m, 0.28H, aromatic minor), 8.30 (d, 1H, aromatic major), 8.27 (d, 1H, aromatic major), 8.24 (m, 0.28H, aromatic minor), 8.18-8.06 (overlapping peaks, 2.56H, aromatic major+minor), 7.96 (d, 0.28H, aromatic minor), 7.90 (m, 0.28H, aromatic minor), 7.84 (m, 0.28H, aromatic minor), 7.80 (d, 1H, aromatic major), 7.71-7.63 (overlapping peaks, 1.56H, aromatic major+minor), 7.62-7.54 (overlapping peaks, 2.56H, aromatic major+minor), 7.50 (m, 0.56H, aromatic minor), 7.41 (overlapping peaks, 2.56H, aromatic major+minor), 7.36-7.22 (overlapping peaks, 4H, aromatic major), 7.20-7.10 (overlapping peaks, 4.28H, aromatic major+minor), 7.01 (m, 1H, aromatic major), 2.15 (s, 3H, MoCHCMe$_2$Ph major), 1.89 (s, 0.84H, MoCHCMe$_2$Ph minor), 1.76 (s, 0.84H, MoCHCMe$_2$Ph minor), 1.59 (s, 3H, MoCHCMe$_2$Ph major); $^{13}$C NMR (100 MHz, CD$_2$Cl$_2$) δ 332.7 (Mo=CH), 161.3, 159.8, 155.4, 155.3, 153.6, 153.4, 152.6, 152.0, 151.7, 151.3, 150.5, 148.6, 148.4, 147.1, 145.9, 145.8, 143.7, 143.3, 142.8, 141.9, 133.8, 131.9, 131.7, 131.6, 131.3, 131.2, 130.3, 130.2, 129.6, 129.5, 128.9, 128.7, 128.2, 127.8, 127.7, 127.3, 127.3, 126.9, 126.7, 126.5, 125.4, 125.3, 123.9, 123.3, 121.7. 118.5, 58.9, 58.4, 30.7, 30.2, 29.6, 29.5; $^{19}$F NMR (376 MHz, CD$_2$Cl$_2$) δ −77.1 (s, 1 F, cis), −78.7 to −79.7 (overlapping peaks, 1.28 F, cis+trans). Anal. Calcd C$_{28}$H$_{24}$ClF$_6$MoN$_3$O$_6$S$_2$: C, 41.62; H, 2.99; N, 5.20. Found: C, 41.50; H, 3.10; N, 5.31.

Mo(NAr$^{tBu}$)(CHCMe$_2$Ph)(OTf)$_2$(bipy) (102f).

The procedure is identical to the synthesis of 102d, employing Mo(NAr$^{tBu}$)(CHCMe$_2$Ph)(OTf)$_2$(DME) (0.5432 g, 0.71 mmol) and bipyridine (0.1111 g, 0.71 mmol); yield 0.4501 g of a red solid (76%): $^1$H NMR (400 MHz, CD$_2$Cl$_2$) δ 14.52 (s, 1H, Mo═CH, J$_{CH}$=125.1 Hz, major), 13.94 (s, 0.13H, Mo═CH, minor), 9.55 (dd, 0.13H, bipy minor), 8.97 (dd, 0.28H, aromatic minor), 8.84 (dd, 1H, bipy major), 8.50-6.80 (overlapping peaks, 18H, aromatics), 2.18 (s, 3H, CMe$_2$Ph major), 1.91 (s, 0.42H, CMe$_2$Ph minor), 1.64 (s, 0.42H, CMe$_2$Ph minor), 1.57 (s, 3H, CMe$_2$Ph major), 1.15 (s, 9H, t-Bu major), 0.98 (s, 1.26H, t-Bu minor). $^{13}$C NMR (100 MHz, CD$_2$Cl$_2$) δ 331.6 (syn MoCH), 159.9, 159.5, 155.5, 155.4, 153.7, 153.6, 152.5, 150.5, 148.7, 147.4, 147.3, 147.2, 147.1, 143.7, 143.5, 142.8, 142.5, 141.9, 141.3, 134.0, 133.0, 130.1, 129.8, 129.5, 129.1, 128.7, 128.2, 127.8, 127.7, 127.4, 127.3, 126.9, 126.8, 124.0, 123.6, 123.2, 122.8, 121.6, 118.5, 58.8, 58.1, 35.7, 35.1, 31.2, 30.8, 30.6, 29.2. Anal. Calcd C$_{32}$H$_{33}$F$_6$MoN$_3$O$_6$S$_2$: C, 46.32; H, 4.01; N, 5.06. Found: C, 46.42; H, 4.21; N, 5.01.

Mo(NAr$^M$)(CHCMe$_2$Ph)(OTf)$^2$(bipy) (102g).

The procedure is identical to the synthesis of 102a, employing Mo(NAr$^M$)(CHCMe$_2$Ph)(OTf)$_2$DME (0.2146 g, 0.26 mmol) and bipy (0.0406 g, 0.26 mmol); yield 0.1696 g of a green solid (73%): $^1$H NMR (400 MHz, CD$_2$Cl$_2$) δ 14.3 (s, 1H, MoCH J$_{CH}$=128 Hz major), 13.9 (s, 0.03H, MoCH minor), 8.64 (d, 1H, aromatic), 8.29 (d, 1H, aromatic), 8.11 (t, 1H, aromatic), 8.00 (d, 1H, aromatic), 7.88 (d, 2H, aromatic), 7.59, (t, 1H, aromatic), 7.49 (d, 2H, aromatic), 7.46 (t, 1H, aromatic), 7.41 (t, 2H, aromatic), 7.31 (dd, 2H, aromatic), 6.77 (d, 2H, aromatic), 6.69 (dd, 1H, aromatic), 6.153 (s, 1H, Mes), 5.901 (s, 1H, Mes), 2.38 (s, 3H, MoCHCMe$_2$Ph), 1.97 (s, 3H, MoCHCMe$_2$Ph), 1.78 (s, 3.27H, Mes), 1.57 (s, 3H, Mes), 0.99 (s, 3H, Mes); $^{13}$C NMR (100 MHz, C$_6$D$_6$) δ 329.7 (syn, MoCH), 329.3 (MoCH), 158.1, 154.3, 153.1, 152.2, 148.0, 146.5, 141.2, 140.8, 138.3, 136.7, 135.7, 135.3, 134.1, 132.1, 130.4, 129.4, 129.2, 129.0, 128.7, 128.2, 128.0, 127.9, 127.2, 126.9, 126.8, 126.6, 126.0, 125.8, 125.6, 123.5, 123.5, 122.9, 120.9, 118.4, 58.4, 30.3, 29.6, 20.8, 20.6, 19.6; $^{19}$F NMR (376 MHz, CD$_2$Cl$_2$) δ −77.1 (s, 1 F, cis), −78.6 (s, 0.06, trans), −79.5 (s br, IF, cis). Anal. Calcd C$_{37}$H$_{35}$F$_6$MoN$_3$O$_6$S$_2$: C, 49.83; H, 3.96; N, 4.71. Found: C, 50.01; H, 3.96; N, 4.56.

Mo(NAr)(CHCMe$_2$Ph)(Pyr)$_2$(bipy) (101a).

Method A: [Mo(NAr)(CHCMe$_2$Ph) (Pyr)$_2$]$_2$ (0.1000 g, 0.09 mmol) was dissolved in Et$_2$O and bipy (0.0292 g, 0.19 mmol) was added. The solution was stirred for 2 h. The precipitate was collected and dried by vacuum filtration to yield 0.0577 g of an orange solid (45%) Method C: 102a (1.1090 g, 1.3 mmol) was suspended in Et$_2$O and LiNC$_4$H$_4$ (0.1888 g, 2.6 mmol) was added in one portion. The solution was left stirring for 12 hours at RT and the orange precipitate was collected and dried by vacuum filtration to yield 0.5490 g (61%). X-ray quality crystals were obtained by crystallization from 1:1 CH$_2$Cl$_2$:n-pentane at −35° C. for 48 hours. $^1$H NMR (400 MHz, CD$_2$Cl$_2$) δ 13.87 (s, 1H, MoCH, J$_{CH}$=116.3 Hz), 9.26 (d, 1H, aromatic), 9.00 (d, 1H, aromatic), 8.20-8.08 (overlapping peaks, 2H, aromatics), 7.83 (d, 1H, aromatics), 7.75-7.57 (overlapping peaks, 4H, aromatics), 7.44-7.32 (overlapping peaks, 3H, aromatics), 7.30-7.20 (overlapping peaks, 2H, aromatics), 7.20-7.14 (overlapping peaks, 2H, aromatics), 5.89 (s, 4H, NC$_4$H$_4$), 5.61 (s, 4H, NC$_4$H$_4$), 3.48 (m, 2H, CHMe$_2$), 1.94 (s, 6H, MoCHCMe$_2$Ph), 0.98 (d, 6H, CHMe$_2$), 0.90 (d, 6H, CHMe$_2$); $^{13}$C NMR (100 MHz, CD$_2$Cl$_2$) δ 316.9 (Mo═CH), 153.5, 151.9, 151.5, 151.4, 150.7, 148.4, 141.2, 139.4, 134.3, 128.9, 128.3, 126.9, 126.8 126.4, 124.1, 123.5, 122.9, 106.8, 57.2, 31.9, 27.7, 26.2, 24.0. Anal. Calcd C$_{40}$H$_{45}$MoN$_5$: C, 69.45; H, 6.56; N, 10.12. Found: C, 69.45; H, 6.41; N, 10.02.

Mo(NAd)(CHCMe$_2$Ph)(Pyr)$_2$(bipy) (101b).

Method A: The procedure is the same as the synthesis of 101a, employing [Mo(NAd)(CHCMe$_2$Ph)(Pyr)$_2$]$_2$ (0.4885 g, 0.48 mmol) and bipy (0.1497 g, 0.96 mmol) to yield a yellow solid (0.4779 g, 75%). Method B: Mo(NAd)(CHCMe$_2$Ph) (OTf)$_2$(DME) (0.3527 g, 0.46 mmol) was dissolved in toluene (15 ml) and cooled down to −35° C. for 1 h. Then, LiNC$_4$H$_4$ (0.0674 g, 0.92 mmol) was added in one portion and the mixture was allowed to stir at RT for 2 h, during which time salts precipitated out. The salts were removed by filtering the solution through celite and washing with toluene until colorless. Finally, bipy (0.0674 g, 0.43 mmol) was added to the solution and the mixture was allowed to stir at RT overnight. Collection and drying of the resulting precipitate by vacuum filtration yielded a yellow solid (0.1007 g, 36%): NMR (400 MHz, CD$_2$Cl$_2$) δ 13.99 (s, 1H, MoCH), 13.40 (s, 1H, MoCH), 12.97 (s, 0.9H, MoCH), 9.53 (dd, 1H, bipy), 9.00 (dd, 0.9H, bipy), 8.69 (dd, 1H, bipy), 8.61 (dd, 0.9H, bipy), 8.10-7.85 (overlapping peaks, 11.9H, aromatics), 7.65-6.70 (overlapping peaks, 22.1H, aromatics), 6.24 (t, 4H, NC$_4$H$_4$), 6.20 (t, 4H, NC$_4$H$_4$), 6.15 (t, 4H, NC$_4$H$_4$), 6.06 (t, 1.6H, NC$_4$H$_4$), 6.04 (t, 1.6H, NC$_4$H$_4$), 5.67 (t, 4H, NC$_4$H$_4$), 5.55 (t, 1.6H, NC$_4$H$_4$), 5.54 (t, 1.6H, NC$_4$H$_4$), 2.40-1.30 (overlapping peaks, 61H, aliphatics). Anal. Calcd C$_{38}$H$_{43}$MoN$_5$: C, 68.56; H, 6.51; N, 10.52. Found: C, 68.33; H, 6.61; N, 10.62.

Mo(NAr')(CHCMe$_2$Ph)(Pyr)$_2$(bipy) (101c).

Method B: The procedure is the same as the synthesis of 101b employing Mo(NAr')(CHCMe$_2$Ph)(OTf)$_2$(DME) (0.3075 g, 0.42 mmol), LiNC$_4$H$_4$ (0.0610 g, 0.84 mmol) and bipy (0.0523 g, 0.33 mmol) to get a yellow solid (0.2047 g, 96%). Method C: The procedure is the same as the synthesis of 101a employing 102c (0.1076 g, 0.13 mmol) and LiNC$_4$H$_4$ (0.0196 g, 0.26 mmol) to yield 0.0660 g of a yellow solid (77%): $^1$H NMR (400 MHz, CD$_2$Cl$_2$) δ 13.78 (s, 1H, MoCH), 9.39 (d, 1H, bipy), 8.90 (d, 1H, bipy), 8.18-8.10 (overlapping peaks, 2H, aromatic), 7.96 (d, 1H, aromatic), 7.87 (m, 1H, aromatic), 7.63-7.55 (overlapping peaks, 3H, aromatic), 7.50 (m, 1H, aromatic), 7.24 (t, 2H, aromatic), 7.10-6.93 (overlapping peaks, 5H, aromatic), 5.93 (s, 4H, NC$_4$H$_4$), 5.58 (s, 4H, NC$_4$H$_4$), 2.03 (s, 6H, Ar' Me), 1.85 (s, 6H, MoCHCMe$_2$Ph). Anal. Calcd C$_{36}$H$_{37}$MoN$_5$: C, 68.02; H, 5.87; N, 11.02. Found: C, 67.86; H, 5.66; N, 11.04.

Mo(NAr$^{iPr}$)(CHCMe$_2$Ph)(Pyr)$_2$(bipy) (101d).

Method B: The procedure is the same as the synthesis of 101b, employing Mo(NAr$^{iPr}$)(CHCMe$_2$Ph)(OTf)$_2$(DME) (0.3231 g, 0.43 mmol), LiNC$_4$H$_4$ (0.0629 g, 0.86 mmol), and bipy (0.0539 g, 0.35 mmol) to get 0.2153 g of yellow 12 (96%). Method C: The procedure is the same as the synthesis of 101a, employing 102d (1.1000 g, 1.3 mmol) and LiNC$_4$H$_4$ (0.1970 g, 2.6 mmol) to yield 0.6800 g of a yellow solid (85%): $^1$H NMR (400 MHz, CD$_2$Cl$_2$) δ 13.61 (s, 1H, MoCH major isomer), 12.75 (s, 0.1H, MoCH minor isomer), 9.47 (dd, 1H, bipy), 8.93 (dd, 1H, bipy), 8.85 (d, 0.1H, bipy), 8.66 (d, 0.2H, CMe$_2$Ph), 8.42 (d, 0.2H, CMe$_2$Ph), 8.12 (m, 0.2H, aromatic), 8.60-7.94 (overlapping peaks, 2H, aromatic), 7.86-7.76 (overlapping peaks, 2H, aromatic), 7.58-7.44 (overlapping peaks, 4H, aromatic), 7.38-7.10 (overlapping peaks, 8H, aromatic), 7.00-6.88 (overlapping peaks, 1H, aromatic), 6.18 (t, 0.2H, NC$_4$H$_4$), 6.09 (t, 4H, NC$_4$H$_4$), 6.01 (t, 0.2H, NC$_4$H$_4$), 5.93 (t, 0.2H, NC$_4$H$_4$), 5.76 (t, 0.2H, NC$_4$H$_4$), 5.68 (t, 4H, NC$_4$H$_4$), 3.69 (m, 0.1H, CHMe$_2$), 3.55 (m, 1H, CHMe$_2$), 1.87 (s, 0.3H, CMe$_2$Ph), 1.79 (s, 6H, CMe$_2$Ph), 1.47 (s, 0.3H, CMe$_2$Ph), 1.07 (d, 6H, CHMe$_2$), 0.95 (d, 6H, CHMe$_2$), 0.85 (d, 6H, CHMe$_2$). Anal. Calcd C$_{37}$H$_{39}$MoN$_5$: C, 68.40; H, 6.05; N, 10.78. Found: C, 68.30; H, 6.04; N, 10.56.

Mo(NAr$^{Cl}$)(CHCMe$_3$)(Pyr)$_2$(bipy) (101e).

Method B: The procedure is the same as the synthesis of 101b, employing Mo(NAr$^{Cl}$)(CHCMe$_2$Ph)(OTf)$_2$(DME) (0.3044 g, 0.41 mmol), LiNC$_4$H$_4$ (0.0599 g, 0.82 mmol) and bipy (0.0513 g, 0.33 mmol) to yield 0.1841 g of orange-yellow 101e (87%): $^1$H NMR (400 MHz, CD$_2$Cl$_2$) δ 13.57 (s, 1H, MoCH), 12.66 (s, 0.2H, MoCH), 9.50 (dd, 1H, bipy), 8.97 (dd, 1H, bipy), 8.18-7.86 (overlapping peaks, 5H, aromatics), 7.58 (m, 2H, CMe$_2$Ph), 7.46 (dd, 2H, CMe$_2$Ph), 7.40-7.35 (overlapping peaks, 1H, CMe$_2$Ph minor isomer), 7.28-6.90 (overlapping peaks, 8H, aromatics), 6.39 (t, 0.2H, NC$_4$H$_4$), 6.17 (t, 4H, NC$_4$H$_4$), 6.06 (t, 0.2H, NC$_4$H$_4$), 5.93 (t, 0.2H, NC$_4$H$_4$), 5.73 (t, 0.2H, NC$_4$H$_4$), 5.67 (t, 4H, NC$_4$H$_4$), 2.34 (s, 1.2H, CMe$_2$Ph minor isomer), 1.76 (s, 6H, CMe$_2$Ph minor isomer). Anal. Calcd C$_{34}$H$_{32}$ClMoN$_5$: C, 63.60; H, 5.02; N, 10.91. Found: C, 63.39; H, 5.05; N, 10.67.

Mo(NAr$^{tBu}$)(CHCMe$_2$Ph)(Pyr)$_2$(bipy) (101f).

Method B: The procedure is the same as the synthesis of 101b, employing Mo(NAr$^{tBu}$)(CHCMe$_2$Ph)(OTf)$_2$(DME) (0.1500 g, 0.20 mmol), LiNC$_4$H$_4$ (0.0287 g, 0.40 mmol), and bipy (0.0245 g, 0.16 mmol) to get 0.0254 g of yellow 101f (24%): $^1$H NMR (400 MHz, CD$_2$Cl$_2$) δ 13.72 (s, 1H, MoCH), 9.33 (dd, 1H, bipy), 9.04 (dd, 1H, bipy), 8.12-8.08 (overlapping peaks, 2H, aromatic), 7.96 (d, 1H, aromatic), 7.88 (td, 1H, aromatic), 7.60-7.56 (overlapping peaks, 3H, aromatic), 7.50 (m, 1H, aromatic), 7.40 (dd, 1H, aromatic), 7.36-7.30 (overlapping peaks, 2H, aromatic), 7.24-7.15 (overlapping peaks, 4H, aromatic), 7.10 (td, 1H, aromatic), 5.96 (d, 4H, NC$_4$H$_4$), 5.62 (d, 4H, NC$_4$H$_4$), 1.84 (s, 6H, CMe$_2$Ph), 1.34 (s, 9H, t-Bu). Anal. Calcd C$_{38}$H$_{41}$MoN$_5$: C, 68.77; H, 6.23; N, 10.55. Found: C, 68.82; H, 6.24; N, 10.37.

Mo(NAr$^M$)(CHCMe$_2$Ph)(Pyr)$_2$(bipy) (101g).

Method B: The procedure is the same as the synthesis of 101b, employing Mo(NAr$^M$)(CHCMe$_2$Ph)(OTf)$_2$(DME) (0.3200 g, 0.39 mmol), LiNC$_4$H$_4$ (0.0566 g, 0.78 mmol), and bipy (0.0484 g, 0.31 mmol) to get 0.1673 g of orange 101g (74%): NMR (400 MHz, CD$_2$Cl$_2$) δ 13.97 (s, 1H, MoCH major isomer), 13.39 (s, 0.7H, MoCH), 12.54 (s, 0.4H, MoCH minor isomer), 9.38 (dd, 0.7H, bipy), 8.94 (dd, 0.7H, bipy), 8.71 (dd, 0.7H, aromatic), 8.10-6.70 (overlapping peaks, 37.8H, aromatic), 6.35 (m, 0.8H, NC$_4$H$_4$ minor isomer), 6.15 (t, 2H, NC$_4$H$_4$ major isomer), 6.08 (m, 0.8H, NC$_4$H$_4$ minor isomer), 5.94 (m, 0.8H, NC$_4$H$_4$ minor isomer), 5.90 (t, 2H, NC$_4$H$_4$ major isomer), 5.77 (t, 2.8H, NC$_4$H$_4$), 5.70 (m, 0.8H, NC$_4$H$_4$ minor isomer), 5.56 (t, 2.8H, NC$_4$H$_4$), 5.39 (m, 2H, NC$_4$H$_4$ major isomer), 5.33-5.31 (m, 2H, NC$_4$H$_4$ major isomer), 2.46 (s, 1.2H, aliphatic minor isomer), 2.34 (s, 1.2H, aliphatic minor isomer), 2.27 (s, 2.1H, aliphatic), 2.16-2.12 (overlapping peaks, 4.2H, aliphatic major+minor isomers), 2.07 (s, 1.2H, aliphatic minor isomer), 2.03 (s, 2.1H, aliphatic), 2.01 (s, 2.1H, aliphatic), 1.80 (s, 6H, aliphatic major isomer), 1.79 (s, 3H, aliphatic major isomer), 1.71 (s, 1.2H, aliphatic minor isomer), 1.54 (s, 3H, aliphatic major isomer), 1.17 (s, 4.2H, aliphatic) Anal. Calcd C$_{43}$H$_{43}$MoN$_5$: C, 71.16; H, 5.97; N, 9.65. Found: C, 70.84; H, 5.86; N, 9.41.

Mo(NAr)(CHCMe$_2$Ph)(Pyr)(OHMT) (103a).

Compound 102a (0.1560 g, 0.23 mmol), HMTOH (0.0745 g, 0.23 mmol), and ZnCl$_2$(dioxane) (0.0546 g, 0.23 mmol) were placed in a 25 mL Schlenk flask (Teflon-sealed cap) and toluene was added until all solids were at the bottom of the flask (10 mL). The flask was sealed and sonicated at RT for 4 h. Then, the solution was filtered through celite and the salts rinsed with toluene. The solvent was removed from the filtrate and the crude was redissolved in pentane and passed through a second plug of celite, and the salts were washed with pentane. The solvent was removed and the crude dissolved in a minimal amount of pentane before placing at −35° C. for 2 days. 103a was obtained as red crystals upon filtration; yield 0.0829 g (46%): $^1$H NMR (400 MHz, C$_6$D$_6$) δ 11.72 (s, 1, MoCH J$_{CH}$=125.5 Hz), 7.20-7.12 (overlapping peaks, 5H, aromatic), 7.50-6.90 (overlapping peaks, 10H, aromatic), 6.83 (t, 2H, NC$_4$H$_4$), 6.78 (t, 2H, NC$_4$H$_4$), 3.30 (m, 2H, CHMe$_2$), 2.16 (s, 6H, Mes), 2.10 (s, 6H, Mes), 2.04 (s, 6H, Mes), 1.51 (s, 3, CMe$_2$Ph), 1.46 (s, 3, CMe$_2$Ph), 1.11 (d, 6H, CHMe$_2$), 1.03 (d, 6H, CHMe$_2$); $^{13}$C NMR (100 MHz, C$_6$D$_6$) δ 293.3 (MoCH), 158.2, 153.7, 148.5, 145.9, 136.8, 136.7, 136.6, 135.9, 132.6, 132.2, 130.0, 129.0, 128.9, 128.4, 127.3, 126.4, 126.2, 123.0, 110.2, 55.7, 31.1, 30.5, 28.6, 24.3, 23.4, 21.1, 20.9, 20.5. Anal. Calcd C$_{50}$H$_{58}$MoN$_2$O: C, 75.17; H, 7.32; N, 3.51. Found: C, 75.16; H, 7.21; N, 3.66.

Mo(NAd)(CHCMe$_2$Ph)(Pyr)(OHMT) (103b).

The procedure is the same as the synthesis of 103a, employing 102b (0.1130 g, 0.17 mmol), HMTOH (0.0561 g, 0.17 mmol), and ZnCl$_2$(dioxane) (0.0381 g, 0.17 mmol) to yield 0.0836 g of yellow crystalline solid (64%). Characterization of this compound has appeared before in the literature ((a) Flook, M. M.; Ng, V. W. L.; Schrock, R. R. *J. Am. Chem. Soc.* 2011, 133, 1784. (b) Flook, M. M. Ph.D. Thesis, 2011, Massachusetts Institute of Technology). Proton NMR spectrum is Provided here as a reference: $^1$H NMR (500 MHz, C$_6$D$_6$) δ 11.04 (s, 1H, MoCH, J$_{CH}$=121.8 Hz), 7.28-6.75 (overlapping peaks, 12H, aromatics), 6.73 (t, 2H, NC$_4$H$_4$), 6.50 (t, 2H, NC$_4$H$_4$), 2.20 (s, 6H, Mes), 2.04 (s, 6H, Mes), 2.02 (s, 6H, Mes), 1.78 (br t, 3H NAd), 1.66 (s, 3H, CHCMe$_2$Ph), 1.62 (br, 3H, NAd), 1.53 (br, 3H, NAd), 1.48 (s 3H, CHCMe$_2$Ph), 1.38 (brs, 6H, NAd).

Mo(NAr')(CHCMe$_2$Ph)(Pyr)(OHMT) (103c).

The procedure is the same as the synthesis of 103a, employing 102c (0.2000 g, 0.31 mmol), HMTOH (0.1150 g, 0.35 mmol), and ZnCl$_2$(dioxane) (0.0800 g, 0.36 mmol) to yield 0.1850 g of yellow solid (79%): $^1$H NMR (500 MHz, C$_6$D$_6$) δ 11.53 (s, 1H, MoCH J$_{CH}$=123.0 Hz), 7.15 (d, 2H, MoCHCMe$_2$Ph), 7.07 (t, 2H, MoCHCMe$_2$Ph), 7.00-6.92 (overlapping peaks, 4H, aromatic), 6.75-6.68 (overlapping peaks, 9H, aromatic), 6.47 (m, 2H, NC$_4$H$_4$), 2.11 (s, 6H, HMTO), 2.05 (s, 6H, HMTO), 2.00 (s, 6H, HMTO), 1.94 (s, 6H, Mo=NAr'), 1.44 (s, 3H, MoCHCMe$_2$Ph), 1.36 (s, 3H, MoCHCMe$_2$Ph); $^{13}$C NMR (125 MHz, C$_6$D$_6$) δ 291.3 (syn, MoCH), 158.1, 155.9, 148.4, 136.9, 136.8, 136.7, 135.8, 135.4, 132.2, 132.0, 128.7, 129.2, 128.6, 127.2, 126.5, 126.3, 122.8, 110.3, 30.7, 29.8, 21.1, 21.0, 20.8, 20.5, 18.9, 18.2. Anal. Calcd C$_{46}$H$_{50}$MoN$_2$O: C, 74.37; H, 6.78; N, 3.77. Found: C, 74.53; H, 6.85; N, 3.74.

Mo(NAr$^{iPr}$)(CHCMe$_2$Ph)(Pyr)(OHMT) (103d).

The procedure is the same as the synthesis of 103a, employing 102d (0.1574 g, 0.24 mmol), HMTOH (0.0801 g, 0.24 mmol), and ZnCl$_2$(dioxane) (0.0544 g, 0.24 mmol) to yield 0.0775 g of yellow crystalline solid (42%). This crystalline material was used to get the x-ray structure of 103d: $^1$H NMR (400 MHz, C$_6$D$_6$) δ 11.46 (s, 1H, MoCH J$_{CH}$=123.9 Hz), 7.25-6.65 (overlapping peaks, 16H, aromatic), 6.58 (t, 2H, NC$_4$H$_4$), 6.39 (t, 2H, NC$_4$H$_4$), 3.18 (m, 1H, CHMe$_2$), 2.09-2.02 (overlapping peaks, 18H, Mes), 1.53 (s, 3H, CMe$_2$Ph), 1.45 (s, 3H, CMe$_2$Ph), 0.93 (d, 6H, CHCMe$_2$)); $^{13}$C NMR (100 MHz, C$_6$D$_6$) δ 289.0 (syn, MoCH), 158.1, 155.1, 148.5, 146.1, 137.2, 137.1, 136.8, 136.5, 135.4, 133.8, 131.9, 131.9, 129.6, 129.2, 128.8, 128.6, 128.5, 127.4, 126.3, 125.7, 125.5, 122.8, 110.0, 54.9, 31.5, 30.2, 28.1, 24.3, 22.5, 21.2, 20.9, 20.5, 20.4. Anal. Calcd $C_{47}H_{52}MoN_2O$: C, 74.58; H, 6.92; N, 3.70. Found: C, 74.16; H, 6.86; N, 3.35.

Mo(NAr$^{Cl}$)(CHCMe$_2$Ph)(Pyr)(OHMT) (103e).

The procedure is the same as the synthesis of 103a, employing 102e (0.1000 g, 0.15 mmol), HMTOH (0.0515 g, 0.15 mmol), and ZnCl$_2$(dioxane) (0.0350 g, 0.15 mmol) to yield 0.0552 g of yellow solid (47%): $^1$H NMR (400 MHz, C$_6$D$_6$) δ 11.53 (s, 1H, MoCH J$_{CH}$=126.3 Hz), 7.19 (dd, 2H, CMe$_2$Ph), 7.08 (td, 2H CMe$_2$Ph), 7.00-6.78 (overlapping peaks, 6H, aromatic), 6.76 (t, 2H, NC$_4$H$_4$), 6.72 (s, 2H, Mes), 6.69 (s, 2H, Mes), 6.63 (td, 1H, aromatic), 6.51 (td, 1H, aromatic), 6.46 (t, 2H, NC$_4$H$_4$), 2.06-1.97 (overlapping peaks, 18H, Mes), 1.53 (s, 3H, CMe$_2$Ph), 1.42 (s, 3H, CMe$_2$Ph); $^{13}$C NMR (100 MHz, C$_6$D$_6$) δ 291.7 (syn, MoCH), 157.9, 153.6, 148.4, 137.3, 137.1, 136.8, 136.6, 136.4, 135.3, 132.2, 132.1, 129.9, 129.5, 129.4, 129.3, 129.0, 128.8, 128.6, 128.4, 126.7, 126.3, 123.2, 110.3, 54.6, 34.4, 30.9, 29.5, 22.7, 21.9, 20.8, 20.5, 14.3. Anal. Calcd $C_{44}H_{45}ClMoN_2O$: C, 70.53; H, 6.05; N, 3.74. Found: C, 70.29; H, 5.91; N, 3.83.

Mo(NAr$^{tBu}$)(CHCMe$_2$Ph)(Pyr)(OHMT) (103f).

The procedure is the same as the synthesis of 103a, employing 102f (0.1194 g, 0.18 mmol), HMTOH (0.0594 g, 0.18 mmol), and ZnCl$_2$(dioxane) (0.0404 g, 0.18 mmol) to yield 0.0504 g of yellow crystalline solid (36%): $^1$H NMR (400 MHz, C$_6$D$_6$) δ 11.30 (s, 1H, MoCH, J$_{CH}$=122.8 Hz), 7.19 (dd, 2H, CMe$_2$Ph), 7.12 (dd, 2H, CMe$_2$Ph), 7.06 (dd, 1H, CMe$_2$Ph), 7.30-6.80 (overlapping peaks, 7H, aromatic), 6.69 (s, 4, Mes), 6.66 (td, 2H, NC$_4$H$_4$), 6.44 (td, 2H, NC$_4$H$_4$), 2.07 (s, 6H, Mes), 2.02 (s, 6H, Mes), 2.01 (s, 6H, Mes), 1.58 (s, 3H, CMe$_2$Ph), 1.44 (s, 3H, CMe$_2$Ph), 1.19 (s, 9H, t-Bu); $^{13}$C NMR (100 MHz, C$_6$D$_6$) δ 288.9 (syn, MoCH), 158.0, 156.0, 148.6, 144.4, 136.7, 136.3, 135.3, 133.3, 132.0, 132.0, 129.6, 129.4, 128.5, 126.8, 126.4, 126.3, 126.2, 125.9, 122.9, 110.0, 55.5, 35.3, 34.4, 31.6, 30.4, 30.2, 22.7, 21.2, 20.9, 20.3. Anal. Calcd $C_{48}H_{54}MoN_2O$: C, 74.78; H, 7.06; N, 3.63. Found: C, 74.63; H, 6.91; N, 3.42.

Mo(NAr$^M$)(CHCMe$_2$Ph)(Pyr)(OHMT) (103g).

The procedure is the same as the synthesis of 103a, employing 102g (0.1000 g, 0.14 mmol), HMTOH (0.0455 g, 0.14 mmol), and ZnCl$_2$(dioxane) (0.0309 g, 0.14 mmol) to yield 0.0375 g of yellow crystalline solid (33%): $^1$H NMR (400 MHz, C$_6$D$_6$) δ 11.00 (s, 1H, MoCH, J$_{CH}$=121.7 Hz), 7.20-7.10 (overlapping peaks, 3H, aromatic), 7.06-6.84 (overlapping peaks, 8H, aromatic), 6.78-6.56 (overlapping peaks, 7H, aromatic), 6.19 (t, 2H, NC$_4$H$_4$), 5.97 (t, 2H, NC$_4$H$_4$), 2.18 (s, 3H, NAr$^M$ Mes), 2.04 (s, 6H, OHMT Mes), 2.01 (s, 6H, OHMT Mes), 1.99 (s, 6H, OHMT Mes), 1.90 (s, 3H, NAr$^M$ Mes), 1.85 (s, 3H, NAr$^M$ Mes), 1.55 (s, 3H, CMe$_2$Ph), 1.45 (s, 3H, CMe$_2$Ph); $^{13}$C NMR (100 MHz, C$_6$D$_6$) δ 286.1 (syn, MoCH), 158.1, 155.5, 148.3, 137.0, 136.6, 136.5, 136.4, 135.9, 135.5, 135.3, 135.2, 131.7, 131.3, 130.6, 129.8, 129.6, 128.9, 128.8, 128.5, 127.2, 126.5, 126.4, 126.4, 109.0, 54.3, 31.2, 30.2, 21.2, 21.2, 21.0, 20.7, 20.6, 20.3. Anal. Calcd $C_{53}H_{56}MoN_2O$: C, 76.42; H, 6.78; N, 3.36. Found: C, 76.41; H, 6.81; N, 3.32.

Mo(NAr)(CCMe$_2$Ph)(NC$_4$H$_2$Me$_2$)(bipy) (104a).

Mo(NAr)(CHCMe$_2$Ph) (NC$_4$H$_2$Me$_2$)$_2$ (0.5000 g, 0.84 mmol), 2,2'-bipyridine (0.1311 g, 0.84 mmol) and benzene (5 mL) were placed in a 25 mL Schlenk flask and sealed with a Teflon-seal cap. The mixture was heated at 60° C. for 18 h and then cooled down to RT. The solvent was removed under vacuum and the crude was triturated with pentane and filtered-off to yield 0.2518 g of purple solid (46%). X-ray quality crystals were obtained by crystallization from 1:7 CH$_2$Cl$_2$: n-pentane at –35° C. for 48 hours: $^1$H NMR (600 MHz, C$_6$D$_6$) δ 8.11 (dd, 1H, bipy), 7.34 (dd, 2H, CMe$_2$Ph), 7.13 (t, 1H, aromatic), 7.08 (m, 1H, aromatic), 6.99 (dd, 2H, CMe$_2$Ph), 6.78-6.64 (overlapping peaks, 8H, aromatic), 6.47 (dd, 1H, aromatic), 6.44 (td, 1H, NC$_4$H$_2$Me$_2$), 6.18 (td, 1H, NC$_4$H$_2$Me$_2$), 4.35 (m, 2H, CHMe$_2$), 3.17 (s, 3H, NC$_4$H$_2$Me$_2$), 2.59 (s, 3H, NC$_4$H$_2$Me$_2$), 1.74 (s, 3H, CMe$_2$Ph), 1.39 (d, 6H, CHMe$_2$), 1.32 (s, 3H, CMe$_2$Ph), 1.14 (d, 6H, CHMe$_2$). Anal. Calcd $C_{38}H_{44}MoN_4$: C, 69.92; H, 6.79; N, 8.58. Found: C, 69.63; H, 6.59; N, 8.36.

Mo(NAd)(CCMe$_2$Ph)(NC$_4$H$_2$Me$_2$)(bipy) (104b).

In an N$_2$-filled glove box, a 50 mL pear-shaped flask containing a magnetic stir bar was charged with Mo(NAd)(CHCMe$_2$Ph)(Me$_2$Pyr)$_2$ (0.1000 g, 0.18 mmol), 2,2'-bipyridine (0.1380 g, 0.88 mmol), and Et$_2$O (8.8 mL); the mixture was allowed to stir for 1 h. At that time, the mixture was concentrated to a black/blue solid, which was redissolved in a minimal amount of Et$_2$O (5 mL). n-Pentane was added until solids began to precipitate (ca. 5 mL). The mixture was placed in the freezer (–35° C.) for 1 h. The solids were then filtered and washed with n-pentane (22° C.). The solids were then dried by pulling the dry box atmosphere through the fit and crushing them with a spatula. Compound 104b (0.0560 g, 44% yield) was recovered as a blue/purple solid for 48 hours: $^1$H NMR (400 MHz, C$_6$D$_6$): δ 8.94 (1H, dd, J=5.6, 0.8 Hz), 8.60 (1H, br s), 7.32-7.27 (2H, m), 7.00-6.95 (1H, m), 6.92-6.87 (2H, m), 6.86-6.81 (1H, m), 6.76-6.62 (3H, m), 6.57-6.50 (2H, m), 6.16 (1H, ddd, J=7.2, 5.6, 1.2 Hz), 3.05 (3H, s), 2.71 (3H, s), 2.31 (5H, br s), 2.18 (4H, br s), 1.92 (3H, s), 1.78 (3H, d, J$_{AB}$=10.8 Hz), 1.70 (3H, d, J$_{AB}$=10.8 Hz), 1.67 (3H, s). Anal. Calcd $C_{36}H_{42}MoN_4$: C, 69.00; H, 6.76; N, 8.94. Found: pending.

Mo(NAr')(CCMe$_2$Ph)(NC$_4$H$_2$Me$_2$)(bipy) (104c).

The procedure is the same as the synthesis of 104a, employing Mo(NAr')(CHCMe$_2$Ph)(NC$_4$H$_2$Me$_2$)$_2$ (0.2213 g, 0.41 mmol) and 2,2'-bipyridine (0.0645 g, 0.41 mmol) to yield 0.1469 g of purple solid (60%). X-ray quality crystals were obtained by crystallization from 1:7 CH$_2$Cl$_2$:n-pentane at –35° C. for 48 hours: $^1$H NMR (600 MHz, C$_6$D$_6$) δ 8.16 (dd, 1H, bipy), 7.22 (d, 2H, CMe$_2$Ph), 7.05 (d, 1H, aromatic), 6.99 (d, 2H, aromatic), 6.93 (td, 1H, aromatic), 6.80 (dd, 1H, aromatic), 6.77-6.64 (overlapping peaks, 7H, aromatic), 6.46 (d, 2H, NC$_4$H$_2$Me$_2$), 6.01 (td, 1H, aromatic), 3.16 (s, 3H, NC$_4$H$_2$Me$_2$), 2.52 (s, 3H, NC$_4$H$_2$Me$_2$), 1.93 (s, 6H, NAr' Me), 1.78 (s, 3H, CMe$_2$Ph), 1.33 (s, 3H, CMe$_2$Ph). Anal. Calcd $C_{34}H_{36}MoN_4$: C, 6845; H, 6.08; N, 9.39. Found: C, 68.35; H, 6.07; N, 9.38.

Mo(NAr$^{iPr}$)(CCMe$_2$Ph)(NC$_4$H$_2$Me$_2$)(bipy) (104d).

(NAr$^{iPr}$)(CHCMe$_2$Ph) (NC$_4$H$_2$Me$_2$)$_2$ (0.2550 g, 0.46 mmoles) and 2,2'-bipyridine (0.0725 g, 0.46 mmoles) in a 1:1 toluene/pentane mixture (7 ml) were stirred at RT for 12 h, during which time a red precipitate formed. Filtration yielded 0.2435 g of red-purple solid (86%): $^1$H NMR (600 MHz, CD$_2$Cl$_2$) δ 8.45 (dd, 1H, bipy), 8.14 (dd, 1H, aromatic), 8.09 (dd, 1H, aromatic), 8.02 (td, 1H, aromatic), 7.87 (td, 1H, aromatic), 7.44 (dd, 1H, aromatic), 7.40 (m, 1H, aromatic), 7.18 (dd, 1H, aromatic), 7.14 (m, 1H, aromatic), 7.01 (m, 1H, aromatic), 6.93 (dd, 2H, CMe$_2$Ph), 6.90-6.88 (overlapping peaks, 5H, aromatic), 5.91 (dd, 1H, NC$_4$H$_2$Me$_2$), 5.75 (t, 2H, NC$_4$H$_2$Me$_2$), 3.50 (m, 1H, CHMe$_2$), 2.49 (s, 3H, NC$_4$H$_2$Me$_2$), 2.15 (s, 3H, NC$_4$H$_2$Me$_2$), 1.56 (s, 3H, CMe$_2$Ph), 1.34 (s, 3H, CMe$_2$Ph), 1.06 (d, 3H, CHMe$_2$), 0.85 (d, 3H, CHMe$_2$). Anal. Calcd $C_{35}H_{38}MoN_4$: C, 68.84; H, 6.27; N, 9.18. Found: C, 68.46; H, 6.18; N, 9.03.

Mo(NAr$^{CF3}$)(CCMe$_3$)(NC$_4$H$_2$Me$_2$)(bipy) (104e).

The procedure is the same as the synthesis of 104a, employing Mo(NAr$^{CF3}$)(CHCMe$_3$)(NC$_4$H$_2$Me$_2$)$_2$ (0.3743 g, 0.73 mmol) and 2,2'-bipyridine (0.1139 g, 0.73 mmol) to yield 0.2899 g of purple solid (69%): NMR (600 MHz, C$_6$D$_6$) δ 8.95 (dd, 1H, bipy), 8.16 (dd, 1H, aromatic), 7.63 (m, 1H, aromatic), 7.21 (td, 1H, aromatic), 6.90-6.60 (overlapping peaks, 7H, aromatic), 6.43 (t, 2H, NC$_4$H$_2$Me$_2$), 6.39 (dd, 1H, aromatic), 6.25 (d, 2H, NC$_4$H$_2$Me$_2$), 3.11 (s, 3H, NC$_4$H$_2$Me$_2$), 2.62 (s, 3H, NC$_4$H$_2$Me$_2$), 1.12 (s, 9H, t-Bu). Anal. Calcd C$_{28}$H$_{29}$F$_3$MoN$_4$: C, 58.54; H, 5.09; N, 9.75. Found: C, 58.38; H, 5.11; N, 9.63.

Mo(NAr$^{M}$)(CCMe$_2$Ph)(NC$_4$H$_2$Me$_2$)(bipy) (104f).

Mo(NAr$^{M}$)(CHCMe$_2$Ph)(NC$_4$H$_2$Me$_2$)$_2$ (0.0520 g, 83 mop and 2,2'-bipyridine (0.0130 g, 83 μmol) were dissolved in C$_6$H$_6$, placed in a 25 mL Schlenk flask, and sealed with a teflon cap. The mixture was left heating at 60° C. for 2 days and then it was cooled down to RT, the solvent was removed in vacuo and the product recrystallized from Et$_2$O at −35° C. to yield 0.0300 g of dark purple solid product (53%): $^1$H NMR (400 MHz, C$_6$D$_6$) δ 8.1 (d, 1H, aromatic), 7.7 (d, 1H, aromatic), 7.50-6.00 (m, 17H, aromatics), 5.90 (s, 2H, Me$_2$C$_4$H$_2$N), 2.50-1.20 (br singlets, 21H, aliphatics). Anal. Calcd C$_{39}$H$_{37}$MoN$_3$: C, 71.71; H, 6.16; N, 8.16. Found: C, 71.61; H, 6.15; N, 8.18.

Mo(NAr$^T$)(CCMe$_3$)(NC$_4$H$_2$Me$_2$)(bipy) (104g).

The procedure is the same as the synthesis of 104f, employing Mo(NAr$^T$)(CHCMe$_3$)(NC$_4$H$_2$Me$_2$)$_2$ (0.0530 g, 82 μmol) and 2,2'-bipyridine (0.0128 g, 82 μmol) to yield 0.0400 g of crystalline purple solid (69%). A small portion of these crystals were used for X-ray chemical structure determination: $^1$H NMR (400 MHz, C$_6$D$_6$) δ 8.4 (m, 1H, aromatic), 8.1 (m, 2H, aromatic), 7.80 (m, 3H, aromatic), 7.50 (m, 1H, aromatic), 7.25 (m, 3H, aromatic), 7.05 (m, 1H, aromatic), 6.95 (m, 3H, aromatic), 6.88 (m, 1H, aromatic), 6.82 (m, 2H, aromatic), 6.60 (m, 2H, aromatic), 5.65 (s, 2H, Me$_2$C$_4$H$_2$N), 2.90 (m, 3H, CHMe$_2$), 2.28 (s, 3H, Me$_2$C$_4$H$_2$N), 2.20 (s, 3H, Me$_2$C$_4$H$_2$N), 1.2 (d, 3H, i-Pr), 0.94 (s, 9H, t-Bu), 0.87 (d, 3H, i-Pr), 0.75 (d, 3H, i-Pr). Anal. Calcd C$_{39}$H$_{37}$MoN$_3$: C, 71.17; H, 7.39; N, 7.90. Found: C, 70.81; H, 7.47; N, 7.91.

General Procedure for ROMP of DCMNBD.

5.0 mg of MAP catalyst is dissolved in 0.5 ml of toluene while 50 equivalents of the monomer are dissolved in 0.7 ml of toluene and stirred in a separate vial. To the monomer vial the catalyst solution is added quickly and left stirring for 2 h until it forms a gel. The reaction is then quenched with 0.5 mL of benzaldehyde and some methylene chloride is added to solubilize the gel. This solution is stirred for another hour, at which point the solution is added to a 100 mL RBF containing 50-70 mL MeOH stirring vigorously. The polymer precipitate and after one hour was collected by filtration. The dry polymer was examined by $^1$H and $^{13}$C NMR spectroscopy to determine the tacticity and cis content according to known literature reports.

TABLE 100

ROMP of DCMNBD with MAP catalysts

| Catalyst | [Mo] (mM) | Monomer Equiv | Time | Polymer Structure |
|---|---|---|---|---|
| 3a | 5.2 | 50 | 2 h | >98% cis, syndiotactic |
| 3b | 8.6 | 100 | 2 h | >98% cis, syndiotactic |
| 3c | 5.6 | 50 | 2 h | >98% cis, syndiotactic |
| 3d | 5.4 | 50 | 2 h | >98% cis, syndiotactic |
| 3e | 5.5 | 50 | 2 h | >98% cis, syndiotactic |
| 3f | 5.6 | 50 | 2 h | >98% cis, syndiotactic |
| 3g | 5.0 | 50 | 2 h | >98% cis, syndiotactic |

X-Ray Crystallographic Procedures:

Low-temperature diffraction data (φ- and ω-scans) were collected on a Bruker-AXS X8 Kappa Duo diffractometer coupled to a Smart Apex2 CCD detector with Mo K$_\alpha$ radiation (λ=0.71073 Å) from a Si-monochromated sealed tube for compounds 101a, 103a, and 103c, on a Bruker D8 three circle diffractometer coupled to a Bruker-AXS Smart Apex CCD detector with graphite-monochromated Cu K$_\alpha$ radiation (λ=1.54178 Å) for the structure of compound 104g, and on a Bruker-AXS X8 Kappa Duo diffractometer coupled to a Smart Apex2 CCD detector with Mo K$_\alpha$ radiation (λ=0.71073 Å) from a 1 μS micro-source for the structure of compound 103d.

For all structures, data reduction was performed with the program SAINT (Chambers, J. L. (2005). SAINT 7.23, Bruker-AXS, Inc., Madison, Wis., USA), absorption correction and scaling were performed with the program SADABS (Sheldrick, G. M. (2006a). SADABS, Bruker AXS, Inc. Madison, Wis., USA). The structures were solved by direct methods using SHELXS (Sheldrick, G. M. (1990). Acta Cryst. A46, 467-473) and refined against F$^2$ on all data by full-matrix least squares with SHELXL-97 (Sheldrick, G. M. (2008). Acta Cryst. A64, 112-122), following established refinement strategies (Müller, P. Crystallography Reviews 2009, 15, 57-83). All non-hydrogen atoms were refined anisotropically. Unless noted otherwise below, all hydrogen atoms were included into the model at geometrically calculated positions and refined using a riding model. The isotropic displacement parameters of all hydrogen atoms were constrained to 1.2 times the U$_{eq}$ value of the atoms they are linked to (1.5 times for methyl groups). Crystal and structural refinement results are listed in Tables 101A-105E.

Compound 101a crystallizes in the monoclinic space group C2/c with one molecule of 101a and one molecule of dichloromethane in the asymmetric unit. Coordinates for the hydrogen atom on C11 which binds directly to Mo, were taken from the difference Fourier synthesis. This hydrogen atom was subsequently refined semi-freely with the help of distance restraints while constraining their U$_{iso}$ to 1.2 times the U$_{eq}$ value of the atoms they are linked to. Phenyl ring on one of the ligands and the solvent dichloromethane were modeled as a two part disorder. The disorder was refined with the help of similarity restraints on 1-2 and 1-3 distances and displacements parameters as well as rigid bond restraints for anisotropic displacement parameters. The ratio between the two components was refined freely and converged at 0.498(10) and 0.447(10), respectively.

Compound 103d crystallizes in the triclinic space group P1 with two molecules of 103d in the asymmetric unit. Coordinates for the hydrogen atoms on carbon binding directly to Mo, C1 and C101, respectively, were taken from the difference Fourier synthesis. Those hydrogen atoms were subsequently refined semi-freely with the help of distance restraints while constraining their U$_{iso}$ to 1.2 times the U$_{eq}$ value of the atoms they are linked to. The structure contains two independent molecules (Z=4); bond lengths are identical within one to three standard uncertainties and for discussion parameters from the first independent molecule were used.

Compound 104a crystallizes in the monoclinic space group P2$_1$/n with one molecule of 104a in the asymmetric unit.

Compound 104c crystallizes in the monoclinic space group P2$_1$/c with one molecule of 104c in the asymmetric unit.

Compound 104g crystallizes in the monoclinic space group P2$_1$/c with two molecules of 104g and six molecules of benzene in the asymmetric unit (Z=8). One of the ligands on the second molecule was modeled as a two part disorder and all structural parameters discussed in the paper refer to the un-distorted molecule. The disorder was refined with the help of similarity restraints on 1-2 and 1-3 distances and displacements parameters as well as rigid bond restraints for anisotropic displacement parameters. The ratio between the two components was refined freely and converged at 0.647(10).

TABLE 101A

Crystal data and structure refinement for 101a.

| | |
|---|---|
| Identification code | (C40H45MoN5)(CH2Cl2) |
| Empirical formula | C41 H47 Cl2 Mo N5 |
| Formula weight | 776.68 |
| Temperature | 130(2) K |
| Wavelength | 0.71073 Å |
| Crystal system | Monoclinic |
| Space group | C2/c |
| Unit cell dimensions | a = 15.8436(8) Å  α = 90° |
| | b = 14.1814(7) Å  β = 94.318(3)° |
| | c = 34.0620(16) Å  γ = 90° |
| Volume | 7631.5(6) Å$^3$ |
| Z | 8 |
| Density (calculated) | 1.352 Mg/m$^3$ |
| Absorption coefficient | 0.519 mm$^{-1}$ |
| F(000) | 3232 |
| Crystal size | 0.04 × 0.03 × 0.02 mm$^3$ |
| Theta range for data collection | 1.93 to 26.00° |
| Index ranges | −19 <= h <= 19, −17 <= k <= 17, −41 <= l <= 40 |
| Reflections collected | 71876 |
| Independent reflections | 7486 [R(int) = 0.1135] |
| Completeness to theta = 26.00° | 99.9% |
| Absorption correction | Semi-empirical from equivalents |
| Max. and min. transmission | 0.9897 and 0.9795 |
| Refinement method | Full-matrix least-squares on F$^2$ |
| Data/restraints/parameters | 7486/67/489 |
| Goodness-of-fit on F$^2$ | 1.007 |
| Final R indices [I > 2sigma(I)] | R1 = 0.0416, wR2 = 0.0775 |
| R indices (all data) | R1 = 0.0759, wR2 = 0.0888 |
| Extinction coefficient | na |
| Largest diff. peak and hole | 0.410 and −0.496 e.Å$^{-3}$ |

TABLE 101B

Atomic coordinates (×10$^4$) and equivalent isotropic displacement parameters (Å$^2$ × 10$^3$) for 101a.

| | x | y | z | U(eq) |
|---|---|---|---|---|
| Mo(1) | 1765 (1) | 7877 (1) | 1428 (1) | 23 (1) |
| N(1) | 1741 (2) | 6790 (2) | 1940 (1) | 34 (1) |
| N(2) | 1430 (2) | 8624 (2) | 2013 (1) | 36 (1) |
| N(3) | 2045 (1) | 7040 (2) | 1091 (1) | 24 (1) |
| N(4) | 2985 (2) | 8299 (2) | 1675 (1) | 40 (1) |
| N(5) | 427 (2) | 7648 (2) | 1421 (1) | 27 (1) |
| C(1) | 1896 (2) | 5873 (3) | 1886 (1) | 44 (1) |
| C(2) | 1734 (3) | 5184 (3) | 2154 (1) | 58 (1) |
| C(3) | 1384 (3) | 5449 (3) | 2492 (1) | 70 (1) |
| C(4) | 1220 (3) | 6387 (3) | 2553 (1) | 59 (1) |
| C(5) | 1412 (2) | 7047 (3) | 2275 (1) | 39 (1) |
| C(6) | 1291 (2) | 8074 (3) | 2326 (1) | 40 (1) |
| C(7) | 1075 (2) | 8460 (3) | 2680 (1) | 55 (1) |
| C(8) | 1010 (3) | 9420 (4) | 2712 (1) | 70 (2) |
| C(9) | 1163 (3) | 9977 (3) | 2400 (1) | 68 (2) |
| C(10) | 1371 (2) | 9553 (3) | 2053 (1) | 50 (1) |
| C(11) | 1616 (2) | 8941 (2) | 1075 (1) | 29 (1) |
| C(12) | 1609 (2) | 9141 (2) | 632 (1) | 29 (1) |
| C(13) | 746 (2) | 8826 (3) | 442 (1) | 51 (1) |
| C(14) | 2284 (3) | 8571 (3) | 440 (1) | 56 (1) |
| C(15) | 1754 (2) | 10189 (2) | 565 (1) | 30 (1) |
| C(16) | 1066 (7) | 10707 (7) | 369 (3) | 28 (1) |
| C(17) | 1151 (6) | 11634 (6) | 283 (3) | 39 (2) |
| C(18) | 1855 (8) | 12126 (8) | 408 (4) | 43 (2) |
| C(19) | 2508 (6) | 11660 (6) | 625 (3) | 44 (2) |
| C(20) | 2394 (6) | 10704 (6) | 712 (3) | 45 (2) |
| C(16X) | 1223 (8) | 10855 (8) | 455 (4) | 45 (2) |
| C(17X) | 1422 (7) | 11798 (7) | 390 (3) | 44 (2) |
| C(18X) | 2237 (7) | 12069 (8) | 466 (3) | 43 (2) |
| C(19X) | 2883 (5) | 11407 (6) | 543 (3) | 39 (2) |
| C(20X) | 2663 (5) | 10478 (5) | 595 (2) | 28 (1) |
| C(21) | 2289 (2) | 6269 (2) | 870 (1) | 32 (1) |
| C(22) | 1675 (3) | 5747 (2) | 647 (1) | 40 (1) |
| C(23) | 1953 (3) | 4965 (3) | 438 (1) | 61 (1) |
| C(24) | 2789 (4) | 4725 (3) | 448 (2) | 77 (2) |
| C(25) | 3378 (3) | 5257 (3) | 663 (2) | 69 (1) |
| C(26) | 3164 (2) | 6041 (2) | 880 (1) | 46 (1) |
| C(27) | 750 (3) | 6000 (2) | 620 (1) | 46 (1) |
| C(28) | 203 (3) | 5200 (3) | 771 (1) | 57 (1) |
| C(29) | 452 (4) | 6262 (3) | 192 (1) | 79 (2) |
| C(30) | 3827 (2) | 6630 (3) | 1096 (1) | 50 (1) |
| C(31) | 4312 (2) | 7209 (3) | 808 (1) | 66 (1) |
| C(32) | 4452 (3) | 6042 (4) | 1363 (2) | 91 (2) |
| C(33) | 3494 (2) | 8982 (3) | 1529 (1) | 46 (1) |
| C(34) | 4281 (2) | 8963 (4) | 1723 (1) | 64 (1) |
| C(35) | 4267 (2) | 8272 (4) | 2002 (1) | 71 (2) |
| C(36) | 3471 (2) | 7869 (4) | 1971 (1) | 64 (1) |
| C(37) | 1 (2) | 6835 (2) | 1499 (1) | 35 (1) |
| C(38) | −850 (2) | 6956 (3) | 1433 (1) | 42 (1) |
| C(39) | −975 (2) | 7887 (3) | 1307 (1) | 45 (1) |
| C(40) | −190 (2) | 8288 (2) | 1303 (1) | 35 (1) |
| C(1S) | 3705 (9) | 7564 (8) | 3519 (3) | 47 (4) |
| Cl(1) | 3312 (8) | 7335 (8) | 3052 (1) | 72 (2) |
| Cl(2) | 3313 (7) | 8620 (8) | 3683 (5) | 94 (4) |
| C(1SX) | 3250 (11) | 7376 (6) | 3577 (3) | 62 (4) |
| Cl(1X) | 3080 (6) | 7123 (7) | 3111 (2) | 76 (2) |
| Cl(2X) | 3328 (4) | 8545 (6) | 3738 (3) | 49 (1) |

U(eq) is defined as one third of the trace of the orthogonalized U$^{ij}$ tensor.

TABLE 101C

Bond lengths [Å] and angles [°] for 101a.

| | |
|---|---|
| Mo(1)—N(3) | 1.730 (2) |
| Mo(1)—C(11) | 1.932 (3) |
| Mo(1)—N(4) | 2.135 (3) |
| Mo(1)—N(5) | 2.143 (2) |
| Mo(1)—N(1) | 2.330 (3) |
| Mo(1)—N(2) | 2.354 (3) |
| N(1)—C(1) | 1.338 (4) |
| N(1)—C(5) | 1.342 (4) |
| N(2)—C(10) | 1.329 (5) |
| N(2)—C(6) | 1.354 (4) |
| N(3)—C(21) | 1.400 (4) |
| N(4)—C(36) | 1.365 (5) |
| N(4)—C(33) | 1.378 (4) |
| N(5)—C(37) | 1.371 (4) |
| N(5)—C(40) | 1.373 (4) |
| C(1)—C(2) | 1.375 (5) |
| C(1)—H(1) | 0.9500 |
| C(2)—C(3) | 1.367 (6) |
| C(2)—H(2) | 0.9500 |
| C(3)—C(4) | 1.374 (6) |
| C(3)—H(3) | 0.9500 |
| C(4)—C(5) | 1.381 (5) |
| C(4)—H(4) | 0.9500 |
| C(5)—C(6) | 1.480 (5) |
| C(6)—C(7) | 1.389 (5) |
| C(7)—C(8) | 1.371 (6) |
| C(7)—H(7) | 0.9500 |
| C(8)—C(9) | 1.360 (6) |
| C(8)—H(8) | 0.9500 |
| C(9)—C(10) | 1.388 (5) |
| C(9)—H(9) | 0.9500 |
| C(10)—H(10) | 0.9500 |
| C(11)—C(12) | 1.534 (5) |
| C(11)—H(11) | 0.944 (17) |
| C(12)—C(15) | 1.525 (4) |
| C(12)—C(14) | 1.527 (4) |
| C(12)—C(13) | 1.536 (5) |
| C(13)—H(13A) | 0.9800 |
| C(13)—H(13B) | 0.9800 |
| C(13)—H(13C) | 0.9800 |
| C(14)—H(14A) | 0.9800 |
| C(14)—H(14B) | 0.9800 |
| C(14)—H(14C) | 0.9800 |
| C(15)—C(20) | 1.318 (10) |

TABLE 101C-continued

Bond lengths [Å] and angles [°] for 101a.

| | |
|---|---|
| C(15)—C(16) | 1.436 (10) |
| C(16)—C(17) | 1.357 (10) |
| C(16)—H(16) | 0.9500 |
| C(17)—C(18) | 1.356 (10) |
| C(17)—H(17) | 0.9500 |
| C(18)—C(19) | 1.394 (11) |
| C(18)—H(18) | 0.9500 |
| C(19)—C(20) | 1.401 (10) |
| C(19)—H(19) | 0.9500 |
| C(20)—H(20) | 0.9500 |
| C(21)—C(22) | 1.400 (5) |
| C(21)—C(26) | 1.422 (5) |
| C(22)—C(23) | 1.407 (5) |
| C(22)—C(27) | 1.504 (5) |
| C(23)—C(24) | 1.365 (7) |
| C(23)—H(23A) | 0.9500 |
| C(24)—C(25) | 1.368 (7) |
| C(24)—H(24) | 0.9500 |
| C(25)—C(26) | 1.391 (5) |
| C(25)—H(25) | 0.9500 |
| C(26)—C(30) | 1.493 (6) |
| C(27)—C(28) | 1.539 (5) |
| C(27)—C(29) | 1.545 (5) |
| C(27)—H(27) | 1.0000 |
| C(28)—H(28A) | 0.9800 |
| C(28)—H(28B) | 0.9800 |
| C(28)—H(28C) | 0.9800 |
| C(29)—H(29A) | 0.9800 |
| C(29)—H(29B) | 0.9800 |
| C(29)—H(29C) | 0.9800 |
| C(30)—C(31) | 1.530 (5) |
| C(30)—C(32) | 1.539 (6) |
| C(30)—H(30) | 1.0000 |
| C(31)—H(31A) | 0.9800 |
| C(31)—H(31B) | 0.9800 |
| C(31)—H(31C) | 0.9800 |
| C(32)—H(32A) | 0.9800 |
| C(32)—H(32B) | 0.9800 |
| C(32)—H(32C) | 0.9800 |
| C(33)—C(34) | 1.365 (5) |
| C(33)—H(33) | 0.9500 |
| C(34)—C(35) | 1.366 (7) |
| C(34)—H(34) | 0.9500 |
| C(35)—C(36) | 1.382 (5) |
| C(35)—H(35) | 0.9500 |
| C(36)—H(36) | 0.9500 |
| C(37)—C(38) | 1.361 (5) |
| C(37)—H(37) | 0.9500 |
| C(38)—C(39) | 1.397 (5) |
| C(38)—H(38) | 0.9500 |
| C(39)—C(40) | 1.369 (4) |
| C(39)—H(39) | 0.9500 |
| C(40)—H(40) | 0.9500 |
| C(1S)—Cl(1) | 1.693 (10) |
| C(1S)—Cl(2) | 1.730 (11) |
| C(1S)—H(1S1) | 0.9900 |
| C(1S)—H(1S2) | 0.9900 |
| N(3)—Mo(1)—C(11) | 98.62 (13) |
| N(3)—Mo(1)—N(4) | 100.60 (11) |
| C(11)—Mo(1)—N(4) | 95.24 (13) |
| N(3)—Mo(1)—N(5) | 101.06 (10) |
| C(11)—Mo(1)—N(5) | 92.16 (11) |
| N(4)—Mo(1)—N(5) | 155.75 (10) |
| N(3)—Mo(1)—N(1) | 93.50 (11) |
| C(11)—Mo(1)—N(1) | 166.88 (11) |
| N(4)—Mo(1)—N(1) | 87.41 (11) |
| N(5)—Mo(1)—N(1) | 80.53 (9) |
| N(3)—Mo(1)—N(2) | 162.76 (11) |
| C(11)—Mo(1)—N(2) | 98.62 (12) |
| N(4)—Mo(1)—N(2) | 78.12 (10) |
| N(5)—Mo(1)—N(2) | 77.95 (9) |
| N(1)—Mo(1)—N(2) | 69.30 (10) |
| C(1)—N(1)—C(5) | 117.9 (3) |
| C(1)—N(1)—Mo(1) | 121.8 (2) |
| C(5)—N(1)—Mo(1) | 119.1 (2) |
| C(10)—N(2)—C(6) | 118.3 (3) |
| C(10)—N(2)—Mo(1) | 123.8 (3) |
| C(6)—N(2)—Mo(1) | 117.9 (2) |
| C(21)—N(3)—Mo(1) | 171.0 (2) |
| C(36)—N(4)—C(33) | 105.5 (3) |
| C(36)—N(4)—Mo(1) | 127.6 (3) |
| C(33)—N(4)—Mo(1) | 126.3 (2) |
| C(37)—N(5)—C(40) | 105.2 (3) |
| C(37)—N(5)—Mo(1) | 128.8 (2) |
| C(40)—N(5)—Mo(1) | 125.8 (2) |
| N(1)—C(1)—C(2) | 123.6 (4) |
| N(1)—C(1)—H(1) | 118.2 |
| C(2)—C(1)—H(1) | 118.2 |
| C(3)—C(2)—C(1) | 118.2 (4) |
| C(3)—C(2)—H(2) | 120.9 |
| C(1)—C(2)—H(2) | 120.9 |
| C(2)—C(3)—C(4) | 119.1 (4) |
| C(2)—C(3)—H(3) | 120.5 |
| C(4)—C(3)—H(3) | 120.5 |
| C(3)—C(4)—C(5) | 120.0 (4) |
| C(3)—C(4)—H(4) | 120.0 |
| C(5)—C(4)—H(4) | 120.0 |
| N(1)—C(5)—C(4) | 121.2 (4) |
| N(1)—C(5)—C(6) | 115.5 (3) |
| C(4)—C(5)—C(6) | 123.3 (3) |
| N(2)—C(6)—C(7) | 121.4 (4) |
| N(2)—C(6)—C(5) | 116.4 (3) |
| C(7)—C(6)—C(5) | 122.2 (4) |
| C(8)—C(7)—C(6) | 119.1 (4) |
| C(8)—C(7)—H(7) | 120.4 |
| C(6)—C(7)—H(7) | 120.4 |
| C(9)—C(8)—C(7) | 119.7 (4) |
| C(9)—C(8)—H(8) | 120.1 |
| C(7)—C(8)—H(8) | 120.1 |
| C(8)—C(9)—C(10) | 118.8 (4) |
| C(8)—C(9)—H(9) | 120.6 |
| C(10)—C(9)—H(9) | 120.6 |
| N(2)—C(10)—C(9) | 122.7 (4) |
| N(2)—C(10)—H(10) | 118.7 |
| C(9)—C(10)—H(10) | 118.7 |
| C(12)—C(11)—Mo(1) | 138.3 (2) |
| C(12)—C(11)—H(11) | 112 (2) |
| Mo(1)—C(11)—H(11) | 109 (2) |
| C(15)—C(12)—C(14) | 109.4 (3) |
| C(15)—C(12)—C(11) | 109.8 (3) |
| C(14)—C(12)—C(11) | 111.8 (3) |
| C(15)—C(12)—C(13) | 111.0 (3) |
| C(14)—C(12)—C(13) | 107.2 (3) |
| C(11)—C(12)—C(13) | 107.6 (3) |
| C(12)—C(13)—H(13A) | 109.5 |
| C(12)—C(13)—H(13B) | 109.5 |
| H(13A)—C(13)—H(13B) | 109.5 |
| C(12)—C(13)—H(13C) | 109.5 |
| H(13A)—C(13)—H(13C) | 109.5 |
| H(13B)—C(13)—H(13C) | 109.5 |
| C(12)—C(14)—H(14A) | 109.5 |
| C(12)—C(14)—H(14B) | 109.5 |
| H(14A)—C(14)—H(14B) | 109.5 |
| C(12)—C(14)—H(14C) | 109.5 |
| H(14A)—C(14)—H(14C) | 109.5 |
| H(14B)—C(14)—H(14C) | 109.5 |
| C(16X)—C(15)—C(20) | 99.8 (6) |
| C(16X)—C(15)—C(16) | 17.0 (7) |
| C(20)—C(15)—C(16) | 115.4 (5) |
| C(16X)—C(15)—C(20X) | 114.9 (6) |
| C(20)—C(15)—C(20X) | 27.3 (4) |
| C(16)—C(15)—C(20X) | 126.0 (5) |
| C(16X)—C(15)—C(12) | 130.5 (5) |
| C(20)—C(15)—C(12) | 127.1 (4) |
| C(16)—C(15)—C(12) | 116.8 (4) |
| C(20X)—C(15)—C(12) | 114.3 (4) |
| C(17)—C(16)—C(15) | 120.7 (7) |
| C(17)—C(16)—H(16) | 119.6 |
| C(15)—C(16)—H(16) | 119.6 |
| C(18)—C(17)—C(16) | 121.6 (9) |
| C(18)—C(17)—H(17) | 119.2 |
| C(16)—C(17)—H(17) | 119.2 |
| C(17)—C(18)—C(19) | 118.9 (9) |
| C(17)—C(18)—H(18) | 120.6 |
| C(19)—C(18)—H(18) | 120.6 |
| C(18)—C(19)—C(20) | 117.9 (8) |

TABLE 101C-continued

Bond lengths [Å] and angles [°] for 101a.

| | |
|---|---|
| C(18)—C(19)—H(19) | 121.0 |
| C(20)—C(19)—H(19) | 121.0 |
| C(15)—C(20)—C(19) | 124.3 (8) |
| C(15)—C(20)—H(20) | 117.9 |
| C(19)—C(20)—H(20) | 117.9 |
| C(15)—C(16X)—C(17X) | 126.3 (9) |
| C(15)—C(16X)—H(16X) | 116.8 |
| C(17X)—C(16X)—H(16X) | 116.8 |
| C(18X)—C(17X)—C(16X) | 117.7 (9) |
| C(18X)—C(17X)—H(17X) | 121.1 |
| C(16X)—C(17X)—H(17X) | 121.1 |
| C(17X)—C(18X)—C(19X) | 121.4 (9) |
| C(17X)—C(18X)—H(18X) | 119.3 |
| C(19X)—C(18X)—H(18X) | 119.3 |
| C(20X)—C(19X)—C(18X) | 118.4 (8) |
| C(20X)—C(19X)—H(19X) | 120.8 |
| C(18X)—C(19X)—H(19X) | 120.8 |
| C(19X)—C(20X)—C(15) | 120.4 (6) |
| C(19X)—C(20X)—H(20X) | 119.8 |
| C(15)—C(20X)—H(20X) | 119.8 |
| C(22)—C(21)—N(3) | 119.8 (3) |
| C(22)—C(21)—C(26) | 122.0 (3) |
| N(3)—C(21)—C(26) | 118.2 (3) |
| C(21)—C(22)—C(23) | 117.3 (4) |
| C(21)—C(22)—C(27) | 122.7 (3) |
| C(23)—C(22)—C(27) | 119.9 (4) |
| C(24)—C(23)—C(22) | 121.6 (4) |
| C(24)—C(23)—H(23A) | 119.2 |
| C(22)—C(23)—H(23A) | 119.2 |
| C(23)—C(24)—C(25) | 119.8 (4) |
| C(23)—C(24)—H(24) | 120.1 |
| C(25)—C(24)—H(24) | 120.1 |
| C(24)—C(25)—C(26) | 122.8 (4) |
| C(24)—C(25)—H(25) | 118.6 |
| C(26)—C(25)—H(25) | 118.6 |
| C(25)—C(26)—C(21) | 116.4 (4) |
| C(25)—C(26)—C(30) | 121.3 (4) |
| C(21)—C(26)—C(30) | 122.2 (3) |
| C(22)—C(27)—C(28) | 112.0 (3) |
| C(22)—C(27)—C(29) | 110.0 (4) |
| C(28)—C(27)—C(29) | 110.6 (3) |
| C(22)—C(27)—H(27) | 108.0 |
| C(28)—C(27)—H(27) | 108.0 |
| C(29)—C(27)—H(27) | 108.0 |
| C(27)—C(28)—H(28A) | 109.5 |
| C(27)—C(28)—H(28B) | 109.5 |
| H(28A)—C(28)—H(28B) | 109.5 |
| C(27)—C(28)—H(28C) | 109.5 |
| H(28A)—C(28)—H(28C) | 109.5 |
| H(28B)—C(28)—H(28C) | 109.5 |
| C(27)—C(29)—H(29A) | 109.5 |
| C(27)—C(29)—H(29B) | 109.5 |
| H(29A)—C(29)—H(29B) | 109.5 |
| C(27)—C(29)—H(29C) | 109.5 |
| H(29A)—C(29)—H(29C) | 109.5 |
| H(29B)—C(29)—H(29C) | 109.5 |
| C(26)—C(30)—C(31) | 110.6 (4) |
| C(26)—C(30)—C(32) | 112.7 (4) |
| C(31)—C(30)—C(32) | 109.7 (3) |
| C(26)—C(30)—H(30) | 107.9 |
| C(31)—C(30)—H(30) | 107.9 |
| C(32)—C(30)—H(30) | 107.9 |
| C(30)—C(31)—H(31A) | 109.5 |
| C(30)—C(31)—H(31B) | 109.5 |
| H(31A)—C(31)—H(31B) | 109.5 |
| C(30)—C(31)—H(31C) | 109.5 |
| H(31A)—C(31)—H(31C) | 109.5 |
| H(31B)—C(31)—H(31C) | 109.5 |
| C(30)—C(32)—H(32A) | 109.5 |
| C(30)—C(32)—H(32B) | 109.5 |
| H(32A)—C(32)—H(32B) | 109.5 |
| C(30)—C(32)—H(32C) | 109.5 |
| H(32A)—C(32)—H(32C) | 109.5 |
| H(32B)—C(32)—H(32C) | 109.5 |
| C(34)—C(33)—N(4) | 110.5 (4) |
| C(34)—C(33)—H(33) | 124.7 |
| N(4)—C(33)—H(33) | 124.7 |
| C(33)—C(34)—C(35) | 106.8 (4) |
| C(33)—C(34)—H(34) | 126.6 |
| C(35)—C(34)—H(34) | 126.6 |
| C(34)—C(35)—C(36) | 107.8 (4) |
| C(34)—C(35)—H(35) | 126.1 |
| C(36)—C(35)—H(35) | 126.1 |
| N(4)—C(36)—C(35) | 109.4 (4) |
| N(4)—C(36)—H(36) | 125.3 |
| C(35)—C(36)—H(36) | 125.3 |
| C(38)—C(37)—N(5) | 111.0 (3) |
| C(38)—C(37)—H(37) | 124.5 |
| N(5)—C(37)—H(37) | 124.5 |
| C(37)—C(38)—C(39) | 106.6 (3) |
| C(37)—C(38)—H(38) | 126.7 |
| C(39)—C(38)—H(38) | 126.7 |
| C(40)—C(39)—C(38) | 106.8 (3) |
| C(40)—C(39)—H(39) | 126.6 |
| C(38)—C(39)—H(39) | 126.6 |
| C(39)—C(40)—N(5) | 110.4 (3) |
| C(39)—C(40)—H(40) | 124.8 |
| N(5)—C(40)—H(40) | 124.8 |
| Cl(1)—C(1S)—Cl(2) | 110.7 (8) |
| Cl(1)—C(1S)—H(1S1) | 109.5 |
| Cl(2)—C(1S)—H(1S1) | 109.5 |
| Cl(1)—C(1S)—H(1S2) | 109.5 |
| Cl(2)—C(1S)—H(1S2) | 109.5 |
| H(1S1)—C(1S)—H(1S2) | 108.1 |
| Cl(1X)—C(1SX)—Cl(2X) | 121.2 (7) |
| Cl(1X)—C(1SX)—H(1S3) | 107.0 |
| Cl(2X)—C(1SX)—H(1S3) | 107.0 |
| Cl(1X)—C(1SX)—H(1S4) | 107.0 |
| Cl(2X)—C(1SX)—H(1S4) | 107.0 |
| H(1S3)—C(1SX)—H(1S4) | 106.8 |

Symmetry transformations used to generate equivalent atoms:

TABLE 101D

Anisotropic displacement parameters ($Å^2 \times 10^3$) for 101a.
The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| Mo(1) | 22 (1) | 27 (1) | 20 (1) | −5 (1) | 2 (1) | 2 (1) |
| N(1) | 36 (2) | 40 (2) | 25 (2) | 2 (1) | 2 (1) | 6 (1) |
| N(2) | 35 (2) | 42 (2) | 33 (2) | −15 (1) | 12 (1) | −7 (1) |
| N(3) | 28 (1) | 25 (1) | 18 (1) | 1 (1) | 2 (1) | 8 (1) |
| N(4) | 30 (2) | 69 (2) | 23 (2) | −8 (2) | 1 (1) | −6 (1) |
| N(5) | 26 (1) | 26 (1) | 29 (1) | 1 (1) | 4 (1) | −1 (1) |
| C(1) | 55 (2) | 45 (2) | 32 (2) | 9 (2) | 5 (2) | 15 (2) |
| C(2) | 81 (3) | 48 (2) | 47 (3) | 19 (2) | 9 (2) | 11 (2) |
| C(3) | 99 (4) | 67 (3) | 46 (3) | 20 (2) | 23 (3) | −3 (3) |
| C(4) | 72 (3) | 74 (3) | 35 (3) | 4 (2) | 23 (2) | −7 (2) |
| C(5) | 39 (2) | 54 (2) | 24 (2) | 0 (2) | 5 (1) | −3 (2) |

TABLE 101D-continued

Anisotropic displacement parameters ($Å^2 \times 10^3$) for 101a.
The anisotropic displacement factor exponent takes the form: $-2\pi^2[h^2 a^{*2} U^{11} + \ldots + 2 h k a^* b^* U^{12}]$.

|        | $U^{11}$ | $U^{22}$ | $U^{33}$ | $U^{23}$ | $U^{13}$ | $U^{12}$ |
|--------|----------|----------|----------|----------|----------|----------|
| C(6)   | 33 (2)   | 58 (3)   | 30 (2)   | −12 (2)  | 9 (2)    | −10 (2)  |
| C(7)   | 56 (2)   | 77 (3)   | 34 (2)   | −18 (2)  | 17 (2)   | −11 (2)  |
| C(8)   | 82 (3)   | 86 (4)   | 46 (3)   | −36 (3)  | 35 (2)   | −18 (3)  |
| C(9)   | 84 (3)   | 56 (3)   | 68 (3)   | −38 (3)  | 33 (3)   | −19 (2)  |
| C(10)  | 55 (2)   | 48 (2)   | 49 (3)   | −21 (2)  | 20 (2)   | −13 (2)  |
| C(11)  | 26 (2)   | 23 (2)   | 39 (2)   | −6 (2)   | 9 (1)    | 0 (1)    |
| C(12)  | 32 (2)   | 23 (2)   | 32 (2)   | 2 (1)    | 7 (1)    | 4 (1)    |
| C(13)  | 61 (3)   | 50 (2)   | 40 (2)   | −6 (2)   | −2 (2)   | −19 (2)  |
| C(14)  | 81 (3)   | 42 (2)   | 50 (3)   | 18 (2)   | 36 (2)   | 29 (2)   |
| C(15)  | 42 (2)   | 22 (2)   | 26 (2)   | 0 (1)    | 2 (2)    | 0 (2)    |
| C(16)  | 26 (3)   | 24 (3)   | 35 (4)   | 4 (3)    | 3 (2)    | 1 (2)    |
| C(17)  | 33 (3)   | 34 (3)   | 50 (4)   | −2 (3)   | 9 (3)    | 3 (2)    |
| C(18)  | 71 (8)   | 19 (3)   | 37 (4)   | −1 (3)   | −17 (5)  | 0 (5)    |
| C(19)  | 48 (5)   | 22 (3)   | 59 (5)   | −1 (3)   | −7 (3)   | −4 (3)   |
| C(20)  | 35 (4)   | 40 (4)   | 60 (5)   | 9 (4)    | 1 (3)    | 2 (3)    |
| C(16X) | 35 (4)   | 40 (4)   | 60 (5)   | 9 (4)    | 1 (3)    | 2 (3)    |
| C(17X) | 48 (5)   | 22 (3)   | 59 (5)   | −1 (3)   | −7 (3)   | −4 (3)   |
| C(18X) | 71 (8)   | 19 (3)   | 37 (4)   | −1 (3)   | −17 (5)  | 0 (5)    |
| C(19X) | 33 (3)   | 34 (3)   | 50 (4)   | −2 (3)   | 9 (3)    | 3 (2)    |
| C(20X) | 26 (3)   | 24 (3)   | 35 (4)   | 4 (3)    | 3 (2)    | 1 (2)    |
| C(21)  | 60 (2)   | 18 (2)   | 21 (2)   | 6 (1)    | 15 (2)   | 8 (2)    |
| C(22)  | 80 (3)   | 22 (2)   | 21 (2)   | 3 (1)    | 13 (2)   | −2 (2)   |
| C(23)  | 127 (4)  | 26 (2)   | 35 (2)   | −4 (2)   | 35 (2)   | −13 (2)  |
| C(24)  | 138 (4)  | 28 (2)   | 75 (3)   | −1 (2)   | 77 (3)   | 4 (2)    |
| C(25)  | 95 (3)   | 32 (2)   | 90 (4)   | 10 (2)   | 63 (3)   | 20 (2)   |
| C(26)  | 61 (2)   | 33 (2)   | 50 (2)   | 13 (2)   | 38 (2)   | 18 (2)   |
| C(27)  | 82 (3)   | 26 (2)   | 28 (2)   | −2 (2)   | −15 (2)  | −9 (2)   |
| C(28)  | 72 (3)   | 38 (2)   | 59 (3)   | −2 (2)   | −11 (2)  | −13 (2)  |
| C(29)  | 138 (5)  | 49 (3)   | 44 (3)   | 1 (2)    | −38 (3)  | −21 (3)  |
| C(30)  | 42 (2)   | 48 (2)   | 63 (3)   | 14 (2)   | 24 (2)   | 18 (2)   |
| C(31)  | 49 (2)   | 63 (3)   | 87 (3)   | 31 (3)   | 18 (2)   | 13 (2)   |
| C(32)  | 82 (4)   | 93 (4)   | 98 (4)   | 56 (3)   | 17 (3)   | 24 (3)   |
| C(33)  | 36 (2)   | 64 (3)   | 38 (2)   | −21 (2)  | 5 (2)    | −15 (2)  |
| C(34)  | 41 (2)   | 106 (4)  | 45 (3)   | −30 (3)  | 6 (2)    | −22 (2)  |
| C(35)  | 32 (2)   | 135 (5)  | 43 (3)   | −20 (3)  | −11 (2)  | −7 (2)   |
| C(36)  | 44 (2)   | 116 (4)  | 30 (2)   | 3 (2)    | −7 (2)   | −12 (2)  |
| C(37)  | 38 (2)   | 34 (2)   | 31 (2)   | 2 (2)    | 1 (2)    | −9 (2)   |
| C(38)  | 36 (2)   | 56 (3)   | 34 (2)   | 1 (2)    | 2 (2)    | −17 (2)  |
| C(39)  | 23 (2)   | 61 (2)   | 51 (2)   | 3 (2)    | 7 (2)    | 3 (2)    |
| C(40)  | 30 (2)   | 34 (2)   | 42 (2)   | 0 (2)    | 6 (2)    | 7 (2)    |
| C(1S)  | 29 (6)   | 60 (6)   | 53 (7)   | 1 (5)    | 9 (5)    | −5 (5)   |
| Cl(1)  | 66 (4)   | 83 (4)   | 64 (3)   | −33 (3)  | −8 (3)   | 9 (3)    |
| Cl(2)  | 104 (6)  | 65 (4)   | 116 (8)  | −15 (4)  | 38 (5)   | −22 (4)  |
| C(1SX) | 59 (8)   | 51 (5)   | 76 (6)   | −2 (5)   | 15 (5)   | 2 (5)    |
| Cl(1X) | 63 (3)   | 104 (4)  | 62 (2)   | −22 (2)  | −2 (2)   | 0 (2)    |
| Cl(2X) | 49 (2)   | 46 (2)   | 53 (2)   | −10 (2)  | 8 (2)    | −14 (2)  |

TABLE 101E

Hydrogen coordinates ($\times 10^4$) and isotropic displacement parameters ($Å^2 \times 10^3$) for 101a.

|        | x        | y         | z        | U(eq) |
|--------|----------|-----------|----------|-------|
| H(1)   | 2130     | 5687      | 1649     | 53    |
| H(2)   | 1863     | 4542      | 2106     | 70    |
| H(3)   | 1256     | 4991      | 2682     | 84    |
| H(4)   | 974      | 6581      | 2786     | 71    |
| H(7)   | 975      | 8064      | 2896     | 66    |
| H(8)   | 859      | 9695      | 2951     | 84    |
| H(9)   | 1127     | 10644     | 2420     | 82    |
| H(10)  | 1476     | 9943      | 1836     | 60    |
| H(11)  | 1447 (19)| 9471 (17) | 1218 (9) | 35    |
| H(13A) | 295      | 9177      | 558      | 76    |
| H(13B) | 670      | 8149      | 487      | 76    |
| H(13C) | 721      | 8949      | 158      | 76    |
| H(14A) | 2846     | 8751      | 557      | 84    |
| H(14B) | 2249     | 8700      | 157      | 84    |
| H(14C) | 2192     | 7897      | 484      | 84    |
| H(16)  | 544      | 10396     | 299      | 34    |
| H(17)  | 707      | 11946     | 131      | 46    |
| H(18)  | 1901     | 12778     | 348      | 52    |
| H(19)  | 3016     | 11979     | 711      | 52    |
| H(20)  | 2805     | 10409     | 888      | 54    |
| H(16X) | 643      | 10683     | 416      | 54    |
| H(17X) | 999      | 12236     | 296      | 52    |
| H(18X) | 2372     | 12721     | 467      | 52    |
| H(19X) | 3461     | 11594     | 559      | 46    |
| H(20X) | 3092     | 10018     | 650      | 34    |
| H(23A) | 1550     | 4595      | 286      | 73    |
| H(24)  | 2961     | 4191      | 306      | 92    |
| H(25)  | 3957     | 5083      | 664      | 83    |
| H(27)  | 678      | 6567      | 789      | 56    |
| H(28A) | 393      | 5053      | 1045     | 86    |
| H(28B) | 258      | 4638      | 607      | 86    |
| H(28C) | −391     | 5400      | 757      | 86    |
| H(29A) | 801      | 6777      | 102      | 119   |
| H(29B) | −142     | 6462      | 180      | 119   |

TABLE 101E-continued

Hydrogen coordinates (×10⁴) and isotropic displacement parameters ($Å^2 \times 10^3$) for 101a.

| | x | y | z | U(eq) |
|---|---|---|---|---|
| H(29C) | 506 | 5711 | 22 | 119 |
| H(30) | 3535 | 7080 | 1267 | 60 |
| H(31A) | 3912 | 7589 | 641 | 99 |
| H(31B) | 4619 | 6783 | 643 | 99 |
| H(31C) | 4714 | 7626 | 956 | 99 |
| H(32A) | 4139 | 5675 | 1548 | 136 |
| H(32B) | 4852 | 6463 | 1510 | 136 |
| H(32C) | 4763 | 5612 | 1201 | 136 |
| H(33) | 3323 | 9406 | 1323 | 55 |
| H(34) | 4747 | 9354 | 1673 | 77 |
| H(35) | 4724 | 8100 | 2185 | 85 |
| H(36) | 3289 | 7370 | 2131 | 77 |
| H(37) | 265 | 6263 | 1587 | 42 |
| H(38) | −1276 | 6498 | 1467 | 51 |
| H(39) | −1503 | 8183 | 1238 | 54 |
| H(40) | −87 | 8921 | 1228 | 42 |
| H(1S1) | 4330 | 7595 | 3528 | 56 |
| H(1S2) | 3548 | 7046 | 3694 | 56 |
| H(1S3) | 3781 | 7056 | 3673 | 74 |
| H(1S4) | 2789 | 7079 | 3715 | 74 |

TABLE 102A

Crystal data and structure refinement for 103d.

| | |
|---|---|
| Identification code | x11172 |
| Empirical formula | C47 H52 Mo N2 O |
| Formula weight | 756.85 |
| Temperature | 100(2) K |
| Wavelength | 0.71073 Å |
| Crystal system | Triclinic |
| Space group | P1̄ |
| Unit cell dimensions | a = 10.6943(6) Å    α = 94.8550(10)° |
| | b = 11.4798(6) Å    β = 91.9520(10)° |
| | c = 34.8506(19) Å   γ = 111.2780(10)° |
| Volume | 3962.9(4) Å³ |
| Z | 4 |
| Density (calculated) | 1.269 Mg/m³ |
| Absorption coefficient | 0.368 mm⁻¹ |
| F(000) | 1592 |
| Crystal size | 0.20 × 0.20 × 0.15 mm³ |
| Theta range for data collection | 1.18 to 30.32°. |
| Index ranges | −15 <= h <= 15, −16 <= k <= 16, −49 <= l <= 49 |
| Reflections collected | 181235 |
| Independent reflections | 23780 [R(int) = 0.0322] |
| Completeness to theta = 30.32° | 99.9% |
| Absorption correction | Semi-empirical from equivalents |
| Max. and min. transmission | 0.9469 and 0.9301 |
| Refinement method | Full-matrix least-squares on F² |
| Data/restraints/parameters | 23780/2/945 |
| Goodness-of-fit on F² | 1.114 |
| Final R indices [I > 2sigma(I)] | R1 = 0.0328, wR2 = 0.0758 |
| R indices (all data) | R1 = 0.0374, wR2 = 0.0783 |
| Largest diff. peak and hole | 0.959 and −0.838 e.Å⁻³ |

TABLE 102B

Atomic coordinates (×10⁴) and equivalent isotropic displacement parameters ($Å^2 \times 10^3$) for 103d.

| | x | y | z | U(eq) |
|---|---|---|---|---|
| Mo(1) | 436 (1) | 5934 (1) | 6119 (1) | 16 (1) |
| C(1) | 1604 (2) | 6245 (2) | 6562 (1) | 21 (1) |
| C(2) | 2710 (2) | 5926 (2) | 6758 (1) | 25 (1) |
| C(3) | 3313 (2) | 5230 (2) | 6468 (1) | 39 (1) |
| C(4) | 2097 (2) | 5057 (2) | 7071 (1) | 37 (1) |
| C(5) | 3786 (2) | 7186 (2) | 6930 (1) | 23 (1) |
| C(6) | 4038 (2) | 7540 (2) | 7326 (1) | 31 (1) |
| C(7) | 4982 (2) | 8716 (2) | 7467 (1) | 41 (1) |
| C(8) | 5679 (2) | 9537 (2) | 7217 (1) | 47 (1) |
| C(9) | 5449 (2) | 9198 (2) | 6822 (1) | 48 (1) |
| C(10) | 4510 (2) | 8032 (2) | 6681 (1) | 35 (1) |
| N(1) | 860 (1) | 4823 (1) | 5844 (1) | 19 (1) |
| C(11) | 1188 (2) | 3944 (1) | 5612 (1) | 18 (1) |
| C(12) | 654 (2) | 2683 (1) | 5686 (1) | 25 (1) |
| C(13) | 997 (2) | 1788 (2) | 5470 (1) | 28 (1) |
| C(14) | 1854 (2) | 2148 (2) | 5174 (1) | 26 (1) |
| C(15) | 2368 (2) | 3393 (2) | 5098 (1) | 22 (1) |
| C(16) | 2060 (1) | 4325 (1) | 5314 (1) | 18 (1) |
| C(17) | 2608 (2) | 5682 (1) | 5224 (1) | 22 (1) |
| C(18) | 1994 (2) | 5814 (2) | 4833 (1) | 29 (1) |
| C(19) | 4150 (2) | 6203 (2) | 5232 (1) | 32 (1) |
| N(2) | 1223 (1) | 7557 (1) | 5876 (1) | 20 (1) |
| C(20) | 688 (2) | 7656 (1) | 5516 (1) | 24 (1) |
| C(21) | 1390 (2) | 8802 (2) | 5399 (1) | 30 (1) |
| C(22) | 2414 (2) | 9452 (2) | 5694 (1) | 33 (1) |
| C(23) | 2290 (2) | 8677 (1) | 5978 (1) | 26 (1) |
| O(1) | −1408 (1) | 5453 (1) | 6240 (1) | 18 (1) |
| C(31) | −2217 (1) | 5350 (1) | 6538 (1) | 16 (1) |
| C(32) | −3190 (1) | 4165 (1) | 6580 (1) | 17 (1) |
| C(41) | −3326 (1) | 3073 (1) | 6294 (1) | 18 (1) |
| C(42) | −2573 (2) | 2319 (1) | 6352 (1) | 24 (1) |
| C(47) | −1611 (2) | 2596 (2) | 6703 (1) | 39 (1) |
| C(43) | −2721 (2) | 1309 (2) | 6077 (1) | 28 (1) |
| C(44) | −3573 (2) | 1045 (1) | 5746 (1) | 27 (1) |
| C(48) | −3730 (3) | −48 (2) | 5449 (1) | 44 (1) |
| C(45) | −4293 (2) | 1820 (1) | 5691 (1) | 24 (1) |
| C(46) | −4188 (2) | 2825 (1) | 5960 (1) | 19 (1) |
| C(49) | −4990 (2) | 3637 (2) | 5888 (1) | 29 (1) |
| C(33) | −4022 (2) | 4050 (1) | 6885 (1) | 21 (1) |
| C(34) | −3912 (2) | 5091 (2) | 7140 (1) | 23 (1) |
| C(35) | −2971 (2) | 6263 (2) | 7088 (1) | 22 (1) |
| C(36) | −2100 (1) | 6419 (1) | 6789 (1) | 18 (1) |
| C(51) | −1070 (1) | 7673 (1) | 6735 (1) | 18 (1) |
| C(52) | 60 (2) | 8224 (1) | 6999 (1) | 20 (1) |
| C(57) | 263 (2) | 7593 (1) | 7347 (1) | 24 (1) |
| C(53) | 1028 (2) | 9385 (1) | 6941 (1) | 24 (1) |
| C(54) | 889 (2) | 10032 (1) | 6631 (1) | 26 (1) |
| C(58) | 1948 (2) | 11292 (2) | 6576 (1) | 39 (1) |
| C(55) | −237 (2) | 9479 (1) | 6373 (1) | 24 (1) |
| C(56) | −1217 (2) | 8308 (1) | 6418 (1) | 21 (1) |
| C(59) | −2407 (2) | 7742 (2) | 6126 (1) | 27 (1) |
| Mo(2) | 4087 (1) | 3635 (1) | 8919 (1) | 16 (1) |
| C(101) | 2647 (2) | 3076 (1) | 8541 (1) | 20 (1) |
| C(102) | 1409 (2) | 3305 (1) | 8399 (1) | 24 (1) |
| C(103) | 616 (2) | 3522 (1) | 8742 (1) | 36 (1) |
| C(104) | 1889 (2) | 4503 (2) | 8190 (1) | 42 (1) |
| C(105) | 517 (2) | 2145 (1) | 8134 (1) | 21 (1) |
| C(106) | 296 (2) | 2151 (2) | 7738 (1) | 30 (1) |
| C(107) | −516 (2) | 1061 (2) | 7511 (1) | 39 (1) |
| C(108) | −1112 (2) | −40 (2) | 7672 (1) | 38 (1) |
| C(109) | −894 (2) | −74 (2) | 8063 (1) | 35 (1) |
| C(110) | −84 (2) | 1010 (2) | 8291 (1) | 28 (1) |
| N(3) | 3719 (2) | 4797 (1) | 9184 (1) | 19 (1) |
| C(111) | 3398 (1) | 5696 (1) | 9408 (1) | 19 (1) |
| C(112) | 3767 (2) | 6908 (1) | 9293 (1) | 24 (1) |
| C(113) | 3420 (2) | 7812 (1) | 9504 (1) | 26 (1) |
| C(114) | 2716 (2) | 7508 (1) | 9832 (1) | 27 (1) |
| C(115) | 2366 (2) | 6309 (1) | 9949 (1) | 25 (1) |
| C(116) | 2695 (2) | 5372 (1) | 9743 (1) | 20 (1) |
| C(117) | 2348 (2) | 4082 (2) | 9882 (1) | 23 (1) |
| C(118) | 833 (2) | 3441 (2) | 9919 (1) | 31 (1) |
| C(119) | 3148 (2) | 4170 (2) | 10262 (1) | 30 (1) |
| N(4) | 3567 (1) | 2143 (1) | 9234 (1) | 20 (1) |
| C(120) | 4358 (2) | 2176 (2) | 9562 (1) | 24 (1) |
| C(121) | 3731 (2) | 1166 (2) | 9758 (1) | 30 (1) |
| C(122) | 2480 (2) | 473 (2) | 9548 (1) | 30 (1) |
| C(123) | 2415 (2) | 1082 (2) | 9233 (1) | 24 (1) |
| O(2) | 5818 (1) | 4148 (1) | 8710 (1) | 18 (1) |
| C(131) | 6586 (1) | 4197 (1) | 8406 (1) | 16 (1) |
| C(132) | 7578 (1) | 5356 (1) | 8348 (1) | 17 (1) |

TABLE 102B-continued

Atomic coordinates (×10⁴) and equivalent isotropic displacement parameters ($Å^2 \times 10^3$) for 103d.

|        | x        | y        | z        | U(eq)  |
|--------|----------|----------|----------|--------|
| C(141) | 7773 (1) | 6515 (1) | 8612 (1) | 17 (1) |
| C(142) | 6922 (2) | 7190 (1) | 8572 (1) | 21 (1) |
| C(147) | 5774 (2) | 6760 (2) | 8265 (1) | 30 (1) |
| C(143) | 7154 (2) | 8284 (1) | 8820 (1) | 24 (1) |
| C(144) | 8216 (2) | 8727 (1) | 9102 (1) | 24 (1) |
| C(148) | 8465 (2) | 9906 (2) | 9371 (1) | 33 (1) |
| C(145) | 9048 (2) | 8044 (1) | 9136 (1) | 22 (1) |
| C(146) | 8840 (1) | 6940 (1) | 8899 (1) | 18 (1) |
| C(149) | 9722 (2) | 6195 (2) | 8962 (1) | 23 (1) |
| C(133) | 8404 (2) | 5394 (1) | 8044 (1) | 21 (1) |
| C(134) | 8265 (2) | 4316 (2) | 7805 (1) | 24 (1) |
| C(135) | 7283 (2) | 3178 (1) | 7869 (1) | 23 (1) |
| C(136) | 6422 (1) | 3095 (1) | 8166 (1) | 18 (1) |
| C(151) | 5343 (2) | 1877 (1) | 8228 (1) | 19 (1) |
| C(152) | 4176 (2) | 1387 (1) | 7976 (1) | 21 (1) |
| C(157) | 3981 (2) | 2057 (2) | 7638 (1) | 29 (1) |
| C(153) | 3154 (2) | 268 (1)  | 8044 (1) | 24 (1) |
| C(154) | 3272 (2) | −390 (1) | 8352 (1) | 26 (1) |
| C(158) | 2154 (2) | −1589 (2)| 8424 (1) | 37 (1) |
| C(155) | 4438 (2) | 102 (1)  | 8596 (1) | 25 (1) |
| C(156) | 5476 (2) | 1225 (1) | 8542 (1) | 22 (1) |
| C(159) | 6720 (2) | 1714 (2) | 8814 (1) | 29 (1) |

U(eq) is defined as one third of the trace of the orthogonalized $U^{ij}$ tensor.

TABLE 102C

Bond lengths [Å] and angles [°] for 103d.

| Mo(1)—N(1)    | 1.7300 (12) |
| Mo(1)—C(1)    | 1.8769 (15) |
| Mo(1)—O(1)    | 1.9186 (10) |
| Mo(1)—N(2)    | 2.0198 (13) |
| C(1)—C(2)     | 1.516 (2)   |
| C(1)—H(1)     | 0.951 (14)  |
| C(2)—C(3)     | 1.535 (2)   |
| C(2)—C(5)     | 1.540 (2)   |
| C(2)—C(4)     | 1.541 (3)   |
| C(3)—H(3A)    | 0.9800      |
| C(3)—H(3B)    | 0.9800      |
| C(3)—H(3C)    | 0.9800      |
| C(4)—H(4A)    | 0.9800      |
| C(4)—H(4B)    | 0.9800      |
| C(4)—H(4C)    | 0.9800      |
| C(5)—C(6)     | 1.393 (2)   |
| C(5)—C(10)    | 1.393 (2)   |
| C(6)—C(7)     | 1.396 (3)   |
| C(6)—H(6)     | 0.9500      |
| C(7)—C(8)     | 1.371 (3)   |
| C(7)—H(7)     | 0.9500      |
| C(8)—C(9)     | 1.384 (4)   |
| C(8)—H(8)     | 0.9500      |
| C(9)—C(10)    | 1.387 (3)   |
| C(9)—H(9)     | 0.9500      |
| C(10)—H(10)   | 0.9500      |
| N(1)—C(11)    | 1.3902 (18) |
| C(11)—C(12)   | 1.400 (2)   |
| C(11)—C(16)   | 1.410 (2)   |
| C(12)—C(13)   | 1.386 (2)   |
| C(12)—H(12)   | 0.9500      |
| C(13)—C(14)   | 1.392 (2)   |
| C(13)—H(13)   | 0.9500      |
| C(14)—C(15)   | 1.386 (2)   |
| C(14)—H(14)   | 0.9500      |
| C(15)—C(16)   | 1.399 (2)   |
| C(15)—H(15)   | 0.9500      |
| C(16)—C(17)   | 1.517 (2)   |
| C(17)—C(18)   | 1.534 (2)   |
| C(17)—C(19)   | 1.535 (2)   |
| C(17)—H(17)   | 1.0000      |
| C(18)—H(18A)  | 0.9800      |
| C(18)—H(18B)  | 0.9800      |
| C(18)—H(18C)  | 0.9800      |

TABLE 102C-continued

Bond lengths [Å] and angles [°] for 103d.

| C(19)—H(19A)  | 0.9800      |
| C(19)—H(19B)  | 0.9800      |
| C(19)—H(19C)  | 0.9800      |
| N(2)—C(23)    | 1.3833 (19) |
| N(2)—C(20)    | 1.390 (2)   |
| C(20)—C(21)   | 1.363 (2)   |
| C(20)—H(20)   | 0.9500      |
| C(21)—C(22)   | 1.418 (3)   |
| C(21)—H(21)   | 0.9500      |
| C(22)—C(23)   | 1.365 (2)   |
| C(22)—H(22)   | 0.9500      |
| C(23)—H(23)   | 0.9500      |
| O(1)—C(31)    | 1.3594 (17) |
| C(31)—C(32)   | 1.4043 (19) |
| C(31)—C(36)   | 1.4086 (19) |
| C(32)—C(33)   | 1.393 (2)   |
| C(32)—C(41)   | 1.4952 (19) |
| C(41)—C(42)   | 1.401 (2)   |
| C(41)—C(46)   | 1.403 (2)   |
| C(42)—C(43)   | 1.397 (2)   |
| C(42)—C(47)   | 1.508 (2)   |
| C(47)—H(47A)  | 0.9800      |
| C(47)—H(47B)  | 0.9800      |
| C(47)—H(47C)  | 0.9800      |
| C(43)—C(44)   | 1.387 (3)   |
| C(43)—H(43)   | 0.9500      |
| C(44)—C(45)   | 1.391 (2)   |
| C(44)—C(48)   | 1.514 (2)   |
| C(48)—H(48A)  | 0.9800      |
| C(48)—H(48B)  | 0.9800      |
| C(48)—H(48C)  | 0.9800      |
| C(45)—C(46)   | 1.392 (2)   |
| C(45)—H(45)   | 0.9500      |
| C(46)—C(49)   | 1.507 (2)   |
| C(49)—H(49A)  | 0.9800      |
| C(49)—H(49B)  | 0.9800      |
| C(49)—H(49C)  | 0.9800      |
| C(33)—C(34)   | 1.394 (2)   |
| C(33)—H(33)   | 0.9500      |
| C(34)—C(35)   | 1.389 (2)   |
| C(34)—H(34)   | 0.9500      |
| C(35)—C(36)   | 1.399 (2)   |
| C(35)—H(35)   | 0.9500      |
| C(36)—C(51)   | 1.494 (2)   |
| C(51)—C(52)   | 1.407 (2)   |
| C(51)—C(56)   | 1.410 (2)   |
| C(52)—C(53)   | 1.396 (2)   |
| C(52)—C(57)   | 1.513 (2)   |
| C(57)—H(57A)  | 0.9800      |
| C(57)—H(57B)  | 0.9800      |
| C(57)—H(57C)  | 0.9800      |
| C(53)—C(54)   | 1.395 (2)   |
| C(53)—H(53)   | 0.9500      |
| C(54)—C(55)   | 1.391 (2)   |
| C(54)—C(58)   | 1.512 (2)   |
| C(58)—H(58A)  | 0.9800      |
| C(58)—H(58B)  | 0.9800      |
| C(58)—H(58C)  | 0.9800      |
| C(55)—C(56)   | 1.398 (2)   |
| C(55)—H(55)   | 0.9500      |
| C(56)—C(59)   | 1.509 (2)   |
| C(59)—H(59A)  | 0.9800      |
| C(59)—H(59B)  | 0.9800      |
| C(59)—H(59C)  | 0.9800      |
| Mo(2)—N(3)    | 1.7263 (12) |
| Mo(2)—C(101)  | 1.8759 (15) |
| Mo(2)—O(2)    | 1.9168 (10) |
| Mo(2)—N(4)    | 2.0294 (13) |
| C(101)—C(102) | 1.516 (2)   |
| C(101)—H(101) | 0.947 (14)  |
| C(102)—C(105) | 1.531 (2)   |
| C(102)—C(104) | 1.539 (2)   |
| C(102)—C(103) | 1.543 (2)   |
| C(103)—H(10A) | 0.9800      |
| C(103)—H(10B) | 0.9800      |
| C(103)—H(10C) | 0.9800      |
| C(104)—H(10D) | 0.9800      |
| C(104)—H(10E) | 0.9800      |

TABLE 102C-continued

Bond lengths [Å] and angles [°] for 103d.

| | |
|---|---|
| C(104)—H(10F) | 0.9800 |
| C(105)—C(106) | 1.392 (2) |
| C(105)—C(110) | 1.396 (2) |
| C(106)—C(107) | 1.394 (3) |
| C(106)—H(106) | 0.9500 |
| C(107)—C(108) | 1.372 (3) |
| C(107)—H(107) | 0.9500 |
| C(108)—C(109) | 1.380 (3) |
| C(108)—H(108) | 0.9500 |
| C(109)—C(110) | 1.390 (2) |
| C(109)—H(109) | 0.9500 |
| C(110)—H(110) | 0.9500 |
| N(3)—C(111) | 1.3915 (18) |
| C(111)—C(112) | 1.401 (2) |
| C(111)—C(116) | 1.410 (2) |
| C(112)—C(113) | 1.388 (2) |
| C(112)—H(112) | 0.9500 |
| C(113)—C(114) | 1.391 (2) |
| C(113)—H(113) | 0.9500 |
| C(114)—C(115) | 1.388 (2) |
| C(114)—H(114) | 0.9500 |
| C(115)—C(116) | 1.400 (2) |
| C(115)—H(115) | 0.9500 |
| C(116)—C(117) | 1.517 (2) |
| C(117)—C(119) | 1.530 (2) |
| C(117)—C(118) | 1.533 (2) |
| C(117)—H(117) | 1.0000 |
| C(118)—H(11A) | 0.9800 |
| C(118)—H(11B) | 0.9800 |
| C(118)—H(11C) | 0.9800 |
| C(119)—H(11D) | 0.9800 |
| C(119)—H(11E) | 0.9800 |
| C(119)—H(11F) | 0.9800 |
| N(4)—C(123) | 1.3821 (19) |
| N(4)—C(120) | 1.387 (2) |
| C(120)—C(121) | 1.364 (2) |
| C(120)—H(120) | 0.9500 |
| C(121)—C(122) | 1.420 (2) |
| C(121)—H(121) | 0.9500 |
| C(122)—C(123) | 1.365 (2) |
| C(122)—H(122) | 0.9500 |
| C(123)—H(123) | 0.9500 |
| O(2)—C(131) | 1.3567 (16) |
| C(131)—C(132) | 1.4044 (19) |
| C(131)—C(136) | 1.4075 (19) |
| C(132)—C(133) | 1.394 (2) |
| C(132)—C(141) | 1.4966 (19) |
| C(141)—C(142) | 1.403 (2) |
| C(141)—C(146) | 1.406 (2) |
| C(142)—C(143) | 1.400 (2) |
| C(142)—C(147) | 1.509 (2) |
| C(147)—H(14A) | 0.9800 |
| C(147)—H(14B) | 0.9800 |
| C(147)—H(14C) | 0.9800 |
| C(143)—C(144) | 1.392 (2) |
| C(143)—H(143) | 0.9500 |
| C(144)—C(145) | 1.390 (2) |
| C(144)—C(148) | 1.512 (2) |
| C(148)—H(14D) | 0.9800 |
| C(148)—H(14E) | 0.9800 |
| C(148)—H(14F) | 0.9800 |
| C(145)—C(146) | 1.394 (2) |
| C(145)—H(145) | 0.9500 |
| C(146)—C(149) | 1.507 (2) |
| C(149)—H(14G) | 0.9800 |
| C(149)—H(14H) | 0.9800 |
| C(149)—H(14I) | 0.9800 |
| C(133)—C(134) | 1.390 (2) |
| C(133)—H(133) | 0.9500 |
| C(134)—C(135) | 1.389 (2) |
| C(134)—H(134) | 0.9500 |
| C(135)—C(136) | 1.396 (2) |
| C(135)—H(135) | 0.9500 |
| C(136)—C(151) | 1.494 (2) |
| C(151)—C(152) | 1.406 (2) |
| C(151)—C(156) | 1.408 (2) |
| C(152)—C(153) | 1.397 (2) |
| C(152)—C(157) | 1.510 (2) |
| C(157)—H(15A) | 0.9800 |
| C(157)—H(15B) | 0.9800 |
| C(157)—H(15C) | 0.9800 |
| C(153)—C(154) | 1.394 (2) |
| C(153)—H(153) | 0.9500 |
| C(154)—C(155) | 1.390 (2) |
| C(154)—C(158) | 1.507 (2) |
| C(158)—H(15D) | 0.9800 |
| C(158)—H(15E) | 0.9800 |
| C(158)—H(15F) | 0.9800 |
| C(155)—C(156) | 1.396 (2) |
| C(155)—H(155) | 0.9500 |
| C(156)—C(159) | 1.506 (2) |
| C(159)—H(15G) | 0.9800 |
| C(159)—H(15H) | 0.9800 |
| C(159)—H(15I) | 0.9800 |
| N(1)—Mo(1)—C(1) | 101.33 (6) |
| N(1)—Mo(1)—O(1) | 116.62 (5) |
| C(1)—Mo(1)—O(1) | 112.16 (6) |
| N(1)—Mo(1)—N(2) | 106.60 (6) |
| C(1)—Mo(1)—N(2) | 101.80 (6) |
| O(1)—Mo(1)—N(2) | 116.33 (5) |
| C(2)—C(1)—Mo(1) | 145.61 (11) |
| C(2)—C(1)—H(1) | 115.1 (12) |
| Mo(1)—C(1)—H(1) | 99.2 (12) |
| C(1)—C(2)—C(3) | 110.99 (13) |
| C(1)—C(2)—C(5) | 106.35 (13) |
| C(3)—C(2)—C(5) | 110.66 (15) |
| C(1)—C(2)—C(4) | 108.41 (14) |
| C(3)—C(2)—C(4) | 108.28 (16) |
| C(5)—C(2)—C(4) | 112.16 (14) |
| C(2)—C(3)—H(3A) | 109.5 |
| C(2)—C(3)—H(3B) | 109.5 |
| H(3A)—C(3)—H(3B) | 109.5 |
| C(2)—C(3)—H(3C) | 109.5 |
| H(3A)—C(3)—H(3C) | 109.5 |
| H(3B)—C(3)—H(3C) | 109.5 |
| C(2)—C(4)—H(4A) | 109.5 |
| C(2)—C(4)—H(4B) | 109.5 |
| H(4A)—C(4)—H(4B) | 109.5 |
| C(2)—C(4)—H(4C) | 109.5 |
| H(4A)—C(4)—H(4C) | 109.5 |
| H(4B)—C(4)—H(4C) | 109.5 |
| C(6)—C(5)—C(10) | 118.09 (17) |
| C(6)—C(5)—C(2) | 122.92 (16) |
| C(10)—C(5)—C(2) | 118.95 (15) |
| C(5)—C(6)—C(7) | 120.78 (19) |
| C(5)—C(6)—H(6) | 119.6 |
| C(7)—C(6)—H(6) | 119.6 |
| C(8)—C(7)—C(6) | 120.2 (2) |
| C(8)—C(7)—H(7) | 119.9 |
| C(6)—C(7)—H(7) | 119.9 |
| C(7)—C(8)—C(9) | 119.9 (2) |
| C(7)—C(8)—H(8) | 120.1 |
| C(9)—C(8)—H(8) | 120.1 |
| C(8)—C(9)—C(10) | 120.1 (2) |
| C(8)—C(9)—H(9) | 119.9 |
| C(10)—C(9)—H(9) | 119.9 |
| C(9)—C(10)—C(5) | 120.96 (19) |
| C(9)—C(10)—H(10) | 119.5 |
| C(5)—C(10)—H(10) | 119.5 |
| C(11)—N(1)—Mo(1) | 178.12 (11) |
| N(1)—C(11)—C(12) | 118.55 (13) |
| N(1)—C(11)—C(16) | 120.33 (13) |
| C(12)—C(11)—C(16) | 121.11 (13) |
| C(13)—C(12)—C(11) | 120.10 (15) |
| C(13)—C(12)—H(12) | 120.0 |
| C(11)—C(12)—H(12) | 120.0 |
| C(12)—C(13)—C(14) | 119.58 (15) |
| C(12)—C(13)—H(13) | 120.2 |
| C(14)—C(13)—H(13) | 120.2 |
| C(15)—C(14)—C(13) | 120.21 (14) |
| C(15)—C(14)—H(14) | 119.9 |
| C(13)—C(14)—H(14) | 119.9 |
| C(14)—C(15)—C(16) | 121.81 (15) |
| C(14)—C(15)—H(15) | 119.1 |
| C(16)—C(15)—H(15) | 119.1 |
| C(15)—C(16)—C(11) | 117.18 (13) |

TABLE 102C-continued

Bond lengths [Å] and angles [°] for 103d.

| | |
|---|---|
| C(15)—C(16)—C(17) | 121.38 (13) |
| C(11)—C(16)—C(17) | 121.42 (13) |
| C(16)—C(17)—C(18) | 110.65 (13) |
| C(16)—C(17)—C(19) | 111.67 (13) |
| C(18)—C(17)—C(19) | 110.79 (14) |
| C(16)—C(17)—H(17) | 107.9 |
| C(18)—C(17)—H(17) | 107.9 |
| C(19)—C(17)—H(17) | 107.9 |
| C(17)—C(18)—H(18A) | 109.5 |
| C(17)—C(18)—H(18B) | 109.5 |
| H(18A)—C(18)—H(18B) | 109.5 |
| C(17)—C(18)—H(18C) | 109.5 |
| H(18A)—C(18)—H(18C) | 109.5 |
| H(18B)—C(18)—H(18C) | 109.5 |
| C(17)—C(19)—H(19A) | 109.5 |
| C(17)—C(19)—H(19B) | 109.5 |
| H(19A)—C(19)—H(19B) | 109.5 |
| C(17)—C(19)—H(19C) | 109.5 |
| H(19A)—C(19)—H(19C) | 109.5 |
| H(19B)—C(19)—H(19C) | 109.5 |
| C(23)—N(2)—C(20) | 106.47 (13) |
| C(23)—N(2)—Mo(1) | 134.22 (11) |
| C(20)—N(2)—Mo(1) | 119.24 (10) |
| C(21)—C(20)—N(2) | 109.78 (15) |
| C(21)—C(20)—H(20) | 125.1 |
| N(2)—C(20)—H(20) | 125.1 |
| C(20)—C(21)—C(22) | 106.82 (15) |
| C(20)—C(21)—H(21) | 126.6 |
| C(22)—C(21)—H(21) | 126.6 |
| C(23)—C(22)—C(21) | 107.43 (15) |
| C(23)—C(22)—H(22) | 126.3 |
| C(21)—C(22)—H(22) | 126.3 |
| C(22)—C(23)—N(2) | 109.51 (15) |
| C(22)—C(23)—H(23) | 125.2 |
| N(2)—C(23)—H(23) | 125.2 |
| C(31)—O(1)—Mo(1) | 143.14 (9) |
| O(1)—C(31)—C(32) | 118.21 (12) |
| O(1)—C(31)—C(36) | 120.36 (12) |
| C(32)—C(31)—C(36) | 121.40 (13) |
| C(33)—C(32)—C(31) | 118.65 (13) |
| C(33)—C(32)—C(41) | 121.90 (13) |
| C(31)—C(32)—C(41) | 119.44 (12) |
| C(42)—C(41)—C(46) | 119.88 (14) |
| C(42)—C(41)—C(32) | 120.51 (13) |
| C(46)—C(41)—C(32) | 119.58 (13) |
| C(43)—C(42)—C(41) | 119.01 (15) |
| C(43)—C(42)—C(47) | 120.40 (15) |
| C(41)—C(42)—C(47) | 120.59 (15) |
| C(42)—C(47)—H(47A) | 109.5 |
| C(42)—C(47)—H(47B) | 109.5 |
| H(47A)—C(47)—H(47B) | 109.5 |
| C(42)—C(47)—H(47C) | 109.5 |
| H(47A)—C(47)—H(47C) | 109.5 |
| H(47B)—C(47)—H(47C) | 109.5 |
| C(44)—C(43)—C(42) | 121.95 (15) |
| C(44)—C(43)—H(43) | 119.0 |
| C(42)—C(43)—H(43) | 119.0 |
| C(43)—C(44)—C(45) | 118.09 (15) |
| C(43)—C(44)—C(48) | 121.81 (17) |
| C(45)—C(44)—C(48) | 120.10 (17) |
| C(44)—C(48)—H(48A) | 109.5 |
| C(44)—C(48)—H(48B) | 109.5 |
| H(48A)—C(48)—H(48B) | 109.5 |
| C(44)—C(48)—H(48C) | 109.5 |
| H(48A)—C(48)—H(48C) | 109.5 |
| H(48B)—C(48)—H(48C) | 109.5 |
| C(44)—C(45)—C(46) | 121.79 (15) |
| C(44)—C(45)—H(45) | 119.1 |
| C(46)—C(45)—H(45) | 119.1 |
| C(45)—C(46)—C(41) | 119.26 (14) |
| C(45)—C(46)—C(49) | 119.89 (14) |
| C(41)—C(46)—C(49) | 120.85 (13) |
| C(46)—C(49)—H(49A) | 109.5 |
| C(46)—C(49)—H(49B) | 109.5 |
| C(46)—C(49)—H(49C) | 109.5 |
| H(49A)—C(49)—H(49C) | 109.5 |
| H(49B)—C(49)—H(49C) | 109.5 |
| C(32)—C(33)—C(34) | 120.90 (14) |
| C(32)—C(33)—H(33) | 119.5 |
| C(34)—C(33)—H(33) | 119.5 |
| C(35)—C(34)—C(33) | 119.66 (14) |
| C(35)—C(34)—H(34) | 120.2 |
| C(33)—C(34)—H(34) | 120.2 |
| C(34)—C(35)—C(36) | 121.36 (14) |
| C(34)—C(35)—H(35) | 119.3 |
| C(36)—C(35)—H(35) | 119.3 |
| C(35)—C(36)—C(31) | 117.98 (13) |
| C(35)—C(36)—C(51) | 121.67 (13) |
| C(31)—C(36)—C(51) | 120.35 (13) |
| C(52)—C(51)—C(56) | 119.56 (14) |
| C(52)—C(51)—C(36) | 120.11 (13) |
| C(56)—C(51)—C(36) | 120.32 (13) |
| C(53)—C(52)—C(51) | 119.49 (14) |
| C(53)—C(52)—C(57) | 118.66 (14) |
| C(51)—C(52)—C(57) | 121.85 (13) |
| C(52)—C(57)—H(57A) | 109.5 |
| C(52)—C(57)—H(57B) | 109.5 |
| H(57A)—C(57)—H(57B) | 109.5 |
| C(52)—C(57)—H(57C) | 109.5 |
| H(57A)—C(57)—H(57C) | 109.5 |
| H(57B)—C(57)—H(57C) | 109.5 |
| C(54)—C(53)—C(52) | 121.64 (15) |
| C(54)—C(53)—H(53) | 119.2 |
| C(52)—C(53)—H(53) | 119.2 |
| C(55)—C(54)—C(53) | 118.22 (15) |
| C(55)—C(54)—C(58) | 121.29 (16) |
| C(53)—C(54)—C(58) | 120.48 (16) |
| C(54)—C(58)—H(58A) | 109.5 |
| C(54)—C(58)—H(58B) | 109.5 |
| H(58A)—C(58)—H(58B) | 109.5 |
| C(54)—C(58)—H(58C) | 109.5 |
| H(58A)—C(58)—H(58C) | 109.5 |
| H(58B)—C(58)—H(58C) | 109.5 |
| C(54)—C(55)—C(56) | 121.94 (15) |
| C(54)—C(55)—H(55) | 119.0 |
| C(56)—C(55)—H(55) | 119.0 |
| C(55)—C(56)—C(51) | 119.13 (14) |
| C(55)—C(56)—C(59) | 119.73 (14) |
| C(51)—C(56)—C(59) | 121.14 (14) |
| C(56)—C(59)—H(59A) | 109.5 |
| C(56)—C(59)—H(59B) | 109.5 |
| H(59A)—C(59)—H(59B) | 109.5 |
| C(56)—C(59)—H(59C) | 109.5 |
| H(59A)—C(59)—H(59C) | 109.5 |
| H(59B)—C(59)—H(59C) | 109.5 |
| N(3)—Mo(2)—C(101) | 100.32 (6) |
| N(3)—Mo(2)—O(2) | 116.09 (5) |
| C(101)—Mo(2)—O(2) | 113.60 (6) |
| N(3)—Mo(2)—N(4) | 106.38 (6) |
| C(101)—Mo(2)—N(4) | 100.26 (6) |
| O(2)—Mo(2)—N(4) | 117.74 (5) |
| C(102)—C(101)—Mo(2) | 143.31 (11) |
| C(102)—C(101)—H(101) | 115.4 (12) |
| Mo(2)—C(101)—H(101) | 100.7 (12) |
| C(101)—C(102)—C(105) | 108.34 (12) |
| C(101)—C(102)—C(104) | 107.58 (13) |
| C(105)—C(102)—C(104) | 112.67 (15) |
| C(101)—C(102)—C(103) | 110.48 (14) |
| C(105)—C(102)—C(103) | 109.36 (13) |
| C(104)—C(102)—C(103) | 108.40 (15) |
| C(102)—C(103)—H(10A) | 109.5 |
| C(102)—C(103)—H(10B) | 109.5 |
| H(10A)—C(103)—H(10B) | 109.5 |
| C(102)—C(103)—H(10C) | 109.5 |
| H(10A)—C(103)—H(10C) | 109.5 |
| H(10B)—C(103)—H(10C) | 109.5 |
| C(102)—C(104)—H(10D) | 109.5 |
| C(102)—C(104)—H(10E) | 109.5 |
| H(10D)—C(104)—H(10E) | 109.5 |
| C(102)—C(104)—H(10F) | 109.5 |
| H(10D)—C(104)—H(10F) | 109.5 |
| H(10E)—C(104)—H(10F) | 109.5 |
| C(106)—C(105)—C(110) | 117.64 (15) |
| C(106)—C(105)—C(102) | 123.29 (15) |
| C(110)—C(105)—C(102) | 119.05 (14) |

TABLE 102C-continued

Bond lengths [Å] and angles [°] for 103d.

| | |
|---|---|
| C(105)—C(106)—C(107) | 120.75 (17) |
| C(105)—C(106)—H(106) | 119.6 |
| C(107)—C(106)—H(106) | 119.6 |
| C(108)—C(107)—C(106) | 120.65 (18) |
| C(108)—C(107)—H(107) | 119.7 |
| C(106)—C(107)—H(107) | 119.7 |
| C(107)—C(108)—C(109) | 119.66 (17) |
| C(107)—C(108)—H(108) | 120.2 |
| C(109)—C(108)—H(108) | 120.2 |
| C(108)—C(109)—C(110) | 119.93 (18) |
| C(108)—C(109)—H(109) | 120.0 |
| C(110)—C(109)—H(109) | 120.0 |
| C(109)—C(110)—C(105) | 121.37 (17) |
| C(109)—C(110)—H(110) | 119.3 |
| C(105)—C(110)—H(110) | 119.3 |
| C(111)—N(3)—Mo(2) | 177.45 (11) |
| N(3)—C(111)—C(112) | 118.73 (14) |
| N(3)—C(111)—C(116) | 119.94 (13) |
| C(112)—C(111)—C(116) | 121.32 (14) |
| C(113)—C(112)—C(111) | 119.99 (15) |
| C(113)—C(112)—H(112) | 120.0 |
| C(111)—C(112)—H(112) | 120.0 |
| C(112)—C(113)—C(114) | 119.57 (15) |
| C(112)—C(113)—H(113) | 120.2 |
| C(114)—C(113)—H(113) | 120.2 |
| C(115)—C(114)—C(113) | 120.23 (15) |
| C(115)—C(114)—H(114) | 119.9 |
| C(113)—C(114)—H(114) | 119.9 |
| C(114)—C(115)—C(116) | 121.91 (15) |
| C(114)—C(115)—H(115) | 119.0 |
| C(116)—C(115)—H(115) | 119.0 |
| C(115)—C(116)—C(111) | 116.98 (14) |
| C(115)—C(116)—C(117) | 121.18 (14) |
| C(111)—C(116)—C(117) | 121.82 (13) |
| C(116)—C(117)—C(119) | 110.53 (13) |
| C(116)—C(117)—C(118) | 111.71 (14) |
| C(119)—C(117)—C(118) | 111.20 (14) |
| C(116)—C(117)—H(117) | 107.7 |
| C(119)—C(117)—H(117) | 107.7 |
| C(118)—C(117)—H(117) | 107.7 |
| C(117)—C(118)—H(11A) | 109.5 |
| C(117)—C(118)—H(11B) | 109.5 |
| H(11A)—C(118)—H(11B) | 109.5 |
| C(117)—C(118)—H(11C) | 109.5 |
| H(11A)—C(118)—H(11C) | 109.5 |
| H(11B)—C(118)—H(11C) | 109.5 |
| C(117)—C(119)—H(11D) | 109.5 |
| C(117)—C(119)—H(11E) | 109.5 |
| H(11D)—C(119)—H(11E) | 109.5 |
| C(117)—C(119)—H(11F) | 109.5 |
| H(11D)—C(119)—H(11F) | 109.5 |
| H(11E)—C(119)—H(11F) | 109.5 |
| C(123)—N(4)—C(120) | 106.31 (13) |
| C(123)—N(4)—Mo(2) | 132.95 (11) |
| C(120)—N(4)—Mo(2) | 119.92 (10) |
| C(121)—C(120)—N(4) | 110.04 (14) |
| C(121)—C(120)—H(120) | 125.0 |
| N(4)—C(120)—H(120) | 125.0 |
| C(120)—C(121)—C(122) | 106.64 (15) |
| C(120)—C(121)—H(121) | 126.7 |
| C(122)—C(121)—H(121) | 126.7 |
| C(123)—C(122)—C(121) | 107.23 (15) |
| C(123)—C(122)—H(122) | 126.4 |
| C(121)—C(122)—H(122) | 126.4 |
| C(122)—C(123)—N(4) | 109.77 (14) |
| C(122)—C(123)—H(123) | 125.1 |
| N(4)—C(123)—H(123) | 125.1 |
| C(131)—O(2)—Mo(2) | 150.15 (9) |
| O(2)—C(131)—C(132) | 118.47 (12) |
| O(2)—C(131)—C(136) | 120.21 (12) |
| C(132)—C(131)—C(136) | 121.27 (13) |
| C(133)—C(132)—C(131) | 118.39 (13) |
| C(133)—C(132)—C(141) | 120.68 (13) |
| C(131)—C(132)—C(141) | 120.90 (12) |
| C(142)—C(141)—C(146) | 119.89 (13) |
| C(142)—C(141)—C(132) | 120.90 (13) |
| C(146)—C(141)—C(132) | 119.20 (13) |
| C(143)—C(142)—C(141) | 119.22 (14) |
| C(143)—C(142)—C(147) | 119.76 (14) |
| C(141)—C(142)—C(147) | 121.02 (14) |
| C(142)—C(147)—H(14A) | 109.5 |
| C(142)—C(147)—H(14B) | 109.5 |
| H(14A)—C(147)—H(14B) | 109.5 |
| C(142)—C(147)—H(14C) | 109.5 |
| H(14A)—C(147)—H(14C) | 109.5 |
| H(14B)—C(147)—H(14C) | 109.5 |
| C(144)—C(143)—C(142) | 121.64 (14) |
| C(144)—C(143)—H(143) | 119.2 |
| C(142)—C(143)—H(143) | 119.2 |
| C(145)—C(144)—C(143) | 118.11 (14) |
| C(145)—C(144)—C(148) | 120.21 (15) |
| C(143)—C(144)—C(148) | 121.68 (15) |
| C(144)—C(148)—H(14D) | 109.5 |
| C(144)—C(148)—H(14E) | 109.5 |
| H(14D)—C(148)—H(14E) | 109.5 |
| C(144)—C(148)—H(14F) | 109.5 |
| H(14D)—C(148)—H(14F) | 109.5 |
| H(14E)—C(148)—H(14F) | 109.5 |
| C(144)—C(145)—C(146) | 122.09 (15) |
| C(144)—C(145)—H(145) | 119.0 |
| C(146)—C(145)—H(145) | 119.0 |
| C(145)—C(146)—C(141) | 119.04 (14) |
| C(145)—C(146)—C(149) | 120.03 (14) |
| C(141)—C(146)—C(149) | 120.90 (13) |
| C(146)—C(149)—H(14G) | 109.5 |
| C(146)—C(149)—H(14H) | 109.5 |
| H(14G)—C(149)—H(14H) | 109.5 |
| C(146)—C(149)—H(14I) | 109.5 |
| H(14G)—C(149)—H(14I) | 109.5 |
| H(14H)—C(149)—H(14I) | 109.5 |
| C(134)—C(133)—C(132) | 121.33 (14) |
| C(134)—C(133)—H(133) | 119.3 |
| C(132)—C(133)—H(133) | 119.3 |
| C(135)—C(134)—C(133) | 119.41 (14) |
| C(135)—C(134)—H(134) | 120.3 |
| C(133)—C(134)—H(134) | 120.3 |
| C(134)—C(135)—C(136) | 121.34 (14) |
| C(134)—C(135)—H(135) | 119.3 |
| C(136)—C(135)—H(135) | 119.3 |
| C(135)—C(136)—C(131) | 118.25 (13) |
| C(135)—C(136)—C(151) | 121.34 (13) |
| C(131)—C(136)—C(151) | 120.40 (13) |
| C(152)—C(151)—C(156) | 119.67 (14) |
| C(152)—C(151)—C(136) | 119.92 (14) |
| C(156)—C(151)—C(136) | 120.40 (14) |
| C(153)—C(152)—C(151) | 119.50 (15) |
| C(153)—C(152)—C(157) | 118.82 (14) |
| C(151)—C(152)—C(157) | 121.66 (14) |
| C(152)—C(157)—H(15A) | 109.5 |
| C(152)—C(157)—H(15B) | 109.5 |
| H(15A)—C(157)—H(15B) | 109.5 |
| C(152)—C(157)—H(15C) | 109.5 |
| H(15A)—C(157)—H(15C) | 109.5 |
| H(15B)—C(157)—H(15C) | 109.5 |
| C(154)—C(153)—C(152) | 121.50 (15) |
| C(154)—C(153)—H(153) | 119.3 |
| C(152)—C(153)—H(153) | 119.3 |
| C(155)—C(154)—C(153) | 118.18 (14) |
| C(155)—C(154)—C(158) | 120.95 (16) |
| C(153)—C(154)—C(158) | 120.86 (16) |
| C(154)—C(158)—H(15D) | 109.5 |
| C(154)—C(158)—H(15E) | 109.5 |
| H(15D)—C(158)—H(15E) | 109.5 |
| C(154)—C(158)—H(15F) | 109.5 |
| H(15D)—C(158)—H(15F) | 109.5 |
| H(15E)—C(158)—H(15F) | 109.5 |
| C(154)—C(155)—C(156) | 122.17 (15) |
| C(154)—C(155)—H(155) | 118.9 |
| C(156)—C(155)—H(155) | 118.9 |
| C(155)—C(156)—C(151) | 118.97 (15) |
| C(155)—C(156)—C(159) | 119.96 (15) |
| C(151)—C(156)—C(159) | 121.06 (14) |
| C(156)—C(159)—H(15G) | 109.5 |
| C(156)—C(159)—H(15H) | 109.5 |
| H(15G)—C(159)—H(15H) | 109.5 |
| C(156)—C(159)—H(15I) | 109.5 |

TABLE 102C-continued

Bond lengths [Å] and angles [°] for 103d.

| | |
|---|---|
| H(15G)—C(159)—H(15I) | 109.5 |
| H(15H)—C(159)—H(15I) | 109.5 |

Symmetry transformations used to generate equivalent atoms:

TABLE 102D

Anisotropic displacement parameters (Å$^2$ × 10$^3$) for 103d. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| Mo(1) | 17 (1) | 13 (1) | 18 (1) | 1 (1) | 3 (1) | 6 (1) |
| C(1) | 23 (1) | 20 (1) | 22 (1) | −1 (1) | 1 (1) | 10 (1) |
| C(2) | 27 (1) | 24 (1) | 25 (1) | −2 (1) | −4 (1) | 13 (1) |
| C(3) | 44 (1) | 45 (1) | 37 (1) | −15 (1) | −13 (1) | 34 (1) |
| C(4) | 38 (1) | 31 (1) | 41 (1) | 11 (1) | −7 (1) | 10 (1) |
| C(5) | 20 (1) | 28 (1) | 25 (1) | −1 (1) | 0 (1) | 12 (1) |
| C(6) | 31 (1) | 37 (1) | 26 (1) | −3 (1) | −1 (1) | 16 (1) |
| C(7) | 37 (1) | 44 (1) | 41 (1) | −16 (1) | −11 (1) | 19 (1) |
| C(8) | 30 (1) | 34 (1) | 70 (2) | −8 (1) | −13 (1) | 8 (1) |
| C(9) | 28 (1) | 46 (1) | 64 (2) | 16 (1) | 4 (1) | 4 (1) |
| C(10) | 27 (1) | 44 (1) | 32 (1) | 7 (1) | 4 (1) | 11 (1) |
| N(1) | 23 (1) | 16 (1) | 19 (1) | 2 (1) | 4 (1) | 9 (1) |
| C(11) | 21 (1) | 16 (1) | 18 (1) | 0 (1) | 1 (1) | 9 (1) |
| C(12) | 32 (1) | 18 (1) | 26 (1) | 4 (1) | 8 (1) | 10 (1) |
| C(13) | 39 (1) | 16 (1) | 30 (1) | 2 (1) | 4 (1) | 13 (1) |
| C(14) | 32 (1) | 21 (1) | 26 (1) | −3 (1) | 2 (1) | 15 (1) |
| C(15) | 23 (1) | 24 (1) | 22 (1) | −1 (1) | 3 (1) | 11 (1) |
| C(16) | 18 (1) | 18 (1) | 20 (1) | 1 (1) | 1 (1) | 8 (1) |
| C(17) | 23 (1) | 18 (1) | 25 (1) | 3 (1) | 7 (1) | 8 (1) |
| C(18) | 27 (1) | 27 (1) | 34 (1) | 13 (1) | 6 (1) | 8 (1) |
| C(19) | 23 (1) | 25 (1) | 42 (1) | 3 (1) | 1 (1) | 3 (1) |
| N(2) | 19 (1) | 15 (1) | 25 (1) | 1 (1) | 2 (1) | 6 (1) |
| C(20) | 27 (1) | 18 (1) | 27 (1) | 2 (1) | 0 (1) | 8 (1) |
| C(21) | 37 (1) | 22 (1) | 32 (1) | 8 (1) | 6 (1) | 11 (1) |
| C(22) | 27 (1) | 20 (1) | 46 (1) | 8 (1) | 6 (1) | 2 (1) |
| C(23) | 21 (1) | 18 (1) | 36 (1) | 2 (1) | 0 (1) | 2 (1) |
| O(1) | 18 (1) | 16 (1) | 18 (1) | 1 (1) | 4 (1) | 5 (1) |
| C(31) | 16 (1) | 16 (1) | 16 (1) | 2 (1) | 1 (1) | 6 (1) |
| C(32) | 16 (1) | 16 (1) | 17 (1) | 2 (1) | 0 (1) | 5 (1) |
| C(41) | 18 (1) | 14 (1) | 19 (1) | 2 (1) | 4 (1) | 4 (1) |
| C(42) | 26 (1) | 19 (1) | 28 (1) | 4 (1) | 2 (1) | 9 (1) |
| C(47) | 44 (1) | 35 (1) | 44 (1) | 3 (1) | −12 (1) | 23 (1) |
| C(43) | 35 (1) | 18 (1) | 37 (1) | 6 (1) | 9 (1) | 14 (1) |
| C(44) | 36 (1) | 15 (1) | 29 (1) | 1 (1) | 12 (1) | 6 (1) |
| C(48) | 69 (2) | 24 (1) | 41 (1) | −5 (1) | 15 (1) | 17 (1) |
| C(45) | 26 (1) | 20 (1) | 21 (1) | 0 (1) | 5 (1) | 4 (1) |
| C(46) | 18 (1) | 18 (1) | 20 (1) | 1 (1) | 4 (1) | 5 (1) |
| C(49) | 31 (1) | 35 (1) | 25 (1) | −4 (1) | −6 (1) | 18 (1) |
| C(33) | 19 (1) | 20 (1) | 20 (1) | 3 (1) | 2 (1) | 4 (1) |
| C(34) | 22 (1) | 27 (1) | 19 (1) | 1 (1) | 6 (1) | 7 (1) |
| C(35) | 24 (1) | 23 (1) | 20 (1) | −2 (1) | 3 (1) | 9 (1) |
| C(36) | 18 (1) | 17 (1) | 18 (1) | 0 (1) | 1 (1) | 6 (1) |
| C(51) | 21 (1) | 14 (1) | 20 (1) | 0 (1) | 4 (1) | 7 (1) |
| C(52) | 26 (1) | 15 (1) | 18 (1) | −1 (1) | 3 (1) | 6 (1) |
| C(57) | 29 (1) | 20 (1) | 19 (1) | 0 (1) | 0 (1) | 6 (1) |
| C(53) | 29 (1) | 17 (1) | 22 (1) | −2 (1) | 1 (1) | 3 (1) |
| C(54) | 34 (1) | 14 (1) | 24 (1) | 0 (1) | 4 (1) | 4 (1) |
| C(58) | 51 (1) | 18 (1) | 34 (1) | 4 (1) | 1 (1) | −2 (1) |
| C(55) | 33 (1) | 18 (1) | 24 (1) | 4 (1) | 4 (1) | 12 (1) |
| C(56) | 24 (1) | 18 (1) | 23 (1) | 0 (1) | 2 (1) | 10 (1) |
| C(59) | 28 (1) | 26 (1) | 29 (1) | 5 (1) | −3 (1) | 12 (1) |
| Mo(2) | 14 (1) | 14 (1) | 19 (1) | 1 (1) | 3 (1) | 5 (1) |
| C(101) | 17 (1) | 17 (1) | 25 (1) | 0 (1) | 3 (1) | 6 (1) |
| C(102) | 19 (1) | 19 (1) | 33 (1) | −1 (1) | −2 (1) | 8 (1) |
| C(103) | 23 (1) | 37 (1) | 47 (1) | −17 (1) | −2 (1) | 15 (1) |
| C(104) | 32 (1) | 22 (1) | 68 (1) | 12 (1) | −13 (1) | 6 (1) |
| C(105) | 17 (1) | 22 (1) | 24 (1) | 0 (1) | 1 (1) | 8 (1) |
| C(106) | 35 (1) | 34 (1) | 26 (1) | 6 (1) | 3 (1) | 19 (1) |
| C(107) | 47 (1) | 51 (1) | 25 (1) | −8 (1) | −8 (1) | 31 (1) |
| C(108) | 29 (1) | 37 (1) | 45 (1) | −19 (1) | −9 (1) | 15 (1) |
| C(109) | 26 (1) | 26 (1) | 45 (1) | −2 (1) | 6 (1) | 1 (1) |
| C(110) | 27 (1) | 27 (1) | 25 (1) | 2 (1) | 4 (1) | 4 (1) |
| N(3) | 18 (1) | 19 (1) | 20 (1) | 1 (1) | 3 (1) | 7 (1) |
| C(111) | 16 (1) | 19 (1) | 21 (1) | −1 (1) | 1 (1) | 7 (1) |
| C(112) | 23 (1) | 22 (1) | 26 (1) | 2 (1) | 4 (1) | 8 (1) |
| C(113) | 29 (1) | 19 (1) | 31 (1) | 0 (1) | 0 (1) | 10 (1) |
| C(114) | 29 (1) | 27 (1) | 27 (1) | −6 (1) | −2 (1) | 17 (1) |
| C(115) | 25 (1) | 31 (1) | 22 (1) | −2 (1) | 2 (1) | 16 (1) |
| C(116) | 17 (1) | 23 (1) | 21 (1) | 0 (1) | 1 (1) | 8 (1) |
| C(117) | 23 (1) | 24 (1) | 24 (1) | 4 (1) | 6 (1) | 9 (1) |
| C(118) | 24 (1) | 34 (1) | 30 (1) | 4 (1) | 3 (1) | 4 (1) |
| C(119) | 23 (1) | 34 (1) | 33 (1) | 14 (1) | 5 (1) | 10 (1) |
| N(4) | 17 (1) | 18 (1) | 25 (1) | 3 (1) | 3 (1) | 6 (1) |
| C(120) | 20 (1) | 19 (1) | 31 (1) | 3 (1) | −2 (1) | 5 (1) |
| C(121) | 28 (1) | 25 (1) | 34 (1) | 9 (1) | −4 (1) | 6 (1) |
| C(122) | 24 (1) | 22 (1) | 40 (1) | 11 (1) | −1 (1) | 1 (1) |
| C(123) | 18 (1) | 19 (1) | 32 (1) | 3 (1) | 0 (1) | 4 (1) |
| O(2) | 16 (1) | 18 (1) | 20 (1) | 2 (1) | 5 (1) | 5 (1) |
| C(131) | 13 (1) | 17 (1) | 17 (1) | 2 (1) | 3 (1) | 4 (1) |
| C(132) | 16 (1) | 16 (1) | 18 (1) | 2 (1) | 0 (1) | 4 (1) |
| C(141) | 16 (1) | 14 (1) | 19 (1) | 2 (1) | 4 (1) | 2 (1) |
| C(142) | 20 (1) | 18 (1) | 24 (1) | 4 (1) | 2 (1) | 5 (1) |
| C(147) | 27 (1) | 28 (1) | 36 (1) | 1 (1) | −8 (1) | 12 (1) |
| C(143) | 25 (1) | 19 (1) | 30 (1) | 4 (1) | 5 (1) | 10 (1) |
| C(144) | 28 (1) | 17 (1) | 24 (1) | 1 (1) | 6 (1) | 6 (1) |
| C(148) | 41 (1) | 22 (1) | 34 (1) | −5 (1) | 4 (1) | 12 (1) |
| C(145) | 22 (1) | 19 (1) | 22 (1) | 0 (1) | 1 (1) | 4 (1) |
| C(146) | 16 (1) | 16 (1) | 21 (1) | 3 (1) | 4 (1) | 3 (1) |
| C(149) | 21 (1) | 23 (1) | 26 (1) | 1 (1) | −1 (1) | 8 (1) |
| C(133) | 18 (1) | 20 (1) | 21 (1) | 3 (1) | 4 (1) | 1 (1) |
| C(134) | 21 (1) | 26 (1) | 21 (1) | 1 (1) | 7 (1) | 5 (1) |
| C(135) | 22 (1) | 20 (1) | 23 (1) | −3 (1) | 6 (1) | 6 (1) |
| C(136) | 17 (1) | 16 (1) | 21 (1) | 1 (1) | 2 (1) | 5 (1) |
| C(151) | 19 (1) | 14 (1) | 24 (1) | 0 (1) | 6 (1) | 5 (1) |
| C(152) | 23 (1) | 17 (1) | 21 (1) | −1 (1) | 4 (1) | 4 (1) |
| C(157) | 28 (1) | 27 (1) | 25 (1) | 4 (1) | 0 (1) | 1 (1) |
| C(153) | 22 (1) | 19 (1) | 24 (1) | −3 (1) | 3 (1) | 0 (1) |
| C(154) | 28 (1) | 17 (1) | 29 (1) | 1 (1) | 10 (1) | 2 (1) |
| C(158) | 37 (1) | 25 (1) | 37 (1) | 6 (1) | 8 (1) | −3 (1) |
| C(155) | 29 (1) | 19 (1) | 29 (1) | 6 (1) | 8 (1) | 9 (1) |
| C(156) | 22 (1) | 18 (1) | 28 (1) | 3 (1) | 5 (1) | 9 (1) |
| C(159) | 25 (1) | 29 (1) | 36 (1) | 9 (1) | 0 (1) | 10 (1) |

TABLE 102E

Hydrogen coordinates (×10$^4$) and isotropic displacement parameters (Å$^2$ × 10$^3$) for 103d.

| | x | y | z | U(eq) |
|---|---|---|---|---|
| H(1) | 1294 (19) | 6799 (17) | 6715 (5) | 25 |
| H(3A) | 2623 | 4419 | 6368 | 58 |
| H(3B) | 4067 | 5090 | 6597 | 58 |
| H(3C) | 3632 | 5736 | 6253 | 58 |
| H(4A) | 1669 | 5470 | 7252 | 56 |
| H(4B) | 2809 | 4880 | 7210 | 56 |
| H(4C) | 1423 | 4267 | 6949 | 56 |
| H(6) | 3563 | 6975 | 7501 | 37 |
| H(7) | 5141 | 8948 | 7738 | 49 |
| H(8) | 6318 | 10338 | 7314 | 56 |
| H(9) | 5936 | 9764 | 6649 | 58 |
| H(10) | 4359 | 7807 | 6410 | 42 |
| H(12) | 56 | 2441 | 5886 | 30 |
| H(13) | 649 | 935 | 5523 | 33 |
| H(14) | 2088 | 1537 | 5023 | 31 |
| H(15) | 2944 | 3621 | 4893 | 26 |
| H(17) | 2338 | 6194 | 5428 | 26 |
| H(18A) | 2273 | 5345 | 4627 | 44 |
| H(18B) | 2306 | 6703 | 4789 | 44 |
| H(18C) | 1011 | 5477 | 4834 | 44 |
| H(19A) | 4521 | 6099 | 5482 | 48 |
| H(19B) | 4473 | 7097 | 5194 | 48 |
| H(19C) | 4440 | 5745 | 5026 | 48 |
| H(20) | −55 | 7020 | 5373 | 29 |

TABLE 102E-continued

Hydrogen coordinates (×10⁴) and isotropic displacement parameters ($Å^2 \times 10^3$) for 103d.

| | x | y | z | U(eq) |
|---|---|---|---|---|
| H(21) | 1224 | 9108 | 5165 | 35 |
| H(22) | 3067 | 10276 | 5693 | 39 |
| H(23) | 2851 | 8876 | 6210 | 31 |
| H(47A) | −1091 | 2047 | 6681 | 59 |
| H(47B) | −2119 | 2444 | 6935 | 59 |
| H(47C) | −997 | 3476 | 6723 | 59 |
| H(43) | −2224 | 788 | 6119 | 34 |
| H(48A) | −4634 | −688 | 5451 | 67 |
| H(48B) | −3059 | −413 | 5512 | 67 |
| H(48C) | −3598 | 247 | 5193 | 67 |
| H(45) | −4872 | 1657 | 5464 | 29 |
| H(49A) | −5438 | 3397 | 5627 | 44 |
| H(49B) | −4387 | 4521 | 5911 | 44 |
| H(49C) | −5668 | 3520 | 6078 | 44 |
| H(33) | −4673 | 3250 | 6920 | 25 |
| H(34) | −4479 | 5000 | 7348 | 28 |
| H(35) | −2918 | 6974 | 7258 | 27 |
| H(57A) | 1227 | 7840 | 7415 | 35 |
| H(57B) | −142 | 6678 | 7287 | 35 |
| H(57C) | −166 | 7851 | 7565 | 35 |
| H(53) | 1800 | 9744 | 7117 | 29 |
| H(58A) | 1948 | 11914 | 6787 | 58 |
| H(58B) | 1749 | 11559 | 6329 | 58 |
| H(58C) | 2834 | 11221 | 6577 | 58 |
| H(55) | −344 | 9911 | 6161 | 29 |
| H(59A) | −2426 | 8372 | 5955 | 41 |
| H(59B) | −3239 | 7467 | 6260 | 41 |
| H(59C) | −2330 | 7019 | 5972 | 41 |
| H(101) | 2913 (19) | 2528 (17) | 8374 (5) | 24 |
| H(10A) | 388 | 2805 | 8895 | 54 |
| H(10B) | −212 | 3610 | 8644 | 54 |
| H(10C) | 1168 | 4290 | 8904 | 54 |
| H(10D) | 2452 | 5216 | 8371 | 63 |
| H(10E) | 1107 | 4669 | 8091 | 63 |
| H(10F) | 2413 | 4388 | 7975 | 63 |
| H(106) | 702 | 2906 | 7622 | 36 |
| H(107) | −658 | 1082 | 7241 | 46 |
| H(108) | −1671 | −777 | 7516 | 45 |
| H(109) | −1297 | −835 | 8176 | 42 |
| H(110) | 64 | 977 | 8560 | 34 |
| H(112) | 4254 | 7111 | 9069 | 28 |
| H(113) | 3663 | 8633 | 9425 | 32 |
| H(114) | 2474 | 8122 | 9978 | 32 |
| H(115) | 1888 | 6120 | 10174 | 30 |
| H(117) | 2619 | 3550 | 9684 | 28 |
| H(11A) | 548 | 3923 | 10120 | 47 |
| H(11B) | 637 | 2587 | 9989 | 47 |
| H(11C) | 346 | 3404 | 9672 | 47 |
| H(11D) | 4110 | 4596 | 10232 | 45 |
| H(11E) | 2982 | 3322 | 10335 | 45 |
| H(11F) | 2865 | 4647 | 10465 | 45 |
| H(120) | 5212 | 2809 | 9638 | 29 |
| H(121) | 4065 | 965 | 9989 | 35 |
| H(122) | 1812 | −276 | 9615 | 36 |
| H(123) | 1687 | 818 | 9041 | 29 |
| H(14A) | 5276 | 7327 | 8287 | 45 |
| H(14B) | 5170 | 5905 | 8300 | 45 |
| H(14C) | 6130 | 6768 | 8010 | 45 |
| H(143) | 6573 | 8737 | 8794 | 29 |
| H(14D) | 8866 | 10645 | 9231 | 50 |
| H(14E) | 9079 | 9938 | 9590 | 50 |
| H(14F) | 7610 | 9900 | 9465 | 50 |
| H(145) | 9782 | 8340 | 9326 | 27 |
| H(14G) | 10414 | 6637 | 9170 | 35 |
| H(14H) | 10154 | 6101 | 8723 | 35 |
| H(14I) | 9172 | 5363 | 9032 | 35 |
| H(133) | 9076 | 6173 | 8001 | 25 |
| H(134) | 8836 | 4359 | 7599 | 28 |
| H(135) | 7196 | 2440 | 7707 | 27 |
| H(15A) | 4426 | 1834 | 7417 | 43 |
| H(15B) | 4373 | 2968 | 7709 | 43 |
| H(15C) | 3018 | 1805 | 7567 | 43 |
| H(153) | 2360 | −52 | 7876 | 29 |
| H(15D) | 2137 | −2270 | 8232 | 55 |
| H(15E) | 1292 | −1472 | 8404 | 55 |
| H(15F) | 2305 | −1805 | 8684 | 55 |
| H(155) | 4531 | −340 | 8807 | 30 |
| H(15G) | 6549 | 1266 | 9046 | 44 |
| H(15H) | 6953 | 2615 | 8888 | 44 |
| H(15I) | 7466 | 1580 | 8687 | 44 |

TABLE 103A

Crystal data and structure refinement for 104a.

| | |
|---|---|
| Identification code | C38H44MoN4 |
| Empirical formula | C38H44MoN4 |
| Formula weight | 652.71 |
| Temperature | 100(2) K |
| Wavelength | 0.71073 Å |
| Crystal system | Monoclinic |
| Space group | P2(1)/n |
| Unit cell dimensions | a = 11.2310(10) Å    α = 90°. |
| | b = 18.7037(18) Å    β = 97.074(6)°. |
| | c = 15.8997(15) Å    γ = 90°. |
| Volume | 3314.5(5) $Å^3$ |
| Z | 4 |
| Density (calculated) | 1.308 $Mg/m^3$ |
| Absorption coefficient | 0.428 $mm^{-1}$ |
| F(000) | 1368 |
| Crystal size | 0.13 × 0.10 × 0.07 $mm^3$ |
| Theta range for data collection | 1.69 to 28.00°. |
| Index ranges | −14 <= h <= 14, −24 <= k <= 22, −21 <= l <= 20 |
| Reflections collected | 58456 |
| Independent reflections | 8003 [R(int) = 0.0972] |
| Completeness to theta = 28.00° | 100.0% |
| Absorption correction | Semi-empirical from equivalents |
| Max. and min. transmission | 0.9707 and 0.9465 |
| Refinement method | Full-matrix least-squares on $F^2$ |
| Data/restraints/parameters | 8003/0/390 |
| Goodness-of-fit on $F^2$ | 1.018 |
| Final R indices [I > 2sigma(I)] | R1 = 0.0475, wR2 = 0.1082 |
| R indices (all data) | R1 = 0.0858, wR2 = 0.1274 |
| Extinction coefficient | na |
| Largest diff. peak and hole | 1.474 and −1.162 e · $Å^{-3}$ |

TABLE 103B

Atomic coordinates (×10⁴) and equivalent isotropic displacement parameters ($Å^2 \times 10^3$) for 104a. U(eq) is defined as one third of the trace of the orthogonalized $U^{ij}$ tensor.

| | x | y | z | U(eq) |
|---|---|---|---|---|
| Mo(1) | −233(1) | 8156(1) | 7506(1) | 18(1) |
| N(1) | −945(2) | 9144(1) | 6709(2) | 23(1) |
| N(2) | 185(2) | 8028(1) | 6193(2) | 21(1) |
| N(3) | −497(2) | 7222(1) | 7702(2) | 19(1) |
| N(4) | −1201(2) | 8597(1) | 8427(2) | 20(1) |
| C(1) | −1487(3) | 9708(2) | 7018(2) | 29(1) |
| C(2) | −2005(3) | 10253(2) | 6510(3) | 34(1) |
| C(3) | −1987(3) | 10206(2) | 5646(2) | 38(1) |
| C(4) | −1420(3) | 9637(2) | 5318(2) | 31(1) |
| C(5) | −888(3) | 9112(2) | 5858(2) | 25(1) |
| C(6) | −227(3) | 8498(2) | 5577(2) | 22(1) |
| C(7) | 7(3) | 8406(2) | 4746(2) | 30(1) |
| C(8) | 690(3) | 7833(2) | 4543(2) | 34(1) |
| C(9) | 1149(3) | 7366(2) | 5181(2) | 29(1) |
| C(10) | 869(3) | 7476(2) | 5985(2) | 25(1) |
| C(11) | −283(3) | 6528(2) | 7987(2) | 18(1) |
| C(12) | −442(3) | 5955(2) | 7406(2) | 22(1) |
| C(13) | −238(3) | 5270(2) | 7696(2) | 25(1) |
| C(14) | 104(3) | 5121(2) | 8550(2) | 25(1) |
| C(15) | 242(3) | 5684(2) | 9125(2) | 24(1) |

TABLE 103B-continued

Atomic coordinates (×10$^4$) and equivalent isotropic displacement parameters (Å$^2$ × 10$^3$) for 104a.
U(eq) is defined as one third of the trace of the orthogonalized U$^{ij}$ tensor.

|       | x       | y       | z        | U(eq) |
|-------|---------|---------|----------|-------|
| C(16) | 53(3)   | 6389(2) | 8865(2)  | 21(1) |
| C(17) | −847(3) | 6101(2) | 6480(2)  | 24(1) |
| C(18) | −177(4) | 5663(2) | 5881(2)  | 32(1) |
| C(19) | −2208(3)| 5995(2) | 6298(2)  | 35(1) |
| C(20) | 142(3)  | 7008(2) | 9486(2)  | 21(1) |
| C(21) | −1108(3)| 7174(2) | 9734(2)  | 28(1) |
| C(22) | 1038(3) | 6884(2) | 10275(2) | 32(1) |
| C(23) | −2452(3)| 8560(2) | 8299(2)  | 22(1) |
| C(24) | −2913(3)| 8931(2) | 8927(2)  | 24(1) |
| C(25) | −1930(3)| 9197(2) | 9481(2)  | 26(1) |
| C(26) | −905(3) | 8991(2) | 9164(2)  | 22(1) |
| C(27) | −3102(3)| 8162(2) | 7573(2)  | 30(1) |
| C(28) | 367(3)  | 9119(2) | 9523(2)  | 31(1) |
| C(29) | 1297(3) | 8334(2) | 7827(2)  | 23(1) |
| C(30) | 2651(3) | 8271(2) | 7939(2)  | 27(1) |
| C(31) | 3018(3) | 7515(2) | 7702(2)  | 24(1) |
| C(32) | 3770(3) | 7375(2) | 7087(2)  | 32(1) |
| C(33) | 4066(4) | 6684(2) | 6880(2)  | 38(1) |
| C(34) | 3585(4) | 6111(2) | 7268(3)  | 39(1) |
| C(35) | 2819(3) | 6234(2) | 7877(2)  | 30(1) |
| C(36) | 2558(3) | 6929(2) | 8094(2)  | 25(1) |
| C(37) | 3110(3) | 8849(2) | 7365(3)  | 43(1) |
| C(38) | 3158(3) | 8424(2) | 8870(2)  | 39(1) |

TABLE 103C

Bond lengths [Å] and angles [°] for 104a.

| Mo(1)—C(29) | 1.764(3) |
|---|---|
| Mo(1)—N(3) | 1.804(3) |
| Mo(1)—N(4) | 2.098(3) |
| Mo(1)—N(2) | 2.209(3) |
| Mo(1)—N(1) | 2.326(3) |
| N(1)—C(1) | 1.341(4) |
| N(1)—C(5) | 1.363(4) |
| N(2)—C(10) | 1.352(4) |
| N(2)—C(6) | 1.355(4) |
| N(3)—C(11) | 1.386(4) |
| N(4)—C(26) | 1.389(4) |
| N(4)—C(23) | 1.397(4) |
| C(1)—C(2) | 1.383(5) |
| C(1)—H(1) | 0.9500 |
| C(2)—C(3) | 1.380(5) |
| C(2)—H(2) | 0.9500 |
| C(3)—C(4) | 1.376(5) |
| C(3)—H(3B) | 0.9500 |
| C(4)—C(5) | 1.391(4) |
| C(4)—H(4) | 0.9500 |
| C(5)—C(6) | 1.467(5) |
| C(6)—C(7) | 1.389(5) |
| C(7)—C(8) | 1.378(5) |
| C(7)—H(7) | 0.9500 |
| C(8)—C(9) | 1.390(5) |
| C(8)—H(8) | 0.9500 |
| C(9)—C(10) | 1.369(5) |
| C(9)—H(9) | 0.9500 |
| C(10)—H(10) | 0.9500 |
| C(11)—C(12) | 1.412(4) |
| C(11)—C(16) | 1.424(4) |
| C(12)—C(13) | 1.372(5) |
| C(12)—C(17) | 1.512(4) |
| C(13)—C(14) | 1.392(4) |
| C(13)—H(13) | 0.9500 |
| C(14)—C(15) | 1.391(4) |
| C(14)—H(14) | 0.9500 |
| C(15)—C(16) | 1.389(4) |
| C(15)—H(15) | 0.9500 |
| C(16)—C(20) | 1.518(4) |
| C(17)—C(18) | 1.522(5) |
| C(17)—C(19) | 1.533(5) |
| C(17)—H(17) | 1.0000 |
| C(18)—H(18A) | 0.9800 |
| C(18)—H(18B) | 0.9800 |
| C(18)—H(18C) | 0.9800 |
| C(19)—H(19A) | 0.9800 |
| C(19)—H(19B) | 0.9800 |
| C(19)—H(19C) | 0.9800 |
| C(20)—C(22) | 1.527(4) |
| C(20)—C(21) | 1.535(5) |
| C(20)—H(20) | 1.0000 |
| C(21)—H(21A) | 0.9800 |
| C(21)—H(21B) | 0.9800 |
| C(21)—H(21C) | 0.9800 |
| C(22)—H(22A) | 0.9800 |
| C(22)—H(22B) | 0.9800 |
| C(22)—H(22C) | 0.9800 |
| C(23)—C(24) | 1.369(5) |
| C(23)—C(27) | 1.488(4) |
| C(24)—C(25) | 1.416(5) |
| C(24)—H(24) | 0.9500 |
| C(25)—C(26) | 1.368(5) |
| C(25)—H(25) | 0.9500 |
| C(26)—C(28) | 1.491(5) |
| C(27)—H(27A) | 0.9800 |
| C(27)—H(27B) | 0.9800 |
| C(27)—H(27C) | 0.9800 |
| C(28)—H(28A) | 0.9800 |
| C(28)—H(28B) | 0.9800 |
| C(28)—H(28C) | 0.9800 |
| C(29)—C(30) | 1.513(5) |
| C(30)—C(31) | 1.532(4) |
| C(30)—C(37) | 1.543(5) |
| C(30)—C(38) | 1.545(5) |
| C(31)—C(36) | 1.392(5) |
| C(31)—C(32) | 1.394(5) |
| C(32)—C(33) | 1.386(5) |
| C(32)—H(32) | 0.9500 |
| C(33)—C(34) | 1.379(6) |
| C(33)—H(33) | 0.9500 |
| C(34)—C(35) | 1.392(5) |
| C(34)—H(34) | 0.9500 |
| C(35)—C(36) | 1.386(5) |
| C(35)—H(35) | 0.9500 |
| C(36)—H(36) | 0.9500 |
| C(37)—H(37A) | 0.9800 |
| C(37)—H(37B) | 0.9800 |
| C(37)—H(37C) | 0.9800 |
| C(38)—H(38A) | 0.9800 |
| C(38)—H(38B) | 0.9800 |
| C(38)—H(38C) | 0.9800 |
| C(29)—Mo(1)—N(3) | 107.91(13) |
| C(29)—Mo(1)—N(4) | 107.07(13) |
| N(3)—Mo(1)—N(4) | 98.64(11) |
| C(29)—Mo(1)—N(2) | 88.93(13) |
| N(3)—Mo(1)—N(2) | 96.71(10) |
| N(4)—Mo(1)—N(2) | 153.05(10) |
| C(29)—Mo(1)—N(1) | 105.36(12) |
| N(3)—Mo(1)—N(1) | 144.12(10) |
| N(4)—Mo(1)—N(1) | 83.95(10) |
| N(2)—Mo(1)—N(1) | 70.74(9) |
| C(1)—N(1)—C(5) | 118.6(3) |
| C(1)—N(1)—Mo(1) | 124.5(2) |
| C(5)—N(1)—Mo(1) | 116.8(2) |
| C(10)—N(2)—C(6) | 118.3(3) |
| C(10)—N(2)—Mo(1) | 120.5(2) |
| C(6)—N(2)—Mo(1) | 121.3(2) |
| C(11)—N(3)—Mo(1) | 159.6(2) |
| C(26)—N(4)—C(23) | 106.3(3) |
| C(26)—N(4)—Mo(1) | 135.0(2) |
| C(23)—N(4)—Mo(1) | 118.5(2) |
| N(1)—C(1)—C(2) | 122.8(3) |
| N(1)—C(1)—H(1) | 118.6 |
| C(2)—C(1)—H(1) | 118.6 |
| C(3)—C(2)—C(1) | 118.6(3) |
| C(3)—C(2)—H(2) | 120.7 |
| C(1)—C(2)—H(2) | 120.7 |
| C(4)—C(3)—C(2) | 119.4(3) |
| C(4)—C(3)—H(3B) | 120.3 |
| C(2)—C(3)—H(3B) | 120.3 |

TABLE 103C-continued

Bond lengths [Å] and angles [°] for 104a.

| | |
|---|---|
| C(3)—C(4)—C(5) | 119.7(3) |
| C(3)—C(4)—H(4) | 120.1 |
| C(5)—C(4)—H(4) | 120.1 |
| N(1)—C(5)—C(4) | 120.8(3) |
| N(1)—C(5)—C(6) | 115.1(3) |
| C(4)—C(5)—C(6) | 124.0(3) |
| N(2)—C(6)—C(7) | 121.2(3) |
| N(2)—C(6)—C(5) | 115.4(3) |
| C(7)—C(6)—C(5) | 123.3(3) |
| C(8)—C(7)—C(6) | 119.7(3) |
| C(8)—C(7)—H(7) | 120.1 |
| C(6)—C(7)—H(7) | 120.1 |
| C(7)—C(8)—C(9) | 119.0(3) |
| C(7)—C(8)—H(8) | 120.5 |
| C(9)—C(8)—H(8) | 120.5 |
| C(10)—C(9)—C(8) | 118.7(3) |
| C(10)—C(9)—H(9) | 120.6 |
| C(8)—C(9)—H(9) | 120.6 |
| N(2)—C(10)—C(9) | 123.1(3) |
| N(2)—C(10)—H(10) | 118.5 |
| C(9)—C(10)—H(10) | 118.5 |
| N(3)—C(11)—C(12) | 119.7(3) |
| N(3)—C(11)—C(16) | 120.4(3) |
| C(12)—C(11)—C(16) | 119.9(3) |
| C(13)—C(12)—C(11) | 119.2(3) |
| C(13)—C(12)—C(17) | 120.9(3) |
| C(11)—C(12)—C(17) | 119.9(3) |
| C(12)—C(13)—C(14) | 121.9(3) |
| C(12)—C(13)—H(13) | 119.0 |
| C(14)—C(13)—H(13) | 119.0 |
| C(15)—C(14)—C(13) | 119.0(3) |
| C(15)—C(14)—H(14) | 120.5 |
| C(13)—C(14)—H(14) | 120.5 |
| C(16)—C(15)—C(14) | 121.4(3) |
| C(16)—C(15)—H(15) | 119.3 |
| C(14)—C(15)—H(15) | 119.3 |
| C(15)—C(16)—C(11) | 118.6(3) |
| C(15)—C(16)—C(20) | 122.3(3) |
| C(11)—C(16)—C(20) | 119.1(3) |
| C(12)—C(17)—C(18) | 113.6(3) |
| C(12)—C(17)—C(19) | 109.4(3) |
| C(18)—C(17)—C(19) | 111.8(3) |
| C(12)—C(17)—H(17) | 107.2 |
| C(18)—C(17)—H(17) | 107.2 |
| C(19)—C(17)—H(17) | 107.2 |
| C(17)—C(18)—H(18A) | 109.5 |
| C(17)—C(18)—H(18B) | 109.5 |
| H(18A)—C(18)—H(18B) | 109.5 |
| C(17)—C(18)—H(18C) | 109.5 |
| H(18A)—C(18)—H(18C) | 109.5 |
| H(18B)—C(18)—H(18C) | 109.5 |
| C(17)—C(19)—H(19A) | 109.5 |
| C(17)—C(19)—H(19B) | 109.5 |
| H(19A)—C(19)—H(19B) | 109.5 |
| C(17)—C(19)—H(19C) | 109.5 |
| H(19A)—C(19)—H(19C) | 109.5 |
| H(19B)—C(19)—H(19C) | 109.5 |
| C(16)—C(20)—C(22) | 113.7(3) |
| C(16)—C(20)—C(21) | 109.4(3) |
| C(22)—C(20)—C(21) | 110.6(3) |
| C(16)—C(20)—H(20) | 107.6 |
| C(22)—C(20)—H(20) | 107.6 |
| C(21)—C(20)—H(20) | 107.6 |
| C(20)—C(21)—H(21A) | 109.5 |
| C(20)—C(21)—H(21B) | 109.5 |
| H(21A)—C(21)—H(21B) | 109.5 |
| C(20)—C(21)—H(21C) | 109.5 |
| H(21A)—C(21)—H(21C) | 109.5 |
| H(21B)—C(21)—H(21C) | 109.5 |
| C(20)—C(22)—H(22A) | 109.5 |
| C(20)—C(22)—H(22B) | 109.5 |
| H(22A)—C(22)—H(22B) | 109.5 |
| C(20)—C(22)—H(22C) | 109.5 |
| H(22A)—C(22)—H(22C) | 109.5 |
| H(22B)—C(22)—H(22C) | 109.5 |
| C(24)—C(23)—N(4) | 109.4(3) |
| C(24)—C(23)—C(27) | 128.8(3) |
| N(4)—C(23)—C(27) | 121.7(3) |
| C(23)—C(24)—C(25) | 107.2(3) |
| C(23)—C(24)—H(24) | 126.4 |
| C(25)—C(24)—H(24) | 126.4 |
| C(26)—C(25)—C(24) | 107.4(3) |
| C(26)—C(25)—H(25) | 126.3 |
| C(24)—C(25)—H(25) | 126.3 |
| C(25)—C(26)—N(4) | 109.6(3) |
| C(25)—C(26)—C(28) | 128.6(3) |
| N(4)—C(26)—C(28) | 121.8(3) |
| C(23)—C(27)—H(27A) | 109.5 |
| C(23)—C(27)—H(27B) | 109.5 |
| H(27A)—C(27)—H(27B) | 109.5 |
| C(23)—C(27)—H(27C) | 109.5 |
| H(27A)—C(27)—H(27C) | 109.5 |
| H(27B)—C(27)—H(27C) | 109.5 |
| C(26)—C(28)—H(28A) | 109.5 |
| C(26)—C(28)—H(28B) | 109.5 |
| H(28A)—C(28)—H(28B) | 109.5 |
| C(26)—C(28)—H(28C) | 109.5 |
| H(28A)—C(28)—H(28C) | 109.5 |
| H(28B)—C(28)—H(28C) | 109.5 |
| C(30)—C(29)—Mo(1) | 161.5(2) |
| C(29)—C(30)—C(31) | 109.9(3) |
| C(29)—C(30)—C(37) | 106.3(3) |
| C(31)—C(30)—C(37) | 112.4(3) |
| C(29)—C(30)—C(38) | 110.2(3) |
| C(31)—C(30)—C(38) | 109.1(3) |
| C(37)—C(30)—C(38) | 109.0(3) |
| C(36)—C(31)—C(32) | 117.2(3) |
| C(36)—C(31)—C(30) | 119.4(3) |
| C(32)—C(31)—C(30) | 123.4(3) |
| C(33)—C(32)—C(31) | 121.7(4) |
| C(33)—C(32)—H(32) | 119.1 |
| C(31)—C(32)—H(32) | 119.1 |
| C(34)—C(33)—C(32) | 120.0(4) |
| C(34)—C(33)—H(33) | 120.0 |
| C(32)—C(33)—H(33) | 120.0 |
| C(33)—C(34)—C(35) | 119.5(3) |
| C(33)—C(34)—H(34) | 120.2 |
| C(35)—C(34)—H(34) | 120.2 |
| C(36)—C(35)—C(34) | 119.7(3) |
| C(36)—C(35)—H(35) | 120.1 |
| C(34)—C(35)—H(35) | 120.1 |
| C(35)—C(36)—C(31) | 121.8(3) |
| C(35)—C(36)—H(36) | 119.1 |
| C(31)—C(36)—H(36) | 119.1 |
| C(30)—C(37)—H(37A) | 109.5 |
| C(30)—C(37)—H(37B) | 109.5 |
| H(37A)—C(37)—H(37B) | 109.5 |
| C(30)—C(37)—H(37C) | 109.5 |
| H(37A)—C(37)—H(37C) | 109.5 |
| H(37B)—C(37)—H(37C) | 109.5 |
| C(30)—C(38)—H(38A) | 109.5 |
| C(30)—C(38)—H(38B) | 109.5 |
| H(38A)—C(38)—H(38B) | 109.5 |
| C(30)—C(38)—H(38C) | 109.5 |
| H(38A)—C(38)—H(38C) | 109.5 |
| H(38B)—C(38)—H(38C) | 109.5 |

Symmetry transformations used to generate equivalent atoms:

TABLE 103D

Anisotropic displacement parameters (Å$^2$ × 10$^3$) for 104a. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| Mo(1) | 13 (1) | 19 (1) | 20 (1) | 0 (1) | −3 (1) | 0 (1) |
| N(1) | 14 (1) | 24 (1) | 29 (2) | 4 (1) | 1 (1) | 0 (1) |
| N(2) | 14 (1) | 24 (1) | 22 (1) | −2 (1) | −3 (1) | −2 (1) |
| N(3) | 16 (1) | 22 (1) | 17 (1) | −2 (1) | −2 (1) | −2 (1) |
| N(4) | 16 (1) | 23 (1) | 21 (1) | −1 (1) | −1 (1) | 1 (1) |
| C(1) | 25 (2) | 25 (2) | 36 (2) | 3 (2) | 4 (2) | 2 (1) |

TABLE 103D-continued

Anisotropic displacement parameters ($Å^2 \times 10^3$) for 104a. The anisotropic displacement factor exponent takes the form: $-2\pi^2[h^2 a^{*2}U^{11} + \ldots + 2 h k a^* b^* U^{12}]$.

|  | $U^{11}$ | $U^{22}$ | $U^{33}$ | $U^{23}$ | $U^{13}$ | $U^{12}$ |
|---|---|---|---|---|---|---|
| C(2) | 24 (2) | 26 (2) | 53 (2) | 6 (2) | 10 (2) | 5 (2) |
| C(3) | 26 (2) | 37 (2) | 50 (2) | 18 (2) | 0 (2) | 6 (2) |
| C(4) | 22 (2) | 38 (2) | 32 (2) | 11 (2) | −2 (2) | −2 (2) |
| C(5) | 15 (2) | 29 (2) | 30 (2) | 6 (1) | −3 (1) | −2 (1) |
| C(6) | 16 (2) | 28 (2) | 21 (2) | 3 (1) | −3 (1) | −6 (1) |
| C(7) | 25 (2) | 39 (2) | 24 (2) | 2 (2) | −2 (1) | −7 (2) |
| C(8) | 30 (2) | 45 (2) | 26 (2) | −8 (2) | 4 (2) | −12 (2) |
| C(9) | 22 (2) | 30 (2) | 34 (2) | −9 (2) | 3 (2) | −5 (2) |
| C(10) | 17 (2) | 29 (2) | 28 (2) | −4 (1) | 0 (1) | −4 (1) |
| C(11) | 14 (2) | 18 (2) | 23 (2) | −2 (1) | 0 (1) | 0 (1) |
| C(12) | 17 (2) | 24 (2) | 23 (2) | 0 (1) | 0 (1) | −1 (1) |
| C(13) | 19 (2) | 32 (2) | 25 (2) | −11 (1) | 2 (1) | 0 (1) |
| C(14) | 27 (2) | 21 (2) | 27 (2) | 4 (1) | 2 (1) | 4 (1) |
| C(15) | 23 (2) | 27 (2) | 21 (2) | 1 (1) | 0 (1) | 4 (1) |
| C(16) | 16 (2) | 25 (2) | 20 (2) | 0 (1) | −1 (1) | 0 (1) |
| C(17) | 28 (2) | 24 (2) | 19 (2) | −1 (1) | −3 (1) | −2 (1) |
| C(18) | 47 (2) | 29 (2) | 21 (2) | −2 (2) | 1 (2) | −2 (2) |
| C(19) | 26 (2) | 46 (2) | 29 (2) | 2 (2) | −10 (2) | −5 (2) |
| C(20) | 22 (2) | 24 (2) | 17 (2) | 0 (1) | −2 (1) | 2 (1) |
| C(21) | 29 (2) | 28 (2) | 28 (2) | −2 (1) | 6 (2) | 1 (2) |
| C(22) | 36 (2) | 34 (2) | 23 (2) | −3 (2) | −9 (2) | 2 (2) |
| C(23) | 16 (2) | 24 (2) | 23 (2) | 4 (1) | −3 (1) | 1 (1) |
| C(24) | 19 (2) | 22 (2) | 29 (2) | 5 (1) | 2 (1) | 4 (1) |
| C(25) | 32 (2) | 22 (2) | 25 (2) | −2 (1) | 3 (2) | 1 (1) |
| C(26) | 22 (2) | 20 (2) | 21 (2) | −1 (1) | −4 (1) | 1 (1) |
| C(27) | 15 (2) | 45 (2) | 30 (2) | −5 (2) | −4 (1) | −3 (2) |
| C(28) | 25 (2) | 31 (2) | 35 (2) | −12 (2) | −7 (2) | 3 (2) |
| C(29) | 18 (2) | 24 (2) | 24 (2) | 0 (1) | −2 (1) | −2 (1) |
| C(30) | 14 (2) | 33 (2) | 33 (2) | −4 (2) | −3 (1) | −3 (1) |
| C(31) | 15 (2) | 29 (2) | 26 (2) | −3 (1) | −9 (1) | −1 (1) |
| C(32) | 20 (2) | 42 (2) | 34 (2) | −1 (2) | 1 (2) | −7 (2) |
| C(33) | 29 (2) | 50 (2) | 36 (2) | −6 (2) | 7 (2) | 4 (2) |
| C(34) | 33 (2) | 36 (2) | 46 (2) | −12 (2) | 0 (2) | 11 (2) |
| C(35) | 25 (2) | 32 (2) | 32 (2) | 2 (2) | −7 (2) | 0 (2) |
| C(36) | 14 (2) | 35 (2) | 24 (2) | −2 (1) | −2 (1) | 1 (1) |
| C(37) | 23 (2) | 34 (2) | 73 (3) | 6 (2) | 10 (2) | −3 (2) |
| C(38) | 18 (2) | 46 (2) | 50 (2) | −19 (2) | −13 (2) | 7 (2) |

TABLE 103E

Hydrogen coordinates ($\times 10^4$) and isotropic displacement parameters ($Å^2 \times 10^3$) for 104a.

|  | x | y | z | U(eq) |
|---|---|---|---|---|
| H(1) | −1516 | 9734 | 7612 | 35 |
| H(2) | −2366 | 10650 | 6751 | 40 |
| H(3B) | −2361 | 10564 | 5281 | 46 |
| H(4) | −1394 | 9602 | 4724 | 37 |
| H(7) | −303 | 8736 | 4320 | 36 |
| H(8) | 844 | 7760 | 3975 | 41 |
| H(9) | 1647 | 6977 | 5062 | 35 |
| H(10) | 1171 | 7149 | 6417 | 30 |
| H(13) | −332 | 4885 | 7303 | 30 |
| H(14) | 241 | 4642 | 8736 | 30 |
| H(15) | 471 | 5585 | 9709 | 28 |
| H(17) | −679 | 6616 | 6375 | 29 |
| H(18A) | 687 | 5749 | 6011 | 49 |
| H(18B) | −444 | 5805 | 5295 | 49 |
| H(18C) | −344 | 5154 | 5953 | 49 |
| H(19A) | −2609 | 6287 | 6691 | 52 |
| H(19B) | −2402 | 5490 | 6373 | 52 |
| H(19C) | −2483 | 6140 | 5714 | 52 |
| H(20) | 415 | 7437 | 9187 | 26 |
| H(21A) | −1670 | 7255 | 9220 | 42 |
| H(21B) | −1066 | 7603 | 10089 | 42 |
| H(21C) | −1385 | 6769 | 10049 | 42 |
| H(22A) | 1830 | 6781 | 10106 | 48 |
| H(22B) | 774 | 6478 | 10595 | 48 |
| H(22C) | 1086 | 7313 | 10631 | 48 |
| H(24) | −3739 | 8998 | 8981 | 28 |
| H(25) | −1973 | 9469 | 9981 | 31 |
| H(27A) | −3968 | 8221 | 7574 | 46 |
| H(27B) | −2896 | 7653 | 7624 | 46 |
| H(27C) | −2868 | 8349 | 7041 | 46 |
| H(28A) | 389 | 9377 | 10061 | 47 |
| H(28B) | 767 | 9404 | 9124 | 47 |
| H(28C) | 781 | 8659 | 9620 | 47 |
| H(32) | 4089 | 7765 | 6802 | 39 |
| H(33) | 4600 | 6604 | 6470 | 46 |
| H(34) | 3775 | 5636 | 7120 | 46 |
| H(35) | 2475 | 5843 | 8144 | 36 |
| H(36) | 2052 | 7008 | 8522 | 30 |
| H(37A) | 2790 | 8756 | 6774 | 64 |
| H(37B) | 3989 | 8836 | 7424 | 64 |
| H(37C) | 2843 | 9320 | 7534 | 64 |
| H(38A) | 2868 | 8060 | 9238 | 59 |
| H(38B) | 2891 | 8897 | 9034 | 59 |
| H(38C) | 4037 | 8412 | 8927 | 59 |

TABLE 104A

Crystal data and structure refinement for 104c.

| | |
|---|---|
| Identification code | C34H36MoN4 |
| Empirical formula | C34H36MoN4 |
| Formula weight | 596.61 |
| Temperature | 100(2) K |
| Wavelength | 0.71073 Å |
| Crystal system | Monoclinic |
| Space group | P2(1)/c |
| Unit cell dimensions | a = 14.9819(3) Å  α = 90°. |
|  | b = 11.6518(3) Å  β = 107.7250(10)°. |
|  | c = 17.4969(4) Å  γ = 90°. |
| Volume | 2909.37(12) Å$^3$ |
| Z | 4 |
| Density (calculated) | 1.362 Mg/m$^3$ |
| Absorption coefficient | 0.480 mm$^{-1}$ |
| F(000) | 1240 |
| Crystal size | 0.12 × 0.04 × 0.03 mm$^3$ |
| Theta range for data collection | 1.43 to 27.49°. |
| Index ranges | −18 <= h <= 19, −14 <= k <= 15, −22 <= l <= 22 |
| Reflections collected | 63038 |
| Independent reflections | 6668 [R(int) = 0.0434] |
| Completeness to theta = 27.49° | 99.8% |
| Absorption correction | Semi-empirical from equivalents |
| Max. and min. transmission | 0.9857 and 0.9446 |
| Refinement method | Full-matrix least-squares on F$^2$ |
| Data/restraints/parameters | 6668/0/356 |
| Goodness-of-fit on F$^2$ | 1.034 |
| Final R indices [I > 2sigma(I)] | R1 = 0.0242, wR2 = 0.0549 |
| R indices (all data) | R1 = 0.0339, wR2 = 0.0587 |
| Extinction coefficient | na |
| Largest diff. peak and hole | 0.386 and −0.323 e · Å$^{-3}$ |

TABLE 104B

Atomic coordinates ($\times 10^4$) and equivalent isotropic displacement parameters ($Å^2 \times 10^3$) for 104c. U(eq) is defined as one third of the trace of the orthogonalized U$^{ij}$ tensor.

|  | x | y | z | U(eq) |
|---|---|---|---|---|
| Mo(1) | 2869(1) | 2163(1) | 1938(1) | 11(1) |
| N(1) | 2913(1) | 975(1) | 1297(1) | 14(1) |
| N(2) | 3526(1) | 3496(1) | 1480(1) | 13(1) |
| N(3) | 3780(1) | 2898(1) | 3156(1) | 14(1) |
| N(4) | 2676(1) | 1092(1) | 2919(1) | 14(1) |
| C(1) | 1688(1) | 2606(1) | 1663(1) | 14(1) |
| C(2) | 631(1) | 2534(2) | 1330(1) | 16(1) |

TABLE 104B-continued

Atomic coordinates (×10⁴) and equivalent isotropic displacement parameters ($Å^2 \times 10^3$) for 104c. U(eq) is defined as one third of the trace of the orthogonalized $U^{ij}$ tensor.

|        | x       | y       | z       | U(eq) |
|--------|---------|---------|---------|-------|
| C(3)   | 255(1)  | 2511(2) | 2056(1) | 15(1) |
| C(4)   | 511(1)  | 3380(2) | 2630(1) | 19(1) |
| C(5)   | 162(1)  | 3414(2) | 3281(1) | 21(1) |
| C(6)   | −451(1) | 2574(2) | 3370(1) | 25(1) |
| C(7)   | −702(1) | 1703(2) | 2811(1) | 26(1) |
| C(8)   | −348(1) | 1666(2) | 2163(1) | 21(1) |
| C(9)   | 220(1)  | 3595(2) | 811(1)  | 21(1) |
| C(10)  | 360(1)  | 1468(2) | 792(1)  | 20(1) |
| C(11)  | 2669(1) | 159(2)  | 700(1)  | 14(1) |
| C(12)  | 2428(1) | 523(2)  | −112(1) | 16(1) |
| C(13)  | 2287(1) | −295(2) | −711(1) | 21(1) |
| C(14)  | 2347(1) | −1462(2)| −537(1) | 24(1) |
| C(15)  | 2565(1) | −1813(2)| 256(1)  | 22(1) |
| C(16)  | 2741(1) | −1025(2)| 882(1)  | 17(1) |
| C(17)  | 2363(1) | 1782(2) | −301(1) | 19(1) |
| C(18)  | 3054(1) | −1430(2)| 1737(1) | 21(1) |
| C(19)  | 4461(1) | 3393(2) | 1503(1) | 15(1) |
| C(20)  | 4806(1) | 4453(2) | 1395(1) | 17(1) |
| C(21)  | 4075(1) | 5256(2) | 1312(1) | 18(1) |
| C(22)  | 3306(1) | 4654(2) | 1365(1) | 16(1) |
| C(23)  | 4962(1) | 2269(2) | 1634(1) | 20(1) |
| C(24)  | 2361(1) | 5116(2) | 1309(1) | 25(1) |
| C(25)  | 4320(1) | 3845(2) | 3243(1) | 17(1) |
| C(26)  | 4992(1) | 4118(2) | 3958(1) | 20(1) |
| C(27)  | 5128(1) | 3393(2) | 4608(1) | 22(1) |
| C(28)  | 4576(1) | 2424(2) | 4531(1) | 18(1) |
| C(29)  | 3895(1) | 2209(2) | 3802(1) | 14(1) |
| C(30)  | 3232(1) | 1249(1) | 3684(1) | 13(1) |
| C(31)  | 3133(1) | 579(2)  | 4311(1) | 17(1) |
| C(32)  | 2454(1) | −260(2) | 4153(1) | 21(1) |
| C(33)  | 1881(1) | −422(2) | 3373(1) | 22(1) |
| C(34)  | 2016(1) | 272(2)  | 2779(1) | 18(1) |

TABLE 104C

Bond lengths [Å] and angles [°] for 104c.

| Bond | Value |
|---|---|
| Mo(1)—C(1) | 1.7643(17) |
| Mo(1)—N(1) | 1.7958(14) |
| Mo(1)—N(2) | 2.1228(14) |
| Mo(1)—N(4) | 2.2100(13) |
| Mo(1)—N(3) | 2.3165(13) |
| N(1)—C(11) | 1.378(2) |
| N(2)—C(22) | 1.389(2) |
| N(2)—C(19) | 1.393(2) |
| N(3)—C(25) | 1.350(2) |
| N(3)—C(29) | 1.353(2) |
| N(4)—C(34) | 1.342(2) |
| N(4)—C(30) | 1.357(2) |
| C(1)—C(2) | 1.514(2) |
| C(2)—C(10) | 1.537(2) |
| C(2)—C(3) | 1.539(2) |
| C(2)—C(9) | 1.546(2) |
| C(3)—C(8) | 1.386(2) |
| C(3)—C(4) | 1.395(2) |
| C(4)—C(5) | 1.390(2) |
| C(4)—H(4) | 0.9500 |
| C(5)—C(6) | 1.383(3) |
| C(5)—H(5) | 0.9500 |
| C(6)—C(7) | 1.380(3) |
| C(6)—H(6) | 0.9500 |
| C(7)—C(8) | 1.391(2) |
| C(7)—H(7) | 0.9500 |
| C(8)—H(8) | 0.9500 |
| C(9)—H(9A) | 0.9800 |
| C(9)—H(9B) | 0.9800 |
| C(9)—H(9C) | 0.9800 |
| C(10)—H(10A) | 0.9800 |
| C(10)—H(10B) | 0.9800 |
| C(10)—H(10C) | 0.9800 |
| C(11)—C(16) | 1.412(2) |
| C(11)—C(12) | 1.419(2) |
| C(12)—C(13) | 1.385(2) |
| C(12)—C(17) | 1.500(2) |
| C(13)—C(14) | 1.390(3) |
| C(13)—H(13) | 0.9500 |
| C(14)—C(15) | 1.387(3) |
| C(14)—H(14) | 0.9500 |
| C(15)—C(16) | 1.392(2) |
| C(15)—H(15) | 0.9500 |
| C(16)—C(18) | 1.501(2) |
| C(17)—H(17A) | 0.9800 |
| C(17)—H(17B) | 0.9800 |
| C(17)—H(17C) | 0.9800 |
| C(18)—H(18A) | 0.9800 |
| C(18)—H(18B) | 0.9800 |
| C(18)—H(18C) | 0.9800 |
| C(19)—C(20) | 1.374(2) |
| C(19)—C(23) | 1.493(2) |
| C(20)—C(21) | 1.414(3) |
| C(20)—H(20) | 0.9500 |
| C(21)—C(22) | 1.375(2) |
| C(21)—H(21) | 0.9500 |
| C(22)—C(24) | 1.490(2) |
| C(23)—H(23A) | 0.9800 |
| C(23)—H(23B) | 0.9800 |
| C(23)—H(23C) | 0.9800 |
| C(24)—H(24A) | 0.9800 |
| C(24)—H(24B) | 0.9800 |
| C(24)—H(24C) | 0.9800 |
| C(25)—C(26) | 1.383(2) |
| C(25)—H(25) | 0.9500 |
| C(26)—C(27) | 1.381(3) |
| C(26)—H(26) | 0.9500 |
| C(27)—C(28) | 1.382(3) |
| C(27)—H(27) | 0.9500 |
| C(28)—C(29) | 1.392(2) |
| C(28)—H(28) | 0.9500 |
| C(29)—C(30) | 1.468(2) |
| C(30)—C(31) | 1.390(2) |
| C(31)—C(32) | 1.377(3) |
| C(31)—H(31) | 0.9500 |
| C(32)—C(33) | 1.386(2) |
| C(32)—H(32) | 0.9500 |
| C(33)—C(34) | 1.380(2) |
| C(33)—H(33) | 0.9500 |
| C(34)—H(34) | 0.9500 |
| C(1)—Mo(1)—N(1) | 106.21(7) |
| C(1)—Mo(1)—N(2) | 103.02(6) |
| N(1)—Mo(1)—N(2) | 102.63(6) |
| C(1)—Mo(1)—N(4) | 91.12(6) |
| N(1)—Mo(1)—N(4) | 95.04(6) |
| N(2)—Mo(1)—N(4) | 153.09(5) |
| C(1)—Mo(1)—N(3) | 113.84(6) |
| N(1)—Mo(1)—N(3) | 137.44(6) |
| N(2)—Mo(1)—N(3) | 82.31(5) |
| N(4)—Mo(1)—N(3) | 71.00(5) |
| C(11)—N(1)—Mo(1) | 162.64(12) |
| C(22)—N(2)—C(19) | 106.24(14) |
| C(22)—N(2)—Mo(1) | 130.44(11) |
| C(19)—N(2)—Mo(1) | 120.25(11) |
| C(25)—N(3)—C(29) | 118.14(14) |
| C(25)—N(3)—Mo(1) | 124.79(11) |
| C(29)—N(3)—Mo(1) | 116.00(11) |
| C(34)—N(4)—C(30) | 118.19(14) |
| C(34)—N(4)—Mo(1) | 121.56(11) |
| C(30)—N(4)—Mo(1) | 120.25(11) |
| C(2)—C(1)—Mo(1) | 159.05(14) |
| C(1)—C(2)—C(10) | 109.32(14) |
| C(1)—C(2)—C(3) | 106.62(13) |
| C(10)—C(2)—C(3) | 113.39(14) |
| C(1)—C(2)—C(9) | 111.35(14) |
| C(10)—C(2)—C(9) | 107.61(14) |
| C(3)—C(2)—C(9) | 108.59(14) |
| C(8)—C(3)—C(4) | 117.77(16) |
| C(8)—C(3)—C(2) | 122.76(15) |
| C(4)—C(3)—C(2) | 119.47(15) |
| C(5)—C(4)—C(3) | 121.37(17) |
| C(5)—C(4)—H(4) | 119.3 |

TABLE 104C-continued

Bond lengths [Å] and angles [°] for 104c.

| | |
|---|---|
| C(3)—C(4)—H(4) | 119.3 |
| C(6)—C(5)—C(4) | 120.04(17) |
| C(6)—C(5)—H(5) | 120.0 |
| C(4)—C(5)—H(5) | 120.0 |
| C(7)—C(6)—C(5) | 119.16(17) |
| C(7)—C(6)—H(6) | 120.4 |
| C(5)—C(6)—H(6) | 120.4 |
| C(6)—C(7)—C(8) | 120.72(18) |
| C(6)—C(7)—H(7) | 119.6 |
| C(8)—C(7)—H(7) | 119.6 |
| C(3)—C(8)—C(7) | 120.94(17) |
| C(3)—C(8)—H(8) | 119.5 |
| C(7)—C(8)—H(8) | 119.5 |
| C(2)—C(9)—H(9A) | 109.5 |
| C(2)—C(9)—H(9B) | 109.5 |
| H(9A)—C(9)—H(9B) | 109.5 |
| C(2)—C(9)—H(9C) | 109.5 |
| H(9A)—C(9)—H(9C) | 109.5 |
| H(9B)—C(9)—H(9C) | 109.5 |
| C(2)—C(10)—H(10A) | 109.5 |
| C(2)—C(10)—H(10B) | 109.5 |
| H(10A)—C(10)—H(10B) | 109.5 |
| C(2)—C(10)—H(10C) | 109.5 |
| H(10A)—C(10)—H(10C) | 109.5 |
| H(10B)—C(10)—H(10C) | 109.5 |
| N(1)—C(11)—C(16) | 121.19(14) |
| N(1)—C(11)—C(12) | 118.72(15) |
| C(16)—C(11)—C(12) | 119.80(15) |
| C(13)—C(12)—C(11) | 119.04(16) |
| C(13)—C(12)—C(17) | 121.40(15) |
| C(11)—C(12)—C(17) | 119.53(15) |
| C(12)—C(13)—C(14) | 121.51(16) |
| C(12)—C(13)—H(13) | 119.2 |
| C(14)—C(13)—H(13) | 119.2 |
| C(15)—C(14)—C(13) | 119.17(17) |
| C(15)—C(14)—H(14) | 120.4 |
| C(13)—C(14)—H(14) | 120.4 |
| C(14)—C(15)—C(16) | 121.56(18) |
| C(14)—C(15)—H(15) | 119.2 |
| C(16)—C(15)—H(15) | 119.2 |
| C(15)—C(16)—C(11) | 118.87(15) |
| C(15)—C(16)—C(18) | 120.26(16) |
| C(11)—C(16)—C(18) | 120.78(15) |
| C(12)—C(17)—H(17A) | 109.5 |
| C(12)—C(17)—H(17B) | 109.5 |
| H(17A)—C(17)—H(17B) | 109.5 |
| C(12)—C(17)—H(17C) | 109.5 |
| H(17A)—C(17)—H(17C) | 109.5 |
| H(17B)—C(17)—H(17C) | 109.5 |
| C(16)—C(18)—H(18A) | 109.5 |
| C(16)—C(18)—H(18B) | 109.5 |
| H(18A)—C(18)—H(18B) | 109.5 |
| C(16)—C(18)—H(18C) | 109.5 |
| H(18A)—C(18)—H(18C) | 109.5 |
| H(18B)—C(18)—H(18C) | 109.5 |
| C(20)—C(19)—N(2) | 109.59(15) |
| C(20)—C(19)—C(23) | 128.09(15) |
| N(2)—C(19)—C(23) | 122.32(15) |
| C(19)—C(20)—C(21) | 107.30(15) |
| C(19)—C(20)—H(20) | 126.3 |
| C(21)—C(20)—H(20) | 126.3 |
| C(22)—C(21)—C(20) | 107.05(16) |
| C(22)—C(21)—H(21) | 126.5 |
| C(20)—C(21)—H(21) | 126.5 |
| C(21)—C(22)—N(2) | 109.81(15) |
| C(21)—C(22)—C(24) | 127.54(16) |
| N(2)—C(22)—C(24) | 122.65(15) |
| C(19)—C(23)—H(23A) | 109.5 |
| C(19)—C(23)—H(23B) | 109.5 |
| H(23A)—C(23)—H(23B) | 109.5 |
| C(19)—C(23)—H(23C) | 109.5 |
| H(23A)—C(23)—H(23C) | 109.5 |
| H(23B)—C(23)—H(23C) | 109.5 |
| C(22)—C(24)—H(24A) | 109.5 |
| C(22)—C(24)—H(24B) | 109.5 |
| H(24A)—C(24)—H(24B) | 109.5 |
| C(22)—C(24)—H(24C) | 109.5 |
| H(24A)—C(24)—H(24C) | 109.5 |
| H(24B)—C(24)—H(24C) | 109.5 |
| N(3)—C(25)—C(26) | 122.39(16) |
| N(3)—C(25)—H(25) | 118.8 |
| C(26)—C(25)—H(25) | 118.8 |
| C(27)—C(26)—C(25) | 119.25(17) |
| C(27)—C(26)—H(26) | 120.4 |
| C(25)—C(26)—H(26) | 120.4 |
| C(26)—C(27)—C(28) | 119.08(16) |
| C(26)—C(27)—H(27) | 120.5 |
| C(28)—C(27)—H(27) | 120.5 |
| C(27)—C(28)—C(29) | 119.08(16) |
| C(27)—C(28)—H(28) | 120.5 |
| C(29)—C(28)—H(28) | 120.5 |
| N(3)—C(29)—C(28) | 122.01(16) |
| N(3)—C(29)—C(30) | 115.18(14) |
| C(28)—C(29)—C(30) | 122.78(15) |
| N(4)—C(30)—C(31) | 121.47(15) |
| N(4)—C(30)—C(29) | 115.28(14) |
| C(31)—C(30)—C(29) | 123.16(15) |
| C(32)—C(31)—C(30) | 119.34(16) |
| C(32)—C(31)—H(31) | 120.3 |
| C(30)—C(31)—H(31) | 120.3 |
| C(31)—C(32)—C(33) | 119.49(16) |
| C(31)—C(32)—H(32) | 120.3 |
| C(33)—C(32)—H(32) | 120.3 |
| C(34)—C(33)—C(32) | 118.24(17) |
| C(34)—C(33)—H(33) | 120.9 |
| C(32)—C(33)—H(33) | 120.9 |
| N(4)—C(34)—C(33) | 123.26(16) |
| N(4)—C(34)—H(34) | 118.4 |
| C(33)—C(34)—H(34) | 118.4 |

Symmetry transformations used to generate equivalent atoms:

TABLE 104D

Anisotropic displacement parameters (Å$^2$ × 10$^3$) for 104c. The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| Mo(1) | 12 (1) | 10 (1) | 12 (1) | 0 (1) | 4 (1) | −1 (1) |
| N(1) | 17 (1) | 12 (1) | 15 (1) | 1 (1) | 6 (1) | −2 (1) |
| N(2) | 15 (1) | 13 (1) | 13 (1) | −2 (1) | 5 (1) | −2 (1) |
| N(3) | 15 (1) | 13 (1) | 14 (1) | −2 (1) | 7 (1) | −1 (1) |
| N(4) | 14 (1) | 12 (1) | 15 (1) | 0 (1) | 5 (1) | 0 (1) |
| C(1) | 16 (1) | 13 (1) | 15 (1) | 2 (1) | 6 (1) | −2 (1) |
| C(2) | 14 (1) | 18 (1) | 17 (1) | 2 (1) | 5 (1) | 0 (1) |
| C(3) | 11 (1) | 16 (1) | 17 (1) | 3 (1) | 3 (1) | 2 (1) |
| C(4) | 17 (1) | 19 (1) | 22 (1) | 1 (1) | 6 (1) | −2 (1) |
| C(5) | 20 (1) | 23 (1) | 20 (1) | −2 (1) | 6 (1) | 3 (1) |
| C(6) | 24 (1) | 33 (1) | 20 (1) | 4 (1) | 10 (1) | 3 (1) |
| C(7) | 26 (1) | 27 (1) | 30 (1) | 2 (1) | 15 (1) | −6 (1) |
| C(8) | 20 (1) | 19 (1) | 24 (1) | −1 (1) | 8 (1) | −3 (1) |
| C(9) | 18 (1) | 24 (1) | 22 (1) | 7 (1) | 5 (1) | 2 (1) |
| C(10) | 18 (1) | 24 (1) | 19 (1) | −3 (1) | 6 (1) | −3 (1) |
| C(11) | 10 (1) | 15 (1) | 17 (1) | −3 (1) | 4 (1) | −1 (1) |
| C(12) | 12 (1) | 18 (1) | 17 (1) | −1 (1) | 5 (1) | −2 (1) |
| C(13) | 20 (1) | 25 (1) | 15 (1) | −2 (1) | 2 (1) | 1 (1) |
| C(14) | 26 (1) | 21 (1) | 22 (1) | −9 (1) | 2 (1) | 3 (1) |
| C(15) | 23 (1) | 13 (1) | 25 (1) | −4 (1) | 2 (1) | 2 (1) |
| C(16) | 15 (1) | 15 (1) | 19 (1) | −2 (1) | 3 (1) | 1 (1) |
| C(17) | 21 (1) | 20 (1) | 16 (1) | 2 (1) | 6 (1) | −4 (1) |
| C(18) | 28 (1) | 13 (1) | 21 (1) | 2 (1) | 4 (1) | 1 (1) |
| C(19) | 14 (1) | 18 (1) | 13 (1) | 0 (1) | 5 (1) | −2 (1) |
| C(20) | 16 (1) | 20 (1) | 16 (1) | −1 (1) | 6 (1) | −6 (1) |
| C(21) | 25 (1) | 14 (1) | 15 (1) | 0 (1) | 7 (1) | −5 (1) |
| C(22) | 21 (1) | 13 (1) | 14 (1) | 0 (1) | 8 (1) | −2 (1) |
| C(23) | 16 (1) | 20 (1) | 22 (1) | 1 (1) | 6 (1) | 1 (1) |
| C(24) | 27 (1) | 15 (1) | 40 (1) | 6 (1) | 18 (1) | 4 (1) |
| C(25) | 20 (1) | 15 (1) | 18 (1) | −2 (1) | 8 (1) | −3 (1) |
| C(26) | 19 (1) | 19 (1) | 22 (1) | −6 (1) | 8 (1) | −6 (1) |
| C(27) | 20 (1) | 26 (1) | 18 (1) | −5 (1) | 4 (1) | −4 (1) |
| C(28) | 19 (1) | 21 (1) | 15 (1) | 0 (1) | 5 (1) | 0 (1) |

TABLE 104D-continued

Anisotropic displacement parameters ($Å^2 \times 10^3$) for 104c. The anisotropic displacement factor exponent takes the form: $-2\pi^2[h^2 a^{*2}U^{11} + \ldots + 2 h k a^* b^* U^{12}]$.

|        | $U^{11}$ | $U^{22}$ | $U^{33}$ | $U^{23}$ | $U^{13}$ | $U^{12}$ |
|--------|----------|----------|----------|----------|----------|----------|
| C(29)  | 15 (1)   | 13 (1)   | 15 (1)   | -1 (1)   | 8 (1)    | 2 (1)    |
| C(30)  | 14 (1)   | 12 (1)   | 16 (1)   | 0 (1)    | 7 (1)    | 3 (1)    |
| C(31)  | 21 (1)   | 15 (1)   | 16 (1)   | 1 (1)    | 6 (1)    | 1 (1)    |
| C(32)  | 29 (1)   | 18 (1)   | 20 (1)   | 6 (1)    | 12 (1)   | -1 (1)   |
| C(33)  | 22 (1)   | 17 (1)   | 26 (1)   | 3 (1)    | 8 (1)    | -6 (1)   |
| C(34)  | 17 (1)   | 18 (1)   | 19 (1)   | 1 (1)    | 4 (1)    | -4 (1)   |

TABLE 104E

Hydrogen coordinates ($\times 10^4$) and isotropic displacement parameters ($Å^2 \times 10^3$) for 104c.

|        | x     | y     | z     | U(eq) |
|--------|-------|-------|-------|-------|
| H(4)   | 931   | 3961  | 2575  | 23    |
| H(5)   | 346   | 4014  | 3664  | 26    |
| H(6)   | -696  | 2596  | 3811  | 30    |
| H(7)   | -1122 | 1122  | 2869  | 31    |
| H(8)   | -521  | 1053  | 1789  | 25    |
| H(9A)  | 382   | 4290  | 1140  | 32    |
| H(9B)  | -463  | 3522  | 603   | 32    |
| H(9C)  | 482   | 3644  | 362   | 32    |
| H(10A) | 610   | 780   | 1106  | 30    |
| H(10B) | 620   | 1533  | 343   | 30    |
| H(10C) | -324  | 1412  | 583   | 30    |
| H(13)  | 2145  | -53   | -1254 | 25    |
| H(14)  | 2240  | -2012 | -957  | 29    |
| H(15)  | 2596  | -2611 | 374   | 26    |
| H(17A) | 2256  | 1891  | -877  | 29    |
| H(17B) | 2948  | 2160  | 0     | 29    |
| H(17C) | 1841  | 2116  | -149  | 29    |
| H(18A) | 2511  | -1476 | 1938  | 32    |
| H(18B) | 3511  | -888  | 2067  | 32    |
| H(18C) | 3342  | -2190 | 1766  | 32    |
| H(20)  | 5421  | 4616  | 1379  | 21    |
| H(21)  | 4108  | 6060  | 1234  | 21    |
| H(23A) | 5606  | 2380  | 1621  | 29    |
| H(23B) | 4637  | 1731  | 1211  | 29    |
| H(23C) | 4974  | 1958  | 2158  | 29    |
| H(24A) | 2381  | 5957  | 1309  | 38    |
| H(24B) | 2176  | 4850  | 1770  | 38    |
| H(24C) | 1906  | 4846  | 812   | 38    |
| H(25)  | 4236  | 4343  | 2796  | 21    |
| H(26)  | 5356  | 4796  | 4002  | 24    |
| H(27)  | 5595  | 3558  | 5101  | 26    |
| H(28)  | 4659  | 1912  | 4970  | 22    |
| H(31)  | 3530  | 699   | 4843  | 21    |
| H(32)  | 2379  | -725  | 4575  | 26    |
| H(33)  | 1408  | -995  | 3251  | 26    |
| H(34)  | 1623  | 165   | 2244  | 22    |

TABLE 105A

Crystal data and structure refinement for 104g.

| | |
|---|---|
| Identification code | d10116 |
| Empirical formula | C60H70MoN4 |
| Formula weight | 943.14 |
| Temperature | 100(2) K |
| Wavelength | 1.54178 Å |
| Crystal system | Monoclinic |
| Space group | P2(1)/c |
| Unit cell dimensions | a = 25.0928(4) Å   α = 90°. |
| | b = 25.8149(4) Å   β = 108.0810(10)°. |
| | c = 17.2021(3) Å   γ = 90°. |
| Volume | 10592.7(3) Å³ |
| Z | 8 |
| Density (calculated) | 1.183 Mg/m³ |
| Absorption coefficient | 2.321 mm⁻¹ |
| F(000) | 4000 |
| Crystal size | 0.30 × 0.20 × 0.10 mm³ |
| Theta range for data collection | 1.85 to 69.31°. |
| Index ranges | -30 <= h <= 30, -31 <= k <= 31, -20 <= l <= 19 |
| Reflections collected | 200905 |
| Independent reflections | 19616 [R(int) = 0.0398] |
| Completeness to theta = 69.31° | 99.0% |
| Absorption correction | Semi-empirical from equivalents |
| Max. and min. transmission | 0.8011 and 0.5427 |
| Refinement method | Full-matrix least-squares on F² |
| Data/restraints/parameters | 19616/2996/1398 |
| Goodness-of-fit on F² | 1.223 |
| Final R indices [I > 2sigma(I)] | R1 = 0.0652, wR2 = 0.1714 |
| R indices (all data) | R1 = 0.0708, wR2 = 0.1744 |
| Largest diff. peak and hole | 3.266 and -1.408 e · Å⁻³ |

TABLE 105B

Atomic coordinates ($\times 10^4$) and equivalent isotropic displacement parameters ($Å^2 \times 10^3$) for 104g. U(eq) is defined as one third of the trace of the orthogonalized $U^{ij}$ tensor.

|        | x        | y        | z        | U(eq)  |
|--------|----------|----------|----------|--------|
| Mo(1)  | 3060(1)  | 8105(1)  | 8559(1)  | 16(1)  |
| C(1)   | 2362(2)  | 8329(2)  | 8383(3)  | 21(1)  |
| C(2)   | 1836(2)  | 8632(2)  | 8307(3)  | 30(1)  |
| C(3)   | 1916(2)  | 9185(2)  | 8033(4)  | 38(1)  |
| C(4)   | 1340(2)  | 8379(3)  | 7653(4)  | 55(2)  |
| C(5)   | 1709(2)  | 8649(2)  | 9121(4)  | 41(1)  |
| N(1)   | 3043(2)  | 7352(2)  | 9021(2)  | 21(1)  |
| C(6)   | 2603(2)  | 7014(2)  | 8980(3)  | 24(1)  |
| C(7)   | 2803(2)  | 6524(2)  | 9164(3)  | 27(1)  |
| C(8)   | 3393(2)  | 6543(2)  | 9315(3)  | 27(1)  |
| C(9)   | 3526(2)  | 7047(2)  | 9231(3)  | 22(1)  |
| C(10)  | 2009(2)  | 7192(2)  | 8768(4)  | 37(1)  |
| C(11)  | 4094(2)  | 7277(2)  | 9337(3)  | 29(1)  |
| N(2)   | 3063(2)  | 7674(2)  | 7386(2)  | 18(1)  |
| C(21)  | 2986(2)  | 7164(2)  | 7268(3)  | 22(1)  |
| C(22)  | 2984(2)  | 6915(2)  | 6544(3)  | 26(1)  |
| C(23)  | 3052(2)  | 7215(2)  | 5910(3)  | 26(1)  |
| C(24)  | 3131(2)  | 7739(2)  | 6020(3)  | 24(1)  |
| C(25)  | 3145(2)  | 7960(2)  | 6770(3)  | 18(1)  |
| C(26)  | 3255(2)  | 8513(2)  | 6945(3)  | 21(1)  |
| C(27)  | 3406(2)  | 8855(2)  | 6428(3)  | 26(1)  |
| C(28)  | 3526(2)  | 9363(2)  | 6654(3)  | 30(1)  |
| C(29)  | 3478(2)  | 9532(2)  | 7392(3)  | 27(1)  |
| C(30)  | 3323(2)  | 9173(2)  | 7886(3)  | 24(1)  |
| N(3)   | 3221(2)  | 8674(2)  | 7685(2)  | 19(1)  |
| N(4)   | 3533(2)  | 8436(2)  | 9441(2)  | 19(1)  |
| C(31)  | 3666(2)  | 8832(2)  | 10006(3) | 18(1)  |
| C(32)  | 3257(2)  | 9187(2)  | 10076(3) | 23(1)  |
| C(33)  | 3391(2)  | 9599(2)  | 10618(3) | 28(1)  |
| C(34)  | 3939(2)  | 9669(2)  | 11107(3) | 29(1)  |
| C(35)  | 4345(2)  | 9322(2)  | 11059(3) | 26(1)  |
| C(36)  | 4223(2)  | 8896(2)  | 10526(3) | 21(1)  |
| C(41)  | 4685(2)  | 8529(2)  | 10521(3) | 21(1)  |
| C(42)  | 4914(2)  | 8200(2)  | 11199(3) | 28(1)  |
| C(47)  | 4683(2)  | 8172(2)  | 11920(3) | 35(1)  |
| C(48)  | 4551(3)  | 7614(2)  | 12103(4) | 46(2)  |
| C(49)  | 5082(3)  | 8424(3)  | 12694(4) | 53(2)  |
| C(43)  | 5360(2)  | 7878(2)  | 11204(3) | 31(1)  |
| C(44)  | 5584(2)  | 7866(2)  | 10562(3) | 31(1)  |
| C(50)  | 6064(2)  | 7508(2)  | 10565(4) | 40(1)  |
| C(51)  | 5898(3)  | 6945(2)  | 10544(6) | 61(2)  |
| C(52)  | 6591(2)  | 7626(3)  | 11291(4) | 51(2)  |
| C(45)  | 5350(2)  | 8187(2)  | 9892(3)  | 28(1)  |
| C(46)  | 4904(2)  | 8519(2)  | 9865(3)  | 22(1)  |
| C(53)  | 4681(2)  | 8876(2)  | 9134(3)  | 22(1)  |
| C(54)  | 4632(2)  | 8604(2)  | 8323(3)  | 28(1)  |
| C(55)  | 5036(2)  | 9365(2)  | 9234(3)  | 33(1)  |
| Mo(2)  | 8045(1)  | 6951(1)  | 3849(1)  | 21(1)  |
| C(101) | 7341(2)  | 6761(2)  | 3731(3)  | 27(1)  |
| C(102) | 6823(2)  | 6473(2)  | 3711(4)  | 35(1)  |

TABLE 105B-continued

Atomic coordinates (×10⁴) and equivalent isotropic displacement parameters ($Å^2 \times 10^3$) for 104g. U(eq) is defined as one third of the trace of the orthogonalized $U^{ij}$ tensor.

| | x | y | z | U(eq) |
|---|---|---|---|---|
| C(103) | 6846(2) | 5931(2) | 3372(4) | 44(1) |
| C(104) | 6305(2) | 6756(3) | 3151(4) | 46(2) |
| C(105) | 6769(2) | 6441(3) | 4577(4) | 45(2) |
| N(101) | 8084(2) | 7706(2) | 4329(2) | 24(1) |
| C(106) | 7674(2) | 8069(2) | 4323(3) | 30(1) |
| C(107) | 7914(2) | 8548(2) | 4508(3) | 32(1) |
| C(108) | 8498(2) | 8492(2) | 4640(3) | 34(1) |
| C(109) | 8589(2) | 7977(2) | 4522(3) | 30(1) |
| C(110) | 7071(2) | 7930(2) | 4147(4) | 41(1) |
| C(111) | 9128(2) | 7717(2) | 4561(4) | 35(1) |
| N(102) | 8037(2) | 7380(2) | 2662(3) | 25(1) |
| C(121) | 8005(2) | 7897(2) | 2567(3) | 30(1) |
| C(122) | 8029(2) | 8142(2) | 1865(3) | 33(1) |
| C(123) | 8091(2) | 7844(2) | 1228(3) | 32(1) |
| C(124) | 8123(2) | 7311(2) | 1317(3) | 29(1) |
| C(125) | 8096(2) | 7091(2) | 2035(3) | 27(1) |
| C(126) | 8128(2) | 6525(2) | 2191(3) | 27(1) |
| C(127) | 8163(2) | 6172(2) | 1600(3) | 34(1) |
| C(128) | 8203(3) | 5652(2) | 1780(3) | 37(1) |
| C(129) | 8211(2) | 5493(2) | 2559(3) | 33(1) |
| C(130) | 8170(2) | 5863(2) | 3116(3) | 27(1) |
| N(103) | 8124(2) | 6374(2) | 2937(2) | 24(1) |
| N(104) | 8521(9) | 6570(10) | 4696(19) | 22(2) |
| C(131) | 8661(6) | 6158(9) | 5218(17) | 22(1) |
| C(132) | 8258(6) | 5805(7) | 5308(13) | 23(2) |
| C(133) | 8398(7) | 5377(7) | 5814(12) | 25(2) |
| C(134) | 8960(7) | 5274(5) | 6232(10) | 25(2) |
| C(135) | 9362(6) | 5615(6) | 6149(12) | 24(2) |
| C(136) | 9231(5) | 6065(5) | 5677(9) | 22(1) |
| C(141) | 9680(6) | 6441(5) | 5647(6) | 22(1) |
| C(142) | 9867(6) | 6481(5) | 4962(7) | 22(1) |
| C(147) | 9616(7) | 6139(6) | 4220(8) | 25(2) |
| C(148) | 9547(10) | 6421(6) | 3411(7) | 27(2) |
| C(149) | 9970(10) | 5650(6) | 4266(13) | 33(3) |
| C(143) | 10288(4) | 6834(4) | 4965(6) | 24(2) |
| C(144) | 10520(4) | 7161(3) | 5630(6) | 23(2) |
| C(150) | 10965(3) | 7560(3) | 5622(5) | 28(2) |
| C(151) | 11551(4) | 7352(7) | 6027(11) | 33(3) |
| C(152) | 10881(4) | 7798(4) | 4786(5) | 38(2) |
| C(145) | 10340(4) | 7112(4) | 6310(6) | 25(2) |
| C(146) | 9921(4) | 6762(4) | 6340(6) | 24(1) |
| C(153) | 9738(4) | 6753(4) | 7104(6) | 30(2) |
| C(154) | 10171(6) | 6470(5) | 7817(6) | 43(3) |
| C(155) | 9616(5) | 7296(4) | 7382(7) | 39(2) |
| N(4A) | 8529(18) | 6612(19) | 4660(40) | 24(2) |
| C(31A) | 8689(11) | 6199(18) | 5180(30) | 22(2) |
| C(32A) | 8293(11) | 5869(13) | 5360(30) | 23(2) |
| C(33A) | 8454(12) | 5447(13) | 5870(20) | 25(2) |
| C(34A) | 9023(13) | 5360(11) | 6290(20) | 25(2) |
| C(35A) | 9412(11) | 5697(11) | 6160(20) | 24(2) |
| C(36A) | 9264(10) | 6116(10) | 5619(17) | 23(2) |
| C(41A) | 9720(11) | 6461(10) | 5522(12) | 23(2) |
| C(42A) | 9887(11) | 6439(10) | 4819(12) | 24(2) |
| C(47A) | 9600(13) | 6083(10) | 4118(13) | 25(2) |
| C(48A) | 9510(20) | 6323(13) | 3270(13) | 29(4) |
| C(49A) | 9900(20) | 5561(11) | 4190(20) | 31(4) |
| C(43A) | 10317(9) | 6764(9) | 4757(11) | 25(2) |
| C(44A) | 10595(7) | 7102(6) | 5393(11) | 27(2) |
| C(50A) | 11055(6) | 7457(5) | 5300(10) | 31(2) |
| C(51A) | 11618(7) | 7334(14) | 5900(20) | 36(5) |
| C(52A) | 10871(6) | 8019(5) | 5264(8) | 27(3) |
| C(45A) | 10416(7) | 7129(7) | 6071(11) | 26(2) |
| C(46A) | 9986(8) | 6813(8) | 6158(10) | 25(2) |
| C(53A) | 9800(8) | 6854(7) | 6913(10) | 31(2) |
| C(54A) | 10236(10) | 6627(9) | 7672(12) | 44(4) |
| C(55A) | 9649(10) | 7413(8) | 7067(13) | 44(4) |
| C(1S) | 6352(4) | 5594(3) | 854(5) | 78(2) |
| C(2S) | 6563(3) | 5171(3) | 1345(5) | 61(2) |
| C(3S) | 6917(3) | 4838(3) | 1136(4) | 57(2) |
| C(4S) | 7072(3) | 4932(3) | 447(4) | 56(2) |
| C(5S) | 6880(3) | 5360(2) | −27(4) | 56(2) |
| C(6S) | 6506(4) | 5688(3) | 164(5) | 75(2) |
| C(1T) | 5279(3) | 941(3) | 4242(4) | 63(2) |
| C(2T) | 5425(3) | 445(3) | 4545(4) | 68(2) |
| C(3T) | 5244(3) | 23(3) | 4030(4) | 69(2) |
| C(4T) | 4918(3) | 101(3) | 3228(4) | 60(2) |
| C(5T) | 4788(3) | 595(3) | 2946(4) | 54(2) |
| C(6T) | 4957(3) | 1016(3) | 3447(4) | 52(2) |
| C(1U) | 2695(2) | 580(2) | 7956(3) | 41(1) |
| C(2U) | 3024(2) | 385(2) | 8702(3) | 36(1) |
| C(3U) | 3585(2) | 508(2) | 8993(3) | 37(1) |
| C(4U) | 3820(3) | 834(2) | 8552(4) | 45(1) |
| C(5U) | 3491(3) | 1030(2) | 7810(4) | 54(2) |
| C(6U) | 2927(3) | 904(2) | 7512(4) | 51(1) |
| C(1V) | 166(4) | 9861(4) | 6680(5) | 83(2) |
| C(2V) | −125(4) | 9459(4) | 6864(5) | 87(2) |
| C(3V) | −184(4) | 8991(4) | 6481(5) | 84(2) |
| C(4V) | 71(4) | 8904(4) | 5896(5) | 88(2) |
| C(5V) | 367(5) | 9304(5) | 5714(7) | 112(3) |
| C(6V) | 428(4) | 9770(4) | 6106(7) | 104(3) |
| C(1W) | 1717(3) | 4979(3) | 592(4) | 65(2) |
| C(2W) | 2002(3) | 5438(3) | 843(5) | 71(2) |
| C(3W) | 1898(3) | 5868(3) | 327(5) | 70(2) |
| C(4W) | 1519(3) | 5828(3) | −441(4) | 54(2) |
| C(5W) | 1243(3) | 5373(2) | −682(4) | 51(2) |
| C(6W) | 1339(3) | 4949(2) | −172(4) | 57(2) |
| C(1X) | 8851(3) | 4238(3) | 3747(4) | 46(1) |
| C(2X) | 8620(2) | 4544(2) | 4216(3) | 38(1) |
| C(3X) | 8047(2) | 4597(2) | 4008(3) | 34(1) |
| C(4X) | 7703(2) | 4347(2) | 3335(4) | 40(1) |
| C(5X) | 7933(3) | 4044(2) | 2862(4) | 42(1) |
| C(6X) | 8505(3) | 3988(2) | 3071(4) | 46(1) |

TABLE 105C

Bond lengths [Å] and angles [°] for 104g.

| | |
|---|---|
| Mo(1)—C(1) | 1.780(5) |
| Mo(1)—N(4) | 1.823(4) |
| Mo(1)—N(1) | 2.105(4) |
| Mo(1)—N(3) | 2.225(4) |
| Mo(1)—N(2) | 2.306(3) |
| C(1)—C(2) | 1.504(7) |
| C(2)—C(5) | 1.531(8) |
| C(2)—C(3) | 1.535(8) |
| C(2)—C(4) | 1.541(7) |
| C(3)—H(3A) | 0.9800 |
| C(3)—H(3B) | 0.9800 |
| C(3)—H(3C) | 0.9800 |
| C(4)—H(4A) | 0.9800 |
| C(4)—H(4B) | 0.9800 |
| C(4)—H(4C) | 0.9800 |
| C(5)—H(5A) | 0.9800 |
| C(5)—H(5B) | 0.9800 |
| C(5)—H(5C) | 0.9800 |
| N(1)—C(6) | 1.391(6) |
| N(1)—C(9) | 1.395(6) |
| C(6)—C(7) | 1.363(7) |
| C(6)—C(10) | 1.492(7) |
| C(7)—C(8) | 1.421(7) |
| C(7)—H(7) | 0.9500 |
| C(8)—C(9) | 1.362(7) |
| C(8)—H(8) | 0.9500 |
| C(9)—C(11) | 1.502(7) |
| C(10)—H(10A) | 0.9800 |
| C(10)—H(10B) | 0.9800 |
| C(10)—H(10C) | 0.9800 |
| C(11)—H(11A) | 0.9800 |
| C(11)—H(11B) | 0.9800 |
| C(11)—H(11C) | 0.9800 |
| N(2)—C(21) | 1.337(6) |
| N(2)—C(25) | 1.359(6) |
| C(21)—C(22) | 1.400(6) |
| C(21)—H(21) | 0.9500 |
| C(22)—C(23) | 1.390(7) |

TABLE 105C-continued

Bond lengths [Å] and angles [°] for 104g.

| | |
|---|---|
| C(22)—H(22) | 0.9500 |
| C(23)—C(24) | 1.374(7) |
| C(23)—H(23) | 0.9500 |
| C(24)—C(25) | 1.400(6) |
| C(24)—H(24) | 0.9500 |
| C(25)—C(26) | 1.466(7) |
| C(26)—N(3) | 1.367(6) |
| C(26)—C(27) | 1.387(7) |
| C(27)—C(28) | 1.375(7) |
| C(27)—H(27) | 0.9500 |
| C(28)—C(29) | 1.382(7) |
| C(28)—H(28) | 0.9500 |
| C(29)—C(30) | 1.390(7) |
| C(29)—H(29) | 0.9500 |
| C(30)—N(3) | 1.339(6) |
| C(30)—H(30) | 0.9500 |
| N(4)—C(31) | 1.379(6) |
| C(31)—C(32) | 1.407(6) |
| C(31)—C(36) | 1.416(6) |
| C(32)—C(33) | 1.385(7) |
| C(32)—H(32) | 0.9500 |
| C(33)—C(34) | 1.383(7) |
| C(33)—H(33) | 0.9500 |
| C(34)—C(35) | 1.378(7) |
| C(34)—H(34) | 0.9500 |
| C(35)—C(36) | 1.403(6) |
| C(35)—H(35) | 0.9500 |
| C(36)—C(41) | 1.499(7) |
| C(41)—C(46) | 1.401(7) |
| C(41)—C(42) | 1.413(7) |
| C(42)—C(43) | 1.392(7) |
| C(42)—C(47) | 1.525(7) |
| C(47)—C(48) | 1.532(8) |
| C(47)—C(49) | 1.541(8) |
| C(47)—H(47) | 1.0000 |
| C(48)—H(48A) | 0.9800 |
| C(48)—H(48B) | 0.9800 |
| C(48)—H(48C) | 0.9800 |
| C(49)—H(49A) | 0.9800 |
| C(49)—H(49B) | 0.9800 |
| C(49)—H(49C) | 0.9800 |
| C(43)—C(44) | 1.386(8) |
| C(43)—H(43) | 0.9500 |
| C(44)—C(45) | 1.392(7) |
| C(44)—C(50) | 1.517(7) |
| C(50)—C(51) | 1.509(9) |
| C(50)—C(52) | 1.541(9) |
| C(50)—H(50) | 1.0000 |
| C(51)—H(51A) | 0.9800 |
| C(51)—H(51B) | 0.9800 |
| C(51)—H(51C) | 0.9800 |
| C(52)—H(52A) | 0.9800 |
| C(52)—H(52B) | 0.9800 |
| C(52)—H(52C) | 0.9800 |
| C(45)—C(46) | 1.396(7) |
| C(45)—H(45) | 0.9500 |
| C(46)—C(53) | 1.519(6) |
| C(53)—C(55) | 1.524(7) |
| C(53)—C(54) | 1.534(6) |
| C(53)—H(53) | 1.0000 |
| C(54)—H(54A) | 0.9800 |
| C(54)—H(54B) | 0.9800 |
| C(54)—H(54C) | 0.9800 |
| C(55)—H(55A) | 0.9800 |
| C(55)—H(55B) | 0.9800 |
| C(55)—H(55C) | 0.9800 |
| Mo(2)—N(4A) | 1.77(3) |
| Mo(2)—C(101) | 1.783(5) |
| Mo(2)—N(104) | 1.854(15) |
| Mo(2)—N(101) | 2.108(4) |
| Mo(2)—N(103) | 2.215(4) |
| Mo(2)—N(102) | 2.317(4) |
| C(101)—C(102) | 1.490(7) |
| C(102)—C(103) | 1.523(8) |
| C(102)—C(105) | 1.538(8) |
| C(102)—C(104) | 1.540(8) |
| C(103)—H(10D) | 0.9800 |
| C(103)—H(10E) | 0.9800 |
| C(103)—H(10F) | 0.9800 |
| C(104)—H(10G) | 0.9800 |
| C(104)—H(10H) | 0.9800 |
| C(104)—H(10I) | 0.9800 |
| C(105)—H(10J) | 0.9800 |
| C(105)—H(10K) | 0.9800 |
| C(105)—H(10L) | 0.9800 |
| N(101)—C(106) | 1.389(6) |
| N(101)—C(109) | 1.393(6) |
| C(106)—C(107) | 1.368(8) |
| C(106)—C(110) | 1.493(8) |
| C(107)—C(108) | 1.421(8) |
| C(107)—H(107) | 0.9500 |
| C(108)—C(109) | 1.374(7) |
| C(108)—H(108) | 0.9500 |
| C(109)—C(111) | 1.493(7) |
| C(110)—H(11D) | 0.9800 |
| C(110)—H(11E) | 0.9800 |
| C(110)—H(11F) | 0.9800 |
| C(111)—H(11G) | 0.9800 |
| C(111)—H(11H) | 0.9800 |
| C(111)—H(11I) | 0.9800 |
| N(102)—C(121) | 1.344(6) |
| N(102)—C(125) | 1.357(7) |
| C(121)—C(122) | 1.382(7) |
| C(121)—H(121) | 0.9500 |
| C(122)—C(123) | 1.386(8) |
| C(122)—H(122) | 0.9500 |
| C(123)—C(124) | 1.386(7) |
| C(123)—H(123) | 0.9500 |
| C(124)—C(125) | 1.380(7) |
| C(124)—H(124) | 0.9500 |
| C(125)—C(126) | 1.482(7) |
| C(126)—N(103) | 1.345(7) |
| C(126)—C(127) | 1.388(7) |
| C(127)—C(128) | 1.375(8) |
| C(127)—H(127) | 0.9500 |
| C(128)—C(129) | 1.395(8) |
| C(128)—H(128) | 0.9500 |
| C(129)—C(130) | 1.379(7) |
| C(129)—H(129) | 0.9500 |
| C(130)—N(103) | 1.354(6) |
| C(130)—H(130) | 0.9500 |
| N(104)—C(131) | 1.367(9) |
| C(131)—C(132) | 1.403(9) |
| C(131)—C(136) | 1.425(9) |
| C(132)—C(133) | 1.383(9) |
| C(132)—H(132) | 0.9500 |
| C(133)—C(134) | 1.395(9) |
| C(133)—H(133) | 0.9500 |
| C(134)—C(135) | 1.380(9) |
| C(134)—H(134) | 0.9500 |
| C(135)—C(136) | 1.395(9) |
| C(135)—H(135) | 0.9500 |
| C(136)—C(141) | 1.499(9) |
| C(141)—C(142) | 1.401(9) |
| C(141)—C(146) | 1.423(9) |
| C(142)—C(143) | 1.396(9) |
| C(142)—C(147) | 1.520(9) |
| C(147)—C(149) | 1.530(10) |
| C(147)—C(148) | 1.533(10) |
| C(147)—H(147) | 1.0000 |
| C(148)—H(14A) | 0.9800 |
| C(148)—H(14B) | 0.9800 |
| C(148)—H(14C) | 0.9800 |
| C(149)—H(14D) | 0.9800 |
| C(149)—H(14E) | 0.9800 |
| C(149)—H(14F) | 0.9800 |
| C(143)—C(144) | 1.394(10) |
| C(143)—H(143) | 0.9500 |
| C(144)—C(145) | 1.384(11) |
| C(144)—C(150) | 1.522(9) |
| C(150)—C(151) | 1.515(11) |
| C(150)—C(152) | 1.518(11) |
| C(150)—H(150) | 1.0000 |
| C(151)—H(15A) | 0.9800 |
| C(151)—H(15B) | 0.9800 |
| C(151)—H(15C) | 0.9800 |

TABLE 105C-continued

Bond lengths [Å] and angles [°] for 104g.

| | |
|---|---|
| C(152)—H(15D) | 0.9800 |
| C(152)—H(15E) | 0.9800 |
| C(152)—H(15F) | 0.9800 |
| C(145)—C(146) | 1.400(10) |
| C(145)—H(145) | 0.9500 |
| C(146)—C(153) | 1.521(10) |
| C(153)—C(155) | 1.544(10) |
| C(153)—C(154) | 1.546(11) |
| C(153)—H(153) | 1.0000 |
| C(154)—H(15G) | 0.9800 |
| C(154)—H(15H) | 0.9800 |
| C(154)—H(15I) | 0.9800 |
| C(155)—H(15J) | 0.9800 |
| C(155)—H(15K) | 0.9800 |
| C(155)—H(15L) | 0.9800 |
| N(4A)—C(31A) | 1.375(13) |
| C(31A)—C(32A) | 1.407(14) |
| C(31A)—C(36A) | 1.421(13) |
| C(32A)—C(33A) | 1.384(14) |
| C(32A)—H(32A) | 0.9500 |
| C(33A)—C(34A) | 1.404(14) |
| C(33A)—H(33A) | 0.9500 |
| C(34A)—C(35A) | 1.379(14) |
| C(34A)—H(34A) | 0.9500 |
| C(35A)—C(36A) | 1.396(13) |
| C(35A)—H(35A) | 0.9500 |
| C(36A)—C(41A) | 1.500(12) |
| C(41A)—C(42A) | 1.398(13) |
| C(41A)—C(46A) | 1.419(13) |
| C(42A)—C(43A) | 1.397(13) |
| C(42A)—C(47A) | 1.509(13) |
| C(47A)—C(49A) | 1.528(14) |
| C(47A)—C(48A) | 1.537(14) |
| C(47A)—H(47A) | 1.0000 |
| C(48A)—H(48D) | 0.9800 |
| C(48A)—H(48E) | 0.9800 |
| C(48A)—H(48F) | 0.9800 |
| C(49A)—H(49D) | 0.9800 |
| C(49A)—H(49E) | 0.9800 |
| C(49A)—H(49F) | 0.9800 |
| C(43A)—C(44A) | 1.404(15) |
| C(43A)—H(43A) | 0.9500 |
| C(44A)—C(45A) | 1.377(16) |
| C(44A)—C(50A) | 1.521(14) |
| C(50A)—C(51A) | 1.500(15) |
| C(50A)—C(52A) | 1.516(15) |
| C(50A)—H(50A) | 1.0000 |
| C(51A)—H(51D) | 0.9800 |
| C(51A)—H(51E) | 0.9800 |
| C(51A)—H(51F) | 0.9800 |
| C(52A)—H(52D) | 0.9800 |
| C(52A)—H(52E) | 0.9800 |
| C(52A)—H(52F) | 0.9800 |
| C(45A)—C(46A) | 1.396(14) |
| C(45A)—H(45A) | 0.9500 |
| C(46A)—C(53A) | 1.515(15) |
| C(53A)—C(54A) | 1.535(15) |
| C(53A)—C(55A) | 1.537(15) |
| C(53A)—H(53A) | 1.0000 |
| C(54A)—H(54D) | 0.9800 |
| C(54A)—H(54E) | 0.9800 |
| C(54A)—H(54F) | 0.9800 |
| C(55A)—H(55D) | 0.9800 |
| C(55A)—H(55E) | 0.9800 |
| C(55A)—H(55F) | 0.9800 |
| C(1S)—C(6S) | 1.379(9) |
| C(1S)—C(2S) | 1.381(8) |
| C(1S)—H(1S) | 0.9500 |
| C(2S)—C(3S) | 1.362(8) |
| C(2S)—H(2S) | 0.9500 |
| C(3S)—C(4S) | 1.379(8) |
| C(3S)—H(3S) | 0.9500 |
| C(4S)—C(5S) | 1.370(8) |
| C(4S)—H(4S) | 0.9500 |
| C(5S)—C(6S) | 1.378(8) |
| C(5S)—H(5S) | 0.9500 |
| C(6S)—H(6S) | 0.9500 |
| C(1T)—C(6T) | 1.370(8) |
| C(1T)—C(2T) | 1.387(9) |
| C(1T)—H(1T) | 0.9500 |
| C(2T)—C(3T) | 1.389(9) |
| C(2T)—H(2T) | 0.9500 |
| C(3T)—C(4T) | 1.382(8) |
| C(3T)—H(3T) | 0.9500 |
| C(4T)—C(5T) | 1.368(8) |
| C(4T)—H(4T) | 0.9500 |
| C(5T)—C(6T) | 1.370(8) |
| C(5T)—H(5T) | 0.9500 |
| C(6T)—H(6T) | 0.9500 |
| C(1U)—C(6U) | 1.378(8) |
| C(1U)—C(2U) | 1.388(7) |
| C(1U)—H(1U) | 0.9500 |
| C(2U)—C(3U) | 1.377(7) |
| C(2U)—H(2U) | 0.9500 |
| C(3U)—C(4U) | 1.381(7) |
| C(3U)—H(3U) | 0.9500 |
| C(4U)—C(5U) | 1.383(8) |
| C(4U)—H(4U) | 0.9500 |
| C(5U)—C(6U) | 1.386(8) |
| C(5U)—H(5U) | 0.9500 |
| C(6U)—H(6U) | 0.9500 |
| C(1V)—C(2V) | 1.363(9) |
| C(1V)—C(6V) | 1.366(10) |
| C(1V)—H(1V) | 0.9500 |
| C(2V)—C(3V) | 1.360(9) |
| C(2V)—H(2V) | 0.9500 |
| C(3V)—C(4V) | 1.368(9) |
| C(3V)—H(3V) | 0.9500 |
| C(4V)—C(5V) | 1.363(10) |
| C(4V)—H(4V) | 0.9500 |
| C(5V)—C(6V) | 1.365(10) |
| C(5V)—H(5V) | 0.9500 |
| C(6V)—H(6V) | 0.9500 |
| C(1W)—C(6W) | 1.363(8) |
| C(1W)—C(2W) | 1.381(9) |
| C(1W)—H(1W) | 0.9500 |
| C(2W)—C(3W) | 1.395(9) |
| C(2W)—H(2W) | 0.9500 |
| C(3W)—C(4W) | 1.372(8) |
| C(3W)—H(3W) | 0.9500 |
| C(4W)—C(5W) | 1.361(8) |
| C(4W)—H(4W) | 0.9500 |
| C(5W)—C(6W) | 1.377(8) |
| C(5W)—H(5W) | 0.9500 |
| C(6W)—H(6W) | 0.9500 |
| C(1X)—C(2X) | 1.377(7) |
| C(1X)—C(6X) | 1.377(7) |
| C(1X)—H(1X) | 0.9500 |
| C(2X)—C(3X) | 1.378(7) |
| C(2X)—H(2X) | 0.9500 |
| C(3X)—C(4X) | 1.372(7) |
| C(3X)—H(3X) | 0.9500 |
| C(4X)—C(5X) | 1.377(7) |
| C(4X)—H(4X) | 0.9500 |
| C(5X)—C(6X) | 1.376(7) |
| C(5X)—H(5X) | 0.9500 |
| C(6X)—H(6X) | 0.9500 |
| C(1)—Mo(1)—N(4) | 109.89(19) |
| C(1)—Mo(1)—N(1) | 103.34(19) |
| N(4)—Mo(1)—N(1) | 101.73(16) |
| C(1)—Mo(1)—N(3) | 92.57(18) |
| N(4)—Mo(1)—N(3) | 92.59(15) |
| N(1)—Mo(1)—N(3) | 153.28(14) |
| C(1)—Mo(1)—N(2) | 106.16(17) |
| N(4)—Mo(1)—N(2) | 140.98(15) |
| N(1)—Mo(1)—N(2) | 83.75(14) |
| N(3)—Mo(1)—N(2) | 71.15(13) |
| C(2)—C(1)—Mo(1) | 167.1(4) |
| C(1)—C(2)—C(5) | 111.2(4) |
| C(1)—C(2)—C(3) | 108.4(4) |
| C(5)—C(2)—C(3) | 109.7(5) |
| C(1)—C(2)—C(4) | 109.3(4) |
| C(5)—C(2)—C(4) | 109.3(5) |
| C(3)—C(2)—C(4) | 108.9(5) |
| C(2)—C(3)—H(3A) | 109.5 |
| C(2)—C(3)—H(3B) | 109.5 |

TABLE 105C-continued

Bond lengths [Å] and angles [°] for 104g.

| | |
|---|---|
| H(3A)—C(3)—H(3B) | 109.5 |
| C(2)—C(3)—H(3C) | 109.5 |
| H(3A)—C(3)—H(3C) | 109.5 |
| H(3B)—C(3)—H(3C) | 109.5 |
| C(2)—C(4)—H(4A) | 109.5 |
| C(2)—C(4)—H(4B) | 109.5 |
| H(4A)—C(4)—H(4B) | 109.5 |
| C(2)—C(4)—H(4C) | 109.5 |
| H(4A)—C(4)—H(4C) | 109.5 |
| H(4B)—C(4)—H(4C) | 109.5 |
| C(2)—C(5)—H(5A) | 109.5 |
| C(2)—C(5)—H(5B) | 109.5 |
| H(5A)—C(5)—H(5B) | 109.5 |
| C(2)—C(5)—H(5C) | 109.5 |
| H(5A)—C(5)—H(5C) | 109.5 |
| H(5B)—C(5)—H(5C) | 109.5 |
| C(6)—N(1)—C(9) | 105.8(4) |
| C(6)—N(1)—Mo(1) | 131.9(3) |
| C(9)—N(1)—Mo(1) | 120.1(3) |
| C(7)—C(6)—N(1) | 110.0(4) |
| C(7)—C(6)—C(10) | 127.6(5) |
| N(1)—C(6)—C(10) | 122.5(4) |
| C(6)—C(7)—C(8) | 107.3(4) |
| C(6)—C(7)—H(7) | 126.4 |
| C(8)—C(7)—H(7) | 126.4 |
| C(9)—C(8)—C(7) | 106.9(5) |
| C(9)—C(8)—H(8) | 126.6 |
| C(7)—C(8)—H(8) | 126.6 |
| C(8)—C(9)—N(1) | 110.1(4) |
| C(8)—C(9)—C(11) | 128.3(5) |
| N(1)—C(9)—C(11) | 121.6(4) |
| C(6)—C(10)—H(10A) | 109.5 |
| C(6)—C(10)—H(10B) | 109.5 |
| H(10A)—C(10)—H(10B) | 109.5 |
| C(6)—C(10)—H(10C) | 109.5 |
| H(10A)—C(10)—H(10C) | 109.5 |
| H(10B)—C(10)—H(10C) | 109.5 |
| C(9)—C(11)—H(11A) | 109.5 |
| C(9)—C(11)—H(11B) | 109.5 |
| H(11A)—C(11)—H(11B) | 109.5 |
| C(9)—C(11)—H(11C) | 109.5 |
| H(11A)—C(11)—H(11C) | 109.5 |
| H(11B)—C(11)—H(11C) | 109.5 |
| C(21)—N(2)—C(25) | 117.8(4) |
| C(21)—N(2)—Mo(1) | 124.6(3) |
| C(25)—N(2)—Mo(1) | 117.6(3) |
| N(2)—C(21)—C(22) | 123.2(4) |
| N(2)—C(21)—H(21) | 118.4 |
| C(22)—C(21)—H(21) | 118.4 |
| C(23)—C(22)—C(21) | 118.4(5) |
| C(23)—C(22)—H(22) | 120.8 |
| C(21)—C(22)—H(22) | 120.8 |
| C(24)—C(23)—C(22) | 119.1(4) |
| C(24)—C(23)—H(23) | 120.4 |
| C(22)—C(23)—H(23) | 120.4 |
| C(23)—C(24)—C(25) | 119.4(4) |
| C(23)—C(24)—H(24) | 120.3 |
| C(25)—C(24)—H(24) | 120.3 |
| N(2)—C(25)—C(24) | 122.0(4) |
| N(2)—C(25)—C(26) | 115.6(4) |
| C(24)—C(25)—C(26) | 122.4(4) |
| N(3)—C(26)—C(27) | 120.8(4) |
| N(3)—C(26)—C(25) | 115.2(4) |
| C(27)—C(26)—C(25) | 124.0(4) |
| C(28)—C(27)—C(26) | 120.4(5) |
| C(28)—C(27)—H(27) | 119.8 |
| C(26)—C(27)—H(27) | 119.8 |
| C(27)—C(28)—C(29) | 119.1(5) |
| C(27)—C(28)—H(28) | 120.4 |
| C(29)—C(28)—H(28) | 120.4 |
| C(28)—C(29)—C(30) | 118.1(5) |
| C(28)—C(29)—H(29) | 120.9 |
| C(30)—C(29)—H(29) | 120.9 |
| N(3)—C(30)—C(29) | 123.5(4) |
| N(3)—C(30)—H(30) | 118.2 |
| C(29)—C(30)—H(30) | 118.2 |
| C(30)—N(3)—C(26) | 118.0(4) |
| C(30)—N(3)—Mo(1) | 121.5(3) |
| C(26)—N(3)—Mo(1) | 120.4(3) |
| C(31)—N(4)—Mo(1) | 152.6(3) |
| N(4)—C(31)—C(32) | 121.2(4) |
| N(4)—C(31)—C(36) | 120.5(4) |
| C(32)—C(31)—C(36) | 118.2(4) |
| C(33)—C(32)—C(31) | 121.8(4) |
| C(33)—C(32)—H(32) | 119.1 |
| C(31)—C(32)—H(32) | 119.1 |
| C(34)—C(33)—C(32) | 119.8(5) |
| C(34)—C(33)—H(33) | 120.1 |
| C(32)—C(33)—H(33) | 120.1 |
| C(35)—C(34)—C(33) | 119.5(5) |
| C(35)—C(34)—H(34) | 120.3 |
| C(33)—C(34)—H(34) | 120.3 |
| C(34)—C(35)—C(36) | 122.2(4) |
| C(34)—C(35)—H(35) | 118.9 |
| C(36)—C(35)—H(35) | 118.9 |
| C(35)—C(36)—C(31) | 118.4(4) |
| C(35)—C(36)—C(41) | 119.1(4) |
| C(31)—C(36)—C(41) | 122.4(4) |
| C(46)—C(41)—C(42) | 119.5(4) |
| C(46)—C(41)—C(36) | 120.9(4) |
| C(42)—C(41)—C(36) | 119.5(4) |
| C(43)—C(42)—C(41) | 119.0(5) |
| C(43)—C(42)—C(47) | 118.4(5) |
| C(41)—C(42)—C(47) | 122.6(5) |
| C(42)—C(47)—C(48) | 111.8(5) |
| C(42)—C(47)—C(49) | 112.0(5) |
| C(48)—C(47)—C(49) | 110.1(5) |
| C(42)—C(47)—H(47) | 107.6 |
| C(48)—C(47)—H(47) | 107.6 |
| C(49)—C(47)—H(47) | 107.6 |
| C(47)—C(48)—H(48A) | 109.5 |
| C(47)—C(48)—H(48B) | 109.5 |
| H(48A)—C(48)—H(48B) | 109.5 |
| C(47)—C(48)—H(48C) | 109.5 |
| H(48A)—C(48)—H(48C) | 109.5 |
| H(48B)—C(48)—H(48C) | 109.5 |
| C(47)—C(49)—H(49A) | 109.5 |
| C(47)—C(49)—H(49B) | 109.5 |
| H(49A)—C(49)—H(49B) | 109.5 |
| C(47)—C(49)—H(49C) | 109.5 |
| H(49A)—C(49)—H(49C) | 109.5 |
| H(49B)—C(49)—H(49C) | 109.5 |
| C(44)—C(43)—C(42) | 122.1(5) |
| C(44)—C(43)—H(43) | 119.0 |
| C(42)—C(43)—H(43) | 119.0 |
| C(43)—C(44)—C(45) | 118.4(5) |
| C(43)—C(44)—C(50) | 121.8(5) |
| C(45)—C(44)—C(50) | 119.8(5) |
| C(51)—C(50)—C(44) | 111.9(5) |
| C(51)—C(50)—C(52) | 111.8(6) |
| C(44)—C(50)—C(52) | 111.4(5) |
| C(51)—C(50)—H(50) | 107.2 |
| C(44)—C(50)—H(50) | 107.2 |
| C(52)—C(50)—H(50) | 107.2 |
| C(50)—C(51)—H(51A) | 109.5 |
| C(50)—C(51)—H(51B) | 109.5 |
| H(51A)—C(51)—H(51B) | 109.5 |
| C(50)—C(51)—H(51C) | 109.5 |
| H(51A)—C(51)—H(51C) | 109.5 |
| H(51B)—C(51)—H(51C) | 109.5 |
| C(50)—C(52)—H(52A) | 109.5 |
| C(50)—C(52)—H(52B) | 109.5 |
| H(52A)—C(52)—H(52B) | 109.5 |
| C(50)—C(52)—H(52C) | 109.5 |
| H(52A)—C(52)—H(52C) | 109.5 |
| H(52B)—C(52)—H(52C) | 109.5 |
| C(44)—C(45)—C(46) | 121.4(5) |
| C(44)—C(45)—H(45) | 119.3 |
| C(46)—C(45)—H(45) | 119.3 |
| C(45)—C(46)—C(41) | 119.6(4) |
| C(45)—C(46)—C(53) | 119.1(4) |
| C(41)—C(46)—C(53) | 121.2(4) |
| C(46)—C(53)—C(55) | 110.9(4) |
| C(46)—C(53)—C(54) | 112.3(4) |
| C(55)—C(53)—C(54) | 111.1(4) |
| C(46)—C(53)—H(53) | 107.5 |

TABLE 105C-continued

Bond lengths [Å] and angles [°] for 104g.

| | |
|---|---|
| C(55)—C(53)—H(53) | 107.5 |
| C(54)—C(53)—H(53) | 107.5 |
| C(53)—C(54)—H(54A) | 109.5 |
| C(53)—C(54)—H(54B) | 109.5 |
| H(54A)—C(54)—H(54B) | 109.5 |
| C(53)—C(54)—H(54C) | 109.5 |
| H(54A)—C(54)—H(54C) | 109.5 |
| H(54B)—C(54)—H(54C) | 109.5 |
| C(53)—C(55)—H(55A) | 109.5 |
| C(53)—C(55)—H(55B) | 109.5 |
| H(55A)—C(55)—H(55B) | 109.5 |
| C(53)—C(55)—H(55C) | 109.5 |
| H(55A)—C(55)—H(55C) | 109.5 |
| H(55B)—C(55)—H(55C) | 109.5 |
| N(4A)—Mo(2)—C(101) | 111.5(15) |
| N(4A)—Mo(2)—N(104) | 3(2) |
| C(101)—Mo(2)—N(104) | 108.6(7) |
| N(4A)—Mo(2)—N(101) | 102(2) |
| C(101)—Mo(2)—N(101) | 102.8(2) |
| N(104)—Mo(2)—N(101) | 104.0(11) |
| N(4A)—Mo(2)—N(103) | 92(2) |
| C(101)—Mo(2)—N(103) | 92.20(19) |
| N(104)—Mo(2)—N(103) | 91.3(12) |
| N(101)—Mo(2)—N(103) | 153.56(15) |
| N(4A)—Mo(2)—N(102) | 138.3(18) |
| C(101)—Mo(2)—N(102) | 107.07(19) |
| N(104)—Mo(2)—N(102) | 140.6(9) |
| N(101)—Mo(2)—N(102) | 83.69(15) |
| N(103)—Mo(2)—N(102) | 71.04(14) |
| C(102)—C(101)—Mo(2) | 165.2(4) |
| C(101)—C(102)—C(103) | 109.3(4) |
| C(101)—C(102)—C(105) | 110.0(5) |
| C(103)—C(102)—C(105) | 110.3(5) |
| C(101)—C(102)—C(104) | 109.7(4) |
| C(103)—C(102)—C(104) | 108.7(5) |
| C(105)—C(102)—C(104) | 108.8(5) |
| C(102)—C(103)—H(10D) | 109.5 |
| C(102)—C(103)—H(10E) | 109.5 |
| H(10D)—C(103)—H(10E) | 109.5 |
| C(102)—C(103)—H(10F) | 109.5 |
| H(10D)—C(103)—H(10F) | 109.5 |
| H(10E)—C(103)—H(10F) | 109.5 |
| C(102)—C(104)—H(10G) | 109.5 |
| C(102)—C(104)—H(10H) | 109.5 |
| H(10G)—C(104)—H(10H) | 109.5 |
| C(102)—C(104)—H(10I) | 109.5 |
| H(10G)—C(104)—H(10I) | 109.5 |
| H(10H)—C(104)—H(10I) | 109.5 |
| C(102)—C(105)—H(10J) | 109.5 |
| C(102)—C(105)—H(10K) | 109.5 |
| H(10J)—C(105)—H(10K) | 109.5 |
| C(102)—C(105)—H(10L) | 109.5 |
| H(10J)—C(105)—H(10L) | 109.5 |
| H(10K)—C(105)—H(10L) | 109.5 |
| C(106)—N(101)—C(109) | 106.3(4) |
| C(106)—N(101)—Mo(2) | 132.5(3) |
| C(109)—N(101)—Mo(2) | 119.1(3) |
| C(107)—C(106)—N(101) | 109.7(5) |
| C(107)—C(106)—C(110) | 127.5(5) |
| N(101)—C(106)—C(110) | 122.9(5) |
| C(106)—C(107)—C(108) | 107.6(5) |
| C(106)—C(107)—H(107) | 126.2 |
| C(108)—C(107)—H(107) | 126.2 |
| C(109)—C(108)—C(107) | 106.6(5) |
| C(109)—C(108)—H(108) | 126.7 |
| C(107)—C(108)—H(108) | 126.7 |
| C(108)—C(109)—N(101) | 109.9(5) |
| C(108)—C(109)—C(111) | 128.2(5) |
| N(101)—C(109)—C(111) | 121.9(4) |
| C(106)—C(110)—H(11D) | 109.5 |
| C(106)—C(110)—H(11E) | 109.5 |
| H(11D)—C(110)—H(11E) | 109.5 |
| C(106)—C(110)—H(11F) | 109.5 |
| H(11D)—C(110)—H(11F) | 109.5 |
| H(11E)—C(110)—H(11F) | 109.5 |
| C(109)—C(111)—H(11G) | 109.5 |
| C(109)—C(111)—H(11H) | 109.5 |
| H(11G)—C(111)—H(11H) | 109.5 |
| C(109)—C(111)—H(11I) | 109.5 |
| H(11G)—C(111)—H(11I) | 109.5 |
| H(11H)—C(111)—H(11I) | 109.5 |
| C(121)—N(102)—C(125) | 117.8(4) |
| C(121)—N(102)—Mo(2) | 124.4(3) |
| C(125)—N(102)—Mo(2) | 117.7(3) |
| N(102)—C(121)—C(122) | 123.0(5) |
| N(102)—C(121)—H(121) | 118.5 |
| C(122)—C(121)—H(121) | 118.5 |
| C(121)—C(122)—C(123) | 118.9(5) |
| C(121)—C(122)—H(122) | 120.5 |
| C(123)—C(122)—H(122) | 120.5 |
| C(124)—C(123)—C(122) | 118.7(5) |
| C(124)—C(123)—H(123) | 120.6 |
| C(122)—C(123)—H(123) | 120.6 |
| C(125)—C(124)—C(123) | 119.4(5) |
| C(125)—C(124)—H(124) | 120.3 |
| C(123)—C(124)—H(124) | 120.3 |
| N(102)—C(125)—C(124) | 122.3(5) |
| N(102)—C(125)—C(126) | 114.2(4) |
| C(124)—C(125)—C(126) | 123.5(5) |
| N(103)—C(126)—C(127) | 122.1(5) |
| N(103)—C(126)—C(125) | 116.2(4) |
| C(127)—C(126)—C(125) | 121.8(5) |
| C(128)—C(127)—C(126) | 119.5(5) |
| C(128)—C(127)—H(127) | 120.2 |
| C(126)—C(127)—H(127) | 120.2 |
| C(127)—C(128)—C(129) | 118.8(5) |
| C(127)—C(128)—H(128) | 120.6 |
| C(129)—C(128)—H(128) | 120.6 |
| C(130)—C(129)—C(128) | 118.8(5) |
| C(130)—C(129)—H(129) | 120.6 |
| C(128)—C(129)—H(129) | 120.6 |
| N(103)—C(130)—C(129) | 122.4(5) |
| N(103)—C(130)—H(130) | 118.8 |
| C(129)—C(130)—H(130) | 118.8 |
| C(126)—N(103)—C(130) | 118.3(4) |
| C(126)—N(103)—Mo(2) | 120.7(3) |
| C(130)—N(103)—Mo(2) | 121.0(3) |
| C(131)—N(104)—Mo(2) | 154.2(15) |
| N(104)—C(131)—C(132) | 122.2(9) |
| N(104)—C(131)—C(136) | 120.2(9) |
| C(132)—C(131)—C(136) | 117.6(7) |
| C(133)—C(132)—C(131) | 122.5(8) |
| C(133)—C(132)—H(132) | 118.7 |
| C(131)—C(132)—H(132) | 118.7 |
| C(132)—C(133)—C(134) | 119.7(8) |
| C(132)—C(133)—H(133) | 120.2 |
| C(134)—C(133)—H(133) | 120.2 |
| C(135)—C(134)—C(133) | 118.6(8) |
| C(135)—C(134)—H(134) | 120.7 |
| C(133)—C(134)—H(134) | 120.7 |
| C(134)—C(135)—C(136) | 123.0(8) |
| C(134)—C(135)—H(135) | 118.5 |
| C(136)—C(135)—H(135) | 118.5 |
| C(135)—C(136)—C(131) | 118.5(7) |
| C(135)—C(136)—C(141) | 121.0(8) |
| C(131)—C(136)—C(141) | 120.5(8) |
| C(142)—C(141)—C(146) | 119.6(7) |
| C(142)—C(141)—C(136) | 121.8(8) |
| C(146)—C(141)—C(136) | 118.5(8) |
| C(143)—C(142)—C(141) | 119.8(7) |
| C(143)—C(142)—C(147) | 119.9(7) |
| C(141)—C(142)—C(147) | 120.3(7) |
| C(142)—C(147)—C(149) | 110.7(8) |
| C(142)—C(147)—C(148) | 112.8(7) |
| C(149)—C(147)—C(148) | 109.9(10) |
| C(142)—C(147)—H(147) | 107.7 |
| C(149)—C(147)—H(147) | 107.7 |
| C(148)—C(147)—H(147) | 107.7 |
| C(144)—C(143)—C(142) | 121.4(7) |
| C(144)—C(143)—H(143) | 119.3 |
| C(142)—C(143)—H(143) | 119.3 |
| C(145)—C(144)—C(143) | 118.4(7) |
| C(145)—C(144)—C(150) | 120.1(7) |
| C(143)—C(144)—C(150) | 121.5(8) |
| C(151)—C(150)—C(152) | 114.1(9) |
| C(151)—C(150)—C(144) | 111.5(8) |

TABLE 105C-continued

Bond lengths [Å] and angles [°] for 104g.

| | |
|---|---|
| C(152)—C(150)—C(144) | 113.3(7) |
| C(151)—C(150)—H(150) | 105.7 |
| C(152)—C(150)—H(150) | 105.7 |
| C(144)—C(150)—H(150) | 105.7 |
| C(144)—C(145)—C(146) | 122.4(7) |
| C(144)—C(145)—H(145) | 118.8 |
| C(146)—C(145)—H(145) | 118.8 |
| C(145)—C(146)—C(141) | 118.3(7) |
| C(145)—C(146)—C(153) | 118.3(7) |
| C(141)—C(146)—C(153) | 123.3(7) |
| C(146)—C(153)—C(155) | 113.3(7) |
| C(146)—C(153)—C(154) | 111.6(7) |
| C(155)—C(153)—C(154) | 110.0(8) |
| C(146)—C(153)—H(153) | 107.2 |
| C(155)—C(153)—H(153) | 107.2 |
| C(154)—C(153)—H(153) | 107.2 |
| C(31A)—N(4A)—Mo(2) | 153(3) |
| N(4A)—C(31A)—C(32A) | 121.7(16) |
| N(4A)—C(31A)—C(36A) | 120.3(15) |
| C(32A)—C(31A)—C(36A) | 117.8(13) |
| C(33A)—C(32A)—C(31A) | 121.9(14) |
| C(33A)—C(32A)—H(32A) | 119.1 |
| C(31A)—C(32A)—H(32A) | 119.1 |
| C(32A)—C(33A)—C(34A) | 120.0(14) |
| C(32A)—C(33A)—H(33A) | 120.0 |
| C(34A)—C(33A)—H(33A) | 120.0 |
| C(35A)—C(34A)—C(33A) | 118.4(14) |
| C(35A)—C(34A)—H(34A) | 120.8 |
| C(33A)—C(34A)—H(34A) | 120.8 |
| C(34A)—C(35A)—C(36A) | 122.9(13) |
| C(34A)—C(35A)—H(35A) | 118.6 |
| C(36A)—C(35A)—H(35A) | 118.6 |
| C(35A)—C(36A)—C(31A) | 118.9(12) |
| C(35A)—C(36A)—C(41A) | 118.6(13) |
| C(31A)—C(36A)—C(41A) | 122.5(14) |
| C(42A)—C(41A)—C(46A) | 119.9(11) |
| C(42A)—C(41A)—C(36A) | 121.1(13) |
| C(46A)—C(41A)—C(36A) | 119.0(13) |
| C(43A)—C(42A)—C(41A) | 119.1(11) |
| C(43A)—C(42A)—C(47A) | 119.6(12) |
| C(41A)—C(42A)—C(47A) | 121.2(12) |
| C(42A)—C(47A)—C(49A) | 111.9(14) |
| C(42A)—C(47A)—C(48A) | 113.8(13) |
| C(49A)—C(47A)—C(48A) | 110.6(16) |
| C(42A)—C(47A)—H(47A) | 106.7 |
| C(49A)—C(47A)—H(47A) | 106.7 |
| C(48A)—C(47A)—H(47A) | 106.7 |
| C(47A)—C(48A)—H(48D) | 109.5 |
| C(47A)—C(48A)—H(48E) | 109.5 |
| H(48D)—C(48A)—H(48E) | 109.5 |
| C(47A)—C(48A)—H(48F) | 109.5 |
| H(48D)—C(48A)—H(48F) | 109.5 |
| H(48E)—C(48A)—H(48F) | 109.5 |
| C(47A)—C(49A)—H(49D) | 109.5 |
| C(47A)—C(49A)—H(49E) | 109.5 |
| H(49D)—C(49A)—H(49E) | 109.5 |
| C(47A)—C(49A)—H(49F) | 109.5 |
| H(49D)—C(49A)—H(49F) | 109.5 |
| H(49E)—C(49A)—H(49F) | 109.5 |
| C(42A)—C(43A)—C(44A) | 121.5(12) |
| C(42A)—C(43A)—H(43A) | 119.3 |
| C(44A)—C(43A)—H(43A) | 119.3 |
| C(45A)—C(44A)—C(43A) | 118.6(11) |
| C(45A)—C(44A)—C(50A) | 121.1(12) |
| C(43A)—C(44A)—C(50A) | 120.1(13) |
| C(51A)—C(50A)—C(52A) | 116.2(17) |
| C(51A)—C(50A)—C(44A) | 112.6(14) |
| C(52A)—C(50A)—C(44A) | 110.5(12) |
| C(51A)—C(50A)—H(50A) | 105.5 |
| C(52A)—C(50A)—H(50A) | 105.5 |
| C(44A)—C(50A)—H(50A) | 105.5 |
| C(50A)—C(51A)—H(51D) | 109.5 |
| C(50A)—C(51A)—H(51E) | 109.5 |
| H(51D)—C(51A)—H(51E) | 109.5 |
| C(50A)—C(51A)—H(51F) | 109.5 |
| H(51D)—C(51A)—H(51F) | 109.5 |
| H(51E)—C(51A)—H(51F) | 109.5 |
| C(50A)—C(52A)—H(52D) | 109.5 |
| C(50A)—C(52A)—H(52E) | 109.5 |
| H(52D)—C(52A)—H(52E) | 109.5 |
| C(50A)—C(52A)—H(52F) | 109.5 |
| H(52D)—C(52A)—H(52F) | 109.5 |
| H(52E)—C(52A)—H(52F) | 109.5 |
| C(44A)—C(45A)—C(46A) | 121.8(12) |
| C(44A)—C(45A)—H(45A) | 119.1 |
| C(46A)—C(45A)—H(45A) | 119.1 |
| C(45A)—C(46A)—C(41A) | 119.0(12) |
| C(45A)—C(46A)—C(53A) | 120.3(12) |
| C(41A)—C(46A)—C(53A) | 120.7(11) |
| C(46A)—C(53A)—C(54A) | 112.0(13) |
| C(46A)—C(53A)—C(55A) | 111.8(13) |
| C(54A)—C(53A)—C(55A) | 111.1(14) |
| C(46A)—C(53A)—H(53A) | 107.2 |
| C(54A)—C(53A)—H(53A) | 107.2 |
| C(55A)—C(53A)—H(53A) | 107.2 |
| C(53A)—C(54A)—H(54D) | 109.5 |
| C(53A)—C(54A)—H(54E) | 109.5 |
| H(54D)—C(54A)—H(54E) | 109.5 |
| C(53A)—C(54A)—H(54F) | 109.5 |
| H(54D)—C(54A)—H(54F) | 109.5 |
| H(54E)—C(54A)—H(54F) | 109.5 |
| C(53A)—C(55A)—H(55D) | 109.5 |
| C(53A)—C(55A)—H(55E) | 109.5 |
| H(55D)—C(55A)—H(55E) | 109.5 |
| C(53A)—C(55A)—H(55F) | 109.5 |
| H(55D)—C(55A)—H(55F) | 109.5 |
| H(55E)—C(55A)—H(55F) | 109.5 |
| C(6S)—C(1S)—C(2S) | 120.7(7) |
| C(6S)—C(1S)—H(1S) | 119.7 |
| C(2S)—C(1S)—H(1S) | 119.7 |
| C(3S)—C(2S)—C(1S) | 119.6(7) |
| C(3S)—C(2S)—H(2S) | 120.2 |
| C(1S)—C(2S)—H(2S) | 120.2 |
| C(2S)—C(3S)—C(4S) | 119.9(7) |
| C(2S)—C(3S)—H(3S) | 120.0 |
| C(4S)—C(3S)—H(3S) | 120.0 |
| C(5S)—C(4S)—C(3S) | 120.8(6) |
| C(5S)—C(4S)—H(4S) | 119.6 |
| C(3S)—C(4S)—H(4S) | 119.6 |
| C(4S)—C(5S)—C(6S) | 119.6(6) |
| C(4S)—C(5S)—H(5S) | 120.2 |
| C(6S)—C(5S)—H(5S) | 120.2 |
| C(5S)—C(6S)—C(1S) | 119.4(7) |
| C(5S)—C(6S)—H(6S) | 120.3 |
| C(1S)—C(6S)—H(6S) | 120.3 |
| C(6T)—C(1T)—C(2T) | 120.7(7) |
| C(6T)—C(1T)—H(1T) | 119.6 |
| C(2T)—C(1T)—H(1T) | 119.6 |
| C(1T)—C(2T)—C(3T) | 119.3(6) |
| C(1T)—C(2T)—H(2T) | 120.4 |
| C(3T)—C(2T)—H(2T) | 120.4 |
| C(4T)—C(3T)—C(2T) | 119.8(7) |
| C(4T)—C(3T)—H(3T) | 120.1 |
| C(2T)—C(3T)—H(3T) | 120.1 |
| C(5T)—C(4T)—C(3T) | 119.5(7) |
| C(5T)—C(4T)—H(4T) | 120.3 |
| C(3T)—C(4T)—H(4T) | 120.3 |
| C(4T)—C(5T)—C(6T) | 121.6(6) |
| C(4T)—C(5T)—H(5T) | 119.2 |
| C(6T)—C(5T)—H(5T) | 119.2 |
| C(5T)—C(6T)—C(1T) | 119.1(7) |
| C(5T)—C(6T)—H(6T) | 120.4 |
| C(1T)—C(6T)—H(6T) | 120.4 |
| C(6U)—C(1U)—C(2U) | 120.0(5) |
| C(6U)—C(1U)—H(1U) | 120.0 |
| C(2U)—C(1U)—H(1U) | 120.0 |
| C(3U)—C(2U)—C(1U) | 120.1(5) |
| C(3U)—C(2U)—H(2U) | 120.0 |
| C(1U)—C(2U)—H(2U) | 120.0 |
| C(2U)—C(3U)—C(4U) | 120.2(5) |
| C(2U)—C(3U)—H(3U) | 119.9 |
| C(4U)—C(3U)—H(3U) | 119.9 |
| C(3U)—C(4U)—C(5U) | 119.7(5) |
| C(3U)—C(4U)—H(4U) | 120.1 |
| C(5U)—C(4U)—H(4U) | 120.1 |
| C(4U)—C(5U)—C(6U) | 120.2(6) |

TABLE 105C-continued

Bond lengths [Å] and angles [°] for 104g.

| | |
|---|---|
| C(4U)—C(5U)—H(5U) | 119.9 |
| C(6U)—C(5U)—H(5U) | 119.9 |
| C(1U)—C(6U)—C(5U) | 119.8(6) |
| C(1U)—C(6U)—H(6U) | 120.1 |
| C(5U)—C(6U)—H(6U) | 120.1 |
| C(2V)—C(1V)—C(6V) | 116.8(9) |
| C(2V)—C(1V)—H(1V) | 121.6 |
| C(6V)—C(1V)—H(1V) | 121.6 |
| C(3V)—C(2V)—C(1V) | 123.3(8) |
| C(3V)—C(2V)—H(2V) | 118.4 |
| C(1V)—C(2V)—H(2V) | 118.4 |
| C(2V)—C(3V)—C(4V) | 119.8(9) |
| C(2V)—C(3V)—H(3V) | 120.1 |
| C(4V)—C(3V)—H(3V) | 120.1 |
| C(5V)—C(4V)—C(3V) | 117.2(9) |
| C(5V)—C(4V)—H(4V) | 121.4 |
| C(3V)—C(4V)—H(4V) | 121.4 |
| C(4V)—C(5V)—C(6V) | 122.7(9) |
| C(4V)—C(5V)—H(5V) | 118.7 |
| C(6V)—C(5V)—H(5V) | 118.7 |
| C(5V)—C(6V)—C(1V) | 120.2(9) |
| C(5V)—C(6V)—H(6V) | 119.9 |
| C(1V)—C(6V)—H(6V) | 119.9 |
| C(6W)—C(1W)—C(2W) | 119.2(7) |
| C(6W)—C(1W)—H(1W) | 120.4 |
| C(2W)—C(1W)—H(1W) | 120.4 |
| C(1W)—C(2W)—C(3W) | 120.5(7) |
| C(1W)—C(2W)—H(2W) | 119.8 |
| C(3W)—C(2W)—H(2W) | 119.8 |
| C(4W)—C(3W)—C(2W) | 119.3(7) |
| C(4W)—C(3W)—H(3W) | 120.3 |
| C(2W)—C(3W)—H(3W) | 120.3 |
| C(5W)—C(4W)—C(3W) | 119.6(7) |
| C(5W)—C(4W)—H(4W) | 120.2 |
| C(3W)—C(4W)—H(4W) | 120.2 |
| C(4W)—C(5W)—C(6W) | 121.4(6) |
| C(4W)—C(5W)—H(5W) | 119.3 |
| C(6W)—C(5W)—H(5W) | 119.3 |
| C(1W)—C(6W)—C(5W) | 120.0(7) |
| C(1W)—C(6W)—H(6W) | 120.0 |
| C(5W)—C(6W)—H(6W) | 120.0 |
| C(2X)—C(1X)—C(6X) | 119.6(5) |
| C(2X)—C(1X)—H(1X) | 120.2 |
| C(6X)—C(1X)—H(1X) | 120.2 |
| C(1X)—C(2X)—C(3X) | 120.1(5) |
| C(1X)—C(2X)—H(2X) | 120.0 |
| C(3X)—C(2X)—H(2X) | 120.0 |
| C(4X)—C(3X)—C(2X) | 120.2(5) |
| C(4X)—C(3X)—H(3X) | 119.9 |
| C(2X)—C(3X)—H(3X) | 119.9 |
| C(3X)—C(4X)—C(5X) | 119.8(5) |
| C(3X)—C(4X)—H(4X) | 120.1 |
| C(5X)—C(4X)—H(4X) | 120.1 |
| C(6X)—C(5X)—C(4X) | 120.0(5) |
| C(6X)—C(5X)—H(5X) | 120.0 |
| C(4X)—C(5X)—H(5X) | 120.0 |
| C(5X)—C(6X)—C(1X) | 120.3(5) |
| C(5X)—C(6X)—H(6X) | 119.9 |
| C(1X)—C(6X)—H(6X) | 119.9 |

Symmetry transformations used to generate equivalent atoms:

TABLE 105D

Anisotropic displacement parameters ($Å^2 \times 10^3$) for 104g.
The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| Mo(1) | 17 (1) | 24 (1) | 9 (1) | −2 (1) | 6 (1) | −1 (1) |
| C(1) | 21 (2) | 30 (2) | 13 (2) | −4 (2) | 5 (2) | −3 (2) |
| C(2) | 18 (2) | 40 (3) | 29 (3) | −10 (2) | 4 (2) | 1 (2) |
| C(3) | 32 (3) | 42 (3) | 40 (3) | 0 (2) | 11 (2) | 12 (2) |
| C(4) | 26 (3) | 58 (4) | 64 (4) | −27 (3) | −11 (3) | 9 (3) |
| C(5) | 35 (3) | 48 (3) | 50 (3) | −11 (3) | 28 (3) | −2 (3) |
| N(1) | 24 (2) | 27 (2) | 15 (2) | −2 (1) | 10 (2) | −2 (1) |
| C(6) | 29 (2) | 30 (2) | 14 (2) | −3 (2) | 11 (2) | −7 (2) |
| C(7) | 36 (2) | 29 (2) | 18 (2) | −4 (2) | 12 (2) | −8 (2) |
| C(8) | 36 (2) | 28 (2) | 18 (2) | −5 (2) | 12 (2) | 0 (2) |
| C(9) | 29 (2) | 29 (2) | 11 (2) | −1 (2) | 8 (2) | 1 (2) |
| C(10) | 28 (2) | 36 (3) | 49 (3) | 0 (3) | 14 (2) | −8 (2) |
| C(11) | 26 (2) | 32 (3) | 28 (3) | 5 (2) | 9 (2) | 3 (2) |
| N(2) | 19 (2) | 31 (2) | 5 (1) | 0 (1) | 4 (1) | 1 (2) |
| C(21) | 28 (2) | 29 (2) | 12 (2) | 1 (2) | 8 (2) | 0 (2) |
| C(22) | 32 (3) | 28 (2) | 19 (2) | −2 (2) | 9 (2) | −1 (2) |
| C(23) | 32 (3) | 35 (2) | 15 (2) | −4 (2) | 10 (2) | 3 (2) |
| C(24) | 27 (2) | 33 (2) | 10 (2) | 1 (2) | 5 (2) | 1 (2) |
| C(25) | 17 (2) | 33 (2) | 6 (2) | 1 (2) | 6 (2) | 2 (2) |
| C(26) | 21 (2) | 31 (2) | 12 (2) | 3 (2) | 6 (2) | 3 (2) |
| C(27) | 32 (3) | 33 (2) | 13 (2) | 2 (2) | 8 (2) | 2 (2) |
| C(28) | 39 (3) | 33 (2) | 19 (2) | 6 (2) | 10 (2) | −1 (2) |
| C(29) | 34 (3) | 27 (2) | 20 (2) | 0 (2) | 7 (2) | −1 (2) |
| C(30) | 25 (2) | 25 (2) | 20 (2) | 2 (2) | 7 (2) | 1 (2) |
| N(3) | 20 (2) | 28 (2) | 10 (2) | 2 (1) | 4 (1) | 2 (2) |
| N(4) | 19 (2) | 27 (2) | 11 (2) | 0 (1) | 5 (1) | −3 (1) |
| C(31) | 21 (2) | 27 (2) | 7 (2) | 2 (2) | 6 (2) | −4 (2) |
| C(32) | 21 (2) | 32 (2) | 18 (2) | −1 (2) | 9 (2) | −2 (2) |
| C(33) | 29 (2) | 31 (2) | 25 (2) | −3 (2) | 12 (2) | 1 (2) |
| C(34) | 34 (2) | 31 (3) | 23 (2) | −8 (2) | 11 (2) | −6 (2) |
| C(35) | 26 (2) | 35 (2) | 12 (2) | −4 (2) | 1 (2) | −5 (2) |
| C(36) | 22 (2) | 28 (2) | 14 (2) | 0 (2) | 6 (2) | −4 (2) |
| C(41) | 20 (2) | 29 (2) | 14 (2) | −1 (2) | 3 (2) | −6 (2) |
| C(42) | 21 (2) | 34 (3) | 23 (2) | 5 (2) | 2 (2) | −4 (2) |
| C(47) | 31 (3) | 47 (3) | 25 (2) | 10 (2) | 8 (2) | 1 (2) |
| C(48) | 36 (3) | 53 (3) | 51 (4) | 23 (3) | 15 (3) | 2 (3) |

TABLE 105D-continued

Anisotropic displacement parameters (Å² × 10³) for 104g.
The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(49) | 59 (4) | 73 (4) | 23 (3) | 6 (3) | 8 (3) | −5 (3) |
| C(43) | 25 (2) | 34 (3) | 33 (3) | 10 (2) | 6 (2) | −1 (2) |
| C(44) | 23 (2) | 33 (3) | 33 (3) | 4 (2) | 5 (2) | −1 (2) |
| C(50) | 29 (3) | 43 (3) | 50 (3) | 13 (2) | 15 (2) | 7 (2) |
| C(51) | 51 (4) | 40 (3) | 102 (6) | 7 (3) | 38 (4) | 12 (3) |
| C(52) | 27 (3) | 68 (4) | 57 (4) | 19 (3) | 12 (2) | 13 (3) |
| C(45) | 22 (2) | 31 (2) | 30 (2) | 1 (2) | 10 (2) | −2 (2) |
| C(46) | 17 (2) | 28 (2) | 19 (2) | −3 (2) | 5 (2) | −5 (2) |
| C(53) | 20 (2) | 33 (2) | 16 (2) | 0 (2) | 9 (2) | 0 (2) |
| C(54) | 27 (2) | 38 (3) | 20 (2) | −2 (2) | 10 (2) | 1 (2) |
| C(55) | 40 (3) | 34 (3) | 24 (3) | 2 (2) | 10 (2) | −6 (2) |
| Mo(2) | 18 (1) | 21 (1) | 24 (1) | 1 (1) | 6 (1) | 1 (1) |
| C(101) | 23 (2) | 28 (2) | 29 (3) | 2 (2) | 7 (2) | 1 (2) |
| C(102) | 23 (2) | 38 (3) | 45 (3) | 12 (2) | 13 (2) | 0 (2) |
| C(103) | 28 (3) | 43 (3) | 58 (4) | 2 (3) | 10 (3) | −12 (2) |
| C(104) | 22 (2) | 53 (3) | 61 (4) | 16 (3) | 9 (2) | −2 (2) |
| C(105) | 31 (3) | 56 (4) | 55 (3) | 19 (3) | 22 (3) | 9 (3) |
| N(101) | 29 (2) | 22 (2) | 23 (2) | −2 (2) | 9 (2) | 3 (1) |
| C(106) | 34 (2) | 31 (2) | 24 (2) | 2 (2) | 9 (2) | 10 (2) |
| C(107) | 46 (3) | 28 (2) | 26 (3) | 3 (2) | 14 (2) | 11 (2) |
| C(108) | 41 (3) | 25 (2) | 34 (3) | −2 (2) | 8 (2) | 0 (2) |
| C(109) | 32 (2) | 23 (2) | 34 (3) | −3 (2) | 10 (2) | −2 (2) |
| C(110) | 35 (2) | 37 (3) | 55 (4) | 3 (3) | 17 (3) | 13 (2) |
| C(111) | 29 (2) | 28 (3) | 47 (3) | −3 (2) | 9 (2) | −3 (2) |
| N(102) | 19 (2) | 26 (2) | 30 (2) | 0 (1) | 7 (2) | 2 (2) |
| C(121) | 29 (2) | 27 (2) | 32 (2) | 2 (2) | 9 (2) | 1 (2) |
| C(122) | 32 (3) | 25 (2) | 41 (3) | 4 (2) | 12 (2) | 0 (2) |
| C(123) | 34 (3) | 31 (2) | 34 (3) | 6 (2) | 15 (2) | −2 (2) |
| C(124) | 28 (2) | 30 (2) | 33 (2) | 1 (2) | 15 (2) | −1 (2) |
| C(125) | 16 (2) | 26 (2) | 36 (2) | 3 (2) | 5 (2) | −2 (2) |
| C(126) | 21 (2) | 25 (2) | 32 (2) | 0 (2) | 5 (2) | −2 (2) |
| C(127) | 44 (3) | 32 (2) | 24 (2) | −3 (2) | 8 (2) | −5 (2) |
| C(128) | 51 (3) | 31 (2) | 30 (2) | −8 (2) | 12 (3) | −4 (2) |
| C(129) | 41 (3) | 24 (2) | 33 (3) | −2 (2) | 7 (2) | −3 (2) |
| C(130) | 27 (2) | 25 (2) | 28 (2) | 1 (2) | 7 (2) | −4 (2) |
| N(103) | 19 (2) | 25 (2) | 26 (2) | 0 (1) | 3 (2) | −3 (2) |
| N(104) | 19 (3) | 23 (4) | 24 (3) | −1 (2) | 7 (2) | 1 (3) |
| C(131) | 22 (2) | 22 (4) | 21 (3) | −1 (2) | 7 (2) | 1 (2) |
| C(132) | 22 (2) | 25 (4) | 23 (4) | −2 (3) | 8 (3) | 0 (2) |
| C(133) | 26 (3) | 26 (5) | 21 (4) | −1 (3) | 7 (3) | −4 (3) |
| C(134) | 29 (4) | 24 (4) | 20 (3) | −1 (3) | 4 (3) | −2 (3) |
| C(135) | 24 (3) | 26 (4) | 19 (3) | 0 (3) | 2 (3) | −1 (3) |
| C(136) | 23 (2) | 24 (3) | 20 (3) | −1 (2) | 6 (2) | 1 (2) |
| C(141) | 20 (2) | 25 (2) | 19 (3) | 2 (2) | 4 (2) | 3 (2) |
| C(142) | 19 (3) | 24 (3) | 20 (3) | 1 (2) | 5 (2) | 4 (2) |
| C(147) | 23 (3) | 30 (3) | 22 (3) | −3 (2) | 7 (3) | 0 (2) |
| C(148) | 33 (5) | 27 (6) | 20 (3) | −7 (3) | 6 (5) | −2 (5) |
| C(149) | 39 (7) | 25 (5) | 31 (6) | −7 (5) | 6 (5) | 1 (5) |
| C(143) | 21 (3) | 28 (3) | 21 (4) | −1 (2) | 7 (3) | 2 (2) |
| C(144) | 20 (3) | 30 (3) | 19 (3) | 0 (2) | 6 (2) | 0 (2) |
| C(150) | 23 (3) | 37 (3) | 27 (3) | −5 (3) | 11 (3) | −5 (2) |
| C(151) | 21 (3) | 48 (5) | 36 (6) | −2 (4) | 18 (4) | −2 (3) |
| C(152) | 39 (4) | 41 (5) | 37 (4) | 5 (3) | 15 (3) | −12 (3) |
| C(145) | 26 (3) | 31 (3) | 19 (3) | 1 (3) | 7 (2) | −4 (2) |
| C(146) | 23 (3) | 29 (3) | 18 (3) | 2 (2) | 5 (2) | −2 (2) |
| C(153) | 34 (4) | 38 (4) | 21 (3) | −1 (3) | 11 (2) | −9 (3) |
| C(154) | 58 (6) | 48 (6) | 19 (4) | 6 (4) | 7 (4) | −9 (4) |
| C(155) | 47 (5) | 46 (4) | 26 (5) | −12 (4) | 13 (4) | −7 (4) |
| N(4A) | 22 (4) | 23 (4) | 25 (3) | −3 (3) | 5 (4) | 2 (3) |
| C(31A) | 22 (2) | 23 (4) | 21 (3) | −3 (3) | 6 (3) | 2 (3) |
| C(32A) | 22 (3) | 24 (5) | 23 (4) | −5 (3) | 6 (3) | 0 (3) |
| C(33A) | 26 (4) | 26 (5) | 22 (4) | −4 (4) | 6 (4) | −4 (3) |
| C(34A) | 28 (4) | 25 (5) | 21 (4) | −1 (4) | 4 (4) | −2 (3) |
| C(35A) | 24 (3) | 26 (5) | 19 (4) | −1 (3) | 2 (3) | −1 (3) |
| C(36A) | 22 (2) | 26 (3) | 19 (3) | −1 (3) | 6 (2) | 1 (2) |
| C(41A) | 22 (3) | 28 (3) | 18 (3) | 1 (3) | 4 (3) | 1 (2) |
| C(42A) | 21 (3) | 29 (4) | 20 (4) | 1 (3) | 6 (3) | 3 (3) |
| C(47A) | 25 (4) | 32 (5) | 19 (4) | 1 (3) | 9 (4) | −1 (3) |
| C(48A) | 36 (8) | 31 (10) | 20 (4) | 0 (5) | 11 (7) | −5 (8) |
| C(49A) | 32 (9) | 27 (6) | 28 (8) | −2 (5) | 3 (7) | −3 (7) |
| C(43A) | 20 (4) | 32 (4) | 22 (5) | −2 (3) | 8 (3) | 2 (3) |
| C(44A) | 20 (3) | 39 (4) | 23 (4) | −4 (3) | 8 (3) | −1 (3) |
| C(50A) | 23 (4) | 47 (4) | 26 (5) | −7 (4) | 11 (3) | −6 (3) |
| C(51A) | 19 (4) | 55 (8) | 38 (10) | −8 (8) | 14 (6) | −2 (5) |

TABLE 105D-continued

Anisotropic displacement parameters (Å² × 10³) for 104g.
The anisotropic displacement factor exponent takes the form: $-2\pi^2[h^2 a^{*2} U^{11} + \ldots + 2 h k a^* b^* U^{12}]$.

|  | $U^{11}$ | $U^{22}$ | $U^{33}$ | $U^{23}$ | $U^{13}$ | $U^{12}$ |
|---|---|---|---|---|---|---|
| C(52A) | 35 (6) | 45 (4) | 5 (6) | 2 (5) | 11 (5) | −6 (4) |
| C(45A) | 22 (4) | 37 (4) | 20 (5) | −3 (4) | 6 (3) | −4 (3) |
| C(46A) | 22 (4) | 34 (4) | 19 (4) | −2 (3) | 6 (3) | −3 (3) |
| C(53A) | 32 (4) | 42 (5) | 21 (4) | −4 (4) | 11 (3) | −8 (4) |
| C(54A) | 52 (8) | 59 (9) | 20 (5) | 2 (6) | 8 (5) | −7 (7) |
| C(55A) | 53 (9) | 50 (7) | 33 (9) | −14 (6) | 19 (8) | −2 (7) |
| C(1S) | 104 (6) | 55 (4) | 95 (6) | 7 (4) | 63 (5) | 25 (4) |
| C(2S) | 80 (5) | 48 (4) | 63 (4) | −6 (3) | 33 (4) | 4 (3) |
| C(3S) | 64 (4) | 52 (4) | 51 (4) | −10 (3) | 12 (3) | 7 (3) |
| C(4S) | 51 (4) | 59 (4) | 56 (4) | −15 (3) | 15 (3) | 5 (3) |
| C(5S) | 67 (4) | 46 (3) | 64 (4) | −16 (3) | 35 (3) | −15 (3) |
| C(6S) | 105 (6) | 44 (4) | 94 (5) | 11 (4) | 55 (5) | 14 (4) |
| C(1T) | 50 (4) | 90 (4) | 46 (3) | −17 (3) | 12 (3) | −8 (4) |
| C(2T) | 56 (4) | 105 (5) | 38 (3) | 2 (3) | 6 (3) | −13 (4) |
| C(3T) | 64 (5) | 81 (4) | 57 (4) | 13 (3) | 13 (3) | −14 (4) |
| C(4T) | 65 (4) | 68 (3) | 45 (3) | −3 (3) | 13 (3) | −17 (3) |
| C(5T) | 58 (4) | 65 (3) | 39 (3) | −5 (2) | 17 (3) | −11 (3) |
| C(6T) | 45 (3) | 71 (4) | 43 (3) | −11 (3) | 17 (3) | −5 (3) |
| C(1U) | 35 (3) | 41 (3) | 41 (3) | −6 (2) | 3 (2) | 10 (2) |
| C(2U) | 34 (2) | 40 (3) | 33 (3) | −6 (2) | 11 (2) | 1 (2) |
| C(3U) | 35 (2) | 44 (3) | 29 (3) | −10 (2) | 7 (2) | 0 (2) |
| C(4U) | 41 (3) | 46 (3) | 49 (3) | −14 (3) | 15 (2) | −12 (2) |
| C(5U) | 71 (4) | 34 (3) | 60 (4) | 4 (3) | 27 (3) | −4 (3) |
| C(6U) | 62 (3) | 40 (3) | 44 (3) | 8 (2) | 7 (3) | 19 (3) |
| C(1V) | 69 (5) | 106 (5) | 60 (5) | 4 (4) | −1 (4) | 5 (4) |
| C(2V) | 116 (7) | 104 (6) | 42 (4) | 14 (4) | 26 (4) | 8 (5) |
| C(3V) | 87 (6) | 111 (5) | 51 (5) | 1 (4) | 16 (4) | −1 (5) |
| C(4V) | 66 (5) | 127 (6) | 63 (5) | −15 (5) | 10 (4) | −4 (5) |
| C(5V) | 83 (6) | 149 (8) | 122 (8) | −15 (6) | 59 (6) | −7 (6) |
| C(6V) | 62 (5) | 134 (7) | 123 (8) | −3 (6) | 38 (5) | −19 (5) |
| C(1W) | 71 (5) | 78 (4) | 51 (3) | 7 (3) | 27 (3) | 30 (3) |
| C(2W) | 44 (4) | 118 (5) | 53 (4) | −12 (3) | 16 (3) | 13 (4) |
| C(3W) | 46 (4) | 77 (4) | 90 (5) | −26 (3) | 26 (3) | −8 (3) |
| C(4W) | 49 (4) | 44 (3) | 75 (4) | 0 (3) | 31 (3) | 3 (3) |
| C(5W) | 66 (4) | 42 (3) | 49 (3) | −1 (2) | 23 (3) | 1 (3) |
| C(6W) | 87 (5) | 42 (3) | 49 (3) | −1 (2) | 31 (3) | 6 (3) |
| C(1X) | 41 (3) | 61 (4) | 36 (3) | 9 (2) | 11 (2) | 17 (3) |
| C(2X) | 38 (2) | 54 (3) | 21 (2) | 6 (2) | 7 (2) | 5 (2) |
| C(3X) | 39 (3) | 38 (3) | 29 (3) | 4 (2) | 17 (2) | 0 (2) |
| C(4X) | 39 (3) | 38 (3) | 45 (3) | 0 (2) | 17 (2) | −11 (2) |
| C(5X) | 60 (3) | 33 (3) | 34 (3) | −3 (2) | 16 (3) | −14 (3) |
| C(6X) | 65 (3) | 37 (3) | 41 (3) | 2 (2) | 23 (3) | 10 (3) |

TABLE 105E

Hydrogen coordinates (×10⁴) and isotropic displacement parameters (Å² × 10³) for 104g.

|  | x | y | z | U(eq) |
|---|---|---|---|---|
| H(3A) | 2216 | 9357 | 8461 | 57 |
| H(3B) | 1566 | 9380 | 7939 | 57 |
| H(3C) | 2016 | 9172 | 7527 | 57 |
| H(4A) | 1424 | 8359 | 7134 | 82 |
| H(4B) | 1002 | 8587 | 7579 | 82 |
| H(4C) | 1279 | 8029 | 7830 | 82 |
| H(5A) | 1657 | 8296 | 9292 | 61 |
| H(5B) | 1367 | 8850 | 9055 | 61 |
| H(5C) | 2023 | 8813 | 9538 | 61 |
| H(7) | 2588 | 6225 | 9186 | 32 |
| H(8) | 3645 | 6259 | 9448 | 32 |
| H(10A) | 1980 | 7465 | 9149 | 55 |
| H(10B) | 1770 | 6900 | 8808 | 55 |
| H(10C) | 1887 | 7328 | 8209 | 55 |
| H(11A) | 4101 | 7430 | 8819 | 43 |
| H(11B) | 4380 | 7004 | 9500 | 43 |
| H(11C) | 4173 | 7545 | 9761 | 43 |
| H(21) | 2931 | 6961 | 7697 | 27 |
| H(22) | 2936 | 6551 | 6487 | 31 |
| H(23) | 3045 | 7058 | 5406 | 32 |
| H(24) | 3175 | 7950 | 5592 | 28 |
| H(27) | 3427 | 8737 | 5915 | 31 |
| H(28) | 3639 | 9596 | 6307 | 36 |
| H(29) | 3550 | 9883 | 7558 | 33 |
| H(30) | 3288 | 9289 | 8392 | 28 |
| H(32) | 2880 | 9143 | 9742 | 28 |
| H(33) | 3107 | 9832 | 10654 | 33 |
| H(34) | 4034 | 9954 | 11474 | 35 |
| H(35) | 4720 | 9373 | 11398 | 31 |
| H(47) | 4323 | 8371 | 11767 | 42 |
| H(48A) | 4338 | 7443 | 11593 | 69 |
| H(48B) | 4330 | 7617 | 12482 | 69 |
| H(48C) | 4903 | 7426 | 12350 | 69 |
| H(49A) | 5448 | 8251 | 12839 | 79 |
| H(49B) | 4925 | 8389 | 13146 | 79 |
| H(49C) | 5129 | 8792 | 12590 | 79 |
| H(43) | 5516 | 7659 | 11662 | 38 |
| H(50) | 6161 | 7579 | 10054 | 48 |
| H(51A) | 5765 | 6870 | 11011 | 92 |
| H(51B) | 6223 | 6727 | 10574 | 92 |
| H(51C) | 5598 | 6874 | 10035 | 92 |
| H(52A) | 6706 | 7986 | 11257 | 77 |

TABLE 105E-continued

Hydrogen coordinates (×10⁴) and isotropic displacement parameters ($\text{Å}^2 \times 10^3$) for 104g.

| | x | y | z | U(eq) |
|---|---|---|---|---|
| H(52B) | 6895 | 7393 | 11272 | 77 |
| H(52C) | 6507 | 7574 | 11805 | 77 |
| H(45) | 5496 | 8181 | 9445 | 33 |
| H(53) | 4295 | 8984 | 9118 | 27 |
| H(54A) | 5007 | 8507 | 8309 | 41 |
| H(54B) | 4457 | 8838 | 7867 | 41 |
| H(54C) | 4402 | 8291 | 8274 | 41 |
| H(55A) | 5056 | 9534 | 9752 | 49 |
| H(55B) | 4867 | 9602 | 8779 | 49 |
| H(55C) | 5415 | 9272 | 9234 | 49 |
| H(10D) | 6876 | 5957 | 2819 | 65 |
| H(10E) | 6504 | 5742 | 3353 | 65 |
| H(10F) | 7173 | 5747 | 3725 | 65 |
| H(10G) | 6285 | 7105 | 3365 | 69 |
| H(10H) | 5966 | 6563 | 3132 | 69 |
| H(10I) | 6336 | 6781 | 2598 | 69 |
| H(10J) | 7090 | 6249 | 4934 | 68 |
| H(10K) | 6421 | 6261 | 4555 | 68 |
| H(10L) | 6764 | 6791 | 4793 | 68 |
| H(107) | 7723 | 8861 | 4542 | 39 |
| H(108) | 8773 | 8758 | 4781 | 41 |
| H(11D) | 6862 | 8234 | 4236 | 62 |
| H(11E) | 7036 | 7650 | 4512 | 62 |
| H(11F) | 6917 | 7817 | 3577 | 62 |
| H(11G) | 9210 | 7446 | 4982 | 53 |
| H(11H) | 9432 | 7972 | 4698 | 53 |
| H(11I) | 9096 | 7560 | 4030 | 53 |
| H(121) | 7964 | 8103 | 3002 | 36 |
| H(122) | 8004 | 8508 | 1819 | 39 |
| H(123) | 8111 | 8003 | 739 | 39 |
| H(124) | 8164 | 7098 | 888 | 35 |
| H(127) | 8159 | 6289 | 1074 | 41 |
| H(128) | 8226 | 5405 | 1382 | 45 |
| H(129) | 8244 | 5136 | 2703 | 40 |
| H(130) | 8174 | 5754 | 3646 | 33 |
| H(132) | 7875 | 5863 | 5011 | 28 |
| H(133) | 8113 | 5154 | 5877 | 30 |
| H(134) | 9064 | 4975 | 6567 | 30 |
| H(135) | 9745 | 5541 | 6425 | 29 |
| H(147) | 9235 | 6028 | 4226 | 30 |
| H(14A) | 9365 | 6756 | 3416 | 40 |
| H(14B) | 9315 | 6211 | 2956 | 40 |
| H(14C) | 9916 | 6476 | 3342 | 40 |
| H(14D) | 10336 | 5745 | 4217 | 49 |
| H(14E) | 9777 | 5415 | 3819 | 49 |
| H(14F) | 10021 | 5476 | 4791 | 49 |
| H(143) | 10420 | 6853 | 4505 | 28 |
| H(150) | 10916 | 7850 | 5979 | 34 |
| H(15A) | 11585 | 7237 | 6583 | 49 |
| H(15B) | 11826 | 7626 | 6049 | 49 |
| H(15C) | 11621 | 7059 | 5709 | 49 |
| H(15D) | 10952 | 7536 | 4417 | 58 |
| H(15E) | 11143 | 8087 | 4836 | 58 |
| H(15F) | 10495 | 7924 | 4565 | 58 |
| H(145) | 10507 | 7324 | 6773 | 30 |
| H(153) | 9381 | 6551 | 6969 | 37 |
| H(15G) | 10203 | 6108 | 7665 | 64 |
| H(15H) | 10048 | 6482 | 8305 | 64 |
| H(15I) | 10536 | 6640 | 7934 | 64 |
| H(15J) | 9967 | 7490 | 7589 | 59 |
| H(15K) | 9442 | 7262 | 7817 | 59 |
| H(15L) | 9360 | 7482 | 6918 | 59 |
| H(32A) | 7906 | 5938 | 5110 | 28 |
| H(33A) | 8178 | 5217 | 5946 | 30 |
| H(34A) | 9138 | 5076 | 6655 | 30 |
| H(35A) | 9798 | 5640 | 6440 | 29 |
| H(47A) | 9218 | 6011 | 4160 | 30 |
| H(48D) | 9332 | 6662 | 3242 | 43 |
| H(48E) | 9275 | 6094 | 2849 | 43 |
| H(48F) | 9877 | 6365 | 3179 | 43 |
| H(49D) | 10289 | 5616 | 4213 | 46 |
| H(49E) | 9710 | 5348 | 3710 | 46 |
| H(49F) | 9886 | 5383 | 4686 | 46 |
| H(43A) | 10425 | 6756 | 4274 | 30 |
| H(50A) | 11088 | 7379 | 4747 | 37 |
| H(51D) | 11907 | 7533 | 5754 | 54 |
| H(51E) | 11694 | 6963 | 5871 | 54 |
| H(51F) | 11620 | 7425 | 6449 | 54 |
| H(52D) | 10785 | 8107 | 5766 | 41 |
| H(52E) | 10536 | 8070 | 4791 | 41 |
| H(52F) | 11174 | 8243 | 5211 | 41 |
| H(45A) | 10589 | 7369 | 6492 | 32 |
| H(53A) | 9451 | 6642 | 6810 | 38 |
| H(54D) | 10352 | 6284 | 7541 | 67 |
| H(54E) | 10072 | 6596 | 8117 | 67 |
| H(54F) | 10563 | 6857 | 7841 | 67 |
| H(55D) | 9993 | 7610 | 7321 | 66 |
| H(55E) | 9417 | 7411 | 7432 | 66 |
| H(55F) | 9440 | 7575 | 6546 | 66 |
| H(1S) | 6098 | 5821 | 992 | 93 |
| H(2S) | 6462 | 5113 | 1827 | 74 |
| H(3S) | 7056 | 4542 | 1464 | 68 |
| H(4S) | 7315 | 4696 | 300 | 67 |
| H(5S) | 7003 | 5430 | −486 | 67 |
| H(6S) | 6356 | 5977 | −175 | 90 |
| H(1T) | 5404 | 1231 | 4590 | 75 |
| H(2T) | 5646 | 395 | 5098 | 82 |
| H(3T) | 5343 | −319 | 4228 | 83 |
| H(4T) | 4787 | −186 | 2875 | 72 |
| H(5T) | 4575 | 648 | 2390 | 64 |
| H(6T) | 4853 | 1356 | 3245 | 63 |
| H(1U) | 2309 | 490 | 7750 | 49 |
| H(2U) | 2862 | 167 | 9012 | 43 |
| H(3U) | 3811 | 369 | 9499 | 44 |
| H(4U) | 4206 | 923 | 8757 | 54 |
| H(5U) | 3652 | 1252 | 7503 | 64 |
| H(6U) | 2702 | 1040 | 7004 | 61 |
| H(1V) | 186 | 10189 | 6939 | 100 |
| H(2V) | −296 | 9507 | 7280 | 104 |
| H(3V) | −401 | 8726 | 6619 | 101 |
| H(4V) | 42 | 8579 | 5627 | 105 |
| H(5V) | 538 | 9256 | 5298 | 134 |
| H(6V) | 653 | 10033 | 5979 | 125 |
| H(1W) | 1785 | 4688 | 947 | 78 |
| H(2W) | 2270 | 5460 | 1372 | 86 |
| H(3W) | 2089 | 6185 | 505 | 84 |
| H(4W) | 1449 | 6116 | −802 | 64 |
| H(5W) | 978 | 5348 | −1213 | 61 |
| H(6W) | 1141 | 4635 | −351 | 69 |
| H(1X) | 9246 | 4201 | 3889 | 56 |
| H(2X) | 8857 | 4717 | 4682 | 46 |
| H(3X) | 7888 | 4808 | 4333 | 41 |
| H(4X) | 7308 | 4383 | 3194 | 48 |
| H(5X) | 7696 | 3873 | 2392 | 51 |
| H(6X) | 8663 | 3775 | 2748 | 55 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

What is claimed is:

1. A compound of formula I:

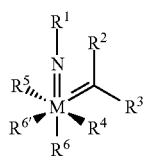

wherein:

M is a suitable metal;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R, provided that $R^2$ and $R^3$ are not simultaneously hydrogen;

each of $R^4$ and $R^5$ is independently halogen, —N(R)$_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 additional heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or:

two R groups on the same nitrogen atom are taken together with the nitrogen to form an optionally substituted 3-8 membered saturated, partially unsaturated, or heteroaryl ring having 0-3 additional heteroatoms not including the same nitrogen atom independently selected from nitrogen, oxygen, or sulfur;

each of $R^6$ and $R^{6'}$ is independently a monodentate ligand, or $R^6$ and $R^{6'}$ are taken together with their intervening atoms to form an optionally substituted bidentate group.

2. A compound of formula II:

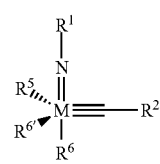

wherein:

M is a suitable metal;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^2$ is —OR, —SR, —N(R)$_2$, —NROR, —OC(O)R, —SOR, —SO$_2$R, —SO$_2$N(R)$_2$, —C(O)N(R)$_2$, —NRC(O)R, —NRC(O)OR, or —NRSO$_2$R, or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^5$ is halogen, —$N(R)_2$, —NRC(O)R, —NRC(O)OR, —NRC(O)N(R)$_2$, —NRSO$_2$R, —NRSO$_2$N(R)$_2$, or —NROR, or an optionally substituted group selected from a 5-6 membered monocyclic heteroaryl ring having at least one nitrogen and 0-3 additional heteroatoms independently selected from nitrogen, oxygen, or sulfur, a 4-7 membered saturated or partially unsaturated heterocyclic ring having at least one nitrogen and 0-2 additional heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 additional heteroatoms independently selected from nitrogen, oxygen, or sulfur;

each R is independently hydrogen or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur, or:

two R groups on the same nitrogen atom are taken together with the nitrogen to form an optionally substituted 3-8 membered saturated, partially unsaturated, or heteroaryl ring having 0-3 additional heteroatoms not including the same nitrogen atom independently selected from nitrogen, oxygen, or sulfur; and each of $R^6$ and $R^{6'}$ is independently a monodentate ligand, or $R^6$ and $R^{6'}$ are taken together with their intervening atoms to form an optionally substituted bidentate group.

3. The compound of claim 1, wherein M is molybdenum or tungsten.

4. The compound of claim 1, wherein $R^1$ is optionally substituted phenyl.

5. The compound of claim 1, wherein one of $R^2$ and $R^3$ is hydrogen and the other is optionally substituted $C_{1-20}$ aliphatic.

6. The compound of claim 1, wherein each of $R^4$ and $R^5$ is

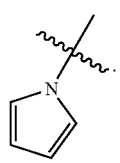 [SMILES: *n1cccc1]

7. The compound of claim 1, wherein both of $R^6$ and $R^{6'}$ are optionally substituted pyridine.

8. The compound of claim 1, wherein $R^6$ and $R^{6'}$ are taken together with their intervening atoms to form an optionally substituted bidentate group.

9. The compound of claim 1, wherein $R^6$ and $R^{6'}$ are taken together to form optionally substituted bipyridyl.

10. The compound of claim 1, wherein $R^6$ and $R^{6'}$ are selected from optionally substituted groups having the structure of

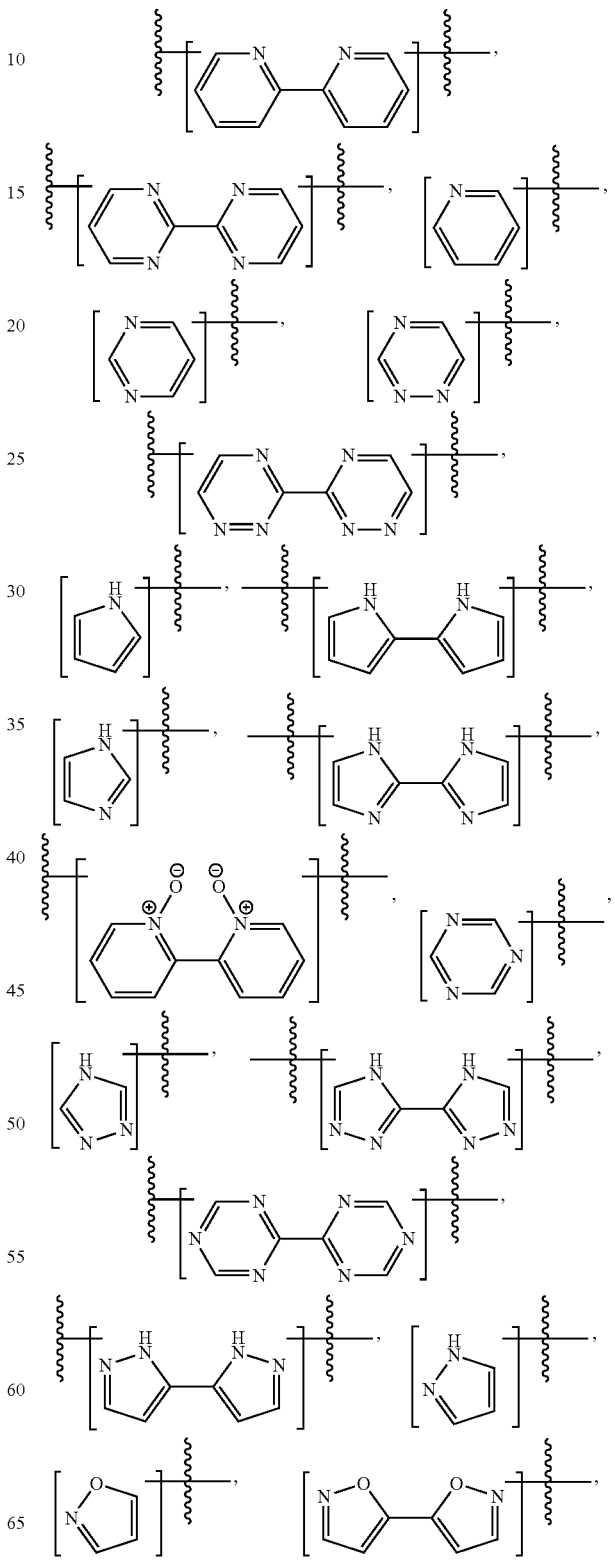

-continued
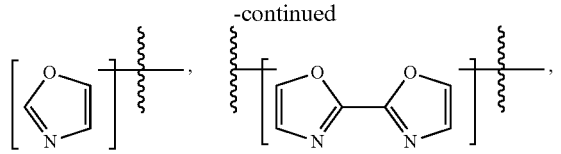
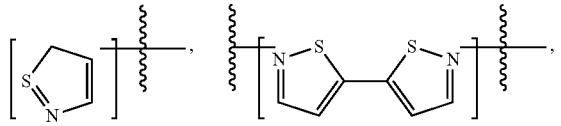
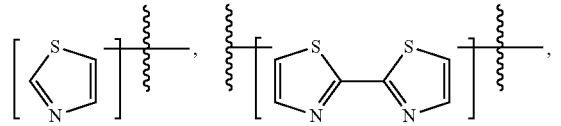
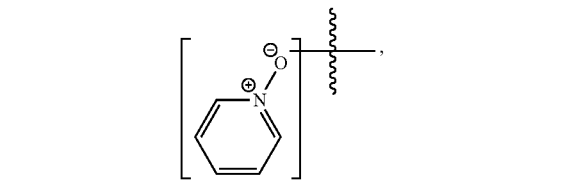
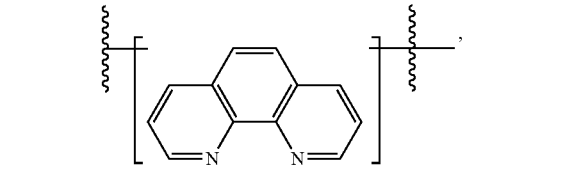
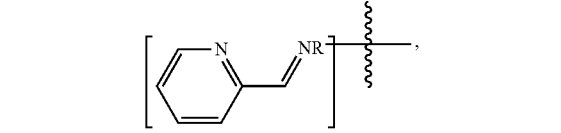
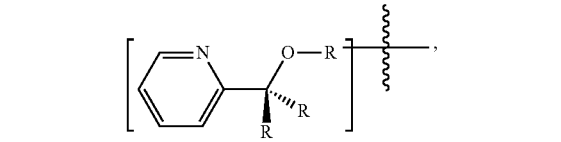
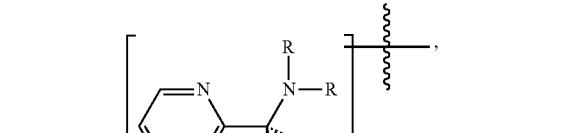
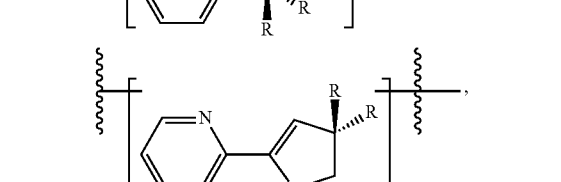
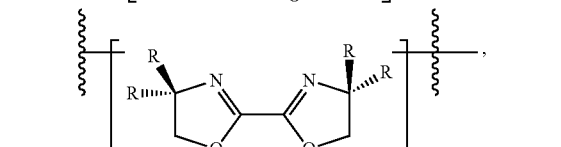
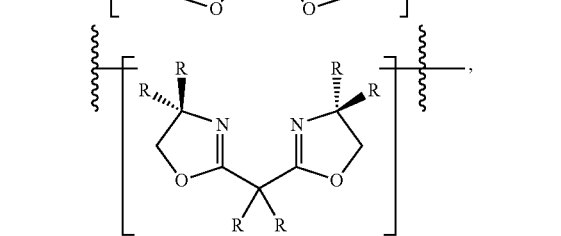
-continued
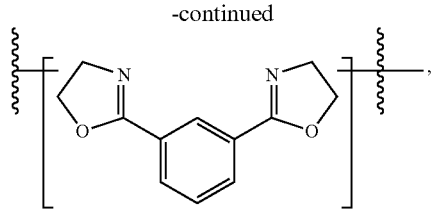
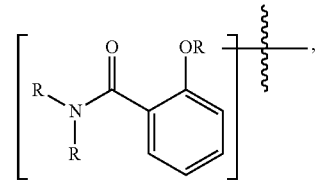
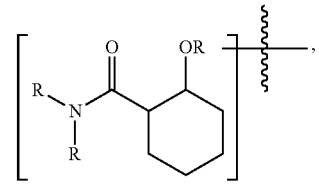
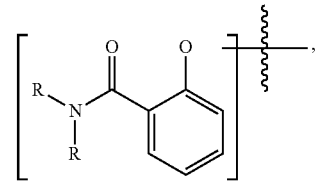
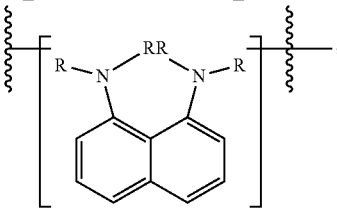
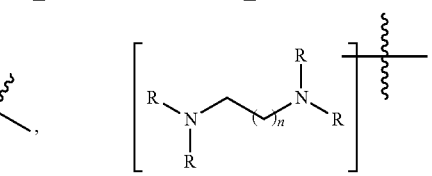
n = 0-100
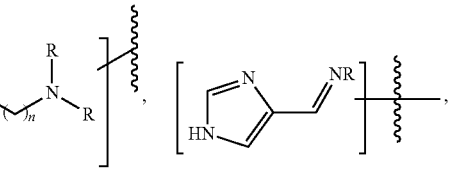
n = 0-100
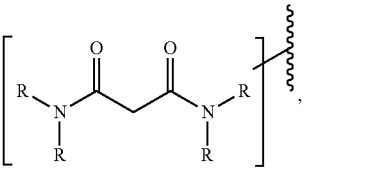
or
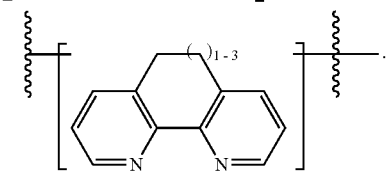

11. The compound of claim 1, wherein the compound is stable to ambient atmosphere.

12. The compound of claim 2, wherein M is molybdenum or tungsten.

13. The compound of claim 2, wherein $R^1$ is optionally substituted phenyl.

14. The compound of claim 2, wherein $R^2$ is optionally substituted $C_{1-20}$ aliphatic.

15. The compound of claim 2, wherein $R^5$ is

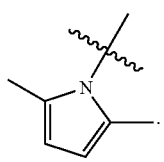

16. The compound of claim 2, wherein both of $R^6$ and $R^{6'}$ are optionally substituted pyridine.

17. The compound of claim 2, wherein $R^6$ and $R^{6'}$ are taken together with their intervening atoms to form an optionally substituted bidentate group.

18. The compound of claim 2, wherein $R^6$ and $R^{6'}$ are taken together to form optionally substituted bipyridyl.

19. The compound of claim 2, wherein $R^6$ and $R^{6'}$ are selected from optionally substituted groups having the structure of

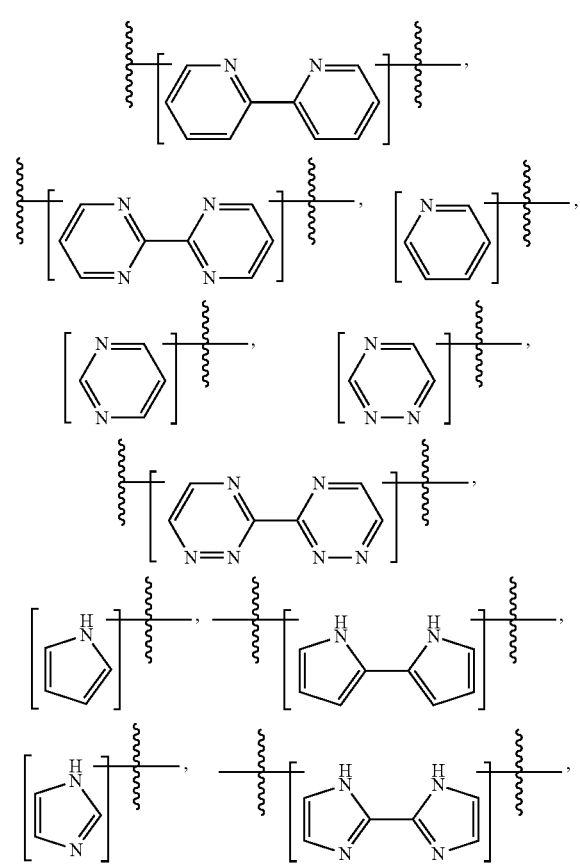

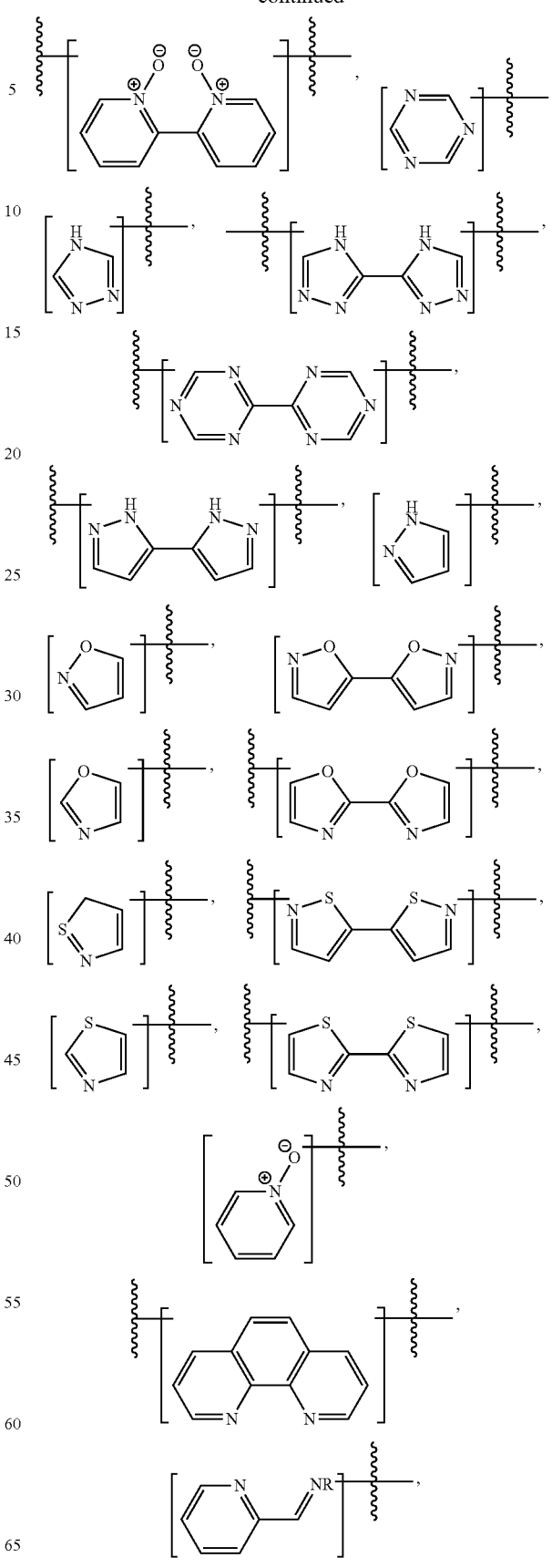

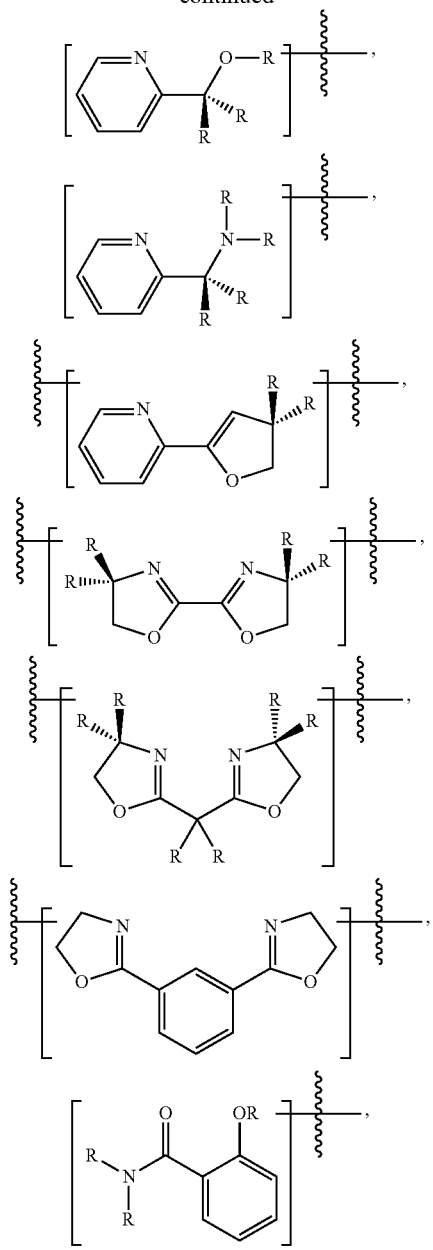
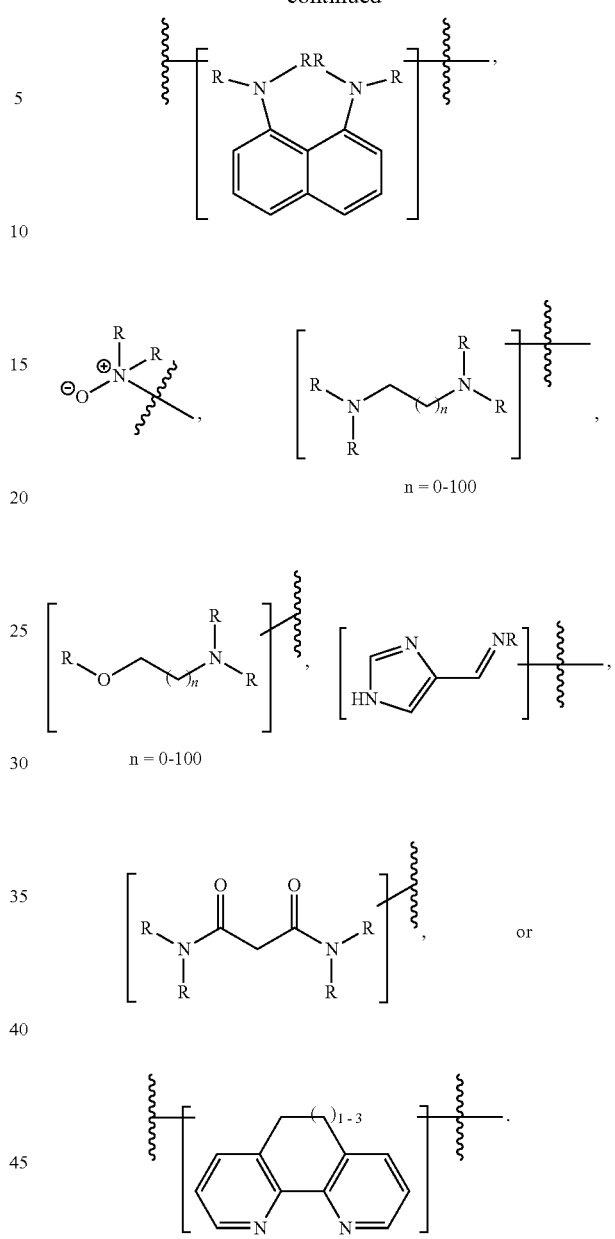
20. A compound selected from
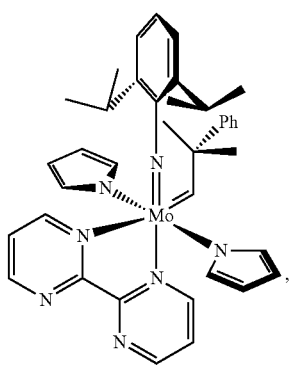

167
-continued
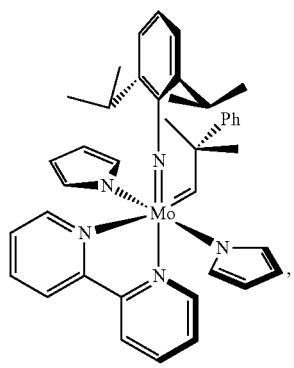
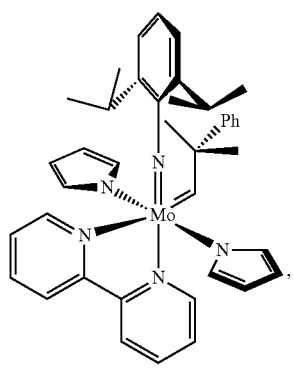
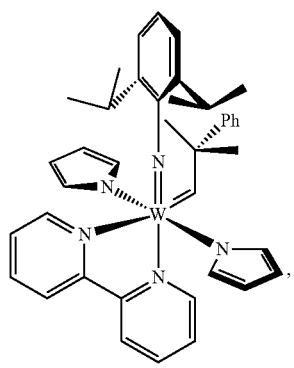
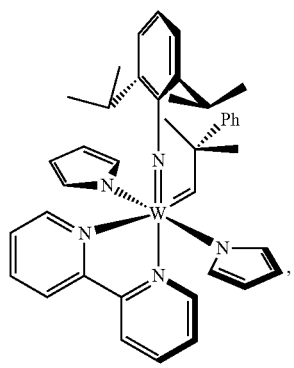
168
-continued
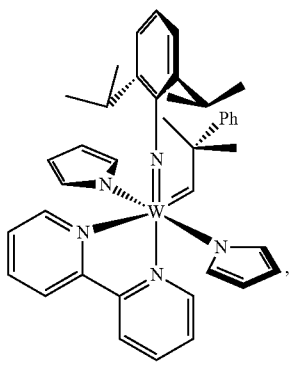
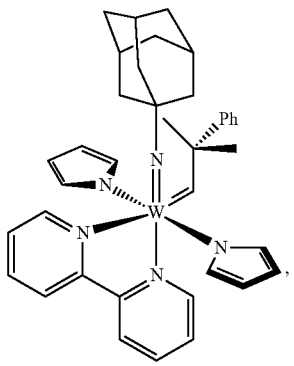
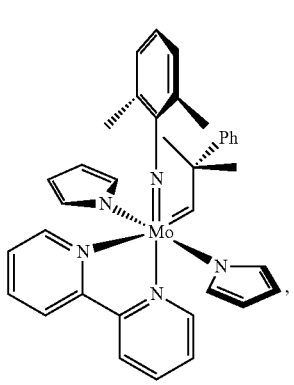
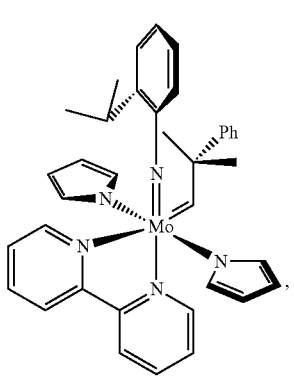

169
-continued
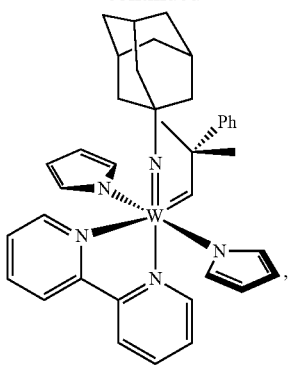
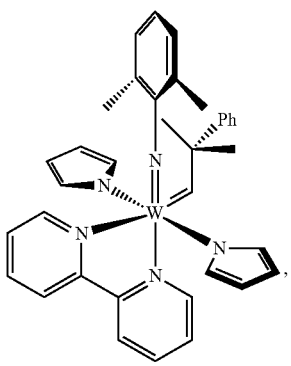
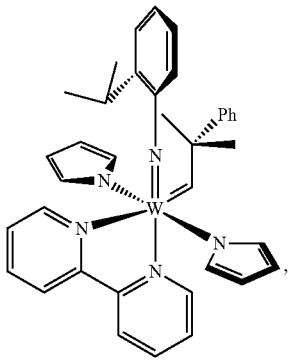
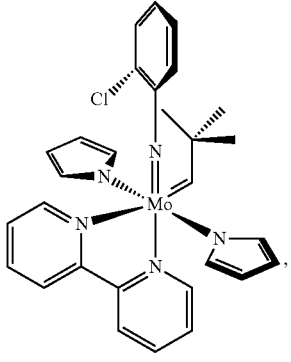
170
-continued
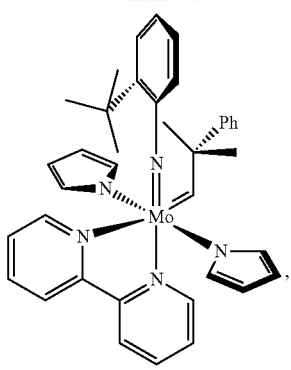
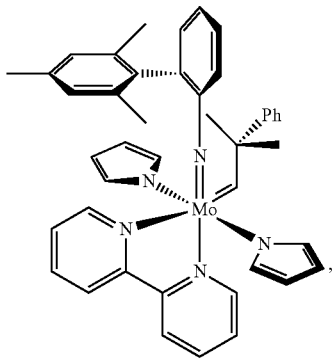
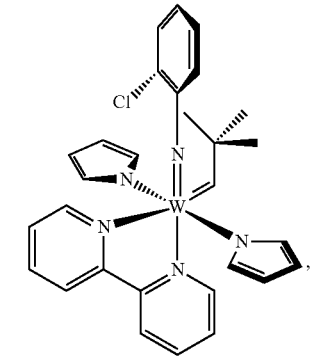
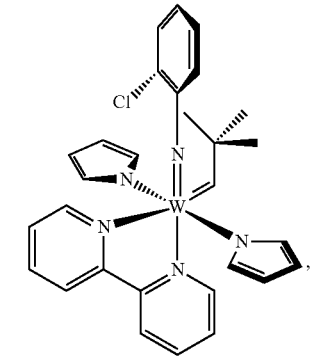

171
-continued
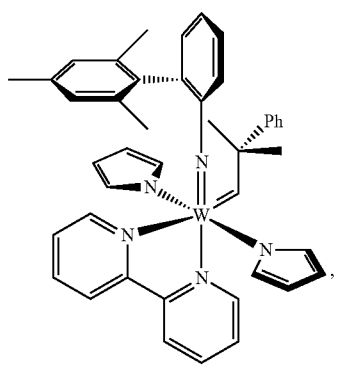
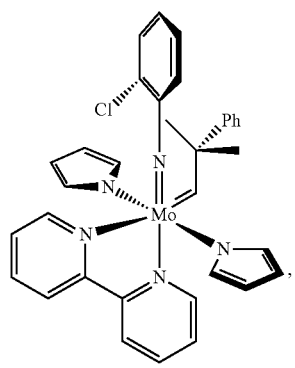
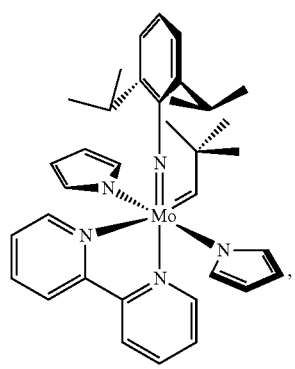
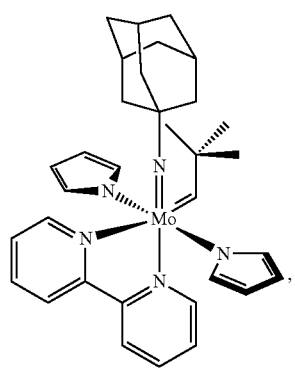
172
-continued
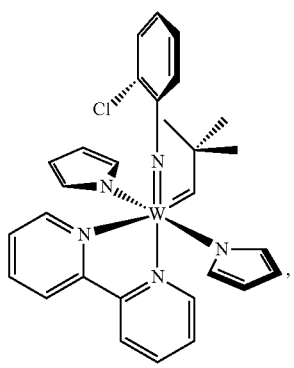
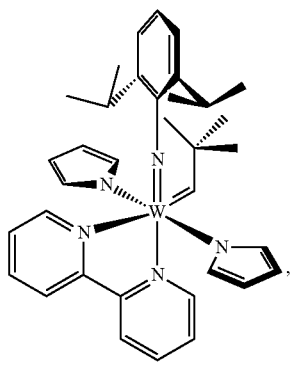
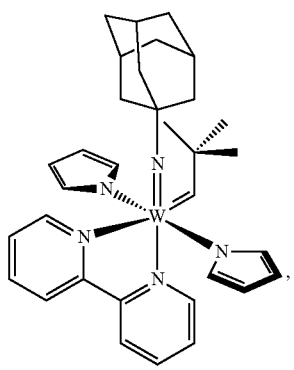
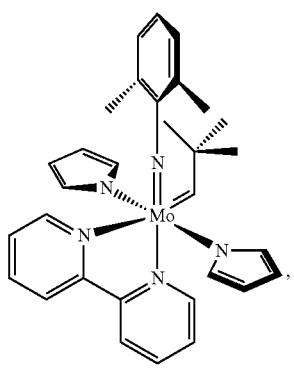

173
-continued
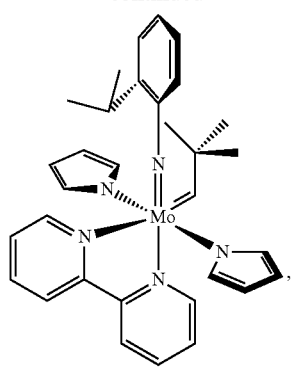
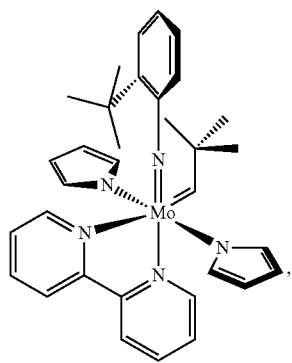
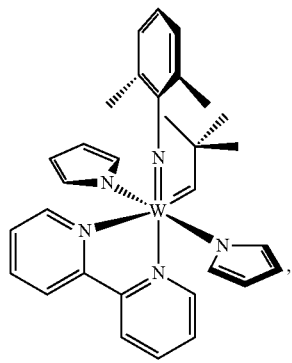
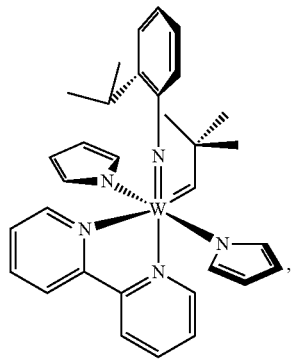
174
-continued
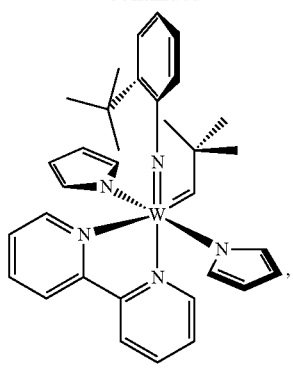
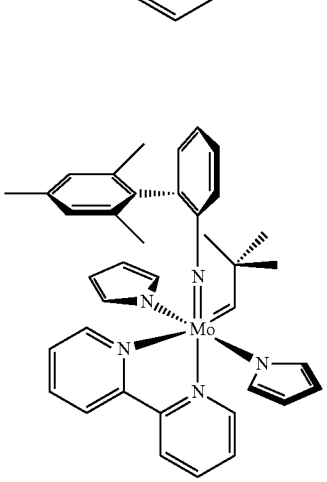
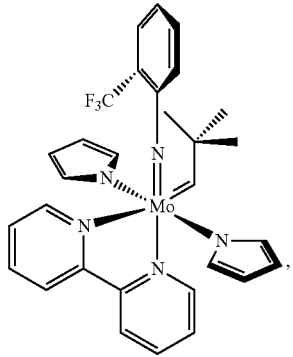
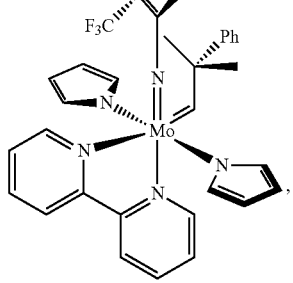

175
-continued
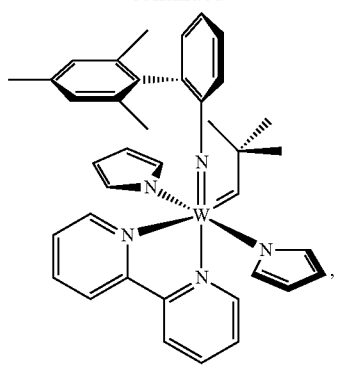
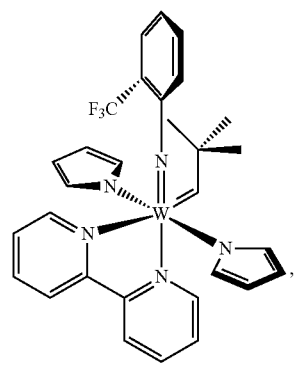
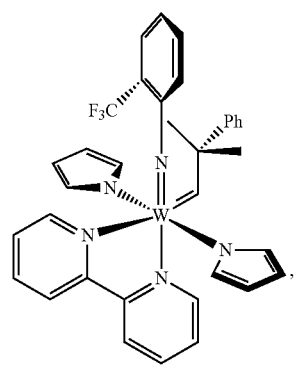
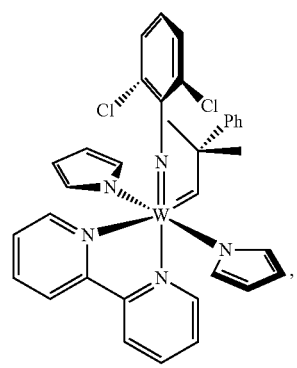
176
-continued
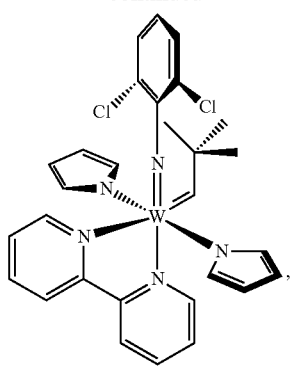
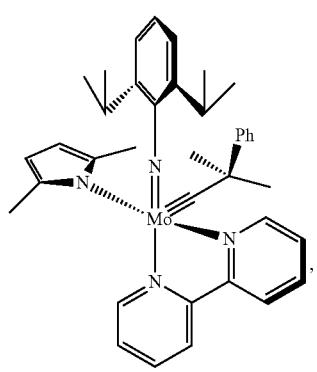
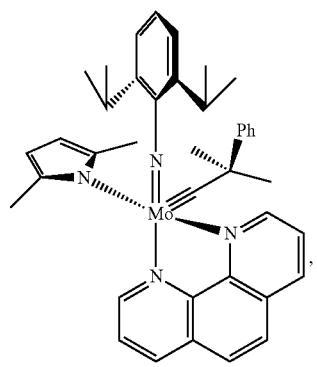
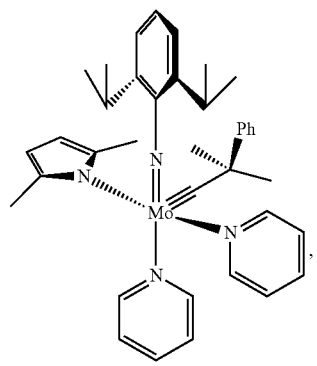

177
-continued
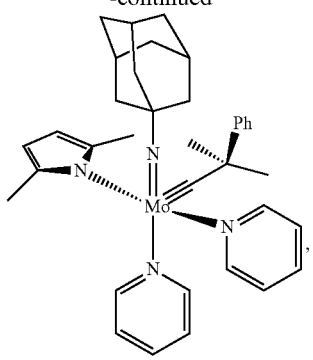
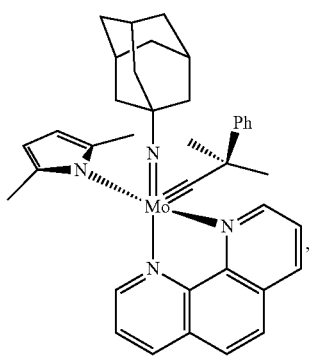
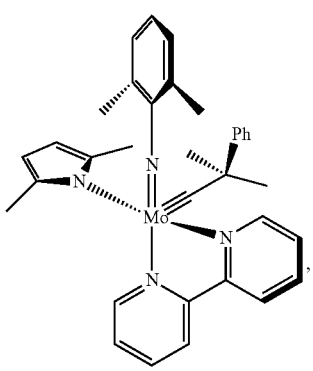
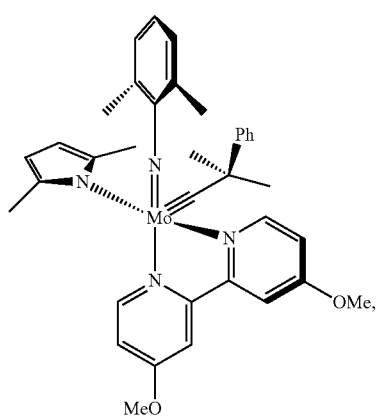
178
-continued
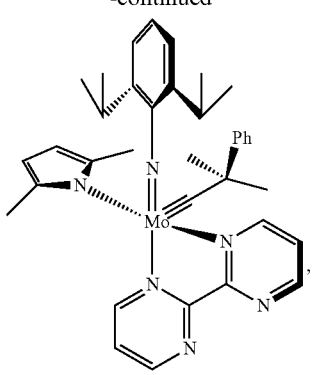
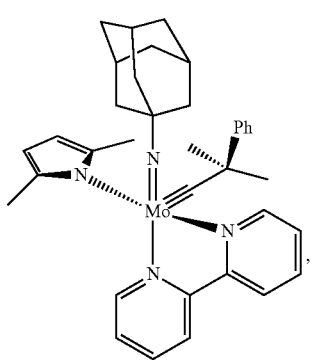
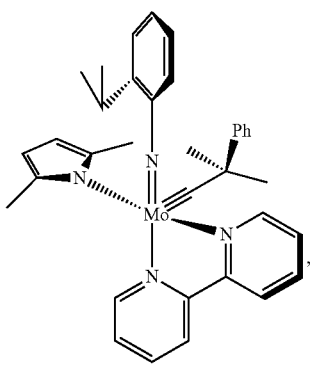
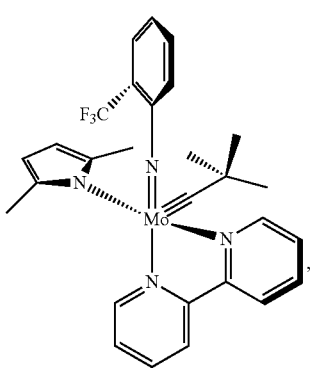

179
-continued
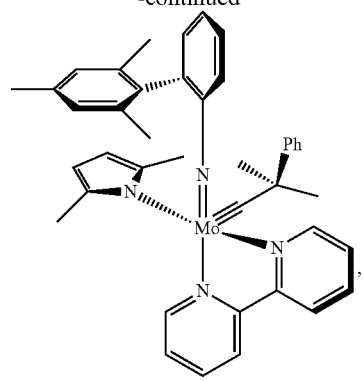
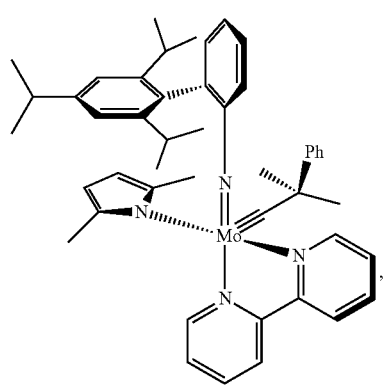
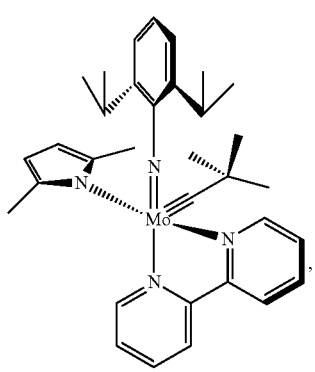
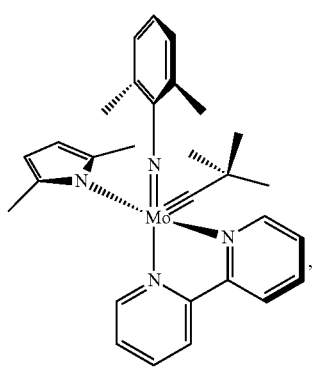
180
-continued
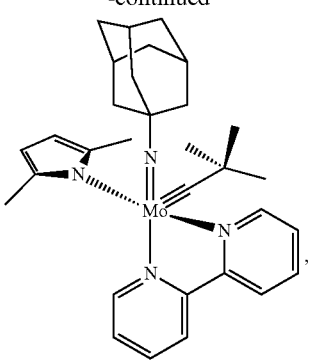
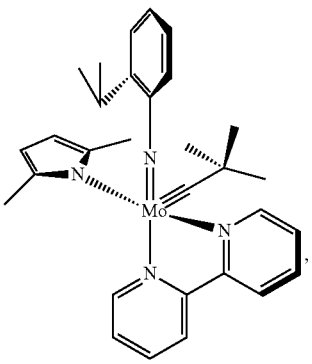
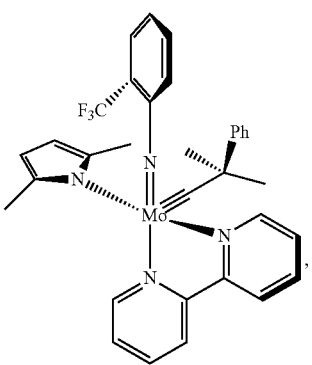
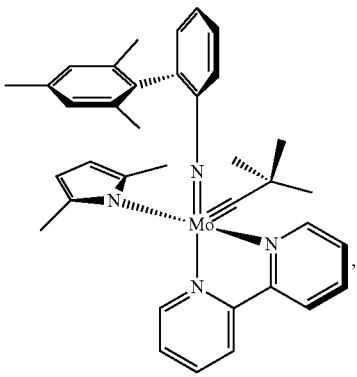

-continued
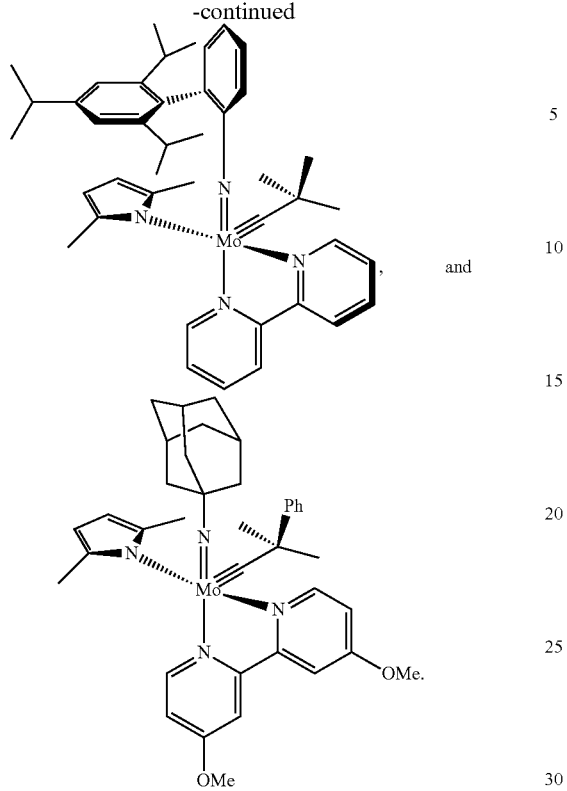
and
* * * * *